(12) United States Patent
Thomas et al.

(10) Patent No.: US 10,034,869 B2
(45) Date of Patent: *Jul. 31, 2018

(54) S1P MODULATING AGENTS

(71) Applicant: BIOGEN MA INC., Cambridge, MA (US)

(72) Inventors: Jermaine Thomas, Chelsea, MA (US); Sha Mi, Belmont, MA (US); Edward Yin-Shiang Lin, Ashland, MA (US); Guo Zhu Zheng, Lexington, MA (US); Bin Ma, Arlington, MA (US); Richard D. Caldwell, Melrose, MA (US); Kevin M. Guckian, Northborough, MA (US); Gnanasambandam Kumaravel, Lexington, MA (US)

(73) Assignee: BIOGEN MA INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/644,352

(22) Filed: Jul. 7, 2017

(65) Prior Publication Data
US 2018/0028511 A1 Feb. 1, 2018

Related U.S. Application Data

(63) Continuation of application No. 14/757,822, filed on Dec. 23, 2015, now Pat. No. 9,808,449, which is a continuation of application No. 13/983,489, filed as application No. PCT/US2012/023799 on Feb. 3, 2012, now Pat. No. 9,340,527.

(60) Provisional application No. 61/440,254, filed on Feb. 7, 2011.

(51) Int. Cl.
*A61K 31/445* (2006.01)
*A61K 38/21* (2006.01)
*C07D 211/62* (2006.01)
*C07D 401/06* (2006.01)
*C07D 405/12* (2006.01)
*C07D 215/20* (2006.01)
*A61K 31/225* (2006.01)
*A61K 39/395* (2006.01)
*A61K 31/517* (2006.01)
*A61K 31/695* (2006.01)
*A61K 31/55* (2006.01)
*C07K 16/28* (2006.01)
*A61K 31/498* (2006.01)
*A61K 31/4709* (2006.01)
*C07D 211/34* (2006.01)
*C07D 211/60* (2006.01)
*A61K 31/4545* (2006.01)

(52) U.S. Cl.
CPC .......... *A61K 31/445* (2013.01); *A61K 31/225* (2013.01); *A61K 31/4545* (2013.01); *A61K 31/4709* (2013.01); *A61K 31/498* (2013.01); *A61K 31/517* (2013.01); *A61K 31/55* (2013.01); *A61K 31/695* (2013.01); *A61K 38/21* (2013.01); *A61K 39/3955* (2013.01); *C07D 211/34* (2013.01); *C07D 211/60* (2013.01); *C07D 211/62* (2013.01); *C07D 215/20* (2013.01); *C07D 401/06* (2013.01); *C07D 405/12* (2013.01); *C07K 16/2842* (2013.01)

(58) Field of Classification Search
CPC .... A61K 31/445; A61K 38/21; A61K 31/225; A61K 39/3955; A61K 31/517; A61K 31/695; A61K 31/55; A61K 31/498; A61K 31/4709; A61K 31/4545; C07D 211/62; C07D 401/06; C07D 405/12; C07D 215/20; C07D 211/34; C07D 211/60; C07K 16/2842
See application file for complete search history.

(56) References Cited

U.S. PATENT DOCUMENTS

| | | | |
|---|---|---|---|
| 5,041,639 | A | 8/1991 | Shroot et al. |
| 5,719,164 | A | 2/1998 | Weidmann et al. |
| 7,750,021 | B2 | 7/2010 | Mi et al. |
| 7,754,896 | B2 | 7/2010 | Azzaoui et al. |
| 7,825,109 | B2 | 11/2010 | Nakade et al. |
| 7,906,549 | B2 | 3/2011 | Habashita et al. |
| 7,919,519 | B2 | 4/2011 | Burli et al. |
| 8,039,674 | B2 | 10/2011 | Habashita et al. |
| 8,802,659 | B2 | 8/2014 | Thomas et al. |

(Continued)

FOREIGN PATENT DOCUMENTS

| | | |
|---|---|---|
| JP | 2007-169194 A | 7/2007 |
| WO | 2003/061567 A2 | 7/2003 |

(Continued)

OTHER PUBLICATIONS

Murakami, A., "Sphingosine 1-phosphate (S1P) regulates vascular contraction via S1P3 receptor: investigation based on a new S1P3 receptor antagonist." Molecular pharmacology 77.4 (2010): 704-713.*

(Continued)

*Primary Examiner* — John M Mauro
(74) *Attorney, Agent, or Firm* — McCarter & English, LLP; Steven G. Davis; Xin Zhang

(57) ABSTRACT

The present invention provides compounds of formula (I) or (II) or a pharmaceutically acceptable salt thereof and their use in modulating the activity of S1P receptors. Also provided is a pharmaceutical composition comprising the compounds of formula (I) or (II) or a pharmaceutically acceptable salt thereof and a pharmaceutically acceptable excipient or carrier.

18 Claims, No Drawings

(56) References Cited

U.S. PATENT DOCUMENTS

| | | |
|---|---|---|
| 9,186,367 B2 | 11/2015 | Thomas et al. |
| 9,340,527 B2 | 5/2016 | Thomas et al. |
| 9,572,824 B2 | 2/2017 | Thomas et al. |
| 2004/0209904 A1 | 10/2004 | Dunn et al. |
| 2004/0254215 A1 | 12/2004 | Arend et al. |
| 2007/0167425 A1 | 7/2007 | Nakade et al. |
| 2008/0027036 A1 | 1/2008 | Burli et al. |
| 2009/0131400 A1 | 5/2009 | Mi et al. |
| 2010/0160258 A1 | 6/2010 | Caldwell et al. |
| 2010/0160357 A1 | 6/2010 | Caldwell et al. |
| 2012/0190649 A1 | 7/2012 | Thomas et al. |
| 2016/0263093 A1 | 9/2016 | Thomas et al. |
| 2017/0239280 A1 | 8/2017 | Thomas et al. |

FOREIGN PATENT DOCUMENTS

| | | |
|---|---|---|
| WO | 2003/062248 A2 | 7/2003 |
| WO | 2003/062252 A1 | 7/2003 |
| WO | 2003/105771 A2 | 12/2003 |
| WO | 2004/103309 A2 | 12/2004 |
| WO | 2004/108681 A1 | 12/2004 |
| WO | 2005/000833 A1 | 1/2005 |
| WO | 2005/020882 A2 | 3/2005 |
| WO | 2005/082905 A1 | 9/2005 |
| WO | 2006/001463 A1 | 1/2006 |
| WO | 2006/064757 A1 | 6/2006 |
| WO | 2006/080477 A1 | 8/2006 |
| WO | 2006/088944 A1 | 8/2006 |
| WO | 2006/099610 A2 | 9/2006 |
| WO | 2007/092638 A1 | 8/2007 |
| WO | 2008/074821 A1 | 6/2008 |
| WO | 2009/023854 A1 | 2/2009 |
| WO | 2010/051030 A1 | 5/2010 |
| WO | 2010/051031 A1 | 5/2010 |
| WO | 2011/017561 A1 | 2/2011 |

OTHER PUBLICATIONS

U.S. Appl. No. 14/338,047, filed Jul. 22, 2014.
Brinkmann, FTY720 (fingolimod) in Multiple Sclerosis: therapeutic effects in the immune and the central nervous system. Br J Pharmacol. Nov. 2009;158(5):1173-82.
Carrigan et al., Synthesis and in vitro pharmacology of substituted quinoline-2,4-dicarboxylic acids as inhibitors of vesicular glutamate transport. J Med Chem. May 23, 2002;45(11):2260-76.
Cee et al., Discovery of AMG 369, a Thiazolo[5,4-b]pyridine Agonist of S1P1 and S1P5. ACS Med Chem Lett. 2011;2:107-112.
European Medicines Agency Press Release, European Medicines Agency starts review of Gilenya (fingolimod). Doctors advised to intensify cardiovascular monitoring after first dose. www.ema.europa.eu. 2 pages. Jan. 20, 2012.
Kurata et al., Structure-activity relationship studies of sphingosine-1-phosphate receptor agonists with N-cinnamyl-beta-alanine moiety. Bioorg Med Chem Lett. Mar. 1, 2011;21(5):1390-3.
Marsolais et al., Chemical modulators of sphingosine-1-phosphate receptors as barrier-oriented therapeutic molecules. Nat Rev Drug Discov. Apr. 2009;8(4):297-307.
Mayo Clinic Staff, Diseases and Conditions. Multiple sclerosis. Retrieved online at: http://www.mayoclinic.org/diseases-conditions/multiple-sclerosis/basics/causes/con-20026689, 8 pages. Jul. 10, 2014.
Meyer zu Heringdorf et al., Pharmacology of the Sphingosine-1-Phosphate Signalling System. Sphingolipids: Basic Science and Drug Development. Springer Vienna, E. Gulbins (Ed.), pp. 239-253 (2013).
Noguchi et al., Roles for lysophospholipid S1P receptors in multiple sclerosis. Crit Rev Biochem Mol Biol. Feb. 2011;46(1):2-10.
Stedman's Medical Dictionary Online, accessed Jun. 17, 2015 at: http://www.stedmansonline.com/popup.aspx?aid=5231018, 1 page.

* cited by examiner

S1P MODULATING AGENTS

REFERENCE TO RELATED APPLICATIONS

This Application is a Continuation of application Ser. No. 14/757,822 filed on Dec. 23, 2015, which is a Continuation of application Ser. No. 13/983,489 filed on Jan. 8, 2014 now U.S. Pat. No. 9,340,527, which is a 35 U.S.C. § 371 national stage application based on International Application PCT/US2012/23799, filed Feb. 3, 2012 which claims the benefit of U.S. Provisional Application 61/440,254 filed on Feb. 7, 2011. The entire contents of each of the foregoing applications, including all drawings, formulae, specification and claims are incorporated herein by reference.

TECHNICAL FIELD

This invention relates to compounds that are S1P modulating agents, and methods of making and using such compounds.

BACKGROUND

Sphingosine 1-phosphate (S1P) is a lysophospholipid mediator that evokes a variety of cellular responses by stimulation of five members of the endothelial cell differentiation gene (EDG) receptor family. The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. Ultimately, this S1P-driven signaling results in cell survival, increased cell migration and, often, mitogenesis. The recent development of agonists targeting S1P receptors has provided insight regarding the role of this signaling system in physiologic homeostasis. For example, the immunomodulator, FTY720 (2-amino-2-[2-(4-octylphenyl) ethyl] propane 1,3-diol), that following phosphorylation, is an agonist at 4 of 5 S1P receptors, revealed that affecting S1P receptor activity influences lymphocyte trafficking. Further, S1P type 1 receptor ($S1P_1$) antagonists cause leakage of the lung capillary endothelium, which suggests that S1P may be involved in maintaining the integrity of the endothelial barrier in some tissue beds. S1P type 4 receptors ($S1P_4$) are expressed mainly in leukocytes, and specifically $S1P_4$ mediates immunosuppressive effects of S1P by inhibiting proliferation and secretion of effector cytokines, while enhancing secretion of the suppressive cytokine IL-10. See, for example, Wang, W. et. al., (2005) *FASEB J*. 19(12): 1731-3, which is incorporated by reference in its entirety. S1P type 5 receptors ($S1P_5$) are exclusively expressed in oligodendrocytes and oligodendrocyte precursor cells (OPCs) and are vital for cell migration. Stimulation of $S1P_5$ inhibits OPC migration, which normally migrate considerable distances during brain development. See, for example, Novgorodov, A. et al., (2007) *FASEB J*, 21: 1503-1514, which is incorporated by reference in its entirety.

S1P has been demonstrated to induce many cellular processes, including those that result in platelet aggregation, cell proliferation, cell morphology, tumor-cell invasion, endothelial cell chemotaxis and angiogenesis. For these reasons, S1P receptors are good targets for therapeutic applications such as wound healing, tumor growth inhibition, and autoimmune diseases.

Sphingosine-1-phosphate signals cells in part via a set of G protein-coupled receptors named $S1P_1$, $S1P_2$, $S1P_3$, $S1P_4$, and $S1P_5$ (formerly EDG1, EDG5, EDG3, EDG6 and EDG8). The EDG receptors are G-protein coupled receptors (GPCRs) and on stimulation propagate second messenger signals via activation of heterotrimeric G-protein alpha ($G_\alpha$) subunits and beta-gamma ($G_{\beta\gamma}$) dimers. These receptors share 50-55% amino acid sequence identity and cluster with three other receptors ($LPA_1$, $LPA_2$, and $LPA_3$ (formerly EDG2, EDG4 and EDG7) for the structurally related lysophosphatidic acid (LPA).

A conformational shift is induced in the G-Protein Coupled Receptor (GPCR) when the ligand binds to that receptor, causing GDP to be replaced by GTP on the α-subunit of the associated G-proteins and subsequent release of the G-proteins into the cytoplasm. The α-subunit then dissociates from the βγ-subunit and each subunit can then associate with effector proteins, which activate second messengers leading to a cellular response. Eventually the GTP on the G-proteins is hydrolyzed to GDP and the subunits of the G-proteins reassociate with each other and then with the receptor. Amplification plays a major role in the general GPCR pathway. The binding of one ligand to one receptor leads to the activation of many G-proteins, each capable of associating with many effector proteins leading to an amplified cellular response.

S1P receptors make good drug targets because individual receptors are both tissue and response specific. Tissue specificity of the S1P receptors is desirable because development of an agonist or antagonist selective for one receptor localizes the cellular response to tissues containing that receptor, limiting unwanted side effects. Response specificity of the S1P receptors is also of importance because it allows for the development of agonists or antagonists that initiate or suppress certain cellular responses without affecting other responses. For example, the response specificity of the S1P receptors could allow for an S1P mimetic that initiates platelet aggregation without affecting cell morphology.

Sphingosine-1-phosphate is formed as a metabolite of sphingosine in its reaction with sphingosine kinase and is stored in abundance in the aggregates of platelets where high levels of sphingosine kinase exist and sphingosine lyase is lacking. S1P is released during platelet aggregation, accumulates in serum, and is also found in malignant ascites. Reversible biodegradation of S1P most likely proceeds via hydrolysis by ectophosphohydrolases, specifically the sphingosine-1-phosphate phosphohydrolases. Irreversible degradation of S1P is catalyzed by S1P lyase yielding ethanolamine phosphate and hexadecenal.

SUMMARY

In one aspect, a compound can have formula (I):

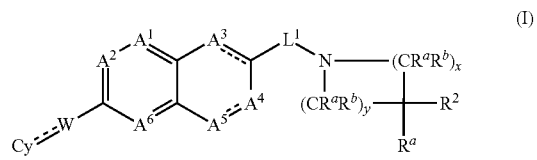

where:
$A^1$ can be —CH= or —N=; $A^2$ can be —CH= or —N=; $A^3$ can be —CH$_2$—, —CH=, or —N=; $A^4$ can be —CH$_2$—, —CH=, or —N=; $A^5$ can be —CH$_2$—, —CH=, or —N=; and $A^6$ can be —CH= or —N=.

W can be —O—, —CR$^5$—, or —CHR$^5$—.

$R^5$ can be hydrogen, halo, alkyl, or haloalkyl.

Cy can be a 4- to 7-membered cycloalkyl group, a 4- to 7-membered cycloalkenyl, or Cy can be a heterocycloalkyl group having 1 heteroatom which can be O; where Cy can be optionally substituted by one to four $R^1$. Each $R^1$, independently, can be halo, alkyl, haloalkyl, hydroxyalkyl, cycloalkyl, trialkylsilyl, alkoxy, cycloalkoxy, alkoxyalkyl, cycloalkoxyalkyl, or aryl. Or, two $R^1$, taken together, can be $C_1$ to $C_5$ alkylene.

$L^1$ can be —C(O)— or —C($R^3$)$_2$—. Each $R^3$, independently, can be hydrogen, alkyl, or haloalkyl.

x can be 0, 1, 2, 3, 4, or 5; y can be 0, 1, 2, 3, 4 or 5; where the sum of x and y is 4 or 5.

Each $R^a$ and each $R^b$, independently, can be hydrogen, halo, hydroxy, —CO$_2R^c$, alkyl, or aryl.

$R^2$ can be —(CH$_2$)$_n$—CO$_2R^c$, wherein n is 0 or 1. $R^c$ can be hydrogen, alkyl, haloalkyl, cycloalkyl, or aryl.

Formula (I) can exclude the compounds 1-((2-(trans-4-tert-butylcyclohexyloxy)naphthalen-6-yl)methyl)piperidine-4-carboxylic acid, 1-((2-(trans-4-tert-butylcyclohexyloxy)naphthalen-6-yl)methyl)piperidine-3R-carboxylic acid, and 1-((2-(trans-4-tert-butylcyclohexyloxy)naphthalen-6-yl)methyl)piperidine-3S-carboxylic acid.

The compound can be in the form of a pharmaceutically acceptable salt.

In some embodiments, Cy can be a 4- to 7-membered cycloalkyl group or Cy can be a heterocycloalkyl group having 1 heteroatom which can be O; where Cy can be optionally substituted by one to four $R^1$, wherein each $R^1$, independently, can be halo, alkyl, haloalkyl, cycloalkyl, alkoxy, cycloalkoxy, alkoxyalkyl, cycloalkoxyalkyl, or aryl, or two $R^1$, taken together, are $C_2$ to $C_5$ alkylene; each $R^a$ and each $R^b$, independently, can be hydrogen, halo, hydroxy, alkyl, or aryl.

In some embodiments, no more than two of $A^1$, $A^2$, $A^3$, $A^4$, $A^5$, and $A^6$ can be —N=.

When $A^1$ is —CH=, $A^2$ can be —CH=, and $A^5$ can be —CH=. In some embodiments, $A^1$, $A^2$, $A^3$, $A^4$, $A^5$, and $A^6$ can be —CH=. When $A^3$ is —CH=, $A^4$ can be —CH=, and $A^5$ can be —CH=; or when $A^3$ is —N=, $A^4$ can be —CH=, and $A^5$ can be —CH=; or when $A^3$ is —N=, $A^4$ can be —N=, and $A^5$ can be —CH=; or when $A^2$ is —N=, $A^6$ can be —N=; or when $A^1$ is —N=, $A^6$ can be —N=; or when $A^3$ is —CH$_2$—, $A^4$ can be —CH$_2$—, and $A^5$ can be —CH$_2$—.

The sum of x and y can be 4. x can be 2 and y can be 2.

Cy can be bicyclic or spiro-bicyclic. Cy can have the formula

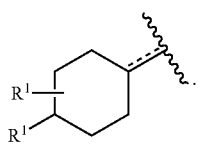

One $R^1$ can be hydrogen and the other $R^1$ can be ethyl, isopropyl, n-butyl, or t-butyl; or both $R^1$, taken together, can be $C_2$ to $C_5$ alkylene. Cy can have the formula:

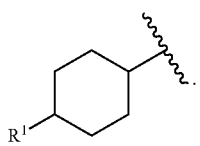

$L^1$ can be —C($R^3$)$_2$—, where at least one $R^3$ is hydrogen. $L^1$ can be —CH$_2$—.

W can be —O—.

In some circumstances, $A^1$ can be —CH=, $A^2$ can be —CH=, $A^3$ can be —CH=, $A^4$ can be —CH=, $A^5$ can be —CH=, and $A^6$ can be —CH=; $L^1$ can be —C($R^3$)$_2$—, where at least one $R^3$ can be hydrogen; the sum of x and y can be 4; Cy has the formula

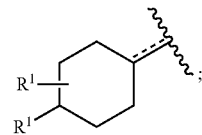

and

W can be —O—.

In another aspect, a compound or pharmaceutically acceptable salt thereof can be selected from the group consisting of: 1-((6-(trans-4-tert-butylcyclohexyloxy)quinazolin-2-yl)methyl)piperidine-4-carboxylic acid; 1-(1-(6-(trans-4-tert-butylcyclohexyloxy)naphthalen-2-yl)-2,2,2-trifluoroethyl)piperidine-4-carboxylic acid; 1-((6-(4-isopropylcyclohexyloxy)naphthalen-2-yl)methyl) piperidine-4-carboxylic acid; 1-((6-(cis-4-tert-butylcyclohexyloxy)naphthalen-2-yl)methyl)piperidine-4-carboxylic acid; 1-((6-(4-(trifluoromethyl)cyclohexyloxy) naphthalen-2-yl)methyl)piperidine-4-carboxylic acid; 1-((6-(4-ethylcyclohexyloxy)naphthalen-2-yl)methyl)piperidine-4-carboxylic acid; 1-((6-(4-butylcyclohexyloxy)naphthalen-2-yl)methyl)piperidine-4-carboxylic acid; 1-((6-(spiro[4.5]decan-8-yloxy)naphthalen-2-yl)methyl)piperidine-4-carboxylic acid; 1-((6-(cis-4-ethylcyclohexyloxy) naphthalen-2-yl)methyl)piperidine-4-carboxylic acid; 1-((6-(trans-4-ethylcyclohexyloxy)naphthalen-2-yl)methyl) pipelidine-4-carboxylic acid; 1-((6-(trans-4-tert-butylcyclohexyloxy)quinolin-2-yl)methyl)piperidine-4-carboxylic acid; 1-(6-(trans-4-tert-butylcyclohexyloxy)-2-naphthoyl)piperidine-4-carboxylic acid; 1-((6-((4-tert-butylcyclohexylidene)methyl)naphthalen-2-yl)methyl) piperidine-4-carboxylic acid; 1-((2-(trans-4-tert-butylcyclohexyloxy)quinolin-6-yl)methyl)piperidine-4-carboxylic acid; 1-[6-(4-tert-butyl-cyclohexyloxy)-naphthalen-2-ylmethyl]-4-ethyl-piperidine-4-carboxylic acid; 1-[6-(4-tert-butyl-cyclohexyloxy)-naphthalen-2-ylmethyl]-4-propyl-piperidine-4-carboxylic acid; 1-[6-(4-tert-butyl-cyclohexyloxy)-naphthalen-2-ylmethyl]-3-methyl-piperidine-4-carboxylic acid; 1-[6-(4-tert-butyl-cyclohexyloxy)-naphthalen-2-ylmethyl]-4-phenyl-piperidine-4-carboxylic acid; 1-[6-(4-tert-butyl-cyclohexyloxy)-naphthalen-2-ylmethyl]-perhydro-azepine-4-carboxylic acid; 1-[6-(4-tert-butyl-cyclohexyloxy)-naphthalen-2-ylmethyl]-4-hydroxy-piperidine-4-carboxylic acid; {1-[6-(4-tert-butyl-cyclohexyloxy)-naphthalen-2-ylmethyl]-piperidin-4-yl}-acetic acid; 1-[7-(trans-4-tert-butyl-cyclohexyloxy)-isoquinolin-3-ylmethyl]-piperidine-4-carboxylic acid; 1-((6-(trans-4-tert-butylcyclohexyloxy) naphthalen-2-yl)methyl)-4-methylpiperidine-4-carboxylic acid; 1-((6-(cyclopentyloxy)naphthalen-2-yl)methyl)piperidine-4-carboxylic acid; 1-((6-(cycloheptyloxy)naphthalen-2-yl)methyl)piperidine-4-carboxylic acid; 1-((6-(tetrahydro-2H-pyran-4-yloxy)naphthalen-2-yl)methyl)piperidine-4-carboxylic acid; 1-((6-(spiro[5.5]undecan-3-yloxy) naphthalen-2-yl)methyl)piperidine-4-carboxylic acid; 1-((6-(spiro[3.5]nonan-7-yloxy)naphthalen-2-yl)methyl)

piperidine-4-carboxylic acid; 1-[6-(4-tert-butyl-cyclohexyloxy)-naphthalen-2-ylmethyl]-piperidine-2-carboxylic acid; 1-((6-((trans-4-(tert-Butyl)cyclohexyl)oxy)-1,2,3,4-tetrahydronaphthalen-2-yl)methyl)piperidine-4-carboxylic acid; 1-((6-((cis-4-phenylcyclohexyl)oxy) naphthalen-2-yl)methyl)piperidine-4-carboxylic acid; 1-((6-((cis-4-(tert-pentyl)cyclohexyl)oxy)naphthalen-2-yl) methyl)piperidine-4-carboxylic acid; 1-((6-((trans-4-(tert-butyl)cyclohexyl)oxy)naphthalen-2-yl)methyl)-3-methylpiperidine-4-carboxylic acid; 1-((6-(((1R,2S,5R)-2-isopropyl-5-methylcyclohexyl)oxy)naphthalen-2-yl) methyl)piperidine-4-carboxylic acid; 1-((6-((4,4-dimethylcyclohexyl)oxy)naphthalen-2-yl)methyl) piperidine-4-carboxylic acid; 1-((6-((4-propylcyclohexyl) oxy)naphthalen-2-yl)methyl)piperidine-4-carboxylic acid; 1-((6-cyclobutoxynaphthalen-2-yl)methyl)piperidine-4-carboxylic acid; 1-(1-(6-((trans-4-(tert-butyl)cyclohexyl)oxy) naphthalen-2-yl)ethyl)piperidine-4-carboxylic acid; 1-((6-((4-(tert-butyl)cyclohexyl)methyl)naphthalen-2-yl)methyl) piperidine-4-carboxylic acid; 1-((6-((tetrahydrofuran-3-yl) oxy)naphthalen-2-yl)methyl)piperidine-4-carboxylic acid; 1-((6-(cyclohexyloxy)naphthalen-2-yl)methyl)piperidine-4-carboxylic acid; 1-((6-(cyclohexyloxy)quinolin-2-yl) methyl)piperidine-4-carboxylic acid; 1-((6-((trans-4-methylcyclohexyl)oxy)quinolin-2-yl)methyl)piperidine-4-carboxylic acid; 1-((6-((trans-4-ethylcyclohexyl)oxy) quinolin-2-yl)methyl)piperidine-4-carboxylic acid; 1-((6-((trans-4-(tert-pentyl)cyclohexyl)oxy)quinolin-2-yl)methyl) piperidine-4-carboxylic acid; 1-((6-((trans-4-(trifluoromethyl)cyclohexyl)oxy)quinolin-2-yl)methyl) piperidine-4-carboxylic acid; 1-((6((4,4-dimethylcyclohexyl)oxy)quinolin-2-yl)methyl)piperidine-4-carboxylic acid; 1-((6-(spiro[3.5]nonan-7-yloxy)quinolin-2-yl)methyl)piperidine-4-carboxylic acid; 1-((6-(spiro[5.5] undecan-3-yloxy)quinolin-2-yl)methyl)piperidine-4-carboxylic acid; 1-((6-((cis-4-ethylcyclohexyl)oxy) quinolin-2-yl)methyl)piperidine-4-carboxylic acid; 1-((6-(spiro[2.5]octan-6-yloxy)naphthalen-2-yl)methyl) piperidine-4-carboxylic acid; 1-((6-(spiro[4.5]decan-8-yloxy)quinolin-2-yl)methyl)piperidine-4-carboxylic acid; 1-((6-((3,3,5-trimethylcyclohexyl)oxy)naphthalen-2-yl) methyl)piperidine-4-carboxylic acid; 1-((6-((cis-4-isopropylcyclohexyl)oxy)quinolin-2-yl)methyl)piperidine-4-carboxylic acid; 1-((6-((3-methylcyclohexyl)oxy)naphthalen-2-yl) methyl)piperidine-4-carboxylic acid; 1-((6-((4-(tert-pentyl) cyclohexyl)oxy)naphthalen-2-yl)methyl)piperidine-4-carboxylic acid; 1-((6-((cis-4-(ethoxymethyl)cyclohexyl) oxy)naphthalen-2-yl)methyl)piperidine-4-carboxylic acid; 1-((6-((octahydro-1H-inden-5-yl)oxy)naphthalen-2-yl) methyl)piperidine-4-carboxylic acid; 1-((6-(spiro[2.5]octan-6-yloxy)quinolin-2-yl)methyl)piperidine-4-carboxylic acid; 1-((6-((3,4-dimethylcyclohexyl)oxy)naphthalen-2-yl) methyl)piperidine-4-carboxylic acid; 1-46-((cis-4-(methoxymethyl)cyclohexyl)oxy)naphthalen-2-yl)methyl) piperidine-4-carboxylic acid; 1-((6-((cis-4-(tert-butoxymethyl)cyclohexyl)oxy)naphthalen-2-yl)methyl) piperidine-4-carboxylic acid; 1-((6-((cis-4-(isobutoxymethyl)cyclohexyl)oxy)naphthalen-2-yl)methyl) piperidine-4-carboxylic acid; 1-((6-((trans-4-(tert-butoxymethypcyclohexypoxy)naphthalen-2-yl)methyl) piperidine-4-carboxylic acid; 1-((6-((trans-4-(isobutoxymethyl)cyclohexyl)oxy)naphthalen-2-yl)methyl) piperidine-4-carboxylic acid; 1-((6-((trans-4-(propoxymethyl)cyclohexyl)oxy)naphthalen-2-yl)methyl) piperidine-4-carboxylic acid; 1-((6-((2-methylcyclohexyl) oxy)naphthalen-2-yl)methyl)piperidine-4-carboxylic acid; 1-((6-(((trans-4-phenylcyclohexyl)oxy)quinolin-2-yl) methyl)piperidine-4-carboxylic acid; 1-((6-(((trans-4-(isopropoxymethyl)cyclohexyl)oxy)naphthalen-2-yl)methyl)piperidine-4-carboxylic acid; 1-((6-((cis-4-(propoxymethyl) cyclohexyl)oxy)naphthalen-2-yl)methyl)piperidine-4-carboxylic acid; 1-((6-((trans-4-(tert-butyl)cyclohexyl)oxy) quinolin-2-yl)methyl)piperidine-3-carboxylic acid; 1-((6-((4,4-difluorocyclohexyl)oxy)naphthalen-2-yl)methyl) piperidine-4-carboxylic acid; 1-((6-((2-methylcyclopentyl) oxy)naphthalen-2-yl)methyl)piperidine-4-carboxylic acid; 1-((6-((4-(2-hydroxypropan-2-yl)cyclohexyl)oxy)naphthalen-2-yl)methyl)piperidine-4-carboxylic acid; 1-((6-((3-methylcyclopentyl)oxy)naphthalen-2-yl)methyl)piperidine-4-carboxylic acid; 1-((6-(bicyclo[3.1.0]hexan-3-yloxy) naphthalen-2-yl)methyl)piperidine-4-carboxylic acid; 1-((6-((trans-4-isopropylcyclohexyl)oxy)naphthalen-2-yl)methyl) piperidine-4-carboxylic acid; 1-((6-((trans-4-(tert-butyl) cyclohexyl)oxy)naphthalen-2-yl)methyl)piperidine-4,4-dicarboxylic acid; 2-(1-((6-((trans-4-(tert-butyl)cyclohexyl) oxy)naphthalen-2-yl)methyl)piperidin-2-yl)acetic acid; 1-((6-((4,4-dimethylcyclohexyl)oxy)naphthalen-2-yl) methyl)piperidine-3-carboxylic acid; 1-((6-((4,4-dimethylcyclohexyl)oxy)naphthalen-2-yl)methyl)-4-methylpiperidine-4-carboxylic acid; 1-((6-((4,4-dimethylcyclohexyl) oxy)naphthalen-2-yl)methyl)-4-ethylpiperidine-4-carboxylic acid; 1-[6-(Bicyclo[2.2.1]hept-5-en-2-yloxy)-naphthalen-2-ylmethyl]-piperidine-4-carboxylic acid; 1-[6-(1,3,3-Trimethyl-bicyclo[2.2.1]hept-2-yloxy)-naphthalen-2-ylmethyl]- piperidine-4-carboxylic acid; 1-[2-(4-tert-Butyl-cyclohexyloxy)-quinoxalin-6-ylmethyl]-piperidine-4-carboxylic acid; 1-[2-(4-tert-Butyl-cyclohexyloxy)-quinazolin-6-ylmethyl]-piperidine-4-carboxylic acid; 1-[7-(4-tert-Butyl-cyclohexyloxy)-[1,8]naphthyridin-3-ylmethyl]-piperidine- 4-carboxylic acid; and 1-((6-(((trans-4-(trimethylsilyl)cyclohexyl)oxy)naphthalen-2-yl)methyl) piperidine-4-carboxylic acid.

The compound can be selective for an S1P receptor, for example, the S1P4 receptor, the S1P1 receptor or the S1P5 receptor. The compound can have a greater affinity for the S1P4 receptor, by at least 5-fold, than for S1P1 receptor, S1P2 receptor, S1P3 receptor, or S1P5 receptor. The compound can have activity as a receptor agonist or a receptor antagonist at one or more S1P receptors.

In another aspect, a pharmaceutical composition can include a compound according to formula (I) or (II), or a pharmaceutically acceptable salt thereof, and a pharmaceutically acceptable excipient or carrier.

In another aspect, a method for prevention or treatment of a pathological condition or symptom in a mammal, wherein the activity of S1P receptors is implicated, comprising administering to said mammal an effective amount of a compound according to formula (I) or (II), or a pharmaceutically acceptable salt thereof.

In another aspect, a compound of formula (I) or (II), or a pharmaceutically acceptable salt thereof, can promote myelination or remyelination. A method of treatment can include administering a compound of formula (I) or (II) to cells to promote myelination or remyelination.

In another aspect, a method for prevention or treatment of multiple sclerosis, an autoimmune disease, a chronic inflammatory disorder, asthma, an inflammatory neuropathy, arthritis, transplantation rejection, Crohn's disease, ulcerative colitis, lupus erythematosis, psoriasis, an ischemia-reperfusion injury, a solid tumor, a tumor metastasis, a disease associated with angiogenesis, a vascular disease, a pain condition, an acute viral disease, an inflammatory bowel condition, insulin-dependent diabetes, or non-insulin dependent diabetes can include administering to said mammal an effective amount of a compound according to formula (I) or (II), or a pharmaceutically acceptable salt thereof.

In another aspect, a method for prevention or treatment of a neurologic disease in a mammal includes administering to said mammal an effective amount of a compound according to formula (I) or (II), or a pharmaceutically acceptable salt thereof. The neurologic disease can be Alzheimer's disease, Parkinson's disease, Huntington's disease, a motor neuron disease, amyotrophic lateral sclerosis, multiple sclerosis, neuronal trauma, or cerebral ischemia. Prevention or treatment of the pathological condition can include remyelination and axon regeneration for multiple sclerosis, blocking astrogliosis, or microglial activation for neural-inflammation related disease.

In another aspect, a method for prevention or treatment of neuropathic pain in a lo mammal includes administering to said mammal an effective amount of a compound according to formula (I) or (II), or a pharmaceutically acceptable salt thereof.

In another aspect, a method for prevention or treatment of an autoimmune disease in a mammal includes administering to said mammal an effective amount of a compound according to formula (I) or (II), or a pharmaceutically acceptable salt thereof.

In another aspect, a compound according to formula (I) or (II), or a pharmaceutically acceptable salt thereof, for use in treating or preventing multiple sclerosis, an autoimmune disease, a chronic inflammatory disorder, asthma, an inflammatory neuropathy, arthritis, transplantation rejection, Crohn's disease, ulcerative colitis, lupus erythematosis, psoriasis, an ischemia-reperfusion injury, a solid tumor, a tumor metastasis, a disease associated with angiogenesis, a vascular disease, a pain condition, an acute viral disease, an inflammatory bowel condition, insulin-dependent diabetes, or non-insulin dependent diabetes.

In another aspect, use of a compound according to formula (I) or (II), or a pharmaceutically acceptable salt thereof, for the manufacture of a medicament for treating or preventing multiple sclerosis, an autoimmune disease, a chronic inflammatory disorder, asthma, an inflammatory neuropathy, arthritis, transplantation rejection, Crohn's disease, ulcerative colitis, lupus erythematosis, psoriasis, an ischemia-reperfusion injury, a solid tumor, a tumor metastasis, a disease associated with angiogenesis, a vascular disease, a pain condition, an acute viral disease, an inflammatory bowel condition, insulin-dependent diabetes, or non-insulin dependent diabetes.

Other features or advantages will be apparent from the following detailed description of several embodiments, and also from the appended claims.

DETAILED DESCRIPTION

The disclosed compounds can have activity as receptor agonists or receptor antagonists at one or more S1P receptors. In particular, the compounds can be S1P$_4$ antagonists.

A compound can have formula (I):

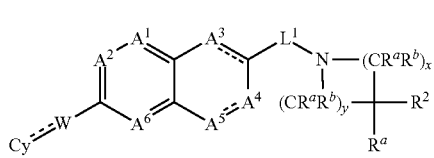

(I)

where:
$A^1$ can be —CH= or —N=, $A^2$ can be —CH= or —N=, $A^3$ can be —CH$_2$—, —CH=, or —N=, $A^4$ can be —CH$_2$—, —CH=, or —N=, $A^5$ can be —CH$_2$—, —CH=, or —N=, and $A^6$ can be —CH= or —N=. W can be —O—, =CR$^5$—, or —CHR$^5$—. $R^5$ can be hydrogen, halo, alkyl, or haloalkyl.

Cy can be a 4- to 7-membered cycloalkyl group, a 4- to 7-membered cycloalkenyl group, or a 4- to 7-membered heterocycloalkyl having 1 heteroatom which is O; wherein Cy is optionally substituted by one to four $R^1$, where each $R^1$, independently, can be halo, alkyl, haloalkyl, hydroxyalkyl, cycloalkyl, trialkylsilyl, alkoxy, cycloalkoxy, alkoxyalkyl, cycloalkoxyalkyl, or aryl, or two $R^1$, taken together, can be $C_1$ to $C_5$ alkylene.

$L^1$ can be —C(O)— or —C(R$^3$)$_2$—. Each $R^3$, independently, can be hydrogen, alkyl, or haloalkyl. x can be 0, 1, 2, 3, 4 or 5, and y can be 0, 1, 2, 3, 4, or 5, where the sum of x and y is 4 or 5.

Each $R^a$ and each $R^b$, independently, can be hydrogen, halo, hydroxy, —CO$_2$R$^c$, alkyl, or aryl.

$R^2$ can be —(CH$_2$)$_n$—CO$_2$R$^c$, where n is 0 or 1. $R^c$ can be hydrogen, alkyl, haloalkyl, cycloalkyl, or aryl.

Formula (I) can exclude the compounds 1-((2-(trans-4-tert-butylcyclohexyloxy)naphthalen-6-yl)methyl)piperidine-4-carboxylic acid, 1-((2-(trans-4-tert-butylcyclohexyloxy)naphthalen-6-yl)methyl)piperidine-3R-carboxylic acid, and 1-((2-(trans-4-tert-butylcyclohexyloxy)naphthalen-6-yl)methyl)piperidine-3S-carboxylic acid.

The compound can be in the form of a pharmaceutically acceptable salt.

In some cases, each $R^1$, independently, is halo, alkyl, haloalkyl, cycloalkyl, alkoxy, cycloalkoxy, alkoxyalkyl, cycloalkoxyalkyl, or aryl, or two $R^1$, taken together, are $C_2$ to $C_5$ alkylene; each $R^a$ and each $R^b$, independently, is hydrogen, halo, hydroxy, alkyl, or aryl; and $R^2$ is —(CH$_2$)$_n$—CO$_2$R$^c$.

In some cases, no more than two of $A^1, A^2, A^3, A^4, A^5$, and $A^6$ is —N=. In some cases, $A^1, A^2, A^3, A^4, A^5$, and $A^6$ are —CH=. In certain compounds, $A^1$ is —CH=, $A^2$ is —CH=, and $A^5$ is —CH=. In some compounds, $A^1, A^2, A^3, A^4, A^5$, and $A^6$ are —CH=. In some compounds, one of the following applies: $A^3$ is —CH=, $A^4$ is —CH=, and $A^5$ is —CH=; or $A^3$ is —N=, $A^4$ is —CH=, and $A^5$ is —CH=; or $A^3$ is —N=, $A^4$ is —N=, and $A^5$ is —CH=; or $A^2$ is —N= and $A^6$ is —N=; or $A^1$ is —N= and $A^6$ is —N=; or $A^3$ is —CH$_2$—, $A^4$ is —CH$_2$—, and $A^5$ is —CH$_2$—.

The sum of x and y can be 4, for example, when x is 2 and y is 2.

Cy can be bicyclic or spiro-bicyclic, e.g., when both $R^1$, taken together, are $C_2$ to $C_5$ alkylene. In this case, if both $R^1$ are attached to different atoms, Cy is bicyclic; if both $R^1$ are attached to the same atom, Cy is spiro-bicyclic. Cy can have the formula:

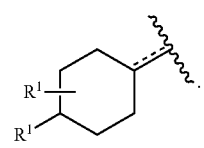

In some cases, one $R^1$ can be hydrogen and the other $R^1$ can be ethyl, isopropyl, n-butyl, or t-butyl, or both $R^1$, taken together, can be $C_2$ to $C_5$ alkylene.

L¹ can be —C(R³)₂—, where at least one R³ is hydrogen.
L¹ can be —CH₂—.
W can be —O—.
In some embodiments, W is —O— and Cy has the formula:

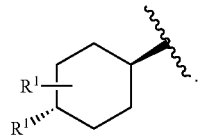

In some embodiments, each of A¹, A², A³, A⁴, A⁵ and A⁶ is —CH═; L¹ is —C(R³)₂—, where at least one R³ is hydrogen; the sum of x and y is 4; Cy has the formula

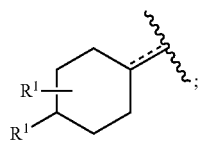

and
W is —O—.
In some cases, Cy can have the formula:

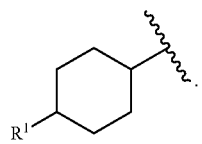

A compound can have formula (II):

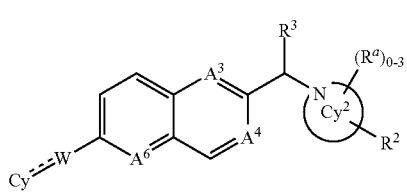

where:
each of A³, A⁴, and A⁶, independently, is —CH═ or —N═;
W is —O—, ═CR⁵—, or —CHR⁵—;
R⁵ is hydrogen, halo, alkyl, or haloalkyl;
Cy is a 4- to 7-membered cycloalkyl group, or a 4- to 7-membered heterocycloalkyl group having 1 heteroatom which is O; wherein Cy is optionally substituted by one to four R¹;
each R¹, independently, is halo, alkyl, haloalkyl, cycloalkyl, alkoxy, cycloalkoxy, alkoxyalkyl, cycloalkoxyalkyl or aryl, or two R¹, taken together, are C₂ to C₅ alkylene;
R³ is hydrogen, alkyl, or haloalkyl;
Cy² is a 6- or 7-membered cycloalkyl group;
each Rᵃ, independently, is hydrogen, halo, hydroxy, alkyl, or aryl;
R² is —(CH₂)ₙ—CO₂Rᶜ, wherein n is 0 or 1; Rᶜ is hydrogen, alkyl, haloalkyl, cycloalkyl, or aryl;

provided that the compound is not 1-((2-(trans-4-tert-butylcyclohexyloxy)naphthalen-6-yl)methyl)piperidine-4-carboxylic acid, 1-((2-(trans-4-tert-butylcyclohexyloxy)naphthalen-6-yl)methyl)piperidine-3R-carboxylic acid, or 1-((2-(trans-4-tert-butylcyclohexyloxy)naphthalen-6-yl)methyl)piperidine-3S-carboxylic acid;
or a pharmaceutically acceptable salt thereof.
In some cases, no more than two of A³, A⁴, and A⁶ are —N═. For example, in certain embodiments, when A³ is —N═, A⁴ can be —N═ or —CH═ and A⁶ can be —CH═; when A⁴ is —N═, A³ can be —N═ or —CH═, and A⁶ can be —CH═; or when A⁶ is —N═, then A³ can be —CH and A⁴ can be —CH═.
Cy can have the formula:

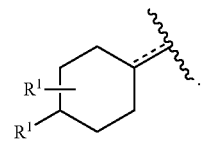

In some cases, one R¹ can be hydrogen and the other R¹ can be ethyl, isopropyl, n-butyl, or t-butyl, or both R¹, taken together, can be C₂ to C₅ alkylene.
In some embodiments, W is —O— and Cy has the formula:

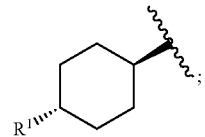

In one embodiment, the invention provides, a compound of formula II, or a pharmaceutically acceptable salt thereof, wherein:
each of A³, A⁴, and A⁶, independently, is —CH═;
W is —O—;
Cy is

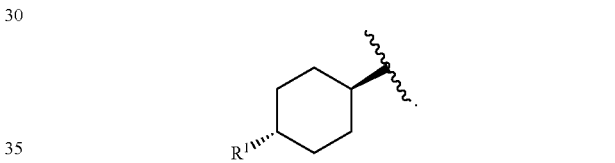

R¹ is halo, alkyl, haloalkyl, or cycloalkyl;
R³ is hydrogen;
Cy² is piperidinyl;
each Rᵃ, independently, is hydrogen, halo, hydroxy, alkyl, or aryl;
R² is —(CH₂)ₙ—O₂Rᶜ, wherein n is 0 or 1; Rᶜ is hydrogen or alkyl.
The compound can be:
1-((6-(trans-4-tert-butylcyclohexyloxy)quinazolin-2-yl)methyl)piperidine-4-carboxylic acid;
1-(1-(6-(trans-4-tert-butylcyclohexyloxy)naphthalen-2-yl)-2,2,2-trifluoroethyl)piperidine-4-carboxylic acid;
1-((6-(4-isopropylcyclohexyloxy)naphthalen-2-yl)methyl)piperidine-4-carboxylic acid;
1-((6-(cis-4-tert-butylcyclohexyloxy)naphthalen-2-yl)methyl)piperidine-4-carboxylic acid;

1-((6-(4-(trifluoromethyl)cyclohexyloxy)naphthalen-2-yl)methyl)piperidine-4-carboxylic acid;
1-((6-(4-ethylcyclohexyloxy)naphthalen-2-yl)methyl)piperidine-4-carboxylic acid;
1-((6-(4-butylcyclohexyloxy)naphthalen-2-yl)methyl)piperidine-4-carboxylic acid;
1-((6- (spiro [4.5]decan-8-yloxy)naphthalen-2-yl)methyl)piperidine-4-carboxylic acid;
1-((6-(cis-4-ethylcyclohexyloxy)naphthalen-2-yl)methyl)piperidine-4-carboxylic acid;
1-((6-(trans-4-ethylcyclohexyloxy)naphthalen-2-yl)methyl)piperidine-4-carboxylic acid;
1-((6-(trans-4-tert-butylcyclohexyloxy)quinolin-2-yl)methyl)piperidine-4-carboxylic acid;
1-(6-(trans-4-tert-butylcyclohexyloxy)-2-naphthoyl)piperidine-4-carboxylic acid;
1-((6-((4-tert-butylcyclohexylidene)methyl)naphthalen-2-yl)methyl)piperidine-4-carboxylic acid;
1-((2-(trans-4-tert-butylcyclohexyloxy)quinolin-6-yl)methyl)piperidine-4-carboxylic acid;
1-[6-(4-tert-butyl-cyclohexyloxy)-naphthalen-2-ylmethyl]-4-ethyl-piperidine-4-carboxylic acid;
1-[6-(4-tert-butyl-cyclohexyloxy)-naphthalen-2-ylmethyl]-4-propyl-piperidine- 4-carboxylic acid;
1-[6-(4-tert-butyl-cyclohexyloxy)-naphthalen-2-ylmethyl]-3-methyl-piperidine-4-carboxylic acid;
1-[6-(4-tert-butyl-cyclohexyloxy)-naphthalen-2-ylmethyl]-4-phenyl-piperidine-4-carboxylic acid;
1-[6-(4-tert-butyl-cyclohexyloxy)-naphthalen-2-ylmethyl]-perhydro-azepine-4-carboxylic acid;
1-[6-(4-tert-butyl-cyclohexyloxy)-naphthalen-2-ylmethyl]-4-hydroxy-piperidine-4-carboxylic acid;
{1-[6-(4-tert-butyl-cyclohexyloxy)-naphthalen-2-ylmethyl]-piperidin-4-yl}-acetic acid;
1- [7-(trans-4-tert-butyl-cyclohexyloxy)-isoquinolin-3-ylmethyl]-piperidine-4-carboxylic acid;
1-((6-(trans-4-tert-butylcyclohexyloxy)naphthalen-2-yl)methyl)-4-methylpiperidine-4-carboxylic acid;
1-((6-(cyclopentyloxy)naphthalen-2-yl)methyl)piperidine-4-carboxylic acid;
1-((6-(cycloheptyloxy)naphthalen-2-yl)methyl)piperidine-4-carboxylic acid;
1-((6-(tetrahydro-2H-pyran-4-yloxy)naphthalen-2-yl)methyl)piperidine-4-carboxylic acid;
1-((6-(spiro[5.5]undecan-3-yloxy)naphthalen-2-yl)methyl)piperidine-4-carboxylic acid;
1-((6-(spiro[3.5]nonan-7-yloxy)naphthalen-2-yl)methyl)piperidine-4-carboxylic acid;
1-[6-(4-tert-butyl-cyclohexyloxy)-naphthalen-2-ylmethyl]-piperidine-2-carboxylic acid;
1-((6-((trans-4-(tert-Butyl)cyclohexyl)oxy)-1,2,3,4-tetrahydronaphthalen-2-yl)methyl)piperidine-4-carboxylic acid;
1-((6-((cis-4-phenylcyclohexyl)oxy)naphthalen-2-yl)methyl)piperidine-4-carboxylic acid;
1-((6-((cis-4-(tert-pentyl)cyclohexyl)oxy)naphthalen-2-yl)methyl)piperidine-4-carboxylic acid;
1-((6-((trans-4-(tert-butyl)cyclohexyl)oxy)naphthalen-2-yl)methyl)-3-methylpiperidine-4-carboxylic acid;
1-((6-(((1R,2S,5R)-2-isopropyl-5-methylcyclohexyl)oxy)naphthalen-2-yl)methyl)piperidine-4-carboxylic acid;
1-((6-((4,4-dimethylcyclohexyl)oxy)naphthalen-2-yl)methyl)piperidine-4-carboxylic acid;
1-((6-((4-propylcyclohexyl)oxy)naphthalen-2-yl)methyl)piperidine-4-carboxylic acid;
1-((6-cyclobutoxynaphthalen-2-yl)methyl)piperidine-4-carboxylic acid;
1-(1-(6-((trans-4-(tert-butyl)cyclohexyl)oxy)naphthalen-2-yl)methyl)piperidine-4-carboxylic acid;
1-((6-((4-(tert-butyl)cyclohexyl)methyl)naphthalen-2-yl)methyl)piperidine-4-carboxylic acid;
1-((6-((tetrahydrofuran-3-yl)oxy)naphthalen-2-yl)methyl)piperidine-4-carboxylic acid;
1-((6-(cyclohexyloxy)naphthalen-2-yl)methyl)piperidine-4-carboxylic acid;
1-((6-(cyclohexyloxy)quinolin-2-yl)methyl)piperidine-4-carboxylic acid;
1-((6-((trans-4-methylcyclohexyl)oxy)quinolin-2-yl)methyl)pipefidine-4-carboxylic acid;
1-((6-((trans-4-ethylcyclohexyl)oxy)quinolin-2-yl)methyl)piperidine-4-carboxylic acid;
1-((6-((trans-4-(tert-pentyl)cyclohexyl)oxy)quinolin-2-yl)methyl)piperidine-4-carboxylic acid;
1-((6-((trans-4-(trifluoromethyl)cyclohexyl)oxy)quinolin-2-yl)methyl)piperidine-4-carboxylic acid;
1-((6-((4,4-dimethylcyclohexyl)oxy)quinolin-2-yl)methyl)piperidine-4-carboxylic acid;
1((6-(spiro[3.5]nonan-7-yloxy)quinolin-2-yl)methyl)piperidine-4-carboxylic acid;
1-((6- (spiro [5.5]undecan-3-yloxy)quinolin- 2-yl)methyl)piperidine- 4-carboxylic acid;
1-((6-((cis-4-ethylcyclohexyl)oxy)quinolin-2-yl)methyl)piperidine-4-carboxylic acid;
1-((6-(spiro [2.5] octan-6-yloxy)naphthalen-2-yl)methyl)piperidine-4-carboxylic acid;
1-((6-(spiro[4.5]decan-8-yloxy)quinolin-2-yl)methyl)piperidine-4-carboxylic acid;
1-((6-((3,3,5-trimethylcyclohexyl)oxy)naphthalen-2-yl)methyl)pipefidine-4-carboxylic acid;
1-((6-((cis-4-isopropylcyclohexyl)oxy)quinolin-2-yl)methyl)piperidine-4-carboxylic acid;
1-((6-((3-methylcyclohexyl)oxy)naphthalen-2-yl)methyl)piperidine-4-carboxylic acid;
1-((6-((4-(tert-pentyl)cyclohexyl)oxy)naphthalen-2-yl)methyl)piperidine-4-carboxylic acid;
1-((6-((cis-4-(ethoxymethyl)cyclohexyl)oxy)naphthalen-2-yl)methyl)piperidine-4-carboxylic acid;
1-((6-((octahydro-1H-inden-5-yl)oxy)naphthalen-2-yl)methyl)piperidine-4-carboxylic acid;
1-((6-(spiro[2.5]octan-6-yloxy)quinolin-2-yl)methyl)piperidine-4-carboxylic acid;
1-((6-((3,4-dimethylcyclohexyl)oxy)naphthalen-2-yl)methyl)piperidine-4-carboxylic acid;
1-((6-((cis-4-(methoxymethyl)cyclohexyl)oxy)naphthalen-2-yl)methyl)piperidine-4-carboxylic acid;
1-((6-((cis-4-(tert-butoxymethyl)cyclohexyl)oxy)naphthalen-2-yl)methyl)piperidine-4-carboxylic acid;
1-((6-((cis-4-(isobutoxymethyl)cyclohexyl)oxy)naphthalen-2-yl)methyl)piperidine-4-carboxylic acid;
1-((6-((trans-4-(tert-butoxymethyl)cyclohexyl)oxy)naphthalen-2-yl)methyl)piperidine-4-carboxylic acid;
1-((6-((trans-4-(isobutoxymethyl)cyclohexyl)oxy)naphthalen-2-yl)methyl)piperidine-4-carboxylic acid;
1-((6-((trans-4-(propoxymethyl)cyclohexyl)oxy)naphthalen-2-yl)methyl)piperidine-4-carboxylic acid;
1-((6-((2-methylcyclohexyl)oxy)naphthalen-2-yl)methyl)piperidine-4-carboxylic acid;
1-((6-((trans-4-phenylcyclohexyl)oxy)quinolin-2-yl)methyl)piperidine-4-carboxylic acid;
1-((6-((trans-4-(isopropoxymethyl)cyclohexyl)oxy)naphthalen-2-yl)methyl)piperidine-4-carboxylic acid;
1-((6-((cis-4-(propoxymethyl)cyclohexyl)oxy)naphthalen-2-yl)methyl)piperidine-4-carboxylic acid;

1-((6-((trans-4-(tert-butyl)cyclohexyl)oxy)quinolin-2-yl)
    methyl)piperidine-3-carboxylic acid;
1-((6-((4,4-difluorocyclohexyl)oxy)naphthalen-2-yl)
    methyl)piperidine-4-carboxylic acid;
1-((6-((2-methylcyclopentyl)oxy)naphthalen-2-yl)methyl)
    piperidine-4-carboxylic acid;
1-((6-((4-(2-hydroxypropan-2-yl)cyclohexyl)oxy)naphtha-
    len-2-yl)methyl)piperidine-4-carboxylic acid;
1-((6-((3-methylcyclopentyl)oxy)naphthalen-2-yl)methyl)
    piperidine-4-carboxylic acid;
1-((6-(bicyclo[3.1.0]hexan-3-yloxy)naphthalen-2-yl)
    methyl)piperidine-4-carboxylic acid;
1-((6-((trans-4-isopropylcyclohexyl)oxy)naphthalen-2-yl)
    methyl)piperidine-4-carboxylic acid;
1-((6-((trans-4-(tert-butyl)cyclohexyl)oxy)naphthalen-2-yl)
    methyl)piperidine-4,4-dicarboxylic acid;
2-(1-((6-((trans-4-(tert-butyl)cyclohexyl)oxy)naphthalen-2-
    yl)methyl)piperidin-2-yl)acetic acid;
1-((6-((4,4-dimethylcyclohexyl)oxy)naphthalen-2-yl)
    methyl)piperidine-3-carboxylic acid;
1-((64,4-dimethylcyclohexyl)oxy)naphthalen-2-yl)
    methyl)-4-methylpiperidine-4-carboxylic acid;
1-((6-((4,4-dimethylcyclohexyl)oxy)naphthalen-2-yl)
    methyl)-4-ethylpipefidine-4-carboxylic acid;
1-[6-(Bicyclo[2.2.1]hept-5-en-2-yloxy)-naphthalen-2-ylm-
    ethyl]-piperidine-4-carboxylic acid;
1-[6-(1,3,3-Trimethyl-bicyclo[2.2.1]hept-2-yloxy)-naphtha-
    len-2-ylmethyl]-piperidine-4-carboxylic acid;
1-[2-(4-tert-Butyl-cyclohexyloxy)-quinoxalin-6-ylmethyl]-
    piperidine-4-carboxylic acid;
1-[2-(4-tert-Butyl-cyclohexyloxy)-quinazolin-6-ylmethyl]-
    piperidine-4-carboxylic acid;
1-[7-(4-tert-Butyl-cyclohexyloxy)-[1,8]naphthyridin-3-yl-
    methyl]-piperidine-4-carboxylic acid; or
1-((6-(((trans-4-(trimethylsilyl)cyclohexyl)oxy)naphthalen-
    2-yl)methyl)piperidine-4-carboxylic acid;
or a pharmaceutically acceptable salt thereof.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

"Alkylene" refers to a divalent alkyl group. Examples of alkylene groups include methylene, ethylene, propylene, n-butylene, and the like. The alkylene is attached to the rest of the molecule through a single bond and to the radical group through a single bond. The points of attachment of the alkylene to the rest of the molecule and to the radical group can be through one carbon or any two carbons within the carbon chain.

As used herein, the term "haloalkyl" refers to an alkyl, as defined herein, that is substituted by one or more halo groups as defined herein. Preferably the haloalkyl can be lo monohaloalkyl, dihaloalkyl or polyhaloalkyl including perhaloalkyl. A monohaloalkyl can have one iodo, bromo, chloro or fluoro substituent. Dihaloalkyl and polyhaloalkyl groups can be substituted with two or more of the same halo atoms or a combination of different halo groups. Non-limiting examples of haloalkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. Preferred haloalkyl groups are trifluoromethyl and difluoromethyl.

"Halogen" or "halo" may be fluoro, chloro, bromo or iodo.

As used herein, the term "hydroxyalkyl" refers to an alkyl group substituted by one or more hydroxy (i.e., —OH) groups.

As used herein, the term "alkenyl" refers to an olefinically unsaturated branched or linear group having at least one double bond. Alkenyl groups include, but are not limited to, 1-propenyl, 2-propenyl, 1,3-butadienyl, 1-butenyl, hexenyl, pentenyl, hexenyl, heptenyl, octenyl and the like.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6 carbon atoms, more preferably about 1-4 carbon atoms.

As used herein, the term "haloalkoxy" refers to haloalkyl-O—, wherein haloalkyl is defined herein above. Representative example of haloalkoxy groups are trifluoromethoxy, difluoromethoxy, and 1,2-dichloroethoxy. Preferably, haloalkoxy groups have about 1-6 carbon atoms, more preferably about 1-4 carbon atoms.

As used herein, the term "alkoxyalkyl" refers to an alkyl group as defined herein, substituted by one or more alkoxy groups as defined herein.

As used herein, the term "carbocyclyl" refers to saturated or partially unsaturated (but not aromatic) monocyclic, bicyclic or tricyclic hydrocarbon groups of 3-14 carbon atoms, preferably 3-9, or more preferably 3-8 carbon atoms. Carbocyclyls include fused, bridged, or spiro ring systems. The term "carbocyclyl" encompasses cycloalkyl groups. The term "cycloalkyl" refers to completely saturated monocyclic, bicyclic or tricyclic hydrocarbon groups of 3-12 carbon atoms, preferably 3-9, or more preferably 3-8 carbon atoms. Exemplary monocyclic carbocyclyl groups include, but are not limited to, cyclopropyl, cyclobutyl, cyclopentyl, cyclopentenyl, cyclohexyl or cyclohexenyl. Exemplary bicyclic carbocyclyl groups include bornyl, decahydronaphthyl, bicyclo[2.1.1]hexyl, bicyclo[2.2.1]heptyl, bicyclo[2.2.1] heptenyl, 6,6-dimethylbicyclo[3.1.1]heptyl, 2,6,6-trimethylbicyclo[3.1.1]heptyl, or bicyclo[2.2.2]octyl. Exemplary tricyclic carbocyclyl groups include adamantyl.

As used herein, the term "halocycloalkyl" refers to a cycloalkyl, as defined herein, that is substituted by one or more halo groups as defined herein. Preferably the halocycloalkyl can be monohalocycloalkyl, dihalocycloalkyl or polyhalocycloalkyl including perhalocycloalkyl. A monohalocycloalkyl can have one iodo, bromo, chloro or fluoro substituent. Dihalocycloalkyl and polyhalocycloalkyl groups can be substituted with two or more of the same halo atoms or a combination of different halo groups.

As used herein, the term "cycloalkenyl" refers to an olefinically unsaturated monocyclic, bicyclic or tricyclic hydrocarbon groups of 3-12 carbon atoms, preferably 3-9, or more preferably 3-8 carbon atoms, and having one or more double bonds. Exemplary monocyclic cycloalkenyl groups include, but are not limited to, cyclopentenyl, cyclopentadienyl, cyclohexenyl, and the like. Exemplary bicyclic cycloalkenyl groups include, but are not limited to, bicyclo [2.2.1]hept-5-enyl and bicycle[2.2.2]oct-2-enyl.

As used herein, the term "cycloalkoxy" refers to cycloalkyl-O—, wherein cycloalkyl is defined herein above.

As used herein, the term "halocycloalkoxy" refers to halocycloalkyl-O—, wherein halocycloalkyl is defined herein above.

As used herein, the term "cycloalkoxyalkyl" refers to an alkyl group as defined herein substituted by one or more cycloalkoxy groups as defined herein.

The term "bicyclic" or "bicyclic ring system," as used herein, can include a fused ring system, a bridged ring system, or a Spiro ring system.

The term "fused ring system," as used herein, is a ring system that has two or three rings (preferably two rings) independently selected from carbocyclyl, heterocyclyl, aryl or heteroaryl rings that share one side A fused ring system may have from 4-15 ring members, preferably form 5-10 ring members. Examples of fused ring systems include octahydroisoquinolin-2(1H)-yl, 2,3-dihydro-1H-indenyl, octahydro-1H-pyrido[1,2-a]pyrazinyl, and decahydroisoquinolinyl).

The term "bridged ring system," as used herein, is a ring system that has a carbocyclyl or heterocyclyl ring wherein two non-adjacent atoms of the ring are connected (bridged) by one or more (preferably from one to three) atoms. A bridged ring system can have more than one bridge within the ring system (e.g., adamantyl). A bridged ring system may have from 6-10 ring members, preferably from 7-10 ring members. Examples of bridged ring systems include adamantly, 9-azabicyclo[3.3.1]nonan-9-yl, 8-azabicyclo[3.2.1]octanyl, bicyclo[2.2.2]octanyl, 3-azabicyclo[3.1.1]heptanyl, bicyclo[2.2.1]heptanyl, (1R,5S)-bicyclo[3.2.1]octanyl, 3-azabicyclo[3.3.1]nonanyl, and bicyclo[2.2.1]heptanyl. More preferably, the bridged ring system is selected from the group consisting of 9-azabicyclo[3.3.1]nonan-9-yl, 8-azabicyclo[3.2.1]octanyl, and bicyclo[2.2.2]octanyl.

The term "spiro ring system," as used herein, is a ring system that has two rings each of which are independently selected from a carbocyclyl or a heterocyclyl, wherein the two ring structures having one atom in common. Spiro ring systems have from 5 to 14 ring members. Example of spiro ring systems include 2-azaspiro[3.3]heptanyl, spiropentanyl, 2-oxa-6-azaspiro[3.3]heptanyl, 2,7-diazaspiro[3.5]nonanyl, 2-oxa-7-azaspiro[3.5]nonanyl, 6-oxa-9-azaspiro[4.5]decanyl, 6-oxa-2-azaspiro[3.4]octanyl, 5-azaspiro[2.3]hexanyl and 2,8-diazaspiro[4.5]decanyl.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

As used herein, the term "heterocyclyl" refers to a saturated or unsaturated, non-aromatic monocyclic, bicyclic or tricyclic ring system which has from 3- to 15-ring members at least one of which is a heteroatom, and up to 10 of which may be heteroatoms, wherein the heteroatoms are independently selected from O, S and N, and wherein N and S can be optionally oxidized to various oxidation states. In one embodiment, a heterocyclyl is a 3-8-membered monocyclic. In another embodiment, a heterocyclyl is a 6-12-membered bicyclic. In yet another embodiment, a heterocyclycyl is a 10-15-membered tricyclic ring system. The heterocyclyl group can be attached at a heteroatom or a carbon atom. Heterocyclyls include fused or bridged ring systems. The term "heterocyclyl" encompasses heterocycloalkyl groups. The term "heterocycloalkyl" refers to completely saturated monocyclic, bicyclic or tricyclic heterocyclyl comprising 3-15 ring members, at least one of which is a heteroatom, and up to 10 of which may be heteroatoms, wherein the heteroatoms are independently selected from O, S and N, and wherein N and S can be optionally oxidized to various oxidation states. Examples of heterocyclyls include dihydrofuranyl, [1,3]dioxolane, 1,4-dioxane, 1,4-dithiane, piperazinyl, 1,3-dioxolane, imidazolidinyl, imidazolinyl, pyrrolidine, dihydropyran, oxathiolane, dithiolane, 1,3-dioxane, 1,3-dithianyl, oxathianyl, thiomorpholinyl, oxiranyl, aziridinyl, oxetanyl, azetidinyl, tetrahydrofuranyl, pyrrolidinyl, tetrahydropyranyl, piperidinyl, morpholinyl, piperazinyl, azepinyl, oxapinyl, oxazepinyl and diazepinyl.

The term "spiroheterocycloalkyl" as used herein, is a heterocycloalkyl that has one ring atom in common with the group to which it is attached. Spiroheterocycloalkyl groups may have from 3 to 15 ring members. In a preferred embodiment, the spiroheterocycloalkyl has from 3 to 8 ring atoms selected from carbon, nitrogen, sulfur and oxygen and is monocyclic.

As used herein, the term "heteroaryl" refers to a 5-14 membered monocyclic-, bicyclic-, or tricyclic-ring system, having 1 to 10 heteroatoms independently selected from N, O or S, wherein N and S can be optionally oxidized to various oxidation states, and wherein at least one ring in the ring system is aromatic. In one embodiment, the heteroaryl is monocyclic and has 5 or 6 ring members. Examples of monocyclic heteroaryl groups include pyridyl, thienyl, furanyl, pyrrolyl, pyrazolyl, imidazoyl, oxazolyl, isoxazolyl, thiazolyl, isothiazolyl, triazolyl, oxadiazolyl, thiadiazolyl and tetrazolyl. In another embodiment, the heteroaryl is bicyclic and has from 8 to 10 ring members. Examples of bicyclic heteroaryl groups include indolyl, benzofuranyl, quinolyl, isoquinolyl indazolyl, indolinyl, isoindolyl, indolizinyl, benzamidazolyl, quinolinyl, 5,6,7,8-tetrahydroquinoline and 6,7-dihydro-5H-pyrrolo[3,2-d]pyrimidine.

An amino is a group having the formula $NH_2$—. The term N-alkylamino is an amino group in which one of the hydrogen atoms is replaced with an alkyl group. The term N,N-dialkylamino is an amino group in which each hydrogen atoms is replaced with an alkyl group which may be the same or different.

The term "trialkylsilyl" refers to $(alkyl)_3$-Si—, wherein each of the alkyl groups may be the same or different.

The number of carbon atoms in a group is specified herein by the prefix "$C_{x-xx}$", wherein x and xx are integers. For example, "$C_{1-4}$alkyl" is an alkyl group which has from 1 to 4 carbon atoms; $C_{1-6}$alkoxy is an alkoxy group having from 1 to 6 carbon atoms; $C_{6-10}$ aryl is an aryl group which has from 6 to 10 carbon atoms; and $C_{1-4}$haloalkyl is a haloalkyl group which has from 1 to 4 carbon atoms.

The disclosed compounds can contain one or more asymmetric centers in the molecule. In accordance with the present disclosure any structure that does not designate the stereochemistry is to be understood as embracing all the various optical isomers (e.g., diastereomers and enantiomers) in pure or substantially pure form, as well as mixtures thereof (such as a racemic mixture, or an enantiomerically enriched mixture). It is well known in the art how to prepare such optically active forms (for example, resolution of the racemic form by recrystallization techniques, synthesis from optically-active starting materials, by chiral synthesis, or chromatographic separation using a chiral stationary phase). The compounds can be isotopically-labeled compounds, for example, compounds including various isotopes of hydrogen, carbon, nitrogen, oxygen, phosphorous, fluorine, iodine, or chlorine. The disclosed compounds may exist in tautomeric forms and mixtures and separate individual tautomers are contemplated. In addition, some compounds may exhibit polymorphism.

A compound of formula (I) or (II) can modulate the activity of S1P receptors. A compound of formula (I) or (II) can have S1P receptor agonist or antagonist activity. The compound can be selective for the S1P4 receptor. The compound can be a selective S1P4 antagonist. Being selective can mean that the compound binds to the receptor (or relatively small group of related molecules or proteins) in a complex mixture, or in other words, when exposed to a variety of closely related receptor types, the compound can bind preferentially to just one of the receptor types. The compound can have a greater affinity for the S1P4 receptor, by at by at least 100-fold, by at least 50-fold, by at least 10-fold, by at least 5-fold or by at least 2-fold, than for S1P1 receptor, S1P2 receptor, S1P3 receptor, or S1P5 receptor.

An inhibitor of S1P4 mediated activity can block S1P interaction with an S1P4 receptor. For example, the inhibitor can be an antagonist of an S1P4 receptor. An antagonist can be a molecule that has affinity for the receptor but does not induce activity or a specific activity from the receptor. The antagonist can bind with an S1P4 receptor with an $IC_{50}$ value of less than 1 µM, less than 750 nM, less than 500 nM, less than 250 nM or less than 100 nM. The antagonist can bind with an S1P4 receptor with an $IC_{50}$ value in a range between 1 nM and 1 µM, between 1 nM and 500 nM, between 10 nM and 250 nM, between 25 nm and 100 nM, or between 50 nM and 100 nM.

The compounds can also promote oligodendrocyte progenitor cell differentiation. The compounds can promote myelination or remyelination.

An "S1P modulating agent" refers a compound or composition that is capable of inducing a detectable change in S1P receptor activity in vivo or in vitro (e.g., at least 10% increase or decrease in S1P activity as measured by a given assay such as the bioassay described in the examples and known in the art. "S1P receptor," refers to all of the S1P receptor subtypes (for example, the S1P receptors $S1P_1$, $S1P_2$, $S1P_3$, $S1P_4$, or $S1P_5$), unless the specific subtype is indicated. It is well known in the art how to determine S1P agonist or antagonist activity using the standard tests described herein, or using other similar tests which are well known in the art. In some cases, depending on the cell type and conditions used, an S1P modulating agent can have agonist or antagonist activity, even at the same receptor subtype.

The biological effects of an S1P modulating agent can be vary depending on whether the compound has S1P receptor agonist or antagonist activity. Potential uses of an S1P modulating agent include, but are not limited to, prevention or treatment of a pathological condition or symptom in a mammal. For example, the condition can include asthma, an inflammatory neuropathies, arthritis, lupus erythematosis, psoriasis, an ischemia reperfusion injury, a solid tumor, a tumor metastasis, a disease associated with angiogenesis, a vascular disease, a pain condition, an acute viral disease, or insulin-dependent diabetes, and non-insulin dependent diabetes. The condition can alter lymphocyte trafficking as a method of treatment for neuropathic pain, inflammation-induced pain (e.g., where prostaglandins are involved) or treatment of autoimmune pathologies such as uveitis, type I diabetes, rheumatoid arthritis, chronic inflammatory disorders, inflammatory bowel diseases (e.g., Crohn's disease and ulcerative colitis), multiple sclerosis, and in drug-eluting stents. Additional uses can include treatment of brain degenerative diseases, heart diseases, cancers, or hepatitis C. See, for example, WO 2005/085295, WO 2004/010987, WO 03/097028, and WO 2006/072562, each of which is incorporated by reference in its entirety. A class of S1P receptor agonists are described in provisional U.S. Application No. 60/956,111, filed Aug. 15, 2007, and PCT/US2008/073378, filed Aug. 15, 2008, each of which is incorporated by reference in its entirety. See also provisional U.S. Application No. 61/231,539, filed Aug. 5, 2009, and PCT/US2010/44607, filed Aug. 5, 2010, each of which is incorporated by reference in its entirety.

Additional potential uses of an S1P modulating agent include, but are not limited to, prevention or treatment of a pathological condition or symptom in a mammal. For example, the condition can include inhibited cell migration of oligodendrocyte precursor cells (OPCs). Potential uses of an S1P receptor antagonist, and $S1P_4$ receptor type selective antagonists particularly, include, but are not limited to, prevention or treatment of a pathological condition or symptom in a mammal.

"Treatment" of multiple sclerosis includes treating various forms of the disease including relapsing-remitting, chronic progressive, and the S1P receptor agonists/antagonists can be used alone or in conjunction with other agents to relieve signs and symptoms of the disease as well as prophylactically.

In addition, the disclosed compounds can be used for altering lymphocyte trafficking as a method for prolonging allograft survival, for example transplantation including solid organ transplants, treatment of graft vs. host disease, bone marrow transplantation, and the like.

In addition, disclosed compounds can be useful for inhibition of S1P lyase. S1P lyase is an intracellular enzyme that irreversibly degrades S1P. Inhibition of S1P lyase disrupts lymphocyte trafficking with concomitant lymphopenia. Accordingly, S1P lyase inhibitors can be useful in modulating immune system function. Therefore, the disclosed compounds can be used to inhibit S1P lyase. This inhibition could be in concert with S1P receptor activity, or be independent of activity at any S1P receptor.

In addition, disclosed compounds can be useful as antagonists of the cannabinoid $CB_1$ receptor. $CB_1$ antagonism is associated with a decrease in body weight and an improvement in blood lipid profiles. The $CB_1$ antagonism could be in concert with S1P receptor activity, or be independent of activity at any S1P receptor.

In addition, disclosed compounds can be useful for inhibition of group IVA cytosolic $PLA_2$ ($cPLA_2$). $cPLA_2$ catalyzes the release of eicosanoic acids (e.g., arachidonic acid). The eicosanoic acids are transformed to pro-inflammatory eicosanoids such as prostaglandins and leukotrienes. Thus, disclosed compounds may be useful as anti-inflammatory agents. This inhibition could be in concert with S1P receptor activity, or be independent of activity at any S1P receptor.

In addition, disclosed compounds may be useful for inhibition of the multiple substrate lipid kinase (MuLK). MuLK is highly expressed in many human tumor cells and thus its inhibition might slow the growth or spread of tumors.

Pharmaceutical compositions can include the compounds of formula (I) or (II). More particularly, such compounds can be formulated as pharmaceutical compositions using standard pharmaceutically acceptable carriers, fillers, solubilizing agents and stabilizers known to those skilled in the art. For example, a pharmaceutical composition including a compound of formula (I) or (II), or a salt, analog, derivative, or modification thereof, as described herein, is used to administer the appropriate compound to a subject.

The compounds of formula (I) or (II) are useful for treating a disease or disorder including administering to a subject in need thereof of a therapeutically acceptable amount of a compound of formula (I) or (II), or a pharmaceutical composition comprising a therapeutically effective amount of a compound of formula (I) or (II), and a pharmaceutically-acceptable carrier.

The compounds of formula (I) or (II) can be used in combination with at least one further active ingredient, such as a medicament used in the treatment of multiple sclerosis such as Tysabri®, dimethyl fumarate, an interferon (such as pegylated or non-pegylated interferons, preferably interferon β-1a or pegylated interferon β-1a), glatiramer acetate, a compound improving vascular function, an immunomodulating agent (such as Fingolimod, cyclosporins, rapamycins or ascomycins, or their immunosuppressive analogs, e.g. cyclosporine A, cyclosporine G, FK-506, ABT-281, ASM981, rapamycin, 40-O-(2-hydroxy)ethyl-rapamycin etc.); corticosteroids; cyclophosphamide; azathioprine; mitoxanthrone, methotrexate; leflunomide; mizoribine; mycophenolic add; mycophenolate mofetil; 15-deoxyspergualine; diflucortolone valerate; difluprednate; Alclometasone dipropionate; amcinonide; amsacrine; asparaginase; azathioprine; basiliximab; beclometasone dipropionate; betamethasone; betamethasone dipropionate; betamethasone phosphate sodique; betamethasone valerate; budesonide; captopril; chlormethine chlorhydrate; clobetasol propionate; cortisone acetate; cortivazol; cyclophosphamide; cytarabine; daclizumab; dactinomycine; desonide; desoximetasone; dexamethasone; dexamethasone acetate; dexamethasone isonicotinate; dexamethasone metasulfobenzoate sodique; dexamethasonephosphate; dexamethasone tebutate; dichlorisone acetate; doxorubicinee chlorhydrate; epirubicine chlorhydrate; fluclorolone acetonide; fludrocortisone acetate; fludroxycortide; flumetasone pivalate; flunisolide; fluocinolone acetonide; fluocinonide; fluocortolone; fluocortolone hexanoate; fluocortolone pivalate; fluorometholone; fluprednidene acetate; fluticasone propionate; gemcitabine chlorhydrate; halcinonide; hydrocortisone; hydrocortisone acetate; hydrocortisone butyrate; hydrocortisone hemisuccinate; melphalan; meprednisone; mercaptopurine; methylprednisolone; methylprednisolone acetate; methylprednisolone hemisuccinate; misoprostol; muromonab-cd3; mycophenolate mofetil; paramethansone acetate; prednazoline, prednisolone; prednisolone acetate; prednisolone caproate; prednisolone metasulfobenzoate sodique; prednisolone phosphate sodique; prednisone; prednylidene; rifampicine; rifampicine sodique; tacrolimus; teriflunomide; thalidomide; thiotepa; tixocortol pivalate; triamcinolone; triamcinolone acetonide hemisuccinate; triamcinolone benetonide; triamcinolone diacetate; triamcinolone hexacetonide; immunosuppressive monoclonal antibodies, e.g., monoclonal antibodies to leukocyte receptors, e.g., MHC, CD2, CD3, CD4, CD7, CD20 (e.g., rituximab and ocrelizumab), CD25, CD28, B7, CD40, CD45, CD56 (e.g., daclizumab), or CD58 or their ligands; or other immunomodulatory compounds, e.g. CTLA41g, or other adhesion molecule inhibitors, e.g. mAbs or low molecular weight inhibitors including Selectin antagonists and VLA-4 antagonists (such as Tysabri®); remyelinating agents such as BIIB033. Compounds of formula (I) or formula (II) can also be used in combination with agents which treat the symptoms of multiple sclerosis such as fampridine.

Axons and dendrites can extend from neurons. The distal tip of an extending axon or neurite can include a specialized region, known as the growth cone. Growth cones can sense the local environment and can guide axonal growth toward a neuron's target cell. Growth cones can respond to environmental cues, for example, surface adhesiveness, growth factors, neurotransmitters and electric fields. The growth cones can advance at a rate of one to two millimeters per day. The growth cone can explore the area ahead of it and on either side, by means of elongations classified as lamellipodia and filopodia. When an elongation contacts an unfavorable surface, it can withdraw. When an elongation contacts a favorable growth surface, it can continue to extend and guides the growth cone in that direction. When the growth cone reaches an appropriate target cell a synaptic connection can be created.

Nerve cell function can be influenced by contact between neurons and other cells in their immediate environment (Rutishauser, et al., 1988, *Physiol. Rev.* 68:819, which is incorporated by reference in its entirety). These cells can include specialized glial cells, oligodendrocytes in the central nervous system (CNS), and Schwann cells in the peripheral nervous system (PNS), which can sheathe the neuronal axon with myelin (Lemke, 1992, in *An Introduction to Molecular Neurobiology*, Z. Hall, Ed., p. 281, Sinauer, each of which is incorporated by reference in its entirety).

CNS neurons can have the inherent potential to regenerate after injury, but they can be inhibited from doing so by inhibitory proteins present in myelin (Brittis et al., 2001, *Neuron* 30:11-14; Jones et al., 2002, *J. Neurosci.* 22:2792-2803; Grimpe et al., 2002, *J. Neurosci.*:22:3144-3160, each of which is incorporated by reference in its entirety).

Several myelin inhibitory proteins found on oligodendrocytes have been characterized. Known examples of myelin inhibitory proteins can include NogoA (Chen et al., Nature, 2000, 403, 434-439; Grandpre et al., *Nature* 2000, 403, 439-444, each of which is incorporated by reference in its entirety), myelin associated glycoprotein (MAG) (McKenacher et al., 1994, *Neuron* 13:805-811; Mukhopadhyay et al., 1994, *Neuron* 13:757-767, each of which is incorporated by reference in its entirety) or oligodendrocyte glycoprotein (OM-gp), Mikol et al., 1988, *J. Cell. Biol.*106:1273-1279, each of which is incorporated by reference in its entirety). Each of these proteins can be a ligand for the neuronal Nogo receptor-1 (NgR1 (Wang et al., *Nature* 2002, 417, 941-944; Grandpre et al., *Nature* 2000, 403, 439-444; Chen et al., *Nature*, 2000, 403, 434-439; Domeniconi et al., *Neuron* 2002, published online Jun. 28, 2002, each of which is incorporated by reference in its entirety).

Nogo receptor-1 (NgR1) can be a GPI-anchored membrane protein that contains 8 leucine rich repeats (Fournier et al., 2001, *Nature* 409:341-346, which is incorporated by reference in its entirety). Upon interaction with inhibitory proteins (e.g., NogoA, MAG and OM-gp), the NgR1 complex can transduce signals that lead to growth cone collapse and inhibition of neurite outgrowth.

There is a need for molecules and methods for inhibiting NgR1-mediated growth cone collapse and the resulting inhibition of neurite outgrowth. Additionally, there is a need for molecules which increase neuronal survival and axon regeneration, particularly for the treatment of disease, disorders or injuries that involve axonal injury, neuronal or oligodendrocyte cell death, demyelination or dymyelination or generally relate to the nervous system.

Such diseases, disorders or injuries can include, but are not limited to, multiple sclerosis (MS), progressive multifocal leukoencephalopathy (PML), encephalomyelitis (EPL), central pontine myelolysis (CPM), adrenoleukodystrophy, Alexander's disease, Pelizaeus Merzbacher disease (PMZ), Globoid cell Leucodystrophy (Krabbe's disease) and Wallerian Degeneration, optic neuritis, transverse myelitis, amylotrophic lateral sclerosis (ALS), Huntington's disease, Alzheimer's disease, Parkinson's disease, spinal cord injury, traumatic brain injury, post radiation injury, neurologic complications of chemotherapy, stroke, acute ischemic optic neuropathy, vitamin E deficiency, isolated vitamin E deficiency syndrome, AR, Bassen-Kornzweig syndrome, Marchiafava-Bignami syndrome, metachromatic leukodystrophy, trigeminal neuralgia, or Bell's palsy. Among these diseases, MS may the most widespread, affecting approximately 2.5 million people worldwide.

MS can begin with a relapsing-remitting pattern of neurologic involvement, which then can progress to a chronic phase with increasing neurological damage. MS can be associated with the destruction of myelin, oligodendrocytes or axons localized to chronic lesions. The demyelination observed in MS may not always permanent and remyelination has been documented in early stages of the disease. Remyelination of neurons can require oligodendrocytes.

Various disease-modifying treatments may be available for MS, including the use of corticosteroids and immunomodulators such as interferon beta or Tysabri®. In addition, because of the central role of oligodendrocytes and myelination in MS, there have been efforts to develop therapies to increase oligodendrocyte numbers or enhance myelination. See, e.g., Cohen et al., U.S. Pat. No. 5,574,009; Chang et al., N. Engl. J. Med. 346: 165-73 (2002), each of which is incorporated by reference in its entirety. However, there remains an urgent need to devise additional therapies for MS and other demyelination and dismyelination disorders.

A compound of formula (I) or (II) can promote myelination or remyelination. A method can include administering a compound of formula (I) or (II) to cells. A method of promoting oligodendrocyte progenitor cell differentiation can include administering a compound of formula (I) or (II) to cells. A method of treating multiple sclerosis can include administering a compound of formula (I) or (II) to a subject.

The dose of a compound of formula (I) or (II) administered to a subject can be less than 10 µg, less than 25 µg, less than 50 µg, less than 75 µg, less than 0.10 mg, less than 0.25 mg, less than 0.5 mg, less than 1 mg, less than 2.5 mg, less than 5 mg, less than 10 mg, less than 15 mg, less than 20 mg, less than 50 mg, less than 75 mg, less than 100 mg, or less than 500 mg.

Administering can include administering by topical, enteral, parenteral, transdermal, transmucosal, inhalational, intracisternal, epidural, intravaginal, intravenous, intramuscular, subcutaneous, intradermal or intravitreal administration.

The duration of administering can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

Administering the inhibitor or compound can include multiple administrations. The duration between administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours or for more than 24 hours.

The duration between successive administrations can be less than 30 seconds, less than 1 minute, about 1 minute, between 1 minute and 5 minutes, between 5 minutes and 10 minutes, between 10 minutes and 20 minutes, between 20 minutes and 30 minutes, between 30 minutes and 1 hour, between 1 hour and 3 hours, between 3 hours and 6 hours, between 6 hours and 12 hours, between 12 hours and 24 hours, between 24 hours and 48 hours, between 48 hours and 72 hours, between 72 hours and 1 week or between 1 week and 2 weeks.

Administering an inhibitor or compound to cells can include cells of an in vitro or in vivo system or model. The cells can be part of a cell line. The cell line can be a primary or secondary cell line. The cell line can be an immortal cell line. The cells can be ruptured and be in the form of a cell lysate. The cells can be part of a living organism, i.e., a subject, for example, a mammal. A mammal can include a rat, a mouse, a gerbil, a hamster, a rabbit or a human. The human can be a subject or a patient.

A method can further include monitoring a property of a sample or a subject. A sample can be removed from a subject. For instance, a sample can include a sample of cells or a tissue from a subject. A sample can include blood, plasma, or neuronal tissue including neurons or glial cells. A sample can also remain in the subject. For example, a sample can be a tissue or cells that are observed within the patient.

A method can further include providing untreated control cells, sample or subject and measuring a property of a sample of the untreated control cells, sample or subject.

A property can include the presence or absence of a molecule, the concentration of a molecule, for example myelin basic protein, myelin associated glycoprotein or myelin oligodendrocyte glycoprotein. In some embodiments, determining the presence of a molecule can include determining the concentration of the molecule, determining the purity of the molecule or determining the quantity of the molecule.

A property can be the conductivity of a tissue or cell. A property can be an emission, for example, electromagnetic radiation.

Monitoring a property can include observing the property of the sample or subject alone. Monitoring a property can include monitoring the property before the sample or subject has been administered a compound of formula (I) or (II). Monitoring a property can include monitoring the property after the sample or subject has been administered a compound. Monitoring a property can include monitoring a property after the sample or subject has been administered a known concentration of a compound.

Monitoring a property of a sample or subject can include observing the property through a microscope. Monitoring a property of the composition can include measuring the property using a microscope. Monitoring a property of the composition can include monitoring the property using still photography or movies. The photography or movies can be on film media or digital form. Monitoring a property can include taking a scan, for example, an MRI or CT scan.

Promoting myelination, remyelination or oligodendrocyte progenitor cell differentiation can prevent or can treat a pathological condition or symptom in a mammal. The pathological condition can be multiple sclerosis, an autoimmune diseases, chronic inflammatory disorders, asthma, inflammatory neuropathies, arthritis, transplantation rejection, Crohn's disease, ulcerative colitis, lupus erythematosis, psoriasis, an ischemia-reperfusion injury, solid tumors, and tumor metastasis, a disease associated with angiogenesis, vascular diseases, pain conditions, acute viral diseases, an inflammatory bowel condition, insulin-dependent diabetes, or non-insulin dependent diabetes.

The compound can be administered as a pharmaceutical composition. A pharmaceutical composition can include a compound of formula (I) or (II). More particularly, a compound of formula (I) or (II) can be formulated as pharmaceutical compositions using standard pharmaceutically acceptable carriers, fillers, solubilizing agents and stabilizers known to those skilled in the art. For example, a pharmaceutical composition including a compound of formula (I) or (II), or a salt, analog, derivative, or modification thereof, as described herein, can be used to administer the appropriate compound to a subject.

A compound of formula (I) or (II) can be useful for treating a disease or disorder, for example, in a method including administering to a subject in need thereof of a therapeutically acceptable amount of compound of formula (I) or (II), or a pharmaceutical composition comprising a therapeutically effective amount of a compound of formula (I) or (II), and a pharmaceutically-acceptable carrier.

In cases where a compound of formula (I) or (II) can be sufficiently basic or acidic to form stable nontoxic acid or base salts, preparation and administration of the compounds as pharmaceutically acceptable salts may be appropriate. Examples of pharmaceutically acceptable salts can be organic acid addition salts formed with acids which form a physiological acceptable anion, for example, tosylate, methanesulfonate, acetate, citrate, malonate, tartarate, succinate, benzoate, ascorbate, α-ketoglutarate, or α-glycerophosphate. Inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion Alkali metal (for example, sodium, potassium or lithium) or alkaline earth metal (for example calcium) salts of carboxylic acids can also be made.

Pharmaceutically-acceptable base addition salts can be prepared from inorganic and organic bases. Salts from inorganic bases, can include but are not limited to, sodium, potassium, lithium, ammonium, calcium or magnesium salts. Salts derived from organic bases can include, but are not limited to, salts of primary, secondary or tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, or mixed di- and tri-amines where at least two of the substituents on the amine can be different and can be alkyl, substituted alkyl, alkenyl, substituted alkenyl, cycloalkyl, substituted cycloalkyl, cycloalkenyl, substituted cycloalkenyl, aryl, heteroaryl, or heterocyclic and the like. Also included can be amines where the two or three substituents, together with the amino nitrogen, form a heterocyclic or heteroaryl group. Non-limiting examples of amines can include, isopropylamine, trimethyl amine, diethyl amine, tri(iso-propyl) amine, tri(n-propyl) amine, ethanolamine, 2-dimethyl-aminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, or N-ethylpiperidine, and the like. Other carboxylic acid derivatives can be useful, for example, carboxylic acid amides, including carboxamides, lower alkyl carboxamides, or dialkyl carboxamides, and the like.

A compound of formula (I) or (II) formulated as a pharmaceutical composition and administered to a mammalian host, such as a human patient in a variety of forms adapted to the chosen route of administration, e.g., orally or parenterally, as eyedrops, by intravenous, intramuscular, topical or subcutaneous routes.

Thus, compound of formula (I) or (II) may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, or wafers, and the like. Such compositions and preparations should contain at least about 0.1% of active compound. The percentage of the compositions and preparations may, of course, be varied and may conveniently be between about 2 to about 60% of the weight of a given unit dosage form. The amount of active compound in such therapeutically useful compositions can be such that an effective dosage level will be obtained.

The tablets, troches, pills, capsules, and the like can include the following: binders such as gum tragacanth, acacia, corn starch or gelatin; excipients such as dicalcium phosphate; a disintegrating agent such as corn starch, potato starch, alginic acid and the like; a lubricant such as magnesium stearate; or a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl or propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

Exemplary pharmaceutical dosage forms for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, or nontoxic glyceryl esters, and mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, or thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate or gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation can be vacuum drying and the freeze drying techniques, which can yield a powder of the active ingredient plus any additional desired ingredient present in the previously sterile-filtered solutions.

For topical administration, a compound of formula (I) or (II) may be applied in pure form, e.g., when they are liquids. However, it can be generally be desirable to administer them to the skin as compositions or formulations, in combination with a dermatologically acceptable carrier, which may be a solid or a liquid.

Exemplary solid carriers can include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts or esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula (I) or (II) to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), each of which is incorporated by reference in its entirety.

Useful dosages of the compounds of formula (I) or (II) can be determined by comparing their in vitro activity, and in vivo activity in animal models. Methods for the extrapolation of effective dosages in mice, and other animals, to humans are known to the art; for example, see U.S. Pat. No. 4,938,949, which is incorporated by reference in its entirety.

Generally, the concentration of the compound(s) of formula (I) or (II) in a liquid composition, such as a lotion, can be from about 0.1 to about 25 weight percent, preferably from about 0.5-10 weight percent. The concentration in a semi-solid or solid composition such as a gel or a powder can be about 0.1-5 wt-%, preferably about 0.5-2.5 weight percent based on the total weight of the composition.

The amount of the compound, or an active salt or derivative thereof, required for use in treatment can vary not only with the particular salt selected but also with the route of administration, the nature of the condition being treated and the age and condition of the patient and can be ultimately at the discretion of the attendant physician or clinician. In general, however, a dose can be in the range of from about 0.1 to about 10 mg/kg of body weight per day.

The compound can be conveniently administered in unit dosage form; for example, containing 0.01 to 10 mg, or 0.05 to 1 mg, of active ingredient per unit dosage form. In some embodiments, a dose of 5 mg/kg or less can be suitable.

The active ingredient can be administered so as to achieve a desired peak plasma concentration of the active compound. The desired peak plasma concentration can be from about 0.5 µM to about 75 µM, preferably, about 1 µM to 50 µM, or about 2 µM to about 30 µM. This may be achieved, for example, by the intravenous injection of a 0.05 to 5% solution of the active ingredient, optionally in saline, or orally administered as a bolus containing between about 1 mg to about 100 mg of the active ingredient.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations; such as multiple inhalations from an insufflator or by application of a plurality of drops into the eye.

The disclosed method can include a kit comprising a compound of formula (I) or (II) and instructional material which can describe administering the compound or a composition comprising the compound to a cell or a subject. This should be construed to include other embodiments of kits that are known to those skilled in the art, such as a kit comprising a (preferably sterile) solvent for dissolving or suspending the compound or composition prior to administering the compound or composition to a cell or a subject. Preferably, the subject can be a human.

In accordance with the disclosed methods, as described above or as discussed in the Examples below, there can be employed conventional chemical, cellular, histochemical, biochemical, molecular biology, microbiology, and in vivo techniques which are known to those of skill in the art. Such techniques are explained fully in the literature.

EXAMPLES

Example 1 cis-4-tert-Butylcyclohexyl methanesulfonate

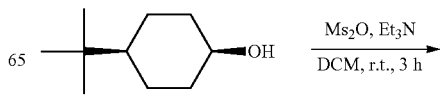

-continued

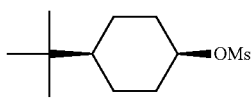

Cis-4-t-butylcyclohexanol (6.0 g, 38.5 mmol, 1.0 eq.) was dissolved in dichloromethane (10 mL). Then methanesulfonic anhydride (8.03 g, 46.2 mmol, 1.1 eq.) was added to the mixture slowly at 0° C. Then triethylamine (6.4 mL, 46.2 mmol, 1.5 eq.) was added to the mixture and the mixture stirred at room temperature for 3 h. The mixture was extracted with dichloromethane and the organic layer was concentrated to give product as a white power (8.0 g, yield: 90%). The product was used to next step without further purification. $^1$H NMR (400 MHz, CDCl$_3$) δ 4.99-4.98 (m, 1H), 3.02 (s, 3H), 2.14-2.12 (m, 2H), 1.65-1.28 (m, 7H), 0.84 (s, 9H).

Example 2

2-Bromo-6-(trans-4-tert-butylcyclohexyloxy)naphthalene

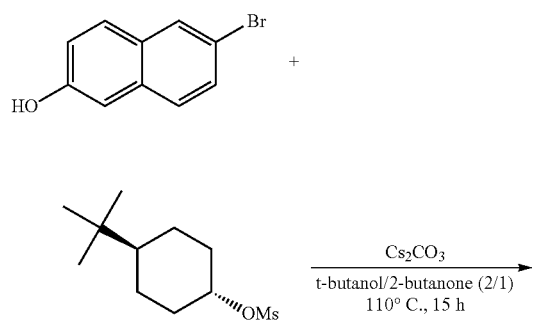

6-bromonaphthalen-2-ol (CAS no. 15231-91-1) (3.0 g, 14.8 mmol, 1.0 eq.) was dissolved in a mixture of t-butanol/2-butanone (4 mL/2 mL). Then cesium carbonate (12 g, 37.2 mmol, 2.5 eq.) was added to the mixture and the mixture was stirred at 110° C. for 10 min. Then trans-4-tert-butylcyclohexyl methanesulfonate (3.48 g, 16.2 mmol, 1.1 eq.) was added to the mixture. The suspension was stirred at 110° C. under a nitrogen atmosphere for 15 h. The reaction mixture was extracted with ethyl acetate and the organic layer was purified by silica gel column chromatography using petroleum ether as eluent to give 2-bromo-6-(trans-4-tert-butylcyclohexyloxy)naphthalene as a slight yellow solid (1.7 g, yield: 32%). ESI-MS: 361.0 (M+H)$^+$. $^1$H NMR (400 MHz, CDCl$_3$) δ 7.89 (s, 1H), 7.63 (d, 1H), 7.56 (d, 1H), 7.47 (d, 1H), 7.15-7.11 (m, 2H), 4.26-4.24 (m, 1H), 2.27-2.25 (m, 2H), 1.89-1.87 (m, 2H), 1.45-1.09 (m, 5H), 0.89 (s, 9H).

Example 3

6-(trans-4-tert-Butylcyclohexyloxy)-2-naphthaldehyde

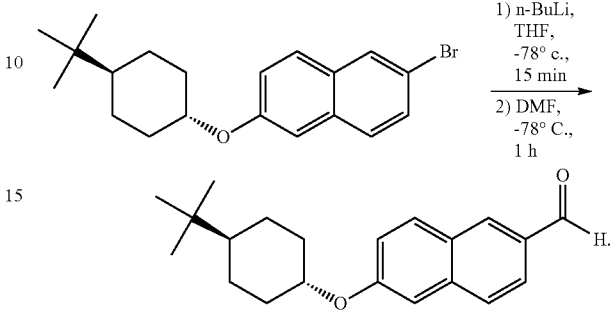

2-bromo-6-(trans-4-tert-butylcyclohexyloxy)naphthalene (2.249 g, 6.25 mmol, 1.0 eq.) was dissolved in THF (10 mL) under nitrogen atmosphere. Then the mixture was cooled down to −78° C. and a solution of n-BuLi in THF (2.5 M, 7.5 mL, 18.8 mmol, 3.0 eq.) was added to the mixture dropwise. The mixture was stirred at −78° C. for 15 min. Then DMF (2.4 mL, 31.2 mmol, 5.0 eq.) was added to the mixture and stirred at −78° C. for 1 h. When the reaction completed, 1 M HCl was added to adjust the pH to 6. The mixture was extracted with EtOAc and the organic layer was concentrated and purified by silica gel chromatography using petroleum ether/ethyl acetate (10/1) as eluent to give 6-(trans-4-tert-butylcyclohexyloxy)-2-naphthaldehyde as a white solid (1.16 g, 60%). EDI-MS: 311.1 (M+H)$^+$. $^1$H NMR (400 MHz, CDCl$_3$) δ 10.08 (s, 1H), 8.24 (s, 1H), 7.92-7.87 (m, 2H), 7.77 (d, 1H), 7.22-7.19 (m, 2H), 4.42-4.30 (m, 1H), 2.30-2.28 (m, 2H), 1.93-1.90 (m, 2H), 1.48-1.11 (m, 5H), 0.82 (s, 9H).

Example 4

6-Bromo-2-(trans-4-tert-butylcyclohexyloxy)-1-iodonaphthalene

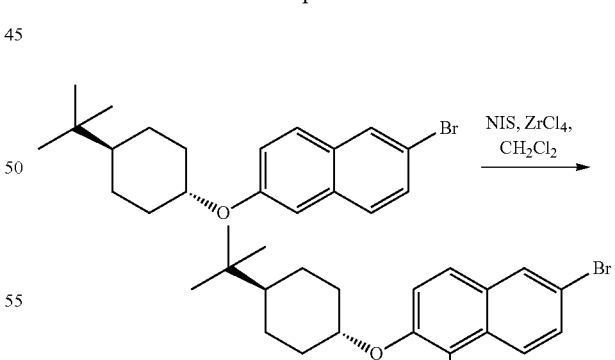

A solution of 2-bromo-6-(trans-4-tert-butylcyclohexyloxy)naphthalene
(160.0 g, 444.4 mmol) in methylene chloride (2.5 L) was purged under an atmosphere of argon. N-iodosuccinimide (202.1 g, 888.8 mmol) and zirconium tetrachloride (20.4 g, 88.9 mmol) was added and the reaction was stirred at room temperature under an atmosphere of argon. The reaction was monitored by ¹H NMR and showed complete conversion to product after 30 minutes. The mixture was then concentrated under reduced pressure to give ~250 g crude as a brown solid. The crude material was purified by silica gel chromatography with hexanes to give 200 g of desired product as a brown solid (yield: 92.6%). EDI-MS: 487.1 (M+H)⁺.

Example 7

(5-Methoxy-2-nitrophenyl)methanol

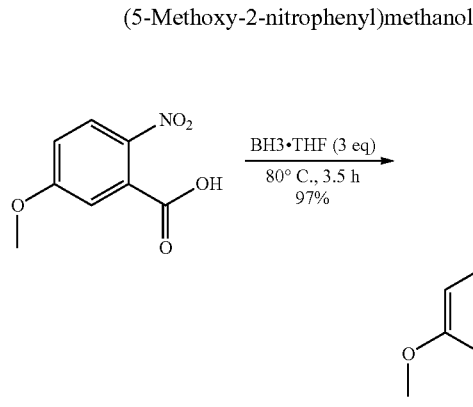

To the solution of 5-methoxy-2-nitrobenzoic acid (20 g, 1.0 mol) in THF (100 mL) was added BH₃ (1.0 M in THF, 30.4 mL, 3.0 eq) at 0° C. The mixture was refluxed for 3 h, diluted with water (200 mL) and extracted with DCM (100 ml*3). The combined organic lays were dried over MgSO₄, evaporated to afford (5-methoxy-2-nitrophenyl)methanol (18 g, yield: 97%), as a white solid. ¹HNMR (400 MHz, DMSO-d₆) δ: 8.13 (d, J=6.4 Hz, 1H), 7.34 (d, J=6.4 Hz, 1H), 7.02 (s, 1H), 5.60-5.58 (m, 1H), 4.84 (d, J=8.0 Hz, 2H), 3.89 (s, 3H); ESI-MS: m/z 184.1 ([M+1]⁺).

Example 8

5-Methoxy-2-nitrobenzaldehyde

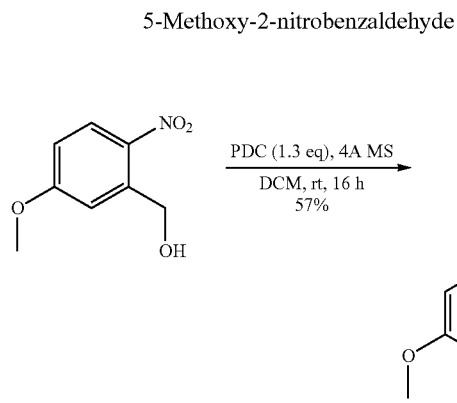

To the solution of (5-methoxy-2-nitrophenyl)methanol (18 g, 0.098 mol) in anhydrous DCM (0.2 L) was added PDC (11.5 g, 0.147 mol, 1.5 eq) and 4A MS (120 g) in portions. The mixture was stirred at room temperature for 16 h, filtered through a Celite pad. The filtrate was evaporated to dryness in vacuum to afford 5-methoxy-2-nitrobenzaldehyde (10 g, yield: 57%) as a light yellow solid. ¹HNMR (400 MHz, DMSO-d₆) δ: 10.24 (s, 1H), 8.14 (d, J=8.8 Hz, 1H), 7.31 (dd, J=8.8, 3.2 Hz, 1H), 7.20 (d, J=3.2 Hz, 1H), 3.89 (s, 3H); ESI-MS: m/z 182.0 ([M+1]⁺).

Example 9

2-(2-Formyl-4-methoxyphenylamino)-2-oxoethyl acetate

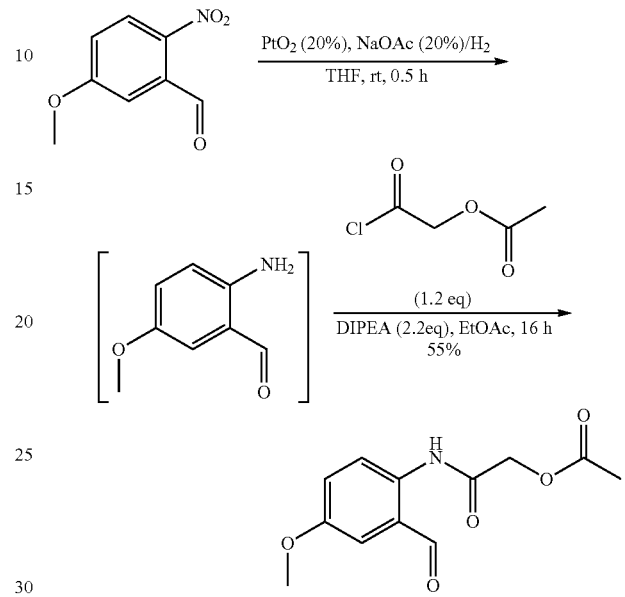

To the solution of 5-methoxy-2-nitrobenzaldehyde (6 g, 0.33 mol) in EtOAc (100 mL) was added 20% PtO₂/C (1.2 g, 20%) and NaOAc (1.2 g, 20%). The reaction was stirred under hydrogen at room temperature for 0.5 h. The mixture was filtered through a Celite pad, and the filtrate was dried over anhydrous Na₂SO₄. After filtration, the solution was cooled to −78° C., and to which was added DIPEA (6.4 g, 0.5 mol, 1.5 eq) and 2-chloro-2-oxoethyl acetate (4.5 g, 0.33 mol, 1.0 eq). The resulting mixture was gradually warmed up to room temperature and stirred overnight. The reaction mixture was washed with water twice, dried over Na₂SO₄ and evaporated most of the solvent in vacuum. Then the solid separating out was collected by filtration to give 2-(2-formyl-4-methoxyphenylamino)-2-oxoethyl acetate (5.6 g, yield: 71%) as a light yellow solid. ¹HNMR (400 MHz, DMSO-d₆) δ: 10.95 (s, 1H), 9.95 (s, 1H), 8.10 (d, J=8.8 Hz, 1H), 7.46 (d, J=3.2 Hz, 1H), 7.30 (dd, J=8.8, 3.2 Hz, 1H), 4.69 (s, 2H), 3.81 (s, 3H), 2.22 (s, 3H); ESI-MS: m/z 252.1 ([M+1]⁺).

Example 10

(6-Methoxyquinazolin-2-yl)methanol

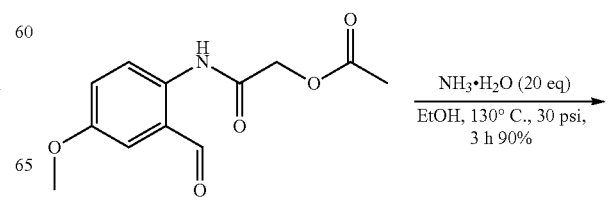

-continued

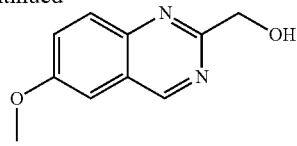

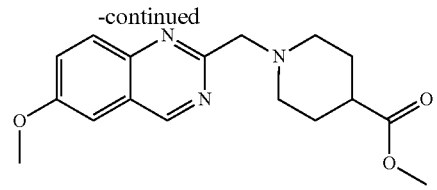

The solution of 2-(2-formyl-4-methoxyphenylamino)-2-oxoethyl acetate (5 g, 0.02 mol) and ammonia (6.8 g, 0.4 mol, 20 eq) in EtOH (30 mL) was reacted under a high pressure (30 psi) at 135° C. for 5 h. After cooling to room temperature, the solvent was evaporated in vacuum. The residual aqueous solution was extracted with DCM (100 mL×3). The combined extracts were dried over anhydrous Na$_2$SO$_4$ and evaporated to dryness in vacuum. The crude product was purified by chromatography (eluting with DCM/MeOH=100/1) to give (6-methoxyquinazolin-2-yl)methanol (4.1 g, yield: 90%) as a white solid. $^1$HNMR (400 MHz, DMSO-d$_6$) δ: 9.46 (s, 1H), 7.90 (d, J =8.8 Hz, 1H), 7.63 (d, J=8.8, 3.2 Hz, 1H), 7.52 (d, J=2.8 Hz, 1H), 5.34 (t, J=6.4 Hz, 1H), 4.72 (d, J=6.4 Hz, 2H), 3.91 (m, 3H); ESI-MS: m/z 191.1 ([M+1]$^+$).

Example 11

6-Methoxyquinazoline-2-carbaldehyde.

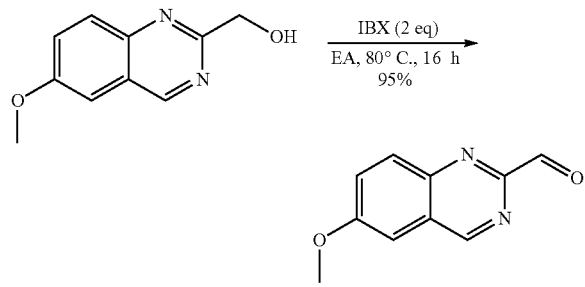

To the solution of (6-methoxyquinazolin-2-yl)methanol (4 g, 0.21 mol) in EA (30 mL) was added IBX (11.6 g, 4.2 mol, 2 eq). The reaction was stirred at 80° C. for 16 h. After filtration, the solution was evaporated in vacuum to give 6-methoxyquinazoline-2-carbaldehyde (3.8 g, yield: 95%) as a white solid. ESI-MS: m/z 189.2 ([M+1]$^+$).

Example 12

Methyl 1-((6-methoxyquinazolin-2-yl)methyl)piperidine-4-carboxylate

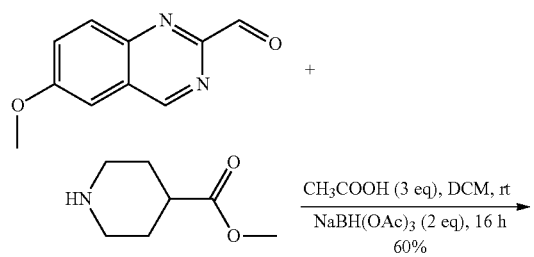

To a solution of compound 6-methoxyquinazoline-2-carbaldehyde (3.8 g, 0.019 mol) and methyl isonipecotic acid ester (2.8 g, 0.021 mmol, 1.1 eq) in CH$_2$Cl$_2$(20 mL) was added acetic acid (3.4 g, 0.057 mol, 3 eq) and NaBH(OAc)$_3$ (8 g, 0.038 mol, 2 eq). The resulting mixture was stirred at room temperature for 16 h. The reaction was quenched by adding 50 mL of saturated aqueous Na$_2$CO$_3$ solution, extracted with DCM (100 mL×3). The combined organic layers were dried over Na$_2$SO$_4$ and concentrated. The residue was purified by a silic gel column (eluting: PE/EA=3/1) to afford methyl 1-((6-methoxyquinazolin-2-yl)methyl)piperidine-4-carboxylate (3.8 g, yield: 60%) as a pale brown solid. $^1$HNMR (400 MHz, DMSO-d$_6$) δ: 9.45 (s, 1H), 7.90 (d, J=9.2 Hz, 1H), 7.62 (dd, J=8.8 Hz, 2.8 Hz, 1H), 7.51 (d, J=2.8 Hz, 1H), 3.92 (s, 3H), 3.78 (s, 2H), 3.57 (s, 3H), 2.88~2.85 (m, 2H), 2.28 (m, 1H), 2.17 (m, 2H),1.78~1.77 (m, 2H), 1.54 (m, 2H); ESI-MS: m/z 316.2 ([M+1]$^+$).

Example 13

Methyl 1-((6-hydroxyquinazolin-2-yl)methyl)piperidine-4-carboxylate

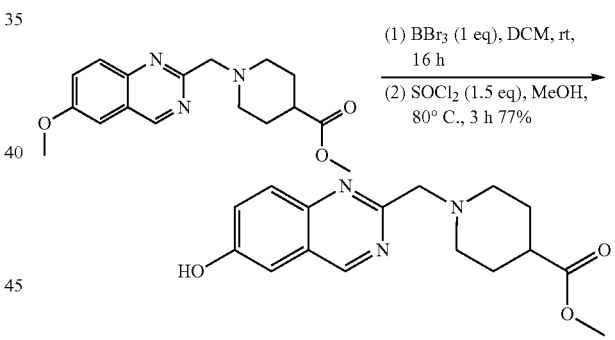

To a solution of methyl 1-((6-methoxyquinazolin-2-yl)methyl)piperidine-4-carboxylate (3.0 g, 9.5 mmol) in DCM (15 mL) was added BBr$_3$ (9.5 mmol, 1.0 eq) at 0° C. under N$_2$. The reaction was stirred at room temperature for 16 h. After the removal of solvent, SOCl$_2$(2.8 g, 0.238 mol, 1.5eq) and MeOH (20 mL) was added at 0° C. The mixture was refluxed at 80° C. for 3 h, poured into the NaHCO$_3$ aqueous solution and extracted with DCM (100 mL*3). The combined extracts were dried over anhydrous Na$_2$SO$_4$ and evaporated to dryness in vacuum. The crude product was purified by chromatography (eluting with DCM/MeOH=25/1) to give methyl 1-((6-hydroxyquinazolin-2-yl)methyl)piperidine-4-carboxylate (1.7 g, yield: 77%) as a yellow solid. $^1$HNMR (400 MHz, DMSO-d$_6$) δ: 10.36 (s, 1H), 9.35 (s, 1H), 7.84 (d, J=9.2 Hz, 1H), 7.51 (dd, J=9.2, 2.4 Hz, 1H), 7.25 (d, J=2.4 Hz, 1H), 3.74 (s, 2H), 3.57 (s, 3H), 2.86~2.84 (m, 2H), 2.27 (m, 1H), 2.16 (m, 2H), 1.77 (m, 2H), 1.56 (m, 2H); ESI-MS: m/z 302.1 ([M+1]$^+$).

Example 14

Methyl 1-((6-((trans-4-tert-butylcyclohexyloxy)quinazolin-2-yl)methyl)piperidine-4-carboxylate

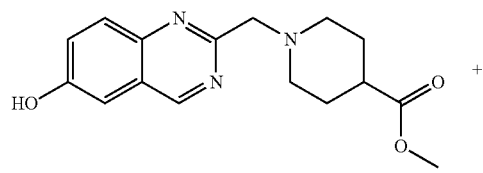

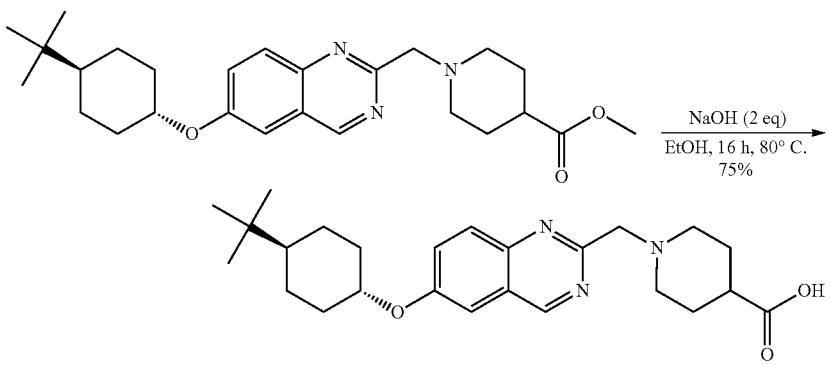

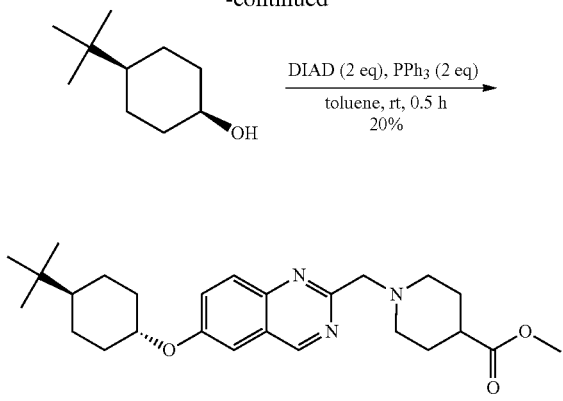

Into a 25 mL round bottom flask was added methyl 1-((6-hydroxyquinazolin-2-yl)methyl)piperidine-4-carboxylate (0.5 g, 1.6 mmol), cis-4-tert-butylcyclohexanol (0.38 g, 0.24 mmol, 1.5 eq), PPh₃ (0.87 g, 3.3 mmol, 2 eq) and dry THF (0.5 mL) under N₂ atmosphere. Then DIAD (0.53 g, 0.33 mmol, 2 eq) was quickly added in one portion at room temperature. The reaction mixture was stirred at rt for 0.5 h, diluted with water (20 mL) and extracted with DCM (20 ml*3). The combined organic lays were dried over MgSO₄ and concentrated. The residue was purified by prep-TLC (DCM/MeOH=15/1) to give methyl 1-((6-(trans-4-tert-butylcyclohexyloxy)quinazolin-2-yl)methyl)piperidine-4-carboxylate (300 mg, yield: 20%) as brown oil.

$^1$HNMR (400 MHz, CDCl₃) δ: 9.27 (s, 1H), 7.87 (d, J=8.8 Hz, 1H), 7.45 (dd, J=8.8, 2.8 Hz, 1H), 7.07 (d, J=2.8 Hz, 1H), 4.30~4.20 (m, 1H), 3.94 (s, 2H), 3.59 (s, 3H), 3.00~2.98 (m, 2H), 2.28~2.18 (m, 4H), 1.85-1.82 (m, 6H), 1.40~1.34 (m, 2H), 1.18~1.03 (m, 4H), 0.86 (s, 9H); ESI-MS: m/z 440.1 (M+1)⁺.

Example 15

1-((6-(trans-4-tert-Butylcyclohexyloxy)quinazolin-2-yl)methyl)piperidine-4-carboxylic acid A mixture of methyl 1-((6-(trans-4-tert-butylcyclohexyloxy)quinazolin-2-yl)methyl)piperidine-4-carboxylate (150 mg, 0.34 mmol) and NaOH (27 mg, 0.68 mmol, 2.0 eq) in EtOH (5 mL) was stirred at 80° C. for 16 h. After cooling to room temperature, 1N HCl (5 ml) aqueous solution was added to adjust pH=3~4. Solvent was evaporated in vacuum. The residue was purified by prep-HPLC (MeOH in 0.05% TFA/H₂O 30-95% v/v as mobile phase) to give 1-((6-(trans-4-tert-butylcyclohexyloxy)quinazolin-2-yl)methyl)piperidine-4-carboxylic acid (105 mg, yield: 75%) as a pale yellow solid.

$^1$HNMR (400 MHz, CD₃OD) δ: 9.45 (s, 1H), 7.96 (d, J=9.6 Hz, 1H), 7.64 (dd, J=9.2, 2.8 Hz, 1H), 7.49 (d, J=2.8 Hz, 1H), 4.69 (s, 2H), 4.47~4.39 (m, 1H), 3.81~3.80 (m, 2H), 3.31~3.27 (m, 1H), 2.70~2.69 (m, 1H), 2.30~2.26 (m, 5H), 2.08~2.07 (m, 2H), 1.92~1.89 (m, 2H), 1.46~1.42 (m, 2H) 1.29~1.26 (m, 2H) 1.12~1.11 (m, 1H), 0.81 (s, 9H) ; ESI-MS: m/z 426 ([M+1]⁺).

Example 16

Ethyl 1-((6-hydroxynaphthalen-2-yl)methyl)piperidine-4-carboxylate

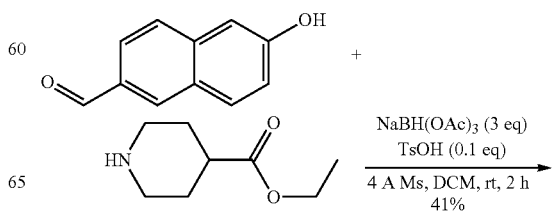

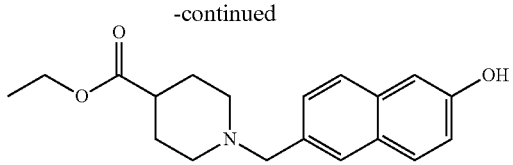

A mixture of 4 Å molecular sieves, 6-hydroxy-2-naphth-aldehyde (1.0 g, 5.81 mmol), ethyl piperidine-4-carboxylate (0.91 g, 5.81 mmol), NaBH(OAc)$_3$ (3.76 g, 17.43 mmol) and TsOH (0.1 g, 0.581 mmol) was stirred at rt for 2 h and then quenched with water (5 mL). The mixture was extracted with DCM (20 mL*2). The combined organics were washed with saturated brine (20 mL*3) and then concentrated. The white precipitates were filtered and dissolved in water (10 mL) and EtOAc (10 mL), NaHCO$_3$ was added to adjust pH=8-9. The mixture was extracted with EtOAc (20 mL*2). The combined organics were washed with saturated brine (20 ml*2), dried over Na$_2$SO$_4$, concentrated and recystallized with EtOAc to give ethyl 1-((6-hydroxynaphthalen-2-yl)methyl)piperidine-4-carboxylate as a white solid (0.83 g, yield: 41%), ESI-MS: 314.1 (M+H)$^+$. $^1$H NMR (400 MHz, DMSO-d6) δ: 9.65 (s, 1H), 7.71 (d, J=8.8 Hz, 1H), 7.61-7.63 (m, 2H), 7.32-7.35 (m, 1H), 7.03-7.08 (m, 2H), 4.02-4.03 (q, J=7.2 Hz, 2H), 3.52 (s, 2H), 2.72-2.75 (m, 2H), 2.25-2.32 (m, 2H), 1.98-2.03 (m, 1H), 1.77-1.79 (m, 2H), 1.51-1.61 (m, 2H), 1.17 (t, J=7.2 Hz, 3H).

Example 17

2,2,2-Trifluoro-1-(6-methoxynaphthalen-2-yl)ethanol

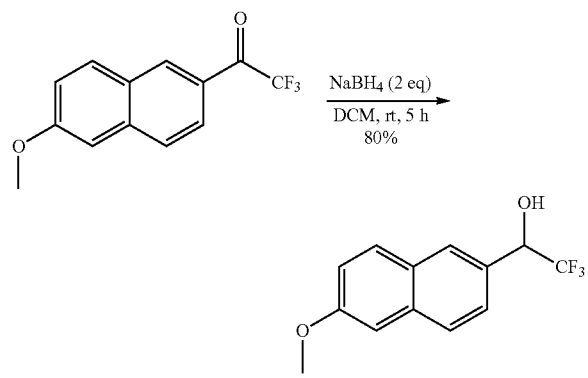

A mixture of 2,2,2-trifluoro-1-(6-methoxynaphthalen-2-yl)ethanone (1 g, 3.9 mmol) and NaBH$_4$ (312 mg, 7.8 mmol, 2 eq) in DCM (20 mL) was stirred at room temperature for 5 h. The reaction mixture was quenched with water (5 mL), washed with brine (10 mL*2), dried over Na$_2$SO$_4$ and concentrated to give 2,2,2-trifluoro-1-(6-methoxynaphthalen-2-yl)ethanol (800 mg, yield: 80%) as a white solid. ESI-MS (M+1)$^+$: 255.1. $^1$HNMR (400 MHz, CDCl$_3$) δ: 7.80 (s, 1H), 7.72-7.68 (m, 2H), 7.46 (d, J=8.4 Hz, 1H), 7.13-7.07 (m, 2H), 5.09 (q, J=6.4 Hz, 1H), 3.85 (s, 3H).

Example 18

2,2,2-Trifluoro-1-(6-methoxynaphthalen-2-yl)ethyl methanesulfonate

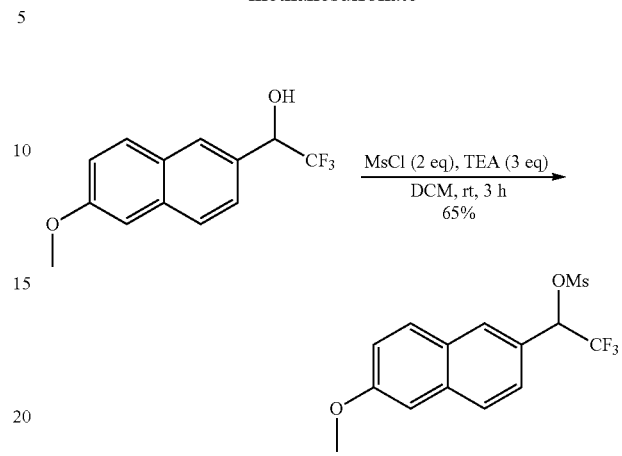

To a solution of 2,2,2-trifluoro-1-(6-methoxynaphthalen-2-yl)ethanol (500 mg, 2 mmol) and TEA (610 mg, 6 mmol, 3 eq) in DCM (10 mL) was added MsCl (680 mg, 6 mmol, 2 eq) at 0° C. dropwise. The reaction mixture was stirred at room temperature for 3 h. The reaction mixture was quenched with sat. NaHCO$_3$ (5 mL), washed with brine (5 mL*3), dried over Na$_2$SO$_4$ and concentrated to give 2,2,2-trifluoro-1-(6-methoxynaphthalen-2-yl)ethyl methanesulfonate (420 mg, yield: 65%) as a white solid. ESI-MS (M+1)$^+$: 335.1. $^1$HNMR (400 MHz, CDCl$_3$) δ: 7.90 (s, 1H), 7.83-7.78 (m, 2H), 7.54 (d, J=8.0 Hz, 1H), 7.22 (dd, J=8.4, 2.4 Hz, 1H), 7.16 (s, 1H), 5.90 (q, J=6.4 Hz, 1H), 3.94 (s, 3H), 2.93 (s, 3H).

Example 19

Methyl 1-(2,2,2-trifluoro-1-(6-methoxynaphthalen-2-yl)ethyl)piperidine-4-carboxylate

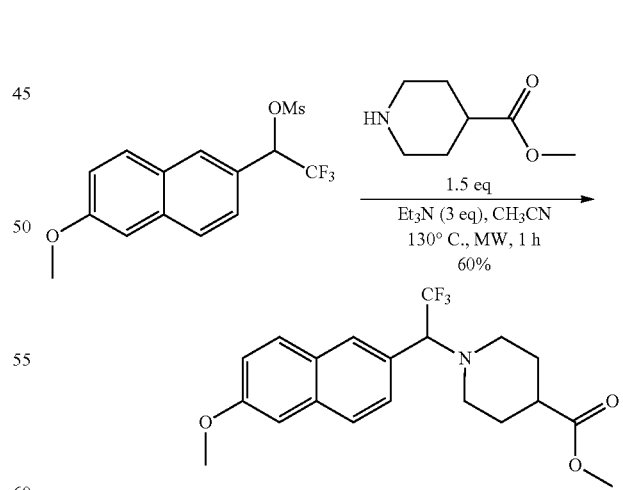

A solution of 2,2,2-trifluoro-1-(6-methoxynaphthalen-2-yl)ethyl methanesulfonate (500 mg, 1.5 mmol), methyl isonipecotic acid ester (330 mg, 2.3 mmol, 1.5 eq) and TEA (450 mg, 4.5 mmol, 3 eq) in CH$_3$CN (4 mL) was stirred at 130° C. under microwave for 1 h. The reaction mixture was stirred at room temperature for 12 h. The reaction mixture was diluted with ethyl acetate (20 mL), washed with brine (5 mL*3), dried over Na₂SO₄ and concentrated to give crude product. The crude product was purified by silica gel column chromatography (Petroleum ether:ethyl acetate=3:1) to give methyl 1-(2,2,2-trifluoro-1-(6-methoxynaphthalen-2-yl)ethyl)piperidine-4-carboxylate (340 mg, yield: 60%) as a yellow solid. ESI-MS (M+1)⁺: 382.1. ¹HNMR (400 MHz, CDCl₃) δ: 7.76-7.73 (m, 3H), 7.46 (d, J=8.4 Hz, 1H), 7.19-7.14 (m, 2H), 4.20 (q, J=8.8 Hz, 1H), 3.93 (s, 3H), 3.65 (s, 3H), 3.04-2.97 (m, 2H), 2.46-2.44 (m, 1H), 2.26-2.22 (m, 2H), 1.87-1.73 (m, 4H).

Example 20

Methyl 1-(2,2,2-trifluoro-1-(6-hydroxynaphthalen-2-yl)ethyl)piperidine-4-carboxylate

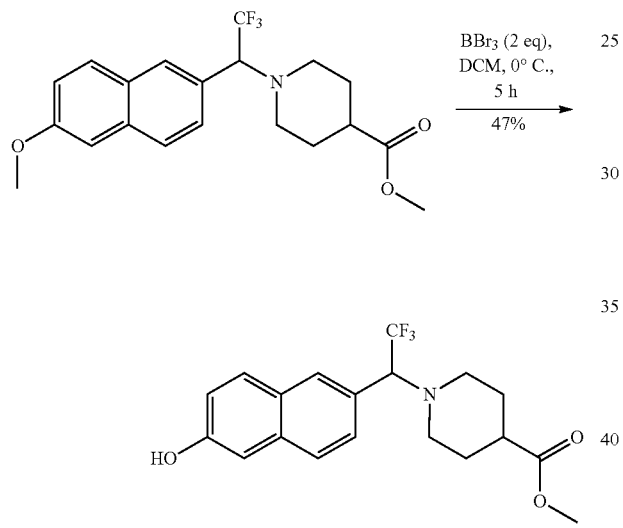

To a solution of methyl 1-(2,2,2-trifluoro-1-(6-methoxynaphthalen-2-yl)ethyl)piperidine-4-carboxylate (500 mg, 1.3 mmol) in DCM (10 mL) was added BBr₃ (3 N in DCM, 0.9 mL, 2.6 mmol, 2 eq) at 0° C. Then the reaction mixture was stirred at 0° C. for 5 h. Methanol (5 mL) was added into the mixture. The reaction was stirred at room temperature for another 2 h, and then was poured into the NaHCO₃ aqueous solution, extracted with DCM (10 mL*3). The combined organic layers were washed with water (5 mL*3) and concentrated to give the crude product, which was purified by chromatography (Petroleum ether:ethyl acetate=1:1) to give methyl 1-(2,2,2-trifluoro-1-(6-hydroxynaphthalen-2-yl)ethyl)piperidine-4-carboxylate as a yellow solid (230 mg, yield: 47%). ESI-MS (M+1)⁺: 368.1. ¹HNMR (400 MHz, CDCl₃) δ: 7.69-7.67 (m, 2H), 7.60 (d, J=8.4 Hz, 1H), 7.37 (d, J=8.8 Hz, 1H), 7.09-7.05 (m, 2H), 4.13 (q, J=8.8 Hz, 1H), 3.59 (s, 3H), 2.97-2.90 (m, 2H), 2.39-2.37 (m, 1H), 2.19-2.17 (m, 2H), 1.72-1.59 (m, 4H).

Example 21

Methyl 1-(1-(6-(trans-4-tert-butylcyclohexyloxy)naphthalen-2-yl)-2,2,2-trifluoroethyl)piperidine-4-carboxylate

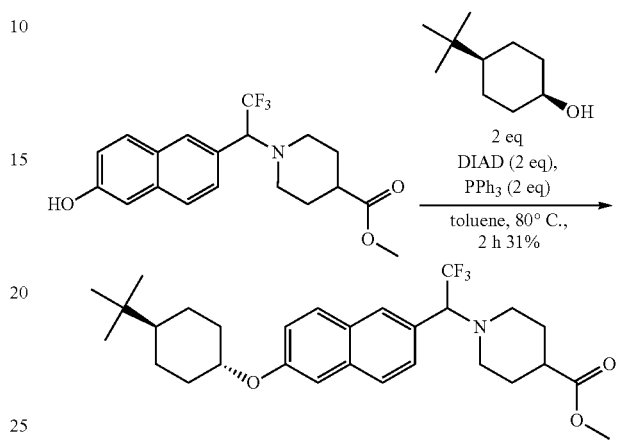

To a stirring mixture of methyl 1-(2,2,2-trifluoro-1-(6-hydroxynaphthalen-2-yl)ethyl)piperidine-4-carboxylate (300 mg, 0.8 mmol), cis-4-(t-butyl)cyclohexanol (245 mg, 1.6 mmol, 2 eq) and PPh₃ (420 mg, 1.6 mmol, 2 eq) in THF (3 mL) was added DIAD (323 g, 1.6 mmol, 2 eq) at room temperate under N₂ atmosphere. The mixture was stirred at 80° C. for 2 h, diluted with ethyl acetate (10 mL) and washed with water (5 mL*3). The organic solvent was removed in vacuum and the residue was purified by silica gel chromatography (petroleum ether:ethyl acetate=1:1) to give methyl 1-(1-(6-(trans-4-tert-butylcyclohexyloxy)naphthalen-2-yl)-2,2,2-trifluoroethyl)piperidine-4-carboxylate (130 mg, yield: 31%) as a yellow solid. ESI-MS (M+1)⁺: 506.1. ¹HNMR (400 MHz, CDCl₃) δ: 7.86~7.80 (m, 3H), 7.46 (d, J=8.8 Hz, 1H), 7.27 (s,1H), 7.16 (d, J=8.8 Hz, 1H), 4.68~4.66 (m, 1H), 4.39~4.36 (m, 1H), 3.56 (s, 3H), 3.32~3.30 (m, 2H), 2.65-2.64 (m, 1H), 2.44-2.43 (m, 1H), 2.30-2.27 (m, 3H), 1.93-1.90 (m, 3H), 1.80-1.79 (m, 2H), 1.44~1.41 (m, 2H), 1.29~1.27 (m, 3H), 1.14~1.13 (m, 1H), 0.90 (s, 9H).

Example 22

1-(1-(6-(trans-4-tert-Butylcyclohexyloxy)naphthalen-2-yl)-2,2,2-trifluoroethyl)piperidine-4-carboxylic acid

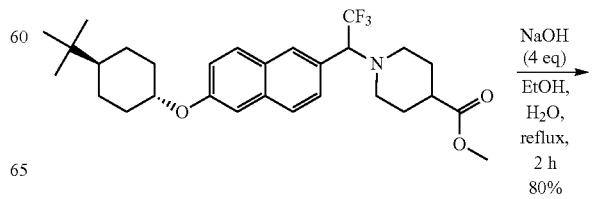

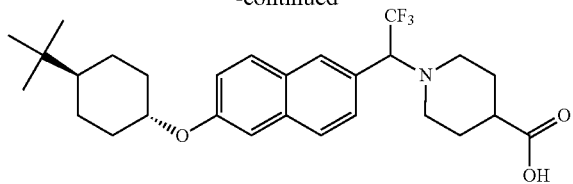

To a solution of methyl 1-(1-(6-(trans-4-tert-butylcyclohexyloxy)naphthalen-2-yl)-2,2,2-trifluoroethyl)piperidine-4-carboxylate (100 mg, 0.2 mmol) in MeOH (5 mL) was added NaOH (32 mg, 0.8 mmol, 4.0 eq) and H$_2$O (0.5 mL). The reaction mixture was stirred at 85° C. for 2 h. Then the reaction was cooled to 0° C., and the pH of the solution was adjusted to 6 with 3 N HCl. The mixture was filtered, and the yellow solid was the desired product 1-(1-(6-(trans-4-tert-butylcyclohexyloxy)naphthalen-2-yl)-2,2,2-trifluoroethyl)piperidine-4-carboxylic acid (78 mg, yield: 80%). ESI-MS (M+1)$^+$: 492.1.

$^1$HNMR (400 MHz, CD$_3$OD) δ: 7.82~7.78 (m, 3H), 7.47 (d, J=8.8 Hz, 1H), 7.27 (s, 1H), 7.16 (dd, J=8.8 Hz, 2.4 Hz, 1H), 4.68~4.67 (m, 1H), 4.38~4.36 (m, 1H), 3.32~3.30 (m, 2H), 2.65-2.64 (m, 1H), 2.44-2.43 (m, 1H), 2.30-2.28 (m, 3H), 1.93-1.90 (m, 3H), 1.80-1.79 (m, 2H), 1.44~1.41 (m, 2H), 1.29~1.26 (m, 3H), 1.13~1.12 (m, 1H), 0.92 (s, 9 H). HPLC: 100.00%.

Into a 25 mL round bottom flask was added ethyl 1-((6-hydroxynaphthalen-2-yl)methyl)piperidine-4-carboxylate (313 mg, 0.1 mmol, 2 eq), 4-isopropylcyclohexanol (284 mg, 0.2 mmol, 2 eq), PPh3 (562 mg, 0.2 mmol, 2 eq) and dry toluene (0.5 mL) under N$_2$. Then DIAD (404 mg, 0.2 mmol, 2 eq) was quickly added in one portion at room temperature. The reaction mixture was stirred at rt for 0.5 h. The solvent was removed under reduced pressure and the residue was purified by silica gel column chromatography (PE:EA=4:1) to give ethyl 1-((6-(4-isopropylcyclohexyloxy)naphthalen-2-yl)methyl)piperidine-4-carboxylate (213 mg, yield: 51%) as slight yellow oil. ESI-MS (M+1)$^+$: 438.1. $^1$H NMR (400 MHz, CDCl$_3$) δ: 7.64-7.57 (m, 3H), 7.36 (d, J=8.4 Hz, 1H), 7.10-7.08 (m, 2H), 4.60-4.58 (m, 1H), 4.05 (q, J=7.2 Hz, 2H), 3.56 (s, 2H), 2.85-2.81 (m, 2H), 2.07-2.04 (m, 1H), 2.01-1.97 (m, 2H), 1.83-1.71 (m, 4H), 1.51-1.40 (m, 6H), 1.24-1.15 (m, 6H), 1.11-1.06 (m, 1H), 0.83 (d, J=6.4Hz, 6H).

Example 24

1-((6-(4-Isopropylcyclohexyloxy)naphthalen-2-yl)methyl)piperidine-4-carboxylic acid

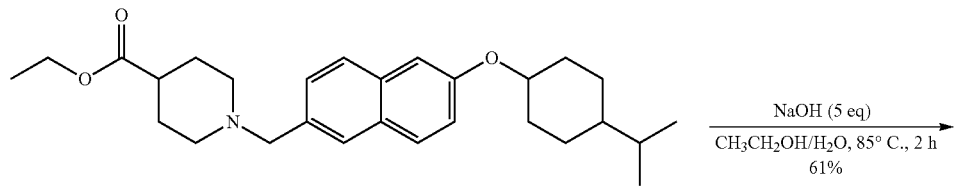

Example 23

Ethyl 1-((6-(4-isopropylcyclohexyloxy)naphthalen-2-yl)methyl)piperidine-4-carboxylate

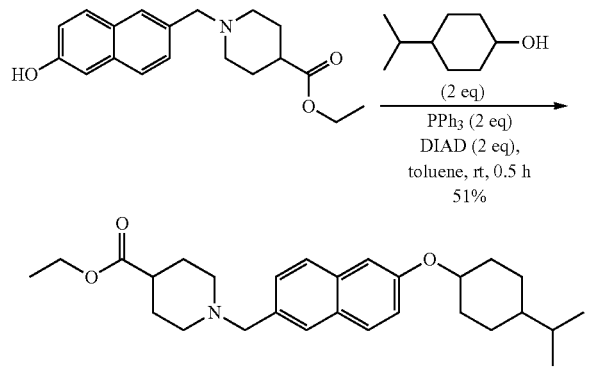

Ethyl 1-((6-(4-isopropylcyclohexyloxy)naphthalen-2-yl)methyl)piperidine-4-carboxylate (120 mg, 0.27 mmol) was dissolved in EtOH (5 mL). NaOH (55 mg, 1.4 mmol, 5 eq) was added in one portion at room temperature. The mixture was stirred at 80° C. for 16 h. Solvent was removed and the residue was dissolved in H$_2$O (3 mL). 1 M aqueous HCl was added to adjust pH=7. The mixture was filtrated to give 1-((6-(4-isopropylcyclohexyloxy)naphthalen-2-yl)methyl)piperidine-4-carboxylic acid as a white solid (85 mg, yield: 61%). ESI-MS (M+1)$^+$: 410.3, HPLC: 100.00%. $^1$H NMR (400 MHz, DMSO-d$_6$) δ: 10.24 (s, 1H), 7.96 (s, 1H), 7.86-7.84 (m, 2H), 7.62-7.60 (m, 1H), 7.39 (s, 1H), 7.24 (d, J=9.2 Hz, 1H), 4.77-4.76 (m, 1H), 4.42-4.36 (m, 2H), 3.40 (s, 2H), 2.95-2.93 (m, 2H), 2.50-2.49 (m, 1H), 2.03-2.00 (m, 4H), 1.85-1.75 (m, 2H), 1.62-1.34 (m, 7H), 1.19-1.12 (m, 1H), 0.88 (d, J=6.8 Hz, 6H).

Example 25

Ethyl 1-((6-(cis-4-tert-butylcyclohexyloxy)naphthalen-2-yl)methyl)piperidine-4-carboxylate

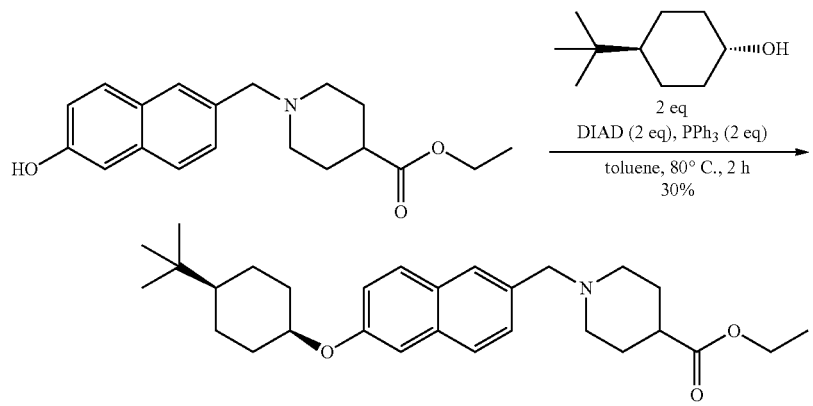

The synthesis was the same as that of ethyl 1-((6-(4-isopropylcyclohexyloxy)naphthalen-2-yl)methyl)piperidine-4-carboxylate. Weight: 120 mg, yellow solid, yield: 30%. ESI-MS (M+1)$^+$: 452.1. $^1$HNMR (400 MHz, CDCl$_3$) δ: 7.75~7.73 (m, 3H), 7.48 (br, 1H), 7.18~7.15 (m, 2H), 4.80~4.76 (m, 1H), 4.40 (s, 2H), 4.05 (q, J=6.8 Hz, 2H), 3.60 (br, 2H), 2.90 (br, 2H), 2.62-2.60 (m, 1H), 2.20-2.16 (m, 4H), 1.80 (br, 2H), 1.63-1.45 (m, 5H), 1.30-1.17 (m, 5H), 0.92 (s, 9H).

Example 26

1-((6-(cis-4-tert-Butylcyclohexyloxy)naphthalen-2-yl)methyl)piperidine-4-carboxylic acid

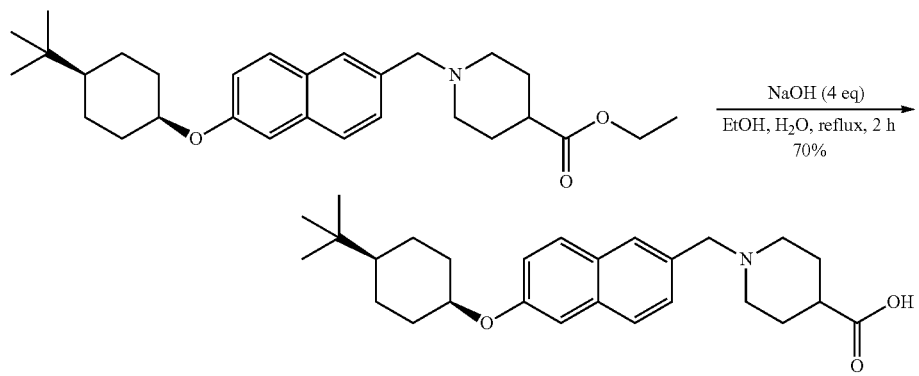

The synthesis was the same as that of 1-((6-(4-isopropylcyclohexyloxy)naphthalen-2-yl)methyl)piperidine-4-carboxylic acid. Weight: 80 mg, yellow solid, yield: 70%. ESI-MS (M+1)$^+$: 424.3. 1HNMR (400 MHz, CD$_3$OD) δ: 7.91 (s, 1H), 7.87~7.83 (m, 2H), 7.48 (dd, J=8.8 Hz, 1.6 Hz, 1H), 7.29 (s, 1H), 7.24 (dd, J=8.8 Hz, 2.0 Hz, 1H), 4.77 (br, 1H), 4.43 (s, 2H), 3.59~3.56 (m, 2H), 3.08-3.07 (m, 2H), 2.62-2.61 (m, 1H), 2.22-2.16 (m, 4H), 1.85-1.77 (m, 2H), 1.63-1.47 (m, 5H), 1.29-1.16 (m, 2H), 0.92 (s, 9H). HPLC: 100.00%.

Example 27

Ethyl 1-((6-(4-(trifluoromethyl)cyclohexyloxy)naphthalen-2-yl)methyl)piperidine-4-carboxylate

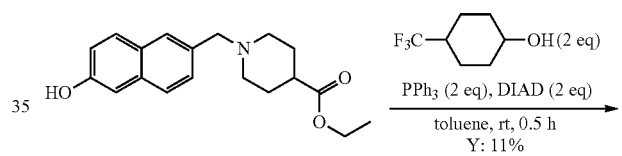

-continued

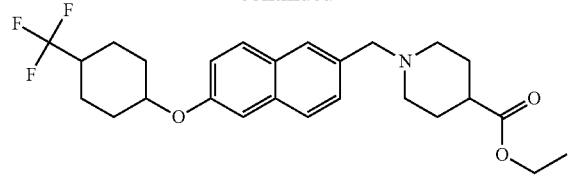

The preparation of ethyl 1-((6-(4-(trifluoromethyl)cyclohexyloxy)naphthalen-2-yl)methyl)piperidine-4-carboxylate was the same as that of ethyl 1-((6-(4-isopropylcyclohexyloxy)naphthalen-2-yl)methyl)piperidine-4-carboxylate. 80 mg, a yellow solid, yield: 11%, ESI-MS (M+H)+: 464.1. ¹H NMR (400 MHz, CDCl₃), δ: 7.66 (m, 3H), 7.59 (d, J=7.6 Hz 1H), 7.19-7.08 (m, 2H), 4.60-4.58 (m, 1H), 4.06 (q, J=7.2 Hz, 2H), 3.54 (s, 2H), 2.86-2.83 (m, 2H), 2.23-2.15 (m, 6H), 1.78-1.70 (m, 8H), 1.34-1.25 (m, 2H), 1.12 (t, J=7.2 Hz, 3H).

Example 28

1-((6-(4-(Trifluoromethyl)cyclohexyloxy)naphthalen-2-yl)methyl)piperidine-4-carboxylic acid

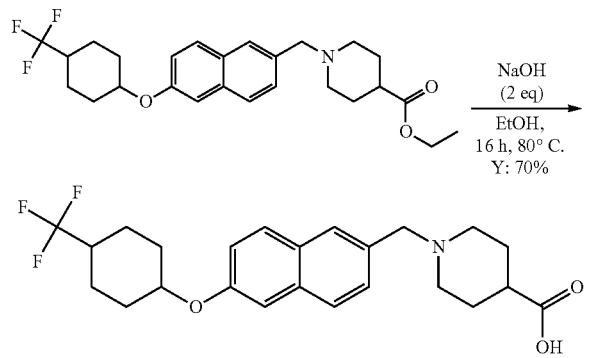

The preparation of 1-((6-(4-(trifluoromethyl)cyclohexyloxy)naphthalen-2-yl)methyl)piperidine-4-carboxylic acid was the same as that of 1-((6-(4-isopropylcyclohexyloxy)naphthalen-2-yl)methyl)piperidine-4-carboxylic acid. 40 mg, a yellow solid, yield: 70%. ESI-MS (M+H)+: 436.1, HPLC: 97.77%.

¹H NMR (400 MHz, CD₃OD) δ: 7.93 (s, 1H), 7.88-7.81 (m, 2H), 7.53 (d, J=8.4 Hz, 1H), 7.34 (d, J=8.4 Hz, 1H), 7.20 (dd, J=8.8, 2.4 Hz, 1H), 4.81-4.80 (m, 0.45H), 4.50-4.46 (m, 0.55H), 4.42 (s, 2H), 3.46-3.45 (m, 2H), 3.15-3.14 (m, 2H), 2.65-2.64 (m, 1H), 2.32-2.03 (m, 6H), 1.77-1.27 (m, 7H).

Example 29

Ethyl 1-((6-(4-ethylcyclohexyloxy)naphthalen-2-yl)methyl)piperidine-4-carboxylate

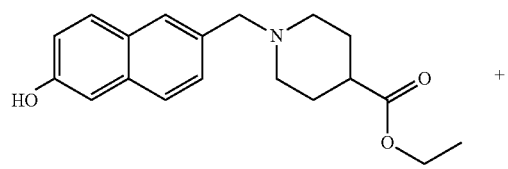 +

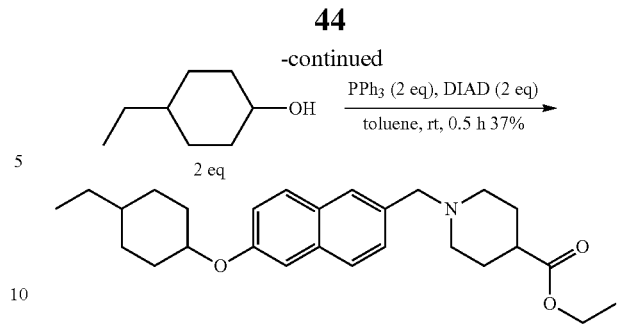

The preparation of ethyl 1-((6-(4-ethylcyclohexyloxy)naphthalen-2-yl)methyl)piperidine-4-carboxylate was the same as that of ethyl 1-((6-(4-isopropylcyclohexyloxy)naphthalen-2-yl)methyl)piperidine-4-carboxylate. Pale yellow solid, 75 mg, yield: 37%, ESI-MS (M+H)+: 424.1. ¹H NMR (400 MHz, CDCl₃), δ: 7.64-7.56 (m, 3H), 7.36 (d, J=8.4 Hz, 1H), 7.09-7.07 (m, 2H), 4.58-4.56 (m, 1H), 4.12 (q, J=6.8 Hz, 2H), 3.53 (s, 2H), 2.83-2.81 (m, 2H), 2.24-1.98 (m, 2H), 1.89-1.69 (m, 6H), 1.56-1.48 (m, 7H), 1.25 (t, J=7.2 Hz, 3H), 1.12-1.10 (m, 2H), 0.86 (t, J=6.8 Hz, 3H).

Example 30

1-((6-(4-Ethylcyclohexyloxy)naphthalen-2-yl)methyl)piperidine-4-carboxylic acid

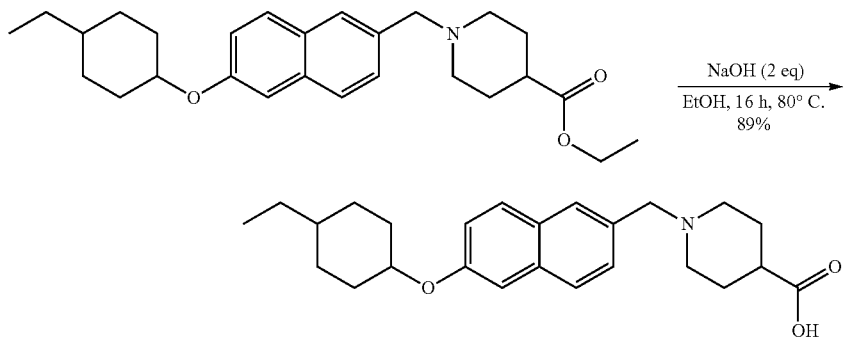

The preparation of 1-((6-(4-ethylcyclohexyloxy)naphthalen-2-yl)methyl)piperidine-4-carboxylic acid was the same as that of 1-((6-(4-isopropylcyclohexyloxy)naphthalen-2-yl)methyl)piperidine-4-carboxylic acid. Yellow oil, 70 mg, yield: 89%.

¹H NMR (400 MHz, CD₃OD) δ: 7.89 (s, 1H), 7.84 (dd, J=8.4, 3.2 Hz, 2H), 7.49 (d, J=8.8 Hz, 1H), 7.29 (d, J=2.0 Hz, 1H), 7.24 (dd, J=8.8, 2.4 Hz 1H), 4.75-4.74 (m, 1H), 4.33 (s, 2H), 3.41-3.32 (m, 2H), 3.03-2.98 (m, 2H), 2.44-2.42 (m, 1H), 2.09-2.06 (m, 4H), 1.91-1.88 (m, 2H), 1.66-1.59 (m, 4H), 1.43-1.41 (m, 2H), 1.34-1.29 (m, 3H), 0.95 (t, J=8.0 Hz, 3H), ESI-MS (M+H)+: 396.1, HPLC: 100.00%.

Example 31

Ethyl 1-((6-(4-butylcyclohexyloxy)naphthalen-2-yl)methyl)piperidine-4-carboxylate

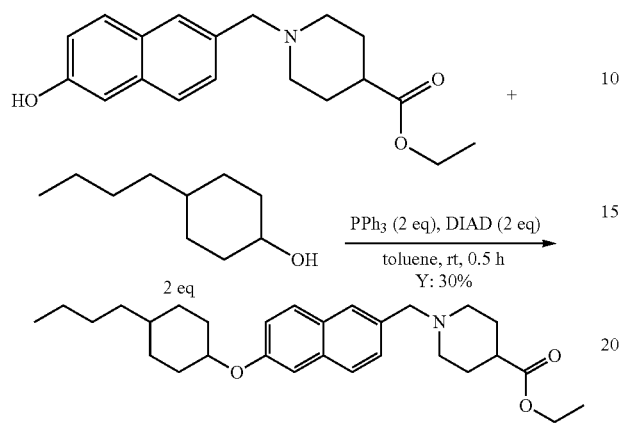

The preparation of ethyl 1-((6-(4-butylcyclohexyloxy)naphthalen-2-yl)methyl)piperidine-4-carboxylate was the same as that of ethyl 1-((6-(4-isopropylcyclohexyloxy)naphthalen-2-yl)methyl)piperidine-4-carboxylate. 170 mg, yellow oil, yield: 30%. ESI-MS (M+H)$^+$: 452.1. $^1$H NMR (400 MHz, CDCl$_3$) (mixture of cis and trans isomers) δ: 7.70-7.62 (m, 3H), 7.42 (d, J=8.8 Hz, 1H), 7.07-7.05 (m, 2H), 4.59-4.56 (m, 0.45H), 4.42-4.34 (m, 0.55H), 4.14 (q, J=6.8 Hz, 2H), 3.52 (s, 2H), 2.80-2.79 (m, 2H), 2.23-1.98 (m, 5H), 1.82-1.80 (m, 5H), 1.78-1.52 (m, 8H), 1.18 (t, J=6.8 Hz, 3H), 1.00 (t, J=7.2 Hz, 3H), 1.12-1.10 (m, 4H).

Example 32

1-((6-(4-Butylcyclohexyloxy)naphthalen-2-yl)methyl)piperidine-4-carboxylic acid

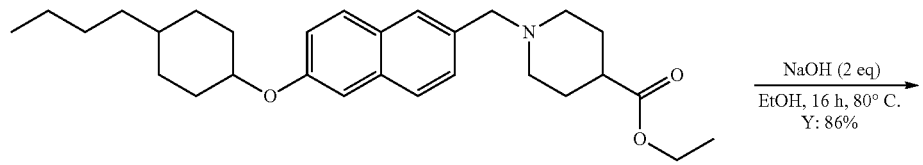

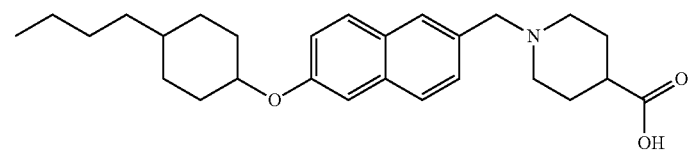

The preparation of 1-((6-(4-butylcyclohexyloxy)naphthalen-2-yl)methyl)piperidine-4-carboxylic acid was the same as that of 1-((6-(4-isopropylcyclohexyloxy)naphthalen-2-yl)methyl)piperidine-4-carboxylic acid. 120 mg, yellow oil, yield: 86%. ESI-MS (M+H)$^+$: 424.1, HPLC: 100.00%. $^1$H NMR (400 MHz, CD$_3$OD) (mixture of cis and trans isomers) δ: 7.89 (s, 1H), 7.85-7.79 (m, 2H), 7.49 (dd, J=8.4, 1.2 Hz, 1H), 7.28 (s, 1H), 7.19 (dd, J=8.8, 2.4 Hz, 1H), 4.81-4.80 (m, 0.45H), 4.42-4.34 (m, 0.55H), 4.33 (s, 2H), 3.42-3.39 (m, 2H), 3.02-3.01 (m, 2H), 2.48-2.47 (m, 1H), 2.20-1.90 (m, 4H), 1.89-1.80 (m, 3H), 1.66-1.58 (m, 4H), 1.34-1.16 (m, 8H), 0.92 (t, J=5.6 Hz, 3H).

Example 33

Ethyl 1-((6-(spiro[4.5]decan-8-yloxy)naphthalen-2-yl)methyl)piperidine-4-carboxylate

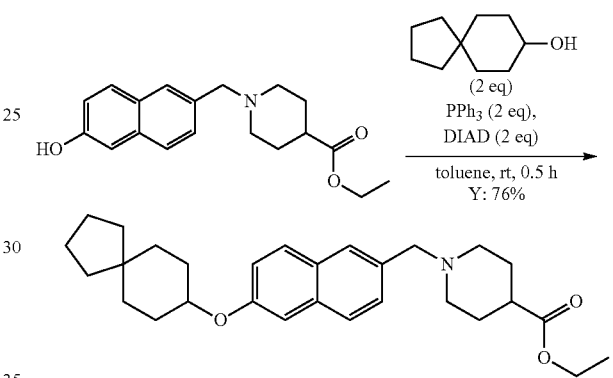

The preparation of ethyl 1-((6-(spiro[4.5]decan-8-yloxy)naphthalen-2-yl)methyl)piperidine-4-carboxylate was the same as that of ethyl 1-((6-(4-isopropylcyclohexyloxy)naphthalen-2-yl)methyl)piperidine-4-carboxylate. 1.01 g, a colorless oil, yield: 76%, ESI-MS (M+H)$^+$: 450.1.

Example 34

1-((6-(Spiro[4.5]decan-8-yloxy)naphthalen-2-yl)methyl)piperidine-4-carboxylic acid

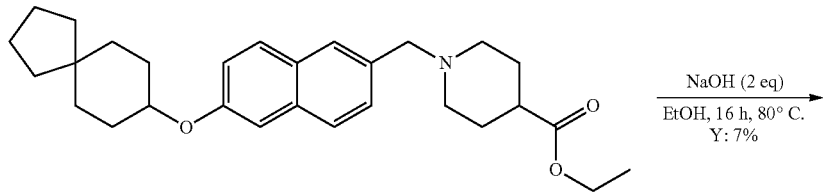

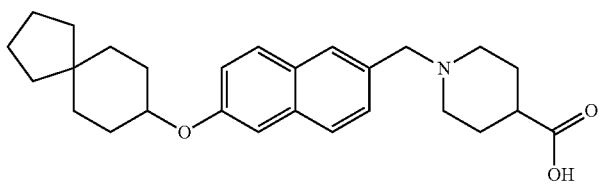

The preparation of 1-((6-(spiro[4.5]decan-8-yloxy)naphthalen-2-yl)methyl)piperidine-4-carboxylic acid was the same as that of 1-((6-(4-isopropylcyclohexyloxy)naphthalen-2-yl)methyl)piperidine-4-carboxylic acid. 62 mg, a yellow solid, yield: 7%, ESI-MS (M+H)$^+$: 422.0, HPLC: 95%. $^1$H NMR (400 MHz, CD$_3$OD)☐☐ δ:☐ 1.37-2.08 (m, 18 H), 2.25 (d, J=15.94 Hz, 2 H), 2.55-2.72 (m, 1 H), 3.09 (td, J=12.74, 1.76 Hz, 2 H), 3.55-3.67 (m, 2 H), 4.44 (s, 2 H), 4.54 (dquin, J=8.09, 3.86, 3.86, 3.86, 3.86 Hz, 1 H), 7.23 (dd, J=8.91, 2.38 Hz, 1 H), 7.31 (s, 1 H), 7.50 (dd, J=8.47, 1.76 Hz, 1 H), 7.84 (d, J=9.04 Hz, 1 H), 7.88 (d, J=8.47 Hz, 1 H), 7.93 (s, 1 H).

Example 35

Ethyl 1-((6-(cis-4-ethylcyclohexyloxy)naphthalen-2-yl)methyl)piperidine-4-carboxylate To a solution of ethyl 1-((6-hydroxynaphthalen-2-yl)methyl)piperidine-4-carboxylate (2.43 g, 8 mmol, 1.0 eq) in the co-solvent t-butanol/2-butanone (40 mL/20 mL) was added cesium carbonate (5.0 g, 16 mmol, 2.0 eq). The mixture was stirred at 80° C. for 10 min and then trans-4-ethylcyclohexyl methanesulfonate (3.2 g, 16 mmol, 2.0 eq) was introduced. The suspension was stirred at 80° C. under N$_2$ for 15 h. Then the reaction mixture was concentrated and the residue was purified by silica gel column chromatography (EtOAc/PE=1:5) to give ethyl 1-((6-(cis-4-ethylcyclohexyloxy)naphthalen-2-yl)methyl)piperidine-4-carboxylate as a slight yellow solid (1.6 g, yield: 46%). ESI-MS (M+H)$^+$: 424.3. $^1$H NMR (400 MHz, CD$_3$OD)δ: 7.63-7.56 (m, 3H), 7.30 (dd, J=8.4, 1.6 Hz, 1H), 7.10 (d, J=2.4 Hz, 1H), 7.03 (dd, J=8.8, 2.4 Hz, 1H), 4.68-4.66 (m, 1 H), 4.01 (q, J=7.2 Hz, 2H), 3.66 (s, 2H), 2.85-2.80 (m, 2H), 2.25-2.22 (m, 1H), 2.11-2.08 (m, 2H), 1.96-1.92 (m, 2H), 1.81-1.77 (m, 2H), 1.65-1.45 (m, 6H), 1.33-1.30 (m, 2H), 1.22-1.12 (m, 3H), 1.13 (t, J=7.2 Hz, 3H), 0.82 (t, J=7.2 Hz, 3H).

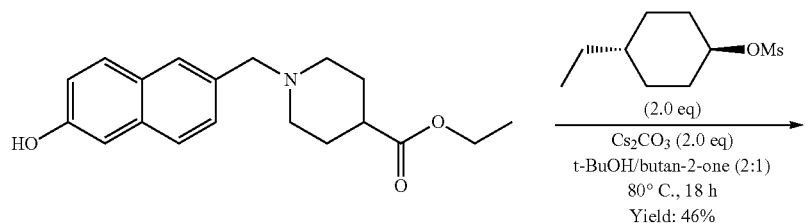

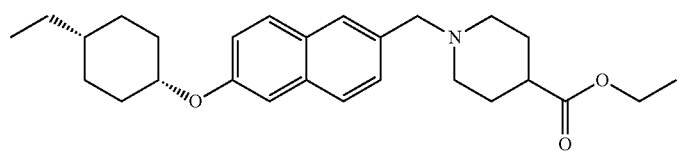

Example 36

1-((6-(cis-4-Ethylcyclohexyloxy)naphthalen-2-yl)methyl)piperidine-4-carboxylic acid

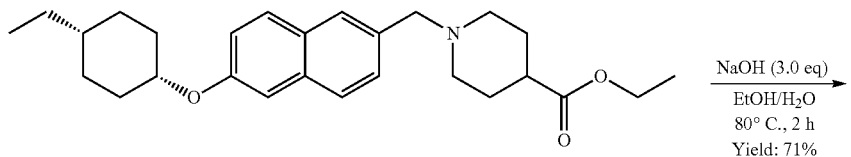

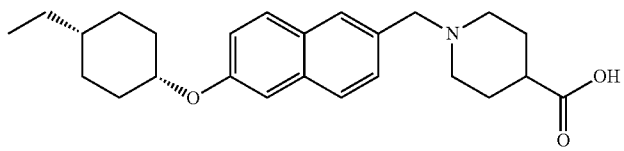

A mixture of ethyl 1-((6-(cis-4-ethylcyclohexyloxy)naphthalen-2-yl)methyl)piperidine-4-carboxylate (1.6 g, 0.004 mol, 1.0 eq) and NaOH (0.48 g, 0.012 mol, 3.0 eq) in ethanol (10 mL) and water (2 mL) was refluxed for 2 h. After the solvent was removed in vacuo, the residue was dissolved in water (20 mL) and acidified with 1 N HCl to pH=7. The mixture was extracted with dichloromethane (50 mL*3) and the combined organic layers were washed with brine (30 mL), dried over sodium sulfate, concentrated and recrystallized in ethyl acetate to give 1-((6-(cis-4-ethylcyclohexyloxy)naphthalen-2-yl)methyl)piperidine-4-carboxylic acid (1.1 g, yield: 71%) as a white solid. ESI-MS (M+H)+: 396.3. HPLC: 100%. 1H NMR (400 MHz, DMSO-d6) δ: 7.77 (d, J=9.2 Hz, 1H), 7.72 (d, J=8.4 Hz, 1H) 7.63 (s, 1H), 7.39 (dd, J=8.4, 1.2 Hz, 1H), 7.29 (d, J=2.0 Hz, 1H), 7.15 (dd, J=8.8, 2.4 Hz, 1H), 4.71-4.69 (m, 1H), 3.54 (s, 2H), 2.78-2.74 (m, 2H), 2.16-2.15 (m, 1H), 2.01-1.93 (m, 4H), 1.77-1.75 (m, 2H), 1.63-1.50 (m, 6H), 1.34-1.24 (m, 5H), 0.87 (t, J=7.2 Hz, 3H).

Example 37

Ethyl 1-((6-(trans-4-ethylcyclohexyloxy)naphthalen-2-yl)methyl)piperidine-4-carboxylate The synthesis of ethyl 1-((6-(trans-4-ethylcyclohexyloxy)naphthalen-2-yl)methyl)piperidine-4-carboxylate was similar to that of ethyl 1-((6-(cis-4-ethylcyclohexyloxy)naphthalen-2-yl)methyl)piperidine-4-carboxylate.

Ethyl 1-((6-(trans-4-ethylcyclohexyloxy)naphthalen-2-yl)methyl)piperidine-4-carboxylate was obtained as a slight yellow solid with yield: 55%. ESI-MS (M+H)+: 424.3. 1H NMR (400 MHz, CD3OD) δ: 7.71 (dd, J=8.8, 3.2 Hz, 2H), 7.66 (s, 1H), 7.42 (dd, J=8.4, 1.6 Hz, 1H), 7.21 (d, J=2.0 Hz, 1H), 7.10 (dd, J=8.8, 2.4 Hz, 1H), 4.42-4.20 (m, 1H), 4.11 (q, J=7.2 Hz, 2H), 3.63 (s, 2H), 2.90-2.87 (m, 2H), 2.38-2.35 (m, 1H), 2.24-2.02 (m, 4H), 1.88-1.85 (m, 4H), 1.76-1.72 (m, 2H), 1.34-1.29 (m, 4H), 1.27-1.11 (m, 6H), 0.94 (t, J=7.2 Hz, 3H).

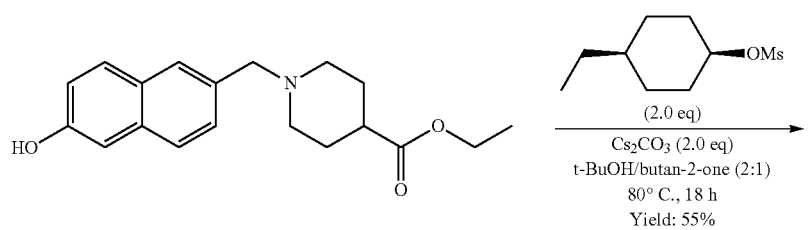

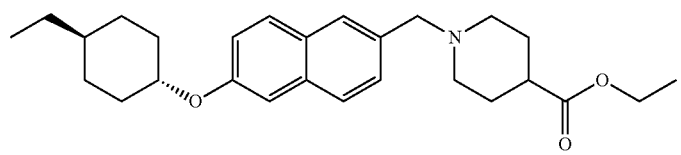

Example 38

1-((6-(trans-4-Ethylcyclohexyloxy)naphthalen-2-yl)methyl)piperidine-4-carboxylic acid

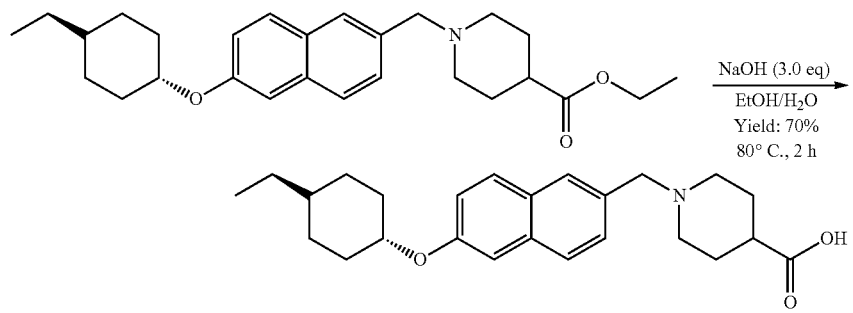

The synthesis of 1-((6-(trans-4-ethylcyclohexyloxy)naphthalen-2-yl)methyl)piperidine-4-carboxylic acid was similar to that of 1-((6-(cis-4-ethylcyclohexyloxy)naphthalen-2-yl)methyl)piperidine-4-carboxylic acid.

1-((6-(trans-4-ethylcyclohexyloxy)naphthalen-2-yl)methyl)piperidine-4-carboxylic acid was obtained as a white solid with yield: 70%. ESI-MS (M+H)$^+$: 396.3. HPLC: 100%. $^1$H NMR (400 MHz, DMSO-d6) δ: 7.78 (d, J=9.2 Hz, 1H), 7.75 (d, J=8.4 Hz, 1H) 7.68 (s, 1H), 7.40 (d, J=8.4 Hz, 1H), 7.33 (d, J=2.4 Hz, 1H), 7.13 (dd, J=8.8, 2.4 Hz, 1H), 4.42-4.40 (m, 1H), 3.57 (s, 2H), 2.78-2.75 (m, 2H), 2.21-2.15 (m, 3H), 2.03-2.02 (m, 2H), 1.84-1.82 (m, 4H), 1.58-1.56 (m, 2H), 1.40-1.37 (m, 2H), 1.29-1.25 (m, 3H), 1.17-1.10 (m, 2H), 0.91 (t, J=7.2 Hz, 3H).

Example 39

6-(trans-4-tert-Butylcyclohexyloxy)-2-methylquinoline

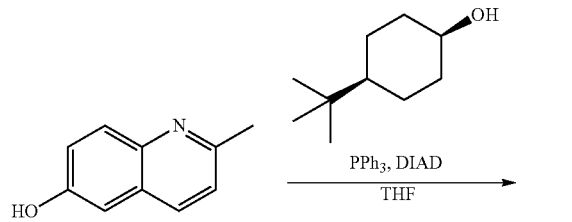

To a solution of 2-Methyl-quinolin-6-ol (4.13 g, 0.0259 mol), cis 4-tert-Butyl-cyclohexanol (4.86 g, 0.0311 mol) and triphenylphosphine (9.53 g, 0.0363 mol) in tetrahydrofuran (100 mL, 1 mol), cooled in an ice bath, was added diisopropyl azodicarboxylate (7.61 mL, 0.0363 mol) in Tetrahydrofuran (10 mL, 0.1 mol). The reaction mixture was stirred for 72 h at room temperature. The solvent was removed under reduced pressure and the residue was taken up in methylene chloride, adsorbed onto silica gel and purified by flash chromatography (0-30% ethyl acetate in hexanes) to give the title compound in 56% yield. ESI-MS (M+H+): 298.3.

Example 40

6-(trans-4-tert-Butylcyclohexyloxy)quinoline-2-carbaldehyde

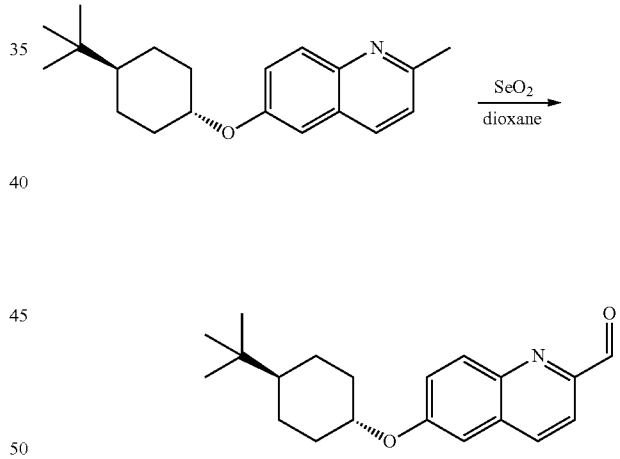

Di-tert-butyl peroxide (1.93 mL, 10.5 mmol) was added to a suspension of selenium dioxide (2.68 g, 24.1 mmol) in 1,4-dioxane (24.00 mL, 307.5 mmol). The mixture was stirred for 30 minutes, then 6-(trans-4-tert-Butyl-cyclohexyloxy)-2-methyl-quinoline (3.12 g, 10.5 mmol) was added as a solution in 1,4-Dioxane and the mixture was heated overnight at 50° C. The reaction mixture was then cooled to room temperature, diluted in chloroform and filtered through a pad of celite. The filtrate was washed with water. The layers were separated and the combined organic phase was dried over MgSO$_4$, filtered, concentrated under reduced pressure, adsorbed onto silica gel and purified by flash chromatography (0-30% EtOAc in hexanes) to give the title compound as a pale yellow solid in 20% yield. ESI-MS (M+H+): 312.27.

Example 41

Methyl 1-((6-(trans-4-tert-butylcyclohexyloxy)quinolin-2-yl)methyl)piperidine-4-carboxylate

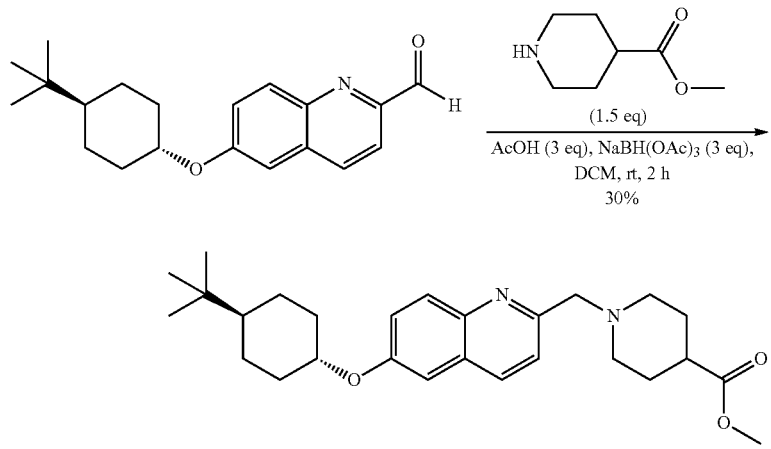

A solution of 6-(trans-4-tert-butylcyclohexyloxy)quinoline-2-carbaldehyde (490 mg, 1.58 mmol), AcOH (283 mg, 4.7 mmol, 3.0 eq) and methyl isonipecotic acid ester (389 mg, 2.36 mmol, 1.5 eq) in DCM (5 mL) was stirred at room temperature for 10 min. Then NaBH(OAc)$_3$ (100 mg, 4.7 mmol, 3.0 eq) was added. The reaction mixture was stirred at room temperature for 1 h. The reaction mixture was quenched with water (5 mL). Then the mixture was extracted with DCM (3×10 mL). The combined organic layer was washed with brine (10 mL), dried over Na$_2$SO$_4$ and concentrated to give crude product. The crude product was purified by silica gel column chromatography (DCM: MeOH=40:1) to give methyl 1-((6-(trans-4-tert-butylcyclohexyloxy)quinolin-2-yl)methyl)piperidine-4-carboxylate (480 mg, yield: 30%) as a yellow oil. ESI-MS (M+1)$^+$: 439.2. $^1$HNMR (400 MHz, CDCl$_3$) δ: 7.98 (d, 1H), 7.94 (d, 1H), 7.56 (d, 1H), 7.32 (d, 1H), 7.08 (s, 1H), 4.30~4.20 (m, 1H), 3.77 (s, 2H), 3.67 (s, 3H), 2.91~2.88 (m, 2H), 2.33~2.14 (m, 5H), 1.91~1.79 (m, 5H), 1.47~1.43 (m, 2H), 1.98~1.10 (m, 4H), 0.89 (s, 9H).

Example 42

1((6-(trans-4-tert-Butylcyclohexyloxy)quinolin-2-yl)methyl)piperidine-4-carboxylic acid

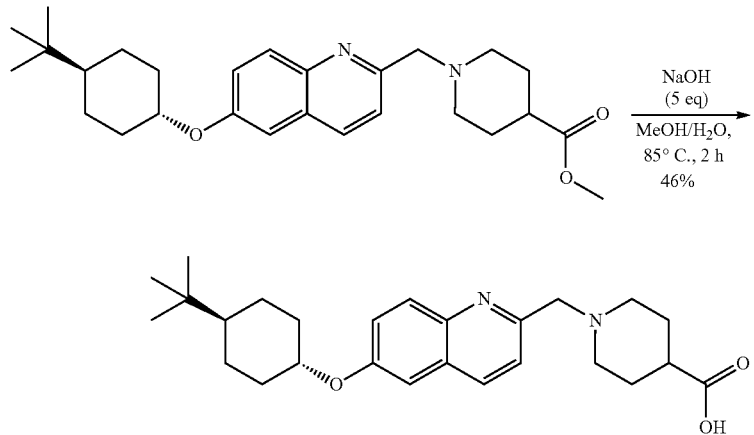

To a solution of methyl 1-((6-(trans-4-tert-butylcyclohexyloxy)quinolin-2-yl)methyl)piperidine-4-carboxylate (150 mg, 0.34 mmol) in MeOH (5 mL) was added NaOH (68 mg, 1.7 mmol, 5.0 eq) and H$_2$O (0.5 mL). The reaction mixture was stirred at 85° C. for 2 h. Then the reaction was cooled to 0° C., the pH of the solution was adjusted to 6 with 3 N HCl. The mixture was filtrated, and the yellow solid was the desired product 1-((6-(trans-4-tert-butylcyclohexyloxy)quinolin-2-yl)methyl)piperidine-4-carboxylic acid (90 mg, yield: 46%). ESI-MS (M+1)$^+$: 425.3, HPLC: 100%. $^1$H NMR (400 MHz, DMSO-d$_6$) δ: 8.32 (d, 1H), 7.93 (d, 1H), 7.70 (d, 1H), 7.48 (s, 1H), 7.41 (d, 1H), 4.53 (br, 1H), 4.44~4.40 (m, 1H), 3.33 (br, 3H), 3.14 (br, 2H), 2.49 (br, 1H), 2.22~2.20 (m, 2H), 2.04~4.80 (m, 6H), 1.37~1.32 (m, 2H), 1.25~1.20 (m, 2H), 1.10~1.08 (m, 1H), 0.87 (s, 9H).

Example 45

Methyl 1-(6-acetoxy-2-naphthoyl)piperidine-4-carboxylate

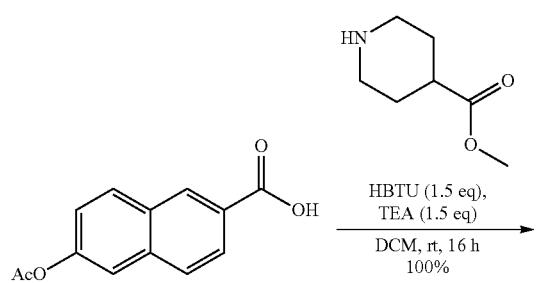

A mixture of 6-acetoxy-2-naphthoic acid (1 g, 4.34 mmol, 1.0 eq), methyl piperidine-4-carboxylate (684 mg, 4.78 mmol, 1.1 eq), HBTU (2.47 g, 6.51 mmol, 1.5 eq) and TEA (658 mg, 6.51 mmol, 1.5 eq) in DCM (20 mL) was stirred at room temperature for 16 h. The reaction mixture was diluted with ethyl acetate (200 mL). The combined organic layers were washed with water (100 mL*2) and brine (100 mL), dried over Na$_2$SO$_4$ and concentrated to give methyl 1-(6-acetoxy-2-naphthoyl)piperidine-4-carboxylate as a yellow oil (2 g, yield: 100%). ESI-MS: 356.0 (M+H)$^+$. $^1$HNMR (400 MHz, DMSO-d$_6$) δ: 8.05 (d, 1H), 8.01-7.96 (m, 2H), 7.73 (s, 1H), 7.53-7.51 (m, 1H), 7.40-7.37 (m, 1H), 3.63 (s, 3H), 3.18-2.95 (m, 2H), 2.71-2.65 (m, 3H), 2.34 (s, 3H), 1.97-1.76 (m, 2H), 1.61-1.50 (m, 2H).

Example 46

Methyl 1-(6-hydroxy-2-naphthoyl)piperidine-4-carboxylate

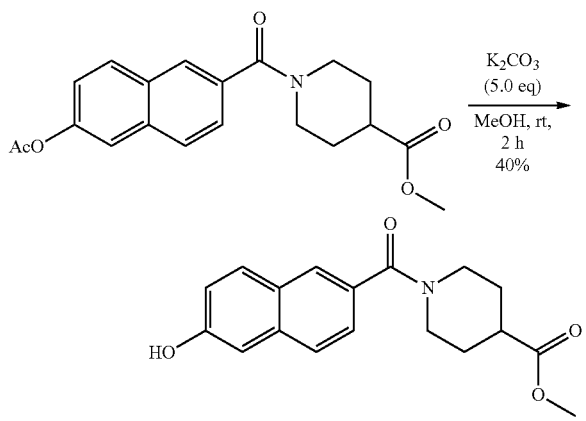

A mixture of methyl 1-(6-acetoxy-2-naphthoyl)piperidine-4-carboxylate (1 g, 2.814 mmol, 1.0 eq), K$_2$CO$_3$ (1.94 g, 14.07 mmol, 5.0 eq) in MeOH (20 mL) was stirred at room temperature for 2 h. The reaction was filtered. The filtrate was concentrated and the residue was purified by prep-HPLC (MeOH: 0.05% TFA/H$_2$O=0-95%) to afford methyl 1-(6-hydroxy-2-naphthoyl)piperidine-4-carboxylate as a white solid (350 mg, yield: 40%). ESI-MS: 314.0 (M+H)$^+$. $^1$HNMR (400 MHz, DMSO-d$_6$) δ: 9.94 (s, 1H), 7.86-7.84 (m, 2H), 7.73 (d, 1H), 7.38 (d, 1H), 7.16-7.12 (m, 2H), 3.63 (s, 3H), 3.16-2.97 (m, 2H), 2.69-2.63 (m, 3H), 1.96-1.79 (m, 2H), 1.61-1.51 (m, 2H).

Example 47

Methyl 1-(6-(trans-4-tert-butylcyclohexyloxy)-2-naphthoyl)piperidine-4-carboxylate

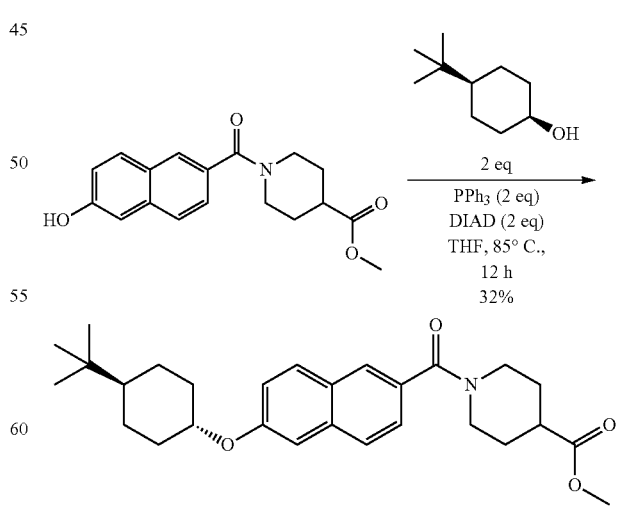

To a stirring mixture of methyl 1-(6-hydroxy-2-naphthoyl)piperidine-4-carboxylate (500 mg, 1.59 mmol), cis-4-(t-butyl)cyclohexanol (487 mg, 3.18 mmol, 2 equiv) and PPh₃ (833 mg, 3.18 mmol, 2 eq) in THF (5 mL) was added DIAD (642 g, 3.18 mmol, 2 eq) at room temperate under N₂ atmosphere, then the mixture was stirred at 80° C. for 12 h. The reaction mixture was diluted with ethyl acetate (20 mL) and washed with water (5 mL*3). The organic solvent was removed in vacuum and the residue was purified by silica gel chromatography (petroleum ether: ethyl acetate=1:1) to give methyl 1-(6-(trans-4-tert-butylcyclohexyloxy)-2-naphthoyl)piperidine-4-carboxylate (230 mg, yield: 32%) as a yellow solid. ESI-MS (M+1)⁺: 453.2. ¹HNMR (400 MHz, CDCl₃) δ: 7.76-7.70 (m, 3H), 7.43 (d, 1H), 7.18 (d, 1H), 7.16 (s, 1H), 4.32-4.26 (m, 1H), 3.71 (s, 3H), 3.08-3.06 (m, 2H), 2.60-2.58 (m, 1H), 2.28-2.26 (m, 2H), 1.91-1.88 (m, 4H), 1.67-1.65 (m, 4H), 1.29-1.26 (m, 2H), 1.12-1.11 (m, 3H), 0.88 (s, 9H).

Example 48

1-(6-(trans-4-tert-Butylcyclohexyloxy)-2-naphthoyl)piperidine-4-carboxylic acid

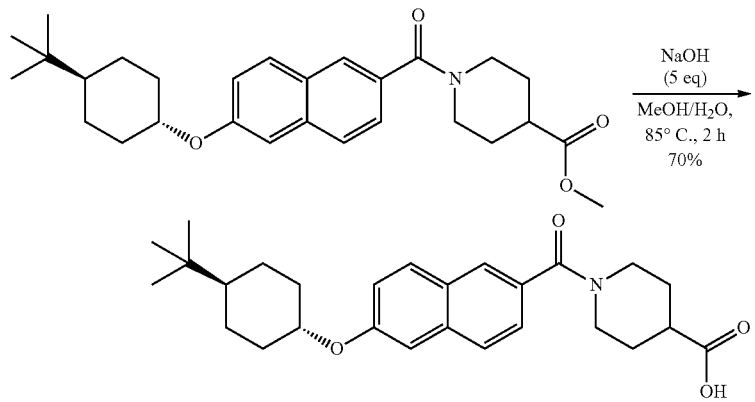

To a solution of methyl 1-(6-(trans-4-tert-butylcyclohexyloxy)-2-naphthoyl)piperidine-4-carboxylate (150 mg, 0.33 mmol) in MeOH (5 mL) was added NaOH (68 mg, 1.7 mmol, 5.0 eq) and H₂O (0.5 mL). The reaction mixture was stirred at 85° C. for 2 h. After the reaction was cooled to 0° C., the pH of the solution was adjusted to 6 with 3 N HCl. The mixture was filtered and the yellow solid was the desired product 1-(6-(trans-4-tert-butylcyclohexyloxy)-2-naphthoyl)piperidine-4-carboxylic acid (90 mg, yield: 70%). ESI-MS (M+1)⁺: 438.3. ¹HNMR (400 MHz, CD₃OD) δ: 7.83~7.81 (m, 3H), 7.41 (d, 1H), 7.28 (s, 1H), 7.16 (d, 1H), 4.44~4.37 (m, 1H), 3.30 (br, 2H), 2.65~2.60 (m, 1H), 2.29~2.27 (m, 2H), 1.93~1.90 (m, 4H), 1.44~1.41 (m, 3H), 1.32-4.31 (m, 2H), 1.28~1.25 (m, 3H), 1.15~1.12 (m, 1H), 0.92 (s, 9H). HPLC: 98.45%

Example 49

1-tert-Butyl-4-methylenecyclohexane

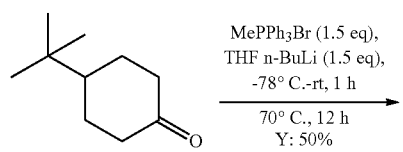

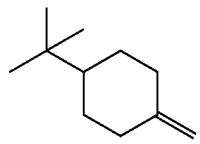

To a solution of methyltriphenylphosphonium bromide (5.36 g, 15 mmol, 1.5 eq) in dried THF (40 mL) was added n-BuLi (2.5 M) (6 mL, 15 mmol, 1.5 eq) at −78° C. The mixture was stirred at room temperature for 1 h. The solution of 4-tert-butylcyclohexanone (1.54 g, 10 mmol) in THF (10 mL) was added to the reaction mixture at −78° C. The mixture was stirred at 70° C. for 12 h. The solvent was removed and the residue was suspended in hexane. The mixture was filtered, and the filtrate was concentrated to give 1-tert-butyl-4-methylenecyclohexane as yellow oil (0.80 g, yield: 50%). ¹HNMR (400 MHz, CDCl₃) δ: 4.58 (s, 2H), 2.34-2.31 (m, 2H), 2.01-1.95 (m, 2H), 1.88-1.84 (m, 2H), 1.14-1.06 (m, 3H), 0.86 (s, 9H).

Example 50

Ethyl 1-((6-(trifluoromethylsulfonyloxy)naphthalen-2-yl)methyl)piperidine-4-carboxylate

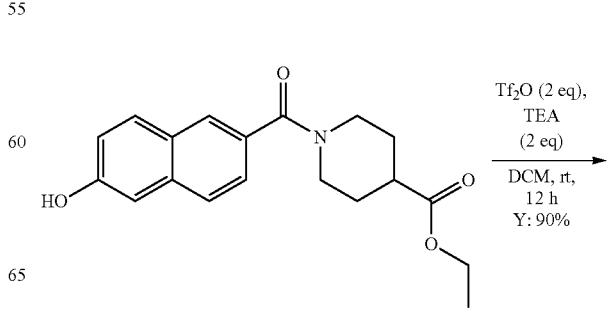

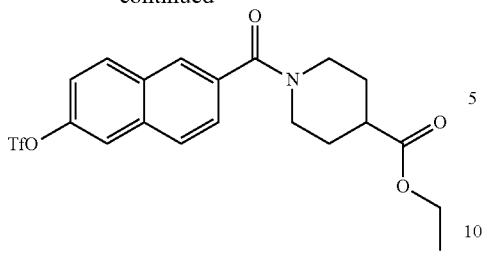

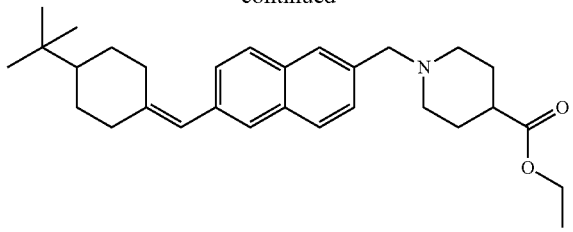

To a solution ethyl 1-((6-hydroxynaphthalen-2-yl)methyl)piperidine-4-carboxylate (1 g, 3.19 mmol) and TEA (0.64 g, 6.38 mmol, 2 eq) in DCM (20 mL) was added Tf$_2$O (1.8 g, 6.38 mmol, 2 eq) dropwise at 0° C. The mixture was stirred at room temperature for 12 h. The reaction was quenched with water at 0° C., washed with sat.NaHCO$_3$ (10 mL) and brine (5 mL*3). The organic layer was dried over Na$_2$SO$_4$ and concentrated to afford ethyl 1-((6-(trifluoromethylsulfonyloxy)naphthalen-2-yl)methyl)piperidine-4-carboxylate as a brown solid (350 mg, yield: 90%). ESI-MS: 446.1 (M+H)$^+$. $^1$HNMR (400 MHz, CDCl$_3$) δ: 7.88 (d, J=9.2 Hz, 1H), 7.84-7.82 (m, 2H), 7.79 (s, 1H), 7.60 (d, J=7.6 Hz, 1H), 7.35 (d, J=9.2 Hz, 1H), 4.13 (q, J=7.6 Hz, 2H), 3.66 (s, 2H), 2.89-2.86 (m, 2H), 2.32-2.28 (m, 1H), 2.11-2.07 (m, 2H), 1.88-1.78 (m, 4H), 1.26 (t, J=7.6 Hz, 3H).

Example 51

Ethyl 1-((6-((4-tert-butylcyclohexylidene)methyl)naphthalen-2-yl)methyl)piperidine-4-carboxylate

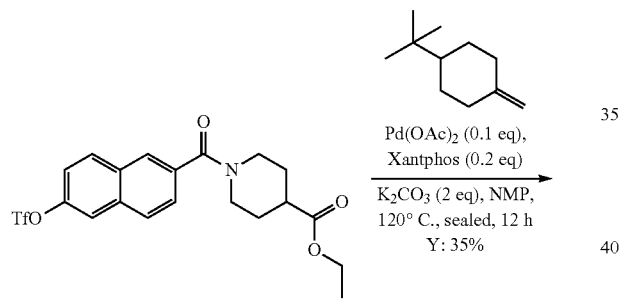

Into a sealed tube were added ethyl 1-((6-(trifluoromethylsulfonyloxy)naphthalen-2-yl)methyl)pipefidine-4-carboxylate (500 mg, 1.12 mmol), 1-tert-butyl-4-methylenecyclohexane (340 mg, 2.24 mmol, 2 eq), K$_2$CO$_3$ (309 mg, 2.24 mmol, 2 eq), Xantphos (130 mg, 0.22 mmol, 0.2 eq), Pd(OAc)$_2$ (25 mg, 0.11 mmol, 0.1 eq) and NMP (2 mL). The mixture was flushed with N$_2$ for 5 min. Then the reaction was stirred at 120° C. for 12 h. The reaction mixture was diluted with ethyl acetate (20 mL) and washed with water (5 mL*3). The organic solvent was removed in vacuum and the residue was purified by silica gel chromatography (petroleum ether: ethyl acetate=2:1) to give ethyl 1-((6-((4-tert-butylcyclohexylidene)methyl)naphthalen-2-yl)methyl)piperidine-4-carboxylate (180 mg, yield: 35%) as a yellow solid. ESI-MS (M+1)$^+$: 448.3. $^1$HNMR (400 MHz, CDCl$_3$) δ: 7.76-7.73 (m, 2H), 7.68 (s, 1H), 7.61 (s, 1H), 7.46 (d, J=8.0 Hz, 1H), 7.34 (d, J=8.8 Hz, 1H), 6.34 (s, 1H), 4.13 (q, J=8.8 Hz, 2H), 3.64 (s, 2H), 2.92-2.89 (m, 2H), 2.30-2.25 (m, 2H), 2.08-2.05 (m, 2H), 1.94-1.77 (m, 8H), 1.60 (br, 2H), 1.26-1.23 (m, 5H), 0.87 (s, 9H).

Example 52

1-((6-((4-tert-Butylcyclohexylidene)methyl)naphthalen-2-yl)methyl)piperidine-4-carboxylic acid

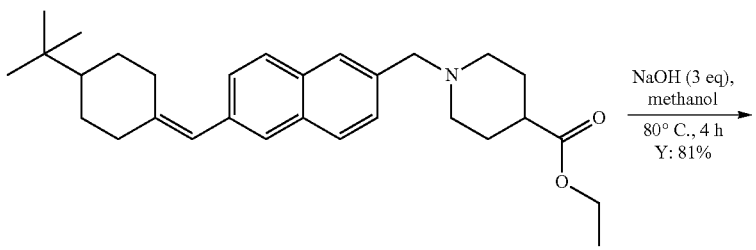

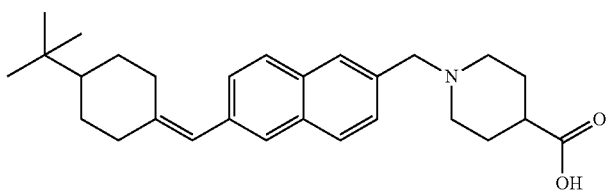

To a solution of ethyl 1-((6-((4-tert-butylcyclohexylidene)methyl)naphthalen-2-yl)methyl)piperidine-4-carboxylate (50 mg, 0.11 mmol) in MeOH (3 mL) was added NaOH (22 mg, 0.55 mmol, 5.0 eq) and H₂O (0.5 mL). The reaction mixture was stirred at 80° C. for 4 h. The pH of the solution was adjusted to 6 with 3 N HCl. The mixture was filtered and the yellow solid was the desired product 1-((6-((4-tert-butylcyclohexylidene)naphthalen-2-yl)methyl)piperidine-4-carboxylic acid (35 mg, yield: 81%). ESI-MS (M+1)⁺: 420.1. ¹HNMR (400 MHz, CD₃OD) δ: 7.86 (s, 1H), 7.83~7.80 (m, 1H), 7.77-7.74 (m, 1H), 7.60 (br, 1H), 7.43 (d, J=8.4 Hz, 1H), 7.35~7.32 (m, 1H), 6.30 (s, 1H), 4.29 (s, 2H), 3.33 (br, 2H), 2.97-2.94 (m, 3H), 2.42-2.38 (m, 2H), 2.20-2.03 (m, 1H), 2.03-2.00 (m, 2H), 1.89-1.80 (m, 5H), 1.22-1.12 (m, 3H), 0.80 (s, 9H). HPLC: 100%.

Example 53

6-Bromo-2-(4-tert-butyl-cyclohexyloxy)-quinoline

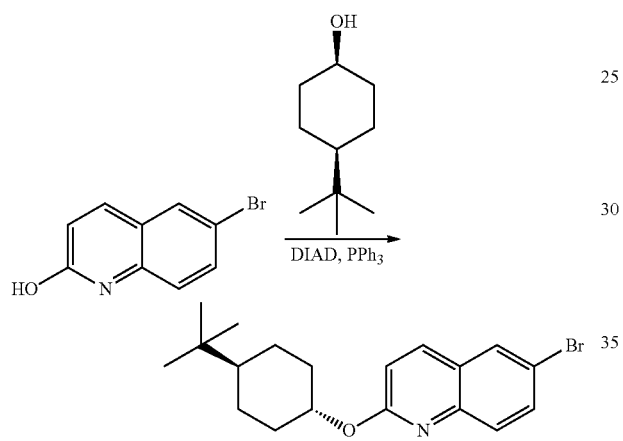

Synthesized as per 2-bromo-6-(trans-4-tert-butylcyclohexyloxy)naphthalene using 6-Bromo-quinolin-2-ol as starting material. ESI-MS (M+H+): 362.1/364.10).

Example 54

2-(trans-4-tert-Butyl-cyclohexyloxy)-quinoline-6-carbaldehyde

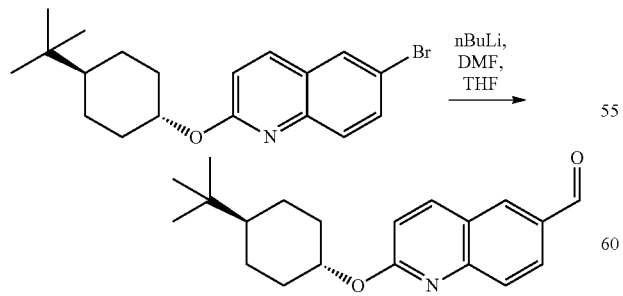

To 6-Bromo-2-(trans-4-tert-butyl-cyclohexyloxy)-quinoline (1.0933 g, 3.0176 mmol) in Tetrahydrofuran (24 mL) was added 1.6 M of n-Butyllithium in hexane (5.6 mL, 9.0 mmol) at −78° C. and the reaction was stirred for 15 min. N,N-Dimethylformamide (1.2 mL) was added and the reaction was stirred for 30 minutes. 1 M HCl was added and the reaction allowed to warm to RT. Saturated sodium bicarbonate solution was added and the mixture extracted with ethyl acetate. The organic layer was washed with saturated sodium chloride, dried with sodium sulfate, filtered and evaporated. The residue was purified by silica gel chromatography using hexanes/ethyl acetate (0-50%) as eluent to give product in 603 mg yield (64%). ESI-MS(M+H+): 312.20.

Example 55

1-((2-(trans-4-tert-Butylcyclohexyloxy)quinolin-6-yl)methyl)piperidine-4-carboxylic acid

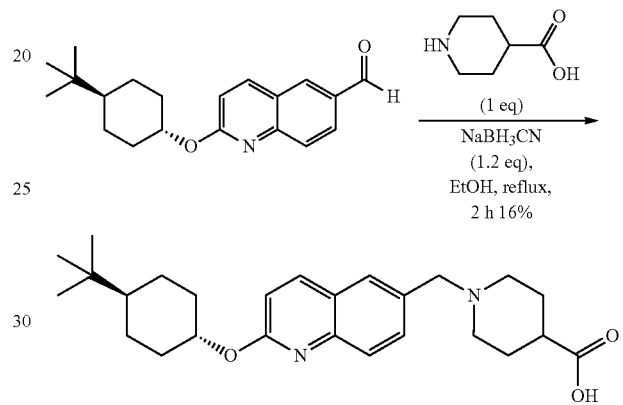

To the solution of 2-(4-tert-butyl-cyclohexyloxy)-quinoline-6-carbaldehyde (350 mg, 1.1 mmol) and piperidine-4-carboxylic acid (145 mg, 1.12 mmol) in ethanol (8 mL, 100 mmol) was heated to reflux for 2 h. The yellow solution was cooled to rt and sodium cyanoborohydride (84.8 mg, 1.35 mmol) was added and was heated to reflux for 1 h. After cooled down to rt, citric acid was added and concentrated down. The solid was suspended in water and filtrate, and the collected solid was washed thoroughly with water. HPLC purification of the solid gives the product. 77 mg, yield: 16%. ESI-MS (M+1)⁺: 425.00. ¹HNMR (400 MHz, d-MeOD) δ: 0.93 (s, 9 H), 1.02-1.57 (m, 10 H), 1.70-2.01 (m, 2 H), 2.30 (br. s., 2 H), 3.03-3.16 (m, 2 H), 3.53-3.68 (m, 2 H), 4.46 (s, 2 H), 5.10-5.27 (m, 1 H), 6.97 (d, J=8.85 Hz, 1 H), 7.71 (dd, J=8.63, 2.04 Hz, 1 H), 7.89 (d, J=8.60 Hz, 1 H), 7.93 (d, J=2.01 Hz, 1 H), 8.15 (d, J=8.97 Hz, 1 H).

Example 56

1-[6-(4-tert-Butyl-cyclohexyloxy)-naphthalen-2-ylmethyl]-4-ethyl-piperidine-4-carboxylic acid

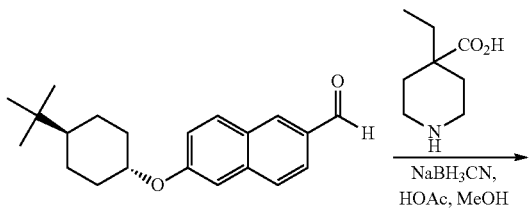

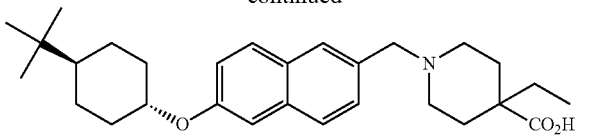

4-ethylpiperidine-4-carboxylic acid (0.184 g, 1.17 mmol) was combined with 6-(4-tert-Butyl-cyclohexyloxy)-naphthalene-2-carbaldehyde (0.3 g, 0.9 mmol), Acetic acid (0.19 mL, 3.4 mmol) in Methanol (1.9 mL, 48 mmol) and stirred for 30 min. The reaction was then cooled to 0° C. on an icebath and sodium cyanoborohydride (90.9 mg, 1.4 mmol) was added. The reaction was then allowed to warm to room temperature while stirring overnight. Reaction was then concentrated to about 4-5 mL then purified directly via reverse phase chromatography (5-95% $CH_3CN$/Water (0.1% TFA), C18, 150 mm). The product was then lyophilized to dryness to give 7 mg 1-[6-(4-tert-Butyl-cyclohexyloxy)-naphthalen-2-ylmethyl]-4-ethyl-piperidine-4-carboxylic acid as a white solid (2%). ESI-MS: 452 (M+1)$^+$. $^1$H NMR (DMSO-$d_6$, 400 MHz): δ (ppm) 7.75-8.00 (m, 3H), 7.47-7.61 (m, 1H), 7.43 (s, 1H), 7.07-7.28 (m, 1H), 4.44 (m, 3H), 3.29-3.54 (m, 2H), 2.74-3.03 (m, 2H), 2.20 (s, 3H), 1.64-1.98 (m, 3H), 1.02-1.65 (m, 9H), 0.89 (s, 9H), 0.76-0.83 (m, 3H)

Example 57

1-[6-(4-tert-Butyl-cyclohexyloxy)-naphthalen-2-ylmethyl]-4-propyl-piperidine-4-carboxylic acid

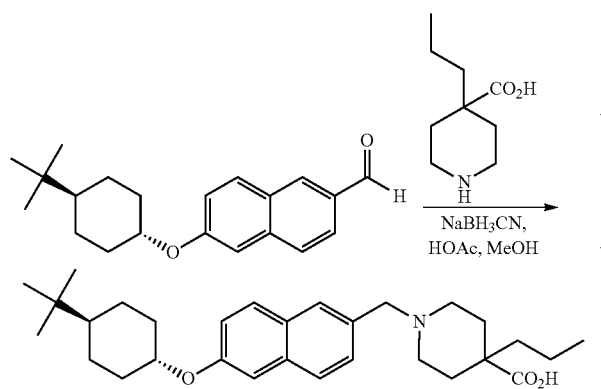

Compound was prepared in a manner similar to that of 1-[6-(4-tert-Butyl-cyclohexyloxy)-naphthalen-2-ylmethyl]-4-ethyl-piperidine-4-carboxylic acid using 4-Propyl-piperidine-4-carboxylic acid (0.185 g, 1.08 mmol), 6-(4-tert-Butyl-cyclohexyloxy)-naphthalene-2-carbaldehyde (0.3 g, 0.9 mmol) and Acetic acid (0.18 mL, 3.1 mmol) in Methanol (1.8 mL, 44 mmol) and Sodium cyanoborohydride (84.101 mg, 1.3383 mmol) to give 16 mg 1-[6-(4-tert-Butyl-cyclohexyloxy)-naphthalen-2-ylmethyl]-4-propyl-piperidine-4-carboxylic acid (4%). ESI-LCMS 466 (M+H). $^1$H NMR (METHANOL-$d_4$, 400 MHz): δ (ppm) 7.54-7.88 (m, 3H), 7.31-7.43 (m, 1H), 7.14-7.25 (m, 1H), 6.98-7.12 (m, 1H), 4.12-4.40 (m, 2H), 3.33-3.50 (m, 2H), 2.82-3.08 (m, 2H), 2.05-2.42 (m, 3H), 1.74-1.95 (m, 2H), 0.94-1.64 (m, 12H), 0.82 (s, 13H).

Example 58

1-[6-(4-tert-Butyl-cyclohexyloxy)-naphthalen-2-ylmethyl]-3-methyl-piperidine-4-carboxylic acid

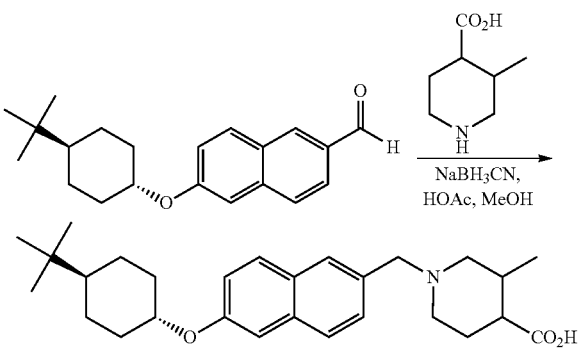

The compound was prepared in a manner similar as to that described for 1-[6-(4-tert-Butyl-cyclohexyloxy)-naphthalen-2-ylmethyl]-4-ethyl-piperidine-4-carboxylic acid using 3-Methyl-piperidine-4-carboxylic acid (0.154 g, 1.08 mmol), 6-(4-tert-Butyl-cyclohexyloxy)-naphthalene-2-carbaldehyde (0.3 g, 0.9 mmol) and Acetic acid (0.18 mL, 3.1 mmol) in Methanol (1.8 mL, 44 mmol) and sodium cyanoborohydride (84.101 mg, 1.3383 mmol) to give 6 mg 1-[6-(4-tert-Butyl-cyclohexyloxy)-naphthalen-2-ylmethyl]-3-methyl-piperidine-4-carboxylic acid (2%). ESI-LCMS 438 (M+H). $^1$H NMR (DMSO-$d_6$, 400 MHz): δ (ppm) 7.73-8.05 (m, 3H), 7.50-7.67 (m, 1H), 7.44 (s, 1H), 7.12-7.30 (m, 1H), 4.45 (br. s., 3H), 2.99-3.49 (m, 3H), 2.59-2.74 (m, 1H), 1.70-2.28 (m, 7H), 1.03-1.48 (m, 6H), 0.96 (d, J=6.8 Hz, 3H), 0.89 (s, 9H)

Example 59

1-[6-(4-tert-Butyl-cyclohexyloxy)-naphthalen-2-ylmethyl]-4-phenyl-piperidine-4-carboxylic acid

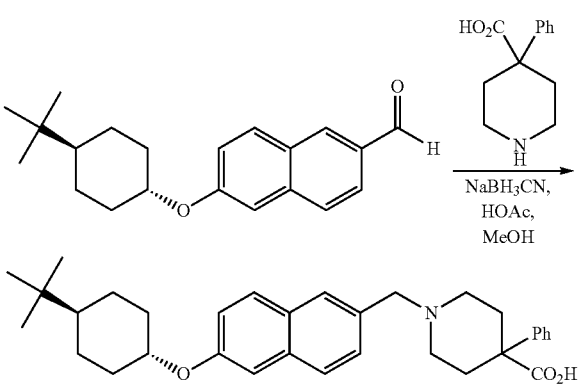

The compound was prepared in a manner similar as to that described for 1-[6-(4-tert-Butyl-cyclohexyloxy)-naphthalen-2-ylmethyl]-4-ethyl-piperidine-4-carboxylic acid using 4-Phenyl-piperidine-4-carboxylic acid (0.198 g, 0.967 mmol), 6-(4-tert-Butyl-cyclohexyloxy)-naphthalene-2-carbaldehyde (0.250 g, 0.805 mmol), acetic acid (0.16 mL, 2.8 mmol), Methanol (1.6 mL, 4.0E1 mmol) and sodium cyanoborohydride (75.314 mg, 1.1985 mmol) to give 21 mg of the title compound as a white solid (5%). ESI-LCMS (500 M+H). 1H NMR (DMSO-d6, 400 MHz): Shift (ppm) 7.80-7.98 (m, 3H), 7.16-7.63 (m, 8 H), 4.51 (br. s., 3H), 3.45-3.64 (m, 2H), 2.96-3.18 (m, 2H), 2.68 (m, 2H), 2.13-2.31 (m, 2H), 1.74-2.09 (m, 4H), 1.00-1.53 (m, 5H), 0.89 (s, 9H)

Example 60

1-[6-(4-tert-Butyl-cyclohexyloxy)-naphthalen-2-ylmethyl]-perhydro-azepine-4-carboxylic acid Step 1: Perhydro-azepine-4-carboxylic acid hydrochloride Perhydro-azepine-1,4-dicarboxylic acid 1-tert-butyl ester (1 g, 4 mmol) was dissolved in 4 M of Hydrogen chloride in 1,4-Dioxane(10 mL, 40 mmol) and stirred at room temperature for 1 hour. Crude reaction was concentrated to dryness and used without additional purification.

Step 2: 1-[6-(4-tert-Butyl-cyclohexyloxy)-naphthalen-2-ylmethyl]-perhydro-azepine-4-carboxylic acid

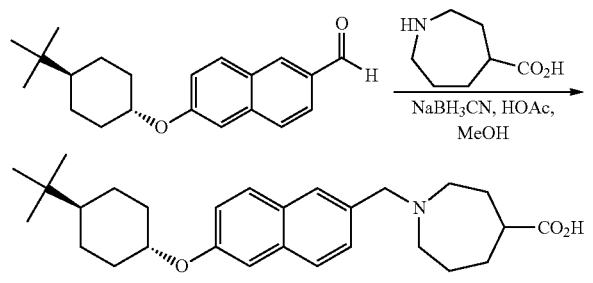

The compound was prepared in a manner similar as to that described for 1-[6-(4-tert-Butyl-cyclohexyloxy)-naphthalen-2-ylmethyl]-4-ethyl-piperidine-4-carboxylic acid using Perhydro-azepine-4-carboxylic acid (0.138 g, 0.967 mmol) HCl, 250 mg solid supported carbonate resin (1.34 mmol/g), Methanol (1.6 mL, 4.0E1 mmol), 6-(4-tert-Butyl-cyclohexyloxy)-naphthalene-2-carbaldehyde (0.250 g, 0.805 mmol) and Acetic acid (0.16 mL, 2.8 mmol) to give 86 mg the title compound as a white solid (24%). ESI-LCMS 438 (M+H). ¹H NMR (DMSO-d₆, 400 MHz): δ (ppm) 7.96 (s, 1H), 7.81-7.91 (m, 2H), 7.51-7.65 (m, 1H), 7.43 (d, J=1.8 Hz, 1H), 7.14-7.26 (m, 1H), 4.45 (br. s., 3H), 3.00-3.57 (m, 4H), 2.63-2.75 (m, 1H), 1.58-2.33 (m, 10H), 1.00-1.51 (m, 6H), 0.89 (s, 9H)

Example 61

1-[6-(4-tert-Butyl-cyclohexyloxy)-naphthalen-2-ylmethyl]-4-hydroxy-piperidine-4-carboxylic acid

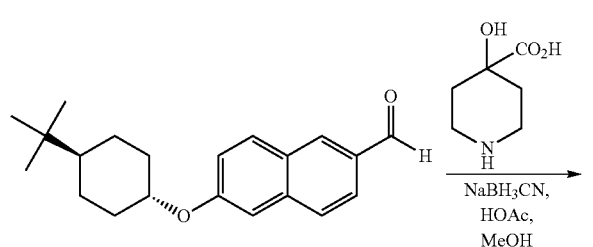

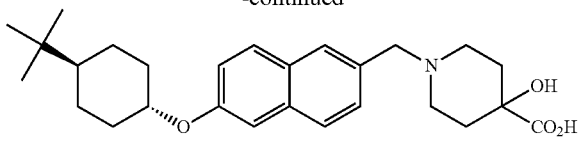

The compound was prepared in a manner similar as to that described for 1-[6-(4-tert-Butyl-cyclohexyloxy)-naphthalen-2-ylmethyl]-4-ethyl-piperidine-4-carboxylic acid 4-Hydroxy-piperidine-4-carboxylic acid (0.0561 g, 0.387 mmol), 6-(4-tert-Butyl-cyclohexyloxy)-naphthalene-2-carbaldehyde (0.100 g, 0.322 mmol), Acetic acid (0.064 mL, 1.1 mmol) and Sodium cyanoborohydride (30.126 mg, 0.47939 mmol) to give 51 mg 1-[6-(4-tert-Butyl-cyclohexyloxy)-naphthalen-2-ylmethyl]-4-hydroxy-piperidine-4-carboxylic acid (36%). ESI-LCMS 440 (M+H). ¹H NMR (DMSO-d₆, 400 MHz): δ (ppm) 9.37-9.69 (m, 1H), 7.75-8.07 (m, 4H), 7.50-7.64 (m, 1H), 7.43 (d, J=2.0 Hz, 1H), 7.13-7.27 (m, 1H), 4.47 (d, J=3.8 Hz, 3H), 3.05-3.47 (m, 4H), 1.97-2.29 (m, 4H), 1.83 (d, J=13.3 Hz, 4H), 1.02-1.45 (m, 5H), 0.89 (s, 9H)

Example 62

{1-[6-(4-tert-Butyl-cyclohexyloxy)-naphthalen-2-ylmethyl]-piperidin-4-yl}-acetic acid

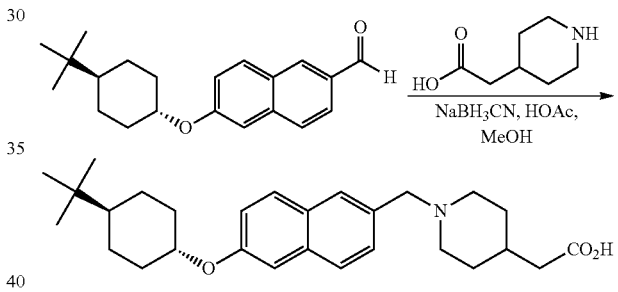

The compound was prepared in a manner similar as to that described for 1-[6-(4-tert-Butyl-cyclohexyloxy)-naphthalen-2-ylmethyl]-4-ethyl-piperidine-4-carboxylic acid using Piperidin-4-yl-acetic acid (0.0554 g, 0.387 mmol), 6-(4-tert-Butyl-cyclohexyloxy)-naphthalene-2-carbaldehyde (0.100 g, 0.322 mmol) and Sodium triacetoxyborohydride (0.212 g, 0.9 mol) to give 85 mg {1-[6-(4-tert-Butyl-cyclohexyloxy)-naphthalen-2-ylmethyl]-piperidin-4-yl}-acetic acid (60%). ESI-LCMS (438 M+H). 1H NMR (DMSO-d6, 400 MHz): Shift (ppm) 7.71-8.01 (m, 3H), 7.43 (d, J=2.0 Hz, 2H), 7.10-7.30 (m, 1H), 4.38 (d, J=4.8 Hz, 3H), 3.28-3.55 (m, 2H), 2.82-3.14 (m, 2H), 2.20 (d, J=6.3 Hz, 4H), 1.85 (br. s., 5H), 1.38 (br. s., 7H), 0.89 (s, 9H)

Example 69

1,1-Dimethoxy-N-(3-methoxybenzyl)propan-2-amine

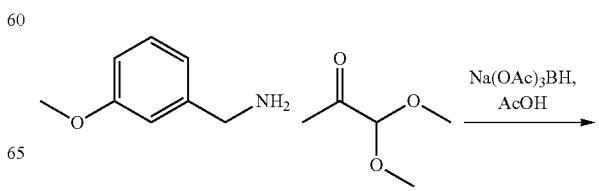

-continued

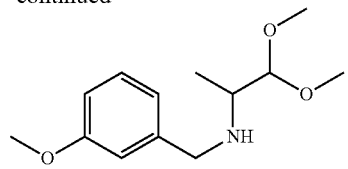

(3-Methoxyphenyl) methanamine (100 g, 730 mmol, 1 equiv.) and 1,1-dimethoxypropan-2-one (172.2 g, 1.46 mol, 2 equiv.) were dissolved in acetic acid (1.8 L). Anhydrous sodium sulfate (207 g, 1.46 mol, 2 equiv.) was added. The mixture was stirred for 1.5 hour at room temperature. Sodium triacetoxyborohydride (463 g, 2.19 mmol, 3 equiv.) was added in portions over 40 minutes. The mixture was stirred for an additional 2 hours. Most of the acetic acid was removed under reduced pressure. The resulting black oil was dissolved in ethyl acetate (2 L) and saturated aqueous sodium bicarbonate (1 L) was added slowly followed by solid potassium carbonate to adjust the pH to 7. The organic layer was separated, dried over sodium sulfate and filtered. The filtrate was concentrated under reduce pressure to give a black oil which was purified by silica gel chromatography to give the title compound (120 g,~85% purity by LC/MS, 68% yield).

Example 70

7-Methoxy-3-methylisoquinoline

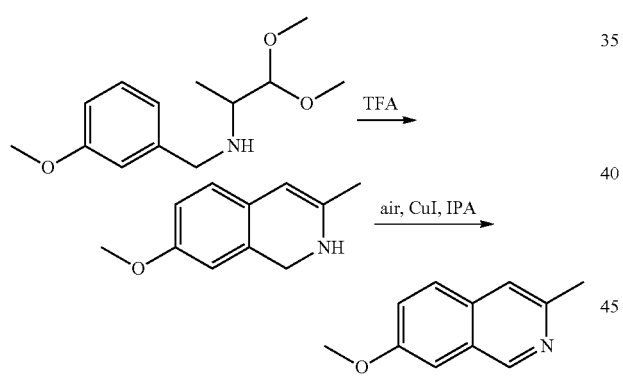

1,1-Dimethoxy-N-(3-methoxybenzyl)propan-2-amine (92.1 g, 385 mmol) was dissolved in trifluoroacetic acid (500 mL). This solution was heated under a nitrogen atmosphere at 55° C. overnight. The trifluoroacetic acid was removed under reduced pressure to give a brown oil (~150 g). This oil was dissolved in isopropyl alcohol (800 mL) and catalytic CuI (8 g) was added. This mixture was stirred at 55° C. open to air for 6 hours then at room temperature for 2 days. This mixture was filtered through a pad of Celite. The Celite cake was washed with methanol (100 mL). The filtrate was concentrated under reduced pressure to give a brown oil. Methylene chloride (1.2 L) was added to dissolve the oil and the solution was washed with a 10% aqueous ammonium hydroxide solution (2×300 mL) and saturated brine. The organic phase was dried over sodium sulfate and filtered. The filtrate was treated with silica gel and concentrated to dryness under reduced pressure. Purification was accomplished by silica gel chromatography to give the title compound (~10 g). The mixed fractions were combined and re-purified by silica gel column. A total of 15 g (15% yield) of product was isolated.

Example 71

3-Methylisoquinolin-7-ol

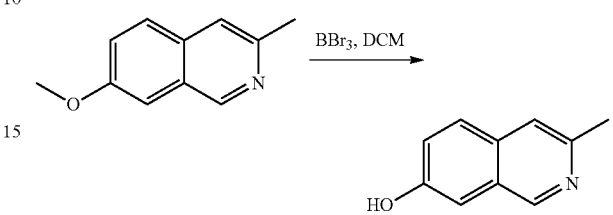

7-Methoxy-3-methylisoquinoline (15 g, 89 mmol, 1 equiv.) was dissolved in methylene chloride (150 mL). A 1.0 M solution of BBr3 in methylene chloride (240 mL, 240 mmol, 2.7 equiv.) was added slowly to this solution at room temperature observing a slight exotherm. This solution was stirred at room temperature for 2.5 hours. After cooling to 0° C., methanol (150 mL) was added slowly to quench the reaction. The solution was stirred for an additional 15 minutes. The solution was concentrated under reduced pressure and treated with methanol (150 mL) and concentrated under reduced pressure. The resulting oil was treated with saturated aqueous sodium bicarbonate slowly with stirring until a pH~7-8 was achieved. The solid resulting was collected under vacuum filtration and was washed with water (300 mL) and methylene chloride (200 mL) giving a tan solid which was dried in a vacuum oven at 50° C. overnight to give 3-methylisoquinolin-7-ol (13.1 g, 92% yield).

Example 72

7-(trans 4-tert-butylcyclohexyloxy)-3-methylisoquinoline

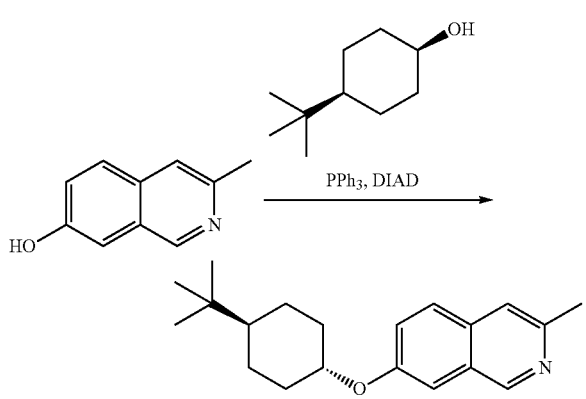

Triphenylphosphine (5.14 g, 19.6 mmol) was added to a solution of 3-Methylisoquinolin-7-ol (2.08 g, 13.1 mmol) and cis-4-tert-butylcyclohexanol (3.06 g, 19.6 mmol) in Toluene (60 mL, 600 mmol). The mixture was stirred for 15 minutes then Diisopropyl azodicarboxylate (3.86 mL, 19.6 mmol) was added. The mixture was then stirred at room temperature overnight. The solvent was removed under vacuum. The crude product was dissolved in methylene chloride, adsorbed onto silica gel and purified by flash chromatography to give the title compound in 2.01 g (52%) yield. ESI-MS(M+H+): 298.46.

Example 73

7-(trans-4-tert-butylcyclohexyloxy)isoquinoline-3-carbaldehyde

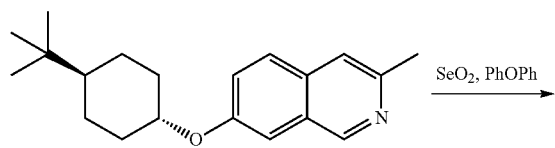

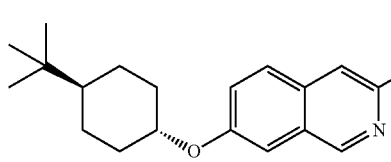

Selenium dioxide (2.25 g, 20.3 mmol) was added to a solution of 7-(trans-4-tert-Butyl-cyclohexyloxy)-3-methyl-isoquinoline (2.01 g, 6.76 mmol) in Diphenyl ether (50 mL, 300 mmol) and the mixture was heated at 200° C. in a sealed tube for 4 hours. The reaction was then cooled to room temperature. Silica gel was added and the flask was placed in a cold water bath to solidify the diphenylether solvent. This solid mixture containing the crude product was purified by flash chormatography to give the title compound in 1.04 g (49%) yield. ESI-MS(M+H+): 312.27

Example 74

1-[7-(trans-4-tert-Butyl-cyclohexyloxy)-isoquinolin-3-ylmethyl]-piperidine-4-carboxylic acid ethyl ester

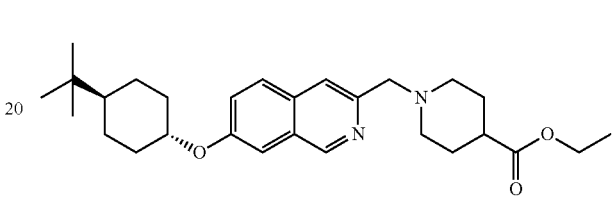

Triethylamine (65 µL, 0.47 mmol) was added to a solution of 7-(trans-4-tert-Butyl-cyclohexyloxy)-isoquinoline-3-carbaldehyde (0.106 g, 0.340 mmol) and Ethyl piperidine-4-carboxylate (79 mg, 0.50 mmol) in 1,2-Dichloroethane (5.00 mL) and the mixture was stirred for 1 hour at room temperature. Sodium triacetoxyborohydride (0.101 g, 0.476 mmol) was then added and stirring was continued for 2 hours. The reaction was diluted in methylene chloride and washed with saturated aqueous sodium bicarbonate. The organic phase was dried over magnesium sulfate, filtered, evaporated. The residue zo was taken up in methylene chloride and silica gel was added. The solvent was removed by evaporation and the residue purified by silica gel chromatography. 101 mg (66%) isolated. ESI-MS(M+H+): 453.10.

Example 75

1-[7-(trans-4-tert-Butyl-cyclohexyloxy)-isoquinolin-3-ylmethyl]-piperidine-4-carboxylic acid

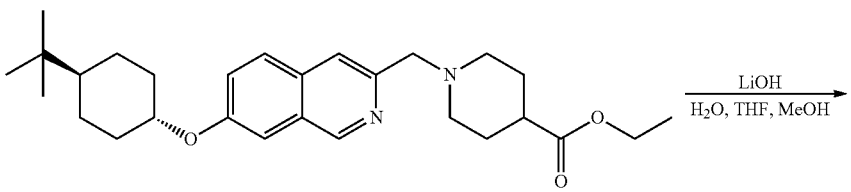

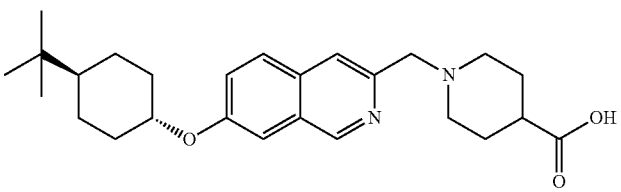

2 M Lithium hydroxide in water (1.00 mL, 2.00 mmol) was added to a solution of 1-[7-(trans -4-tert-Butyl-cyclohexyloxy)-isoquinolin-3-ylmethyl]-piperidine-4-carboxylic acid ethyl ester (0.101 g, 0.223 mmol) in tetrahydrofuran (1.00 mL) and methanol (1.00 mL). The mixture was stirred at room temperature. After 1 hour, the solvent was concentrated under vacuum. The residue was taken up in DMSO and concentrated. HCl (250 uL) was added to solubilize. Purification by preparative HPLC gave the product in 13.2 mg yield (9%) as bis-TFA salt. ESI-MS(M+H+): 425.0. $^1$H NMR (400 MHz, DMSO-$d_6$) δ 12.49 (br. s., 1H), 9.24 (s, 1H), 7.87 (d, J=9.04 Hz, 1H), 7.83 (s, 1H), 7.61 (d, J=1.76 Hz, 1H), 7.40 (dd, J=2.26, 8.78 Hz, 1H), 4.33-4.49 (m, 3H), 3.04 (br. s., 1H), 2.16 (d, J=10.29 Hz, 2H), 1.95 (d, J=11.80 Hz, 2H), 1.71-1.86 (m, 4H), 1.24-1.38 (m, 2H), 1.09-1.23 (m, 2H), 0.96-1.08 (m, 1H), 0.82 (s, 9H).

Example 76

Ethyl 1-((6-(trans-4-tert-butyleyelohexyloxy)naphthalen-2-yl)methyl)-4-methylpiperidine-4-carboxylate

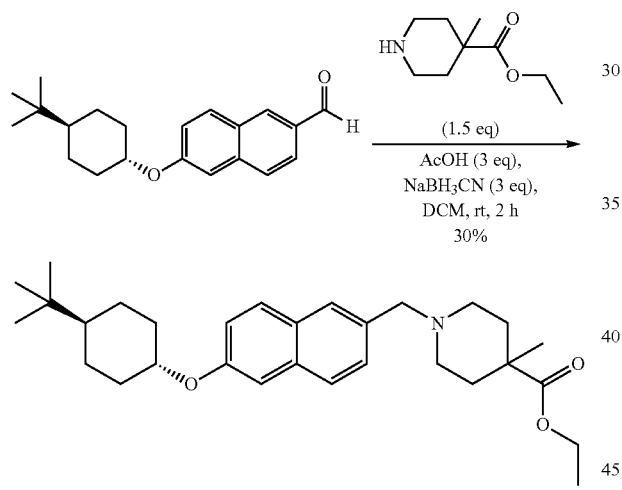

A solution of 6-(trans-4-tert-butylcyclohexyloxy)-2-naphthaldehyde (500 mg, 1.6 mmol), AcOH (288 mg, 4.8 mmol, 3.0 eq) and ethyl 4-methylpiperidine-4-carboxylate (410 mg, 2.4 mmol, 1.5 eq) in DCM (5 mL) was stirred at room temperature for 10 min. Then NaBH$_3$CN (300 mg, 4.8 mmol, 3.0 eq) was added. The reaction mixture was stirred at room temperature for 12 h, quenched with water (5 mL) and extracted with DCM (3×10 mL). The combined organic layers were washed with brine (10 mL), dried over Na$_2$SO$_4$ and concentrated. The residue was purified by silica gel column chromatography (Petroleum ether: ethyl acetate=3:1) to give ethyl 1-((6-(trans-4-tert-butylcyclohexyloxy)naphthalen-2-yl)methyl)-4-methylpiperidine-4-carboxylate (480 mg, yield: 30%) as a yellow oil. ESI-MS (M+1)$^+$: 466.2. $^1$HNMR (400 MHz, CDCl$_3$) δ: 7.75~7.73 (m, 3H), 7.48 (d, 1H), 7.18~7.15 (m, 2H), 4.28~4.26 (m, 1H), 4.19~4.12 (q, 2H), 4.01 (s, 2H), 3.17~3.15 (m, 2H), 2.59 (br, 2H), 2.29~2.17 (m, 4H), 1.91~1.82 (m, 4H), 1.46~1.43 (m, 3H), 1.30~1.18 (m, 8H), 0.88 (s, 9H).

Example 77

1-((6-(trans-4-tert-Butylcyclohexyloxy)naphthalen-2-yl)methyl)-4-methylpiperidine-4-carboxylic acid

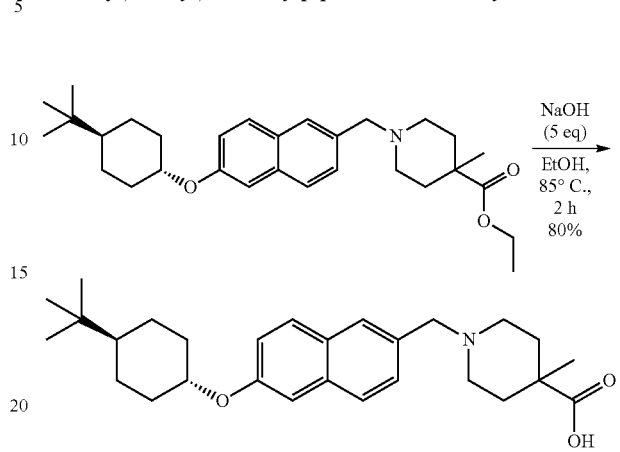

To a solution of ethyl 1-((6-(trans-4-tert-butylcyclohexyloxy)naphthalen-2-yl)methyl)-4-methylpiperidine-4-carboxylate (150 mg, 0.3 mmol) in MeOH (5 mL) was added NaOH (60 mg, 1.5 mmol, 5.0 eq) and H$_2$O (0.5 mL). The reaction mixture was stirred at 85° C. for 2 h. The pH of the solution was adjusted to 6 with 3 N HCl. The mixture was filtered and the yellow solid was the desired product 1-((6-(trans-4-tert-butylcyclohexyloxy)naphthalen-2-yl)methyl)-4-methylpiperidine-4-carboxylic acid (100 mg, yield: 80%). ESI-MS (M+1)$^+$: 438.3, HPLC: 100%. $^1$HNMR (400 MHz, DMSO-$d_6$) δ: 10.21 (s, 1H), 8.02 (br, 1H), 7.93~7.88 (m, 2H), 7.67 (br, 1H), 7.48 (s, 1H), 7.26 (d, 1H), 4.51~4.45 (m, 2H), 3.35 (s, 2H), 3.32 (br, 1H), 2.92 (br, 1H), 2.29~2.14 (m, 4H), 1.92~1.76 (m, 4H), 1.47~1.12 (m, 9H), 0.93 (s, 9H).

Example 78

Ethyl 1-((6-(cyclopentyloxy)naphthalen-2-yl)methyl)piperidine-4-carboxylate

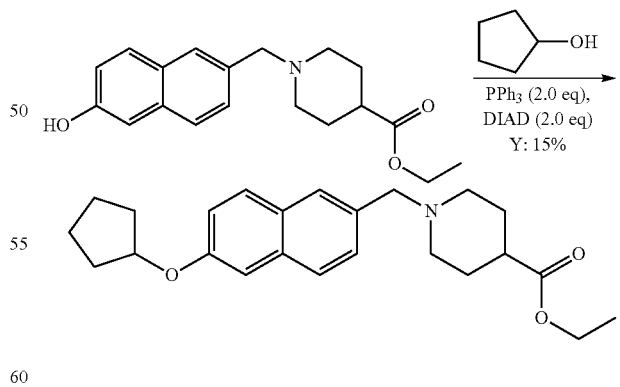

The preparation of ethyl 1-((6-(cyclopentyloxy)naphthalen-2-yl)methyl)piperidine-4-carboxylate was the same as that of ethyl 1-((6-(4-isopropylcyclohexyloxy)naphthalen-2-yl)methyl)piperidine-4-carboxylate. 140 mg, yellow oil, yield: 15%. ESI-MS (M+H)$^+$: 382.3. $^1$H NMR (400 MHz, CDCl$_3$) δ: 7.62-7.55 (m, 3H), 7.34 (d, J=10 Hz, 1H), 7.02-7.01 (m, 2H), 4.82-4.81 (m, 1H), 4.04 (q, J=7.2 Hz, 2H), 3.52 (s, 2H), 2.83-2.80 (m, 2H), 2.21-2.17 (m, 1H), 1.97-1.72 (m, 12H), 1.58-1.56 (m, 2H), 1.18-1.14 (m, 3H).

Example 79

1-((6-(Cyclopentyloxy)naphthalen-2-yl)methyl)piperidine-4-carboxylic acid

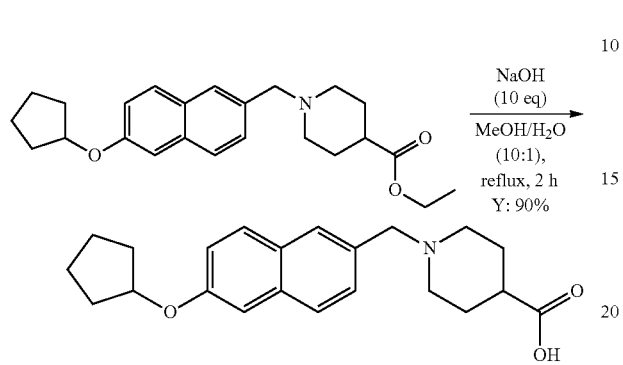

The preparation of 1-((6-(Cyclopentyloxy)naphthalen-2-yl)methyl)piperidine-4-carboxylic acid as the same as that of 1-((6-(4-isopropylcyclohexyloxy)naphthalen-2-yl)methyl)piperidine-4-carboxylic acid. 100 mg, a yellow solid, yield: 90%. ESI-MS (M+H)+: 354.2, HPLC: 97.41%. $^1$H NMR (400 MHz, CD$_3$OD), δ: 7.94 (s, 1H), 7.87 (d, J=8.4 Hz, 1H), 7.83 (d, J=8.8 Hz, 1H), 7.53 (dd, J=8.4, 1.2 Hz, 1H), 7.26 (s, 1H), 7.11 (dd, J=8.8, 2.4 Hz, 1H), 5.00-4.98 (m, 1H), 4.43 (s, 2H), 3.48-3.46 (m, 2H), 3.15-3.12 (m, 2H), 2.63-2.61 (m, 1H), 2.19-2.15 (m, 2H), 2.03-2.00 (m, 3H), 1.91-1.87 (m, 5H), 1.72-1.68 (m, 2H).

Example 80

Ethyl 1-((6-(cycloheptyloxy)naphthalen-2-yl)methyl)piperidine-4-carboxylate

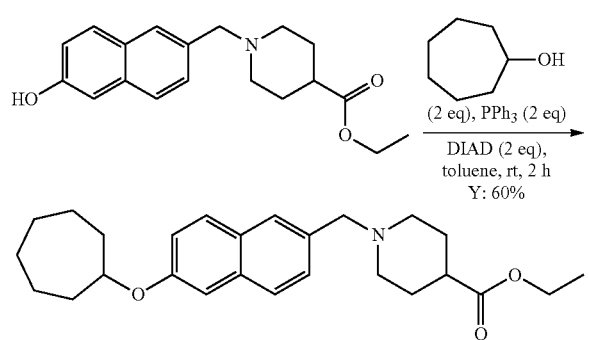

The preparation of ethyl 1-((6-(cycloheptyloxy)naphthalen-2-yl)methyl)piperidine-4-carboxylate was the same as that of ethyl 1-((6-(4-isopropylcyclohexyloxy)naphthalen-2-yl)methyl)piperidine-4-carboxylate. 200 mg, colorless oil, yield: 60%. ESI-MS (M+H)+: 410.1. 1H NMR (400 MHz, DMSO-d$_6$), δ: 7.78-7.71 (m, 2H), 7.66 (s, 1H), 7.38 (dd, J=8.4, 1.6 Hz, 1H), 7.23 (d, J=2.0 Hz, 1H), 7.10 (dd, J=8.8, 2.8 Hz, 1H), 4.66-4.62 (m, 1H), 4.04 (q, J=7.2 Hz, 2H), 3.54 (s, 2H), 2.79-2.75 (m, 2H), 2.31-2.56 (m, 1H), 2.04-1.98 (m, 4H), 1.79-1.71 (m, 6H), 1.59-1.45 (m, 11H).

Example 81

1-((6-(cycloheptyloxy)naphthalen-2-yl)methyl)piperidine-4-carboxylic acid

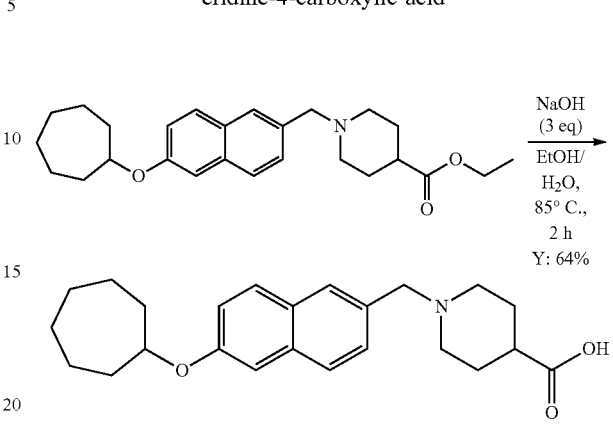

The preparation of 1-((6-(cycloheptyloxy)naphthalen-2-yl)methyl)piperidine-4-carboxylic acid was the same as that of 1-((6-(4-isopropylcyclohexyloxy)naphthalen-2-yl)methyl)piperidine-4-carboxylic acid. 60 mg, a white solid, yield: 64%. ESI-MS (M+H)+: 382.1. HPLC: 100%. 1H NMR (400 MHz, DMSO-d$_6$), δ: 7.78-7.71 (m, 2H), 7.66 (s, 1H), 7.38 (dd, J=8.4, 1.6 Hz, 1H), 7.23 (d, J=2.0 Hz, 1H), 7.09 (dd, J=9.2, 2.4 Hz, 1H), 4.65-4.61 (m, 1H), 3.53 (s, 2H), 2.76-2.73 (m, 2H), 2.16-2.13 (m, 1H), 2.06-1.95 (m, 4H), 1.79-1.66 (m, 6H), 1.59-1.49 (m, 8H).

Example 82 ethyl 1-((6-(tetrahydro-2H-pyran-4-yloxy)naphthalen-2-yl)methyl)piperidine-4-carboxylate

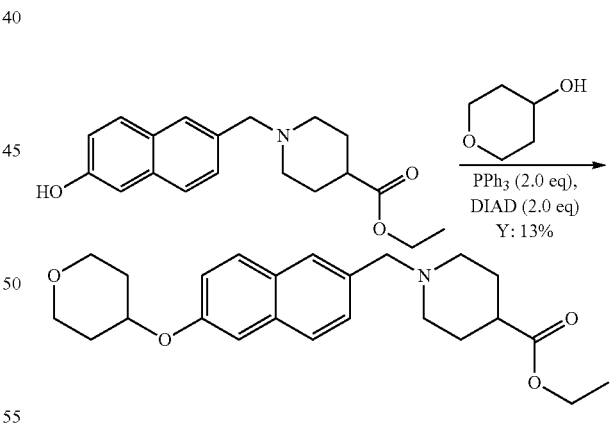

The preparation of ethyl 1-((6-(tetrahydro-2H-pyran-4-yloxy)naphthalen-2-yl)methyl)piperidine-4-carboxylate was the same as that of ethyl 1-((6-(4-isopropylcyclohexyloxy)naphthalen-2-yl)methyl)piperidine-4-carboxylate. 120 mg, yellow oil, yield: 13%. ESI-MS (M+H)+: 398.1. $^1$H NMR (400 MHz, CDCl$_3$) δ: 7.65 (d, J=9.2 Hz, 1H), 7.60-7.58 (m, 2H), 7.38 (d, J=9.6 Hz, 1H), 7.07-7.06 (m, 2H), 4.58-4.54 (m, 1H), 4.05 (q, J=7.2 Hz, 2H,), 3.97-3.92 (m, 2H), 3.58-3.52 (m, 4H), 2.83-2.80 (m, 2H), 2.23-2.17 (m, 1H), 2.04-1.99 (m, 4H), 1.83-1.72 (m, 6H), 1.17 (t, J=7.2 Hz, 3H).

Example 83

1-((6-(tetrahydro-2H-pyran-4-yloxy)naphthalen-2-yl)methyl)piperidine-4-carboxylic acid

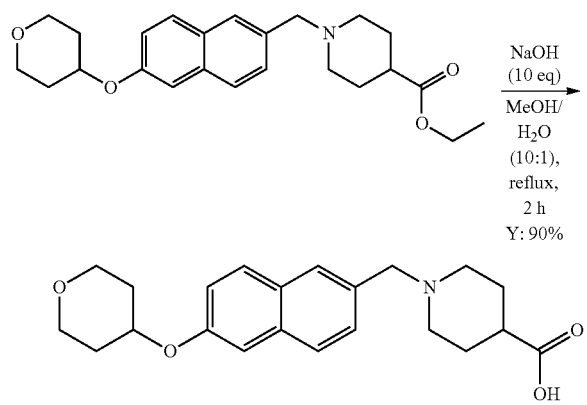

The preparation of 1-((6-(tetrahydro-2H-pyran-4-yloxy)naphthalen-2-yl)methyl)piperidine-4-carboxylic acid was the same as that of 1-((6-(4-isopropylcyclohexyloxy)naphthalen-2-yl)methyl)piperidine-4-carboxylic acid. 90 mg, a slight yellow solid, yield: 90%. ESI-MS (M+H)$^+$: 370.1, HPLC: 97.18%. $^1$H NMR (400 MHz, CD$_3$OD) δ: 7.85 (s, 1H), 7.78-7.74 (m, 2H), 7.43 (d, J=8.8 Hz, 1H), 7.26 (s, 1H), 7.14 (dd, J=9.2, 2.4 Hz, 1H), 4.69-4.65 (m,1H), 4.32 (s, 2H), 3.91-3.82 (m, 2H), 3.58-3.52 (m, 2H), 3.37-3.35 (m, 2H), 3.06-3.03 (m, 2H), 2.54-2.52 (m, 1H), 2.07-1.99 (m, 4H), 1.87-1.86 (m, 2H), 1.73-1.64 (m, 2H).

Example 84

Ethyl 1-((6-(spiro[5.5]undecan-3-yloxy)naphthalen-2-yl)methyl)piperidine-4-carboxylate

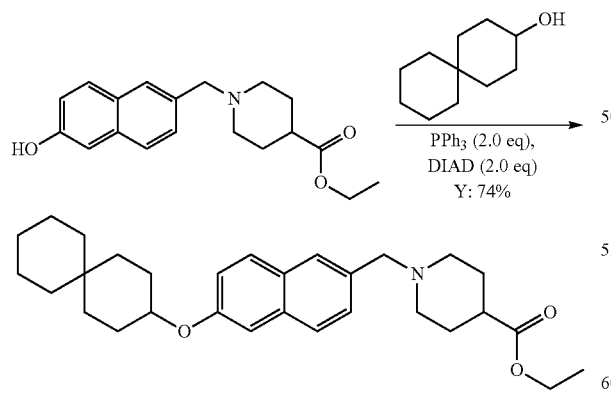

The preparation of ethyl 1-((6-(spiro[5.5]undecan-3-yloxy)naphthalen-2-yl)methyl)piperidine-4-carboxylate was the same as that of ethyl 1-((6-(4-isopropylcyclohexyloxy)naphthalen-2-yl)methyl)piperidine-4-carboxylate. 1.03 g, yellow oil, yield: 74%. ESI-MS (M+H)$^+$: 464.10.

Example 85

1-((6-(spiro[5.5]undecan-3-yloxy)naphthalen-2-yl)methyl)piperidine-4-carboxylic acid

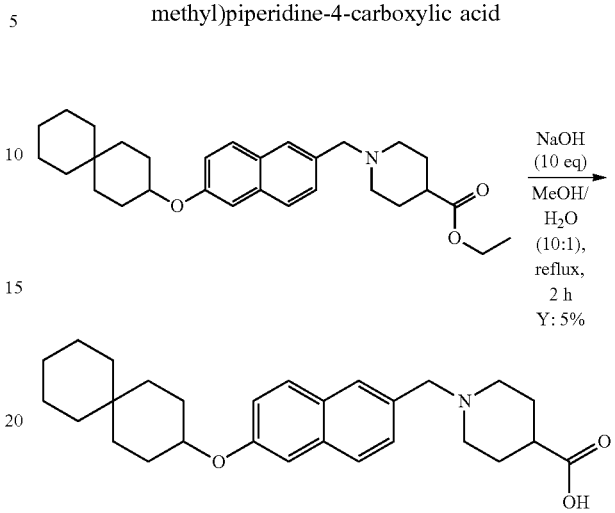

The preparation of 1-((6-(spiro[5.5]undecan-3-yloxy)naphthalen-2-yl)methyl)piperidine-4-carboxylic acid was the same as that of 1-((6-(4-isopropylcyclohexyloxy)naphthalen-2-yl)methyl)piperidine-4-carboxylic acid. 14 mg, a slight yellow solid, yield: 5%. ESI-MS (M+H)$^+$: 436.0, HPLC: 95%. $^1$H NMR (400 MHz, CD$_3$OD) δ: 7.92 (s, 1 H), 7.88 (d, J=8.47 Hz, 1 H), 7.84 (d, J=9.04 Hz, 1 H), 7.50 (dd, J=8.47, 1.76 Hz, 1 H), 7.30 (s, 1 H), 7.22 (dd, J=8.97, 2.38 Hz, 1 H), 4.53 (dquin, J=8.07, 4.18, 4.18, 4.18, 4.18 Hz, 1 H), 4.44 (s, 2 H), 3.59 (d, J=12.74 Hz, 2 H), 3.09 (td, J=13.13, 2.85 Hz, 2 H), 2.57-2.70 (m, 1 H), 2.17-2.32 (m, 2 H), 1.21-2.01 (m, 20 H).

Example 86

Ethyl 1-((6-(spiro[3.5]nonan-7-yloxy)naphthalen-2-yl)methyl)piperidine-4-carboxylate

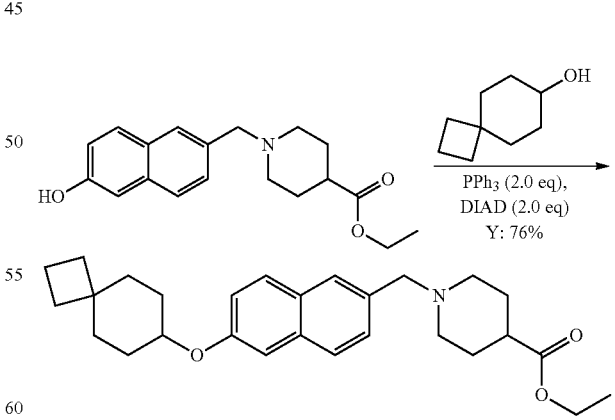

The preparation of ethyl 1-((6-(spiro[3.5]nonan-7-yloxy)naphthalen-2-yl)methyl)piperidine-4-carboxylate was the same as that of ethyl 1-((6-(4-isopropylcyclohexyloxy)naphthalen-2-yl)methyl)piperidine-4-carboxylate. 977 mg, yellow oil, yield: 76%. ESI-MS (M+H)$^+$: 436.0.

Example 87

1-((6-(spiro[3.5]nonan-7-yloxy)naphthalen-2-yl)methyl)piperidine-4-carboxylic acid

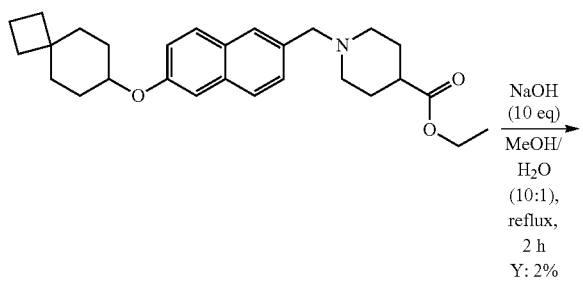

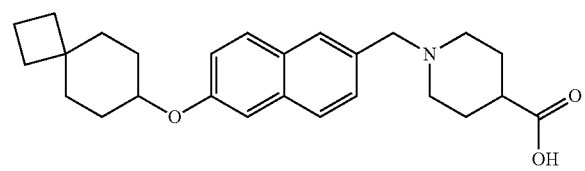

The preparation of 1-((6-(spiro[3.5]nonan-7-yloxy)naphthalen-2-yl)methyl)piperidine-4-carboxylic acid was the same as that of 1-((6-(4-isopropylcyclohexyloxy)nahthalen-2-yl)methyl)piperidine-4-carboxylic acid. 14 mg, a slight yellow solid, yield: 2%. ESI-MS (M+H)$^+$: 408.0, HPLC: 95%. $^1$H NMR (400 MHz, CD$_3$OD) δ: 1.43-2.06 (m, 16 H), 2.25 (d, J=16.82 Hz, 2 H), 2.64 (tt, J=12.44, 3.78 Hz, 1 H), 3.00-3.14 (m, 2 H), 3.59 (d, J=13.68 Hz, 2 H), 4.44 (s, 2 H) 4.46-4.56 (m, 1 H), 7.22 (dd, J=8.88, 2.48 Hz, 1 H), 7.30 (s, 1 H), 7.50 (dd, J=8.53, 1.76 Hz, 1 H), 7.84 (d, J=9.04 Hz, 1 H), 7.88 (d, J=8.66 Hz, 1 H), 7.92 (s, 1 H).

Example 88

1-[6-(4-tert-Butyl-cyclohexyloxy)-naphthalen-2-ylmethyl]-piperidine-2-carboxylic acid

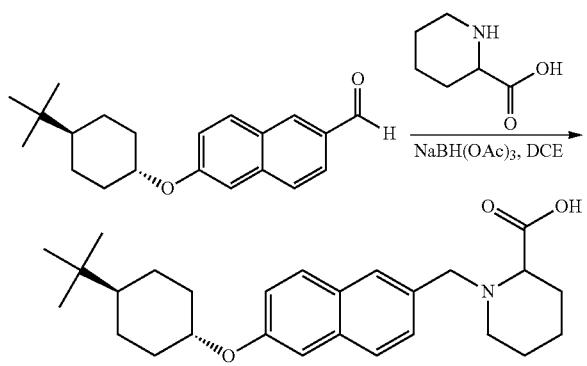

Piperidine-2-carboxylic acid (0.125 g, 0.967 mmol) as HCl salt was combined with 6-(4-tert-Butyl-cyclohexyloxy)-naphthalene-2-carbaldehyde (0.250 g, 0.805 mmol) in 1,2-dichloroethane (5 mL, 60 mmol) and acetic acid (0.500 mL, 8.79 mmol). The mixture was heated to reflux while stirring overnight. Reaction cooled to room temperature and then sodium triacetoxyborohydride (546 mg, 2.58 mmol) was added in small portions. The reaction was then left stirring overnight. Reaction was then purified directly via reverse phase chromatography (5-95% CH$_3$CN/Water (0.1% TFA), C18, 150 mm). The product was then lyophilized to dryness to give 3 mg 1-[6-(4-tert-Butyl-cyclohexyloxy)-naphthalen-2-ylmethyl]piperidine-2-carboxylic acid as a yellow solid (0.8%). ESI-LCMS (424 M+H). $^1$H NMR (DMSO-d$_6$ 400 MHz): δ (ppm) 12.34-12.58 (m, 1H), 11.20-11.53 (m, 1H), 8.01 (s, 1H), 7.68-7.93 (m, 3H), 7.41 (s, 1H), 7.02-7.22 (m, 1H), 4.35 (br. s., 3H), 3.23-3.43 (m, 2H), 2.86-3.09 (m, 2H), 1.74-2.30 (m, 8H), 1.00-1.52 (m, 5H), 0.87 (s, 9H)

Example 89

Methyl 6-hydroxy-1,2,3,4-tetrahydronaphthalene-2-carboxylate

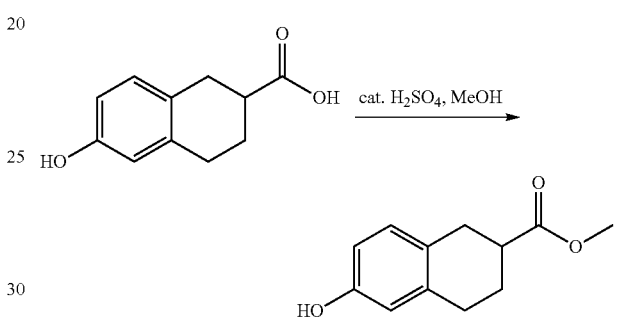

To a solution of 6-hydroxy-1,2,3,4-tetrahydronaphthalene-2-carboxylic acid (0.5 g, 3 mmol) in methanol (6 mL, 200 mmol) was added sulfuric acid (0.05 g, 0.5 mmol) and stirred over weekend. After concentration, the residue was dissolved in EtOAc and washed with water, brine and dried over Na$_2$SO$_4$ to give the pure product as a white solid (0.55g, 100%). LCMS: Rt=1.17 min, m/z=207.00 [M+], 100%.

Example 90

Methyl 6-((trans-4-(tert-butyl)cyclohexyl)oxy)-1,2,3,4-tetrahydronaphthalene-2-carboxylate

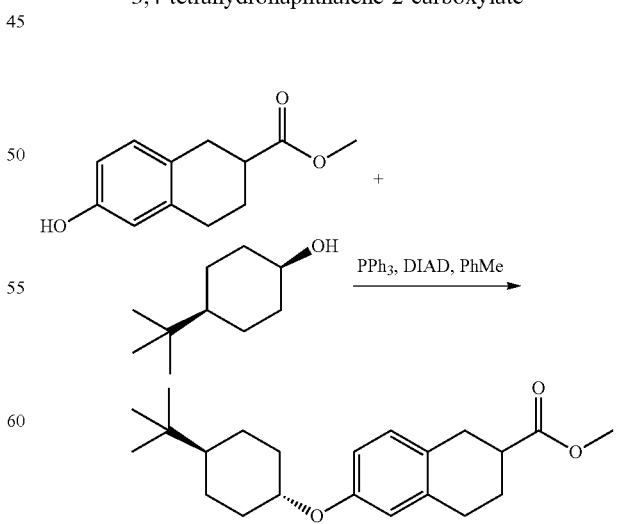

To a mixture of 6-hydroxy-1,2,3,4-tetrahydro-naphthalene-2-carboxylic acid methyl ester (0.280 g, 1.36 mmol), trans-4-tert-butylcyclohexanol (0.2338 g, 1.496 mmol) and triphenylphosphine (0.7122 g, 2.715 mmol) in toluene (5 mL, 50 mmol) was stirred for 20 min, then,diisopropyl azodicarboxylate (0.34 mL, 1.6 mmol) was added dropwise at 0° C. The solution was stirred at reflux overnight. The reaction was added silica gel and the solvent was concentrated. The residue was purified with silica gel eluted with EtOAc in hexanes from 0 to 20% to give the product as a white precipitate (73 mg, 16%). LCMS Rt=1.50 min, m/z=450.10 [M+H].

Example 91

(6-(((trans-4-(tert-Butyl)cyclohexyBoxy)-1,2,3,4-tetrahydronaphthalen-2-yl)methanol

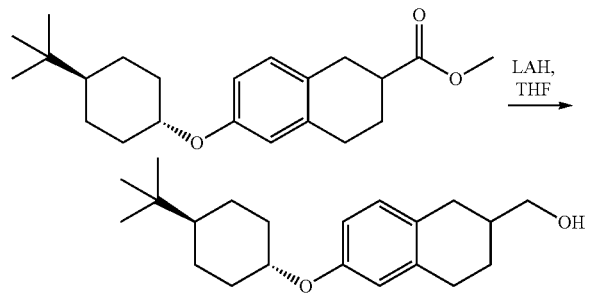

To 6-(trans-4-tert-Butyl-cyclohexyloxy)-1,2,3,4-tetrahydro-naphthalene-2-carboxylic acid methyl ester (73 mg, 0.21 mmol) in tetrahydrofuran (0.86 mL,1.0E1 mmol) was added 1.00 M of lithium tetrahydroaluminate in tetrahydrofuran (0.64 mL, 0.64 mmol). After stirring at room temperature for 1h, EtOAc and Rochele's salt solution was added and stirred for 30 min. The mixture was extracted with EtOAc and was purified with silica gel to give product (73 mg, 100%). LCMS: Rf=2.24 min, m/z=317.10.

Example 92

6-((trans-4-(tert-Butyl)cyclohexyl)oxy)-1,2,3,4-tetrahydronaphthalene-2-carbaldehyde

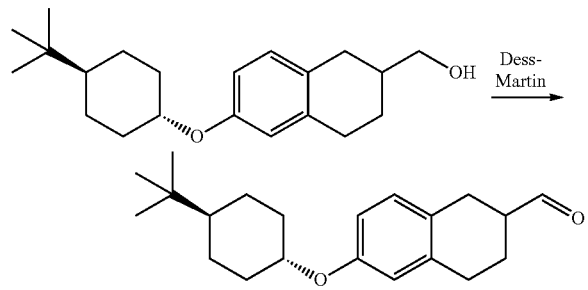

To a solution of [6-(trans-4-tert-butyl-cyclohexyloxy)-1,2,3,4-tetrahydro-naphthalen-2-yl]-methanol (73 mg, 0.23 mmol) in methylene chloride (1.478 mL, 23.07 mmol) was added Dess-Martin periodinane (0.1468 g, 0.3460 mmol) and was stirred at room temperature for 1 hour. After being passed through silica gel plug, the solvent was concentrated down to give product (27 mg, 37%). LCMS: Rf=2.39 min, m/z=315.00.

Example 93

1-((6-((trans-4-(tert-Butyl)cyclohexyl)oxy)-1,2,3,4-tetrahydronaphthalen-2-yl)methyl)piperidine-4-carboxylic acid

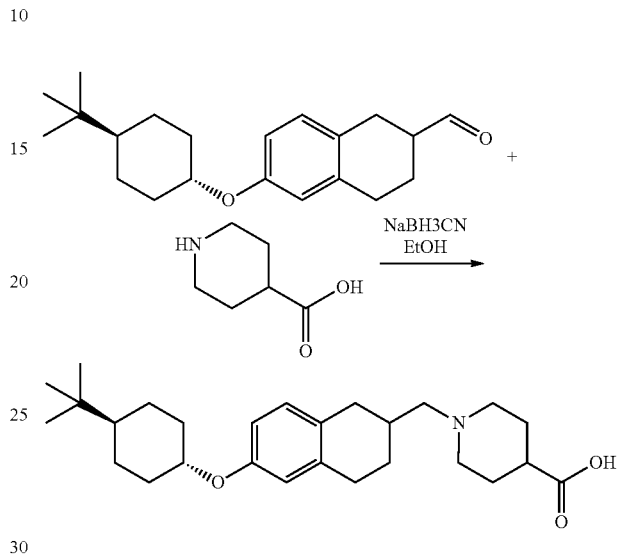

A solution of 6-(trans-4-tert-butyl-cyclohexyloxy)-1,2,3,4-tetrahydro-naphthalene-2-carbaldehyde (34.5 mg, 0.110 mmol) and piperidine-4-carboxylic acid (14.2 mg, 0.110 mmol) in ethanol (0.8 mL, 10 mmol) was heated to reflux for 2 h. The yellow solution was cooled to room temperature and sodium cyanoborohydride (8.27 mg, 0.132 mmol) was added and heated to reflux for 1 h. After cooled down to room temperature, citric acid was added and concentrated down. The solid was suspended in water and filtered and the collected solid was washed thoroughly with water. HPLC purification of the solid gave the product (1.6 mg (3.4%). LCMS Rt=1.76 min, m/z=428.42 [M-F1]. $^1$H NMR (400 MHz, METHANOL-d4) δ ppm 0.91 (s, 9 H), 1.02-1.48 (m, 10 H), 1.80-2.47 (m, 11 H), 2.47-3.01 (m, 3 H), 3.66-3.96 (m, 3 H), 4.07-4.26 (m, 1 H), 6.67-6.83 (m, 2 H), 6.99-7.15 (m, 1 H).

Example 94 ethyl 1-((6-((cis-4-phenylcyclohexyl)oxy)naphthalen-2-yl)methyl)piperidine-4-carboxylate

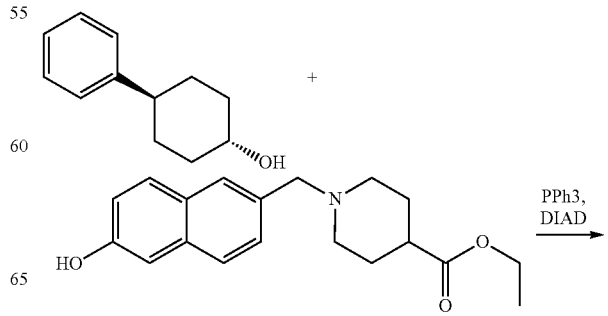

-continued

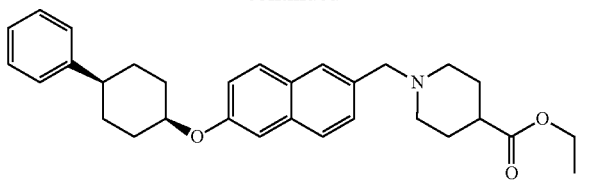

A mixture of 1-(6-hydroxy-naphthalen-2-ylmethyl)-piperidine-4-carboxylic acid ethyl ester (0.400 g, 1.28 mmol), 4-phenyl-cyclohexanol (0.2479 g, 1.406 mmol) and triphenylphosphine (0.6695 g, 2.553 mmol) in toluene (5 mL, 40 mmol) was stirred for 20 min, then diisopropyl azodicarboxylate (0.32 mL, 1.5 mmol) was added dropwise at 0° C. The solution was stirred at reflux overnight. The reaction was added silica gel and the solvent was concentrated. The residue was purified with silica gel eluted with EtOAc in hexanes from 0 to 20% to give product as an oil (0.3 g, 50%). LCMS: Rt=1.75 min, m/z=472.45 [M+H].

Example 95

1-((6-((cis-4-phenylcyclohexyl)oxy)naphthalen-2-yl)methyl)piperidine-4-carboxylic acid

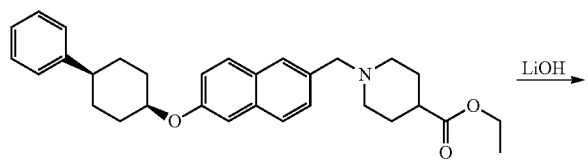

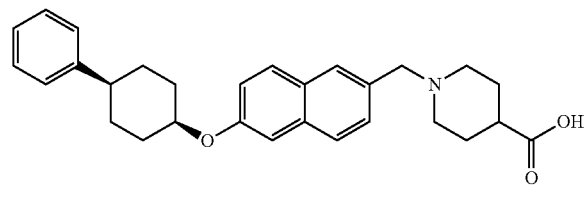

A solution of 1-[6-(cis-4-phenyl-cyclohexyloxy)-naphthalen-2-ylmethyl]-piperidine-4-carboxylic acid ethyl ester (0.9 g, 2 mmol) and lithium hydroxide (457 mg, 19.1 mmol) in tetrahydrofuran (7.74 mL, 95.4 mmol) and water (1.72 mL, 95.4 mmol) was stirred at room temperature overnight. LCMS showed a single desired product peak Rt=1.60 min, m/z=444.35, [M+1], 100%. The solvent was concentrated and neutralized with conc. HCl and concentrated and purified on HPLC to give product (245 mg, 30%). $^1$H NMR (400 MHz, METHANOL-d4) δ ppm 1.59-2.17 (m, 13 H), 2.26 (d, J=10.35 Hz, 2 H), 2.59-2.73 (m, 1 H), 2.93 (d, J=11.61 Hz, 2 H), 3.64 (s, 2 H), 4.84 (br. s., 1 H), 7.19 (s, 1 H), 7.23 (d, J=11.36 Hz, 1 H), 7.28 (s, 5 H), 7.45 (d, J=8.41 Hz, 1 H), 7.65-7.74 (m, 2 H), 7.77 (d, J=8.97 Hz, 1 H).

Example 96 ethyl 1-((6-((cis-4-(tert-pentyl)cyclohexyl)oxy)naphthalen-2-yl)methyl)piperidine-4-carboxylate A mixture of 1-(6-hydroxy-naphthalen-2-ylmethyl)-piperidine-4-carboxylic acid ethyl ester (0.400 g, 1.28 mmol), trans-4-(1,1-dimethyl-propyl)-cyclohexanol (0.2395 g, 1.406 mmol) and triphenylphosphine (0.6695 g, 2.553 mmol) in toluene (5 mL, 40 mmol) was stirred for 20 min, then, diisopropyl azodicarboxylate (0.32 mL, 1.5 mmol) was added drop wise at 0° C. The solution was stirred at reflux overnight. The reaction was added to silica gel and the solvent was concentrated. The residue was purified with silica gel eluted with EtOAc in hexanes from 0 to 20% to give product as oil (0.6 g, 100%). LCMS: Rt=1.95 min, m/z=466.49 [M+H].

Example 97

1-((6-((cis-4-(tert-pentyl)cyclohexyl)oxy)naphthalen-2-yl)methyl)piperidine-4-carboxylic acid A solution of 1-{6-[cis-4-(1,1-dimethyl-propyl)-cyclohexyloxy]-naphthalen-2-ylmethyl}-piperidine-4-carboxylic acid ethyl ester (0.382 g, 0.820 mmol) and lithium hydroxide (196 mg, 8.20 mmol) in tetrahydrofuran (3.32 mL, 41.0 mmol) and water (0.738 mL, 41.0 mmol) was stirred at room temperature overnight. LCMS showed a single desired product peak Rt=1.78 min, m/z=438.40 [M+1], 100%. The solvent was concentrated and neutralized with concentrated HCl. The solid was suspended with water and filtered and washed thoroughly with water and ether then dried to give a white solid (86.9 mg, 24%). ¹H NMR (400 MHz, METHANOL-d4) δ ppm 0.81-0.90 (m, 9 H), 1.19-1.70 (m, 10 H), 2.19 (d, J=13.99 Hz, 2 H), 2.67 (s, 2 H), 4.45 (s, 2 H), 4.78 (t, J=2.45 Hz, 1 H), 7.26 (dd, J=8.91, 2.45 Hz, 1 H), 7.31 (d, J=2.26 Hz, 1 H), 7.53 (dd, J=8.50, 1.73 Hz, 1 H), 7.86 (dd, J=8.69, 3.42 Hz, 2 H), 7.96 (s, 1 H).

Example 98

Synthesis of ethyl 3-methylpiperidine-4-carboxylate hydrochloride:

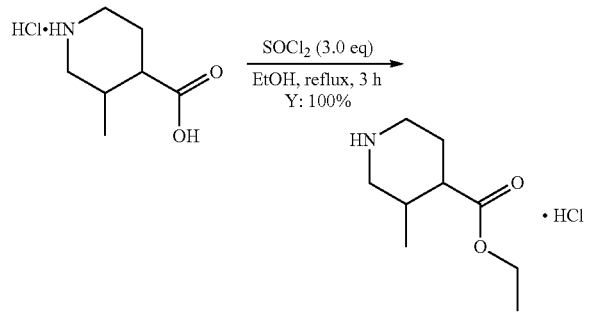

The mixture of 3-methylpiperidine-4-carboxylic acid hydrochloride (3.3 g, 18.4 mmol, 1.0 eq) and SOCl₂ (6.6 g, 55.3 mmol, 3.0 equiv) in EtOH (30 mL) was stirred at reflux for 3 h, and then the reaction mixture was concentrated by vacuum to give compound ethyl 3-methylpiperidine-4-carboxylate hydrochloride as a yellow oil which was used for next step. ESI-MS (M+H)⁺: 172.2.

Example 99

Synthesis of ethyl 1-((6-((trans-4-(tert-butyl)cyclohexyl)oxy)naphthalen-2-yl)methyl)-3-methylpiperidine-4-carboxylate:

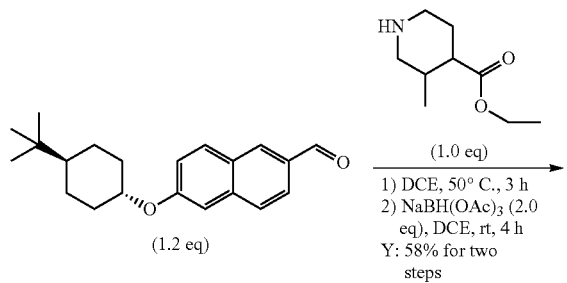

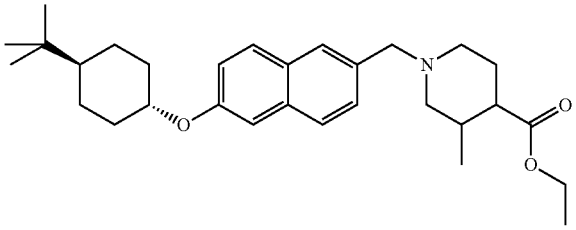

The mixture of 6-((trans-4-(tert-butyl)cyclohexyl)oxy)-2-naphthaldehyde (6.85 g, 22.10 mmol, 1.2 eq) and ethyl 3-methylpiperidine-4-carboxylate hydrochloride (3.15 g, 18.42 mmol, 1.0 equiv) in anhydrous DCE (30 mL) was stirred at 50° C. for 3 h, and then cooled to room temperature, NaBH(OAc)₃ (7.81 g, 36.84 mmol, 2.0 equiv) was added. The resulted mixture was stirred at room temperature for 4 h. The reaction mixture was adjusted to pH=7 with aq. Na₂CO₃. Then the mixture was diluted with water (20 mL) and extracted with DCM (30 mL×3). The combined organic layers were dried over anhydrous Na₂SO₄ and concentrated in vacuum to give the residue, which was purified by silica gel column chromatography (PE/EA=5:1) to give ethyl 1-((6-((trans-4-(tert-butyl)cyclohexyl)oxy)naphthalen-2-yl)methyl)-3-methylpiperidine-4-carboxylate as a yellow oil (5.0 g, Y: 58% for two steps). ESI-MS (M+H)⁺: 466.2. ¹H NMR (400 MHz, CDCl₃) (mixture of isomers) δ ppm 7.63-7.56 (m, 3H), 7.38-7.37 (m, 1H), 7.07-7.03 (m, 2H), 4.21-4.16 (m, 1H), 4.09-4.03 (m, 2H), 3.58-3.41 (m, 2H), 2.82-2.78 (m, 1H), 2.62-2.59 (m, 1H), 2.44-2.38 (m, 1H), 2.22-1.80 (m, 8H), 1.64-1.52 (m, 1H), 1.40-1.31 (m, 2H), 1.17 (t, J=6.8 Hz, 3H), 1.13-1.02 (m, 3H), 0.93 (d, J=6.8 Hz, 3H), 0.82 (s, 9H).

Example 100

1-((6-((trans-4-(tert-butyl)cyclohexyl)oxy)naphthalen-2-yl)methyl)-3-methylpiperidine-4-carboxylic acid

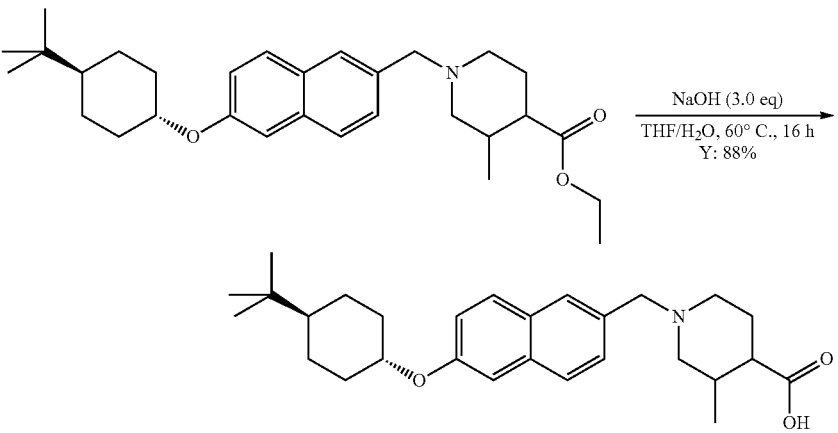

To a solution of ethyl 1-((6-((trans-4-(tert-butyl)cyclohexyl)oxy)naphthalen-2-yl)methyl)-3-methylpiperidine-4-carboxylate (750 mg, 1.62 mmol, 1.0 eq) in THF/H₂O (8/1, 9.0 mL) was added NaOH (130 mg, 3.24 mmol, 2.0 eq). The mixture was heated to 60° C. and stirred for 16 h. After cooling down to room temperature, the reaction mixture was adjusted to pH=7 with aq. HCl. The solvent was removed in vacuo to give the residue, which was purified by silica gel (DCM/MeOH=15:1) to give 1-((6-((trans-4-(tert-butyl)cyclohexyl)oxy)naphthalen-2-yl)methyl)-3-methylpiperidine-4-carboxylic acid as a white solid (620 mg, Y: 88%). ESI-MS (M+H)⁺: 438.3. HPLC: 100.00%; ¹H NMR (400 MHz, CDCl₃) δ ppm 10.82 (br, 1H), 7.65-7.54 (m, 3H), 7.41-7.40 (m, 1H), 7.04-7.02 (m, 2H), 4.20-4.14 (m, 1H), 3.85 (s, 2H), 3.15-3.07 (m, 2H), 2.77-2.71 (m, 1H), 2.50-2.46 (m, 1H), 2.18-2.16 (m, 3H), 1.96-1.92 (m, 2H), 1.81-1.78 (m, 2H), 1.36-0.96 (m, 9H), 0.82 (s, 9H).

1-[6-(4-tert-Butyl-cyclohexyloxy)-naphthalen-2-ylmethyl]-3-methyl-piperidine-4-carboxylic acid (2.8 g, 6.4 mmol) was separated with SFC on IC (2×15 cm) under 20% ethanol(0.2% DEA)/CO₂, (100 bar, 60 mL/min, 220 nm. inj vol.: 1 mL, 3 mg/mL 1:2 DCM: methanol) yielded 1.4 g of isomer-1 (chemical purity >95%, ee >99%), and 1.4 g of isomer 2 (chemical purity >99%, ee >99%). Isomer-1: LCMS Rt=1.66 min, m/z=438.20. ¹H NMR (400 MHz, METHANOL-d4) δ ppm 7.75 (d, J=6.53 Hz, 3H), 7.47 (d, J=8.53 Hz, 1H), 7.25 (s, 1H), 7.13 (d, J=8.78 Hz, 1H), 4.36 (t, J=11.42 Hz, 1H), 3.62 (q, J=7.19 Hz, 4H), 2.84-3.06 (m, 4H), 1.10-2.46 (m, 22H), 1.06 (d, J=6.8 Hz, 3H), 0.94 (s, 12H);

Isomer-2: LCMS Rt=1.66 min, m/z=438.20. ¹H NMR (400 MHz, METHANOL-d4) δ ppm 7.75 (d, J=6.53 Hz, 3H), 7.47 (d, J=8.53 Hz, 1H), 7.25 (s, 1H), 7.13 (d, J=8.78 Hz, 1H), 4.36 (t, J=11.42 Hz, 1H), 3.62 (q, J=7.19 Hz, 4H), 2.84-3.06 (m, 4H), 1.10-2.46 (m, 22H), 1.06 (d, J=6.8 Hz, 3H), 0.94 (s, 12H).

Example 101 ethyl 1-((6-(((1R,2S,5R)-2-isopropyl-5-methylcyclohexyl)oxy)naphthalen-2-yl)methyl)piperidine-4-carboxylate

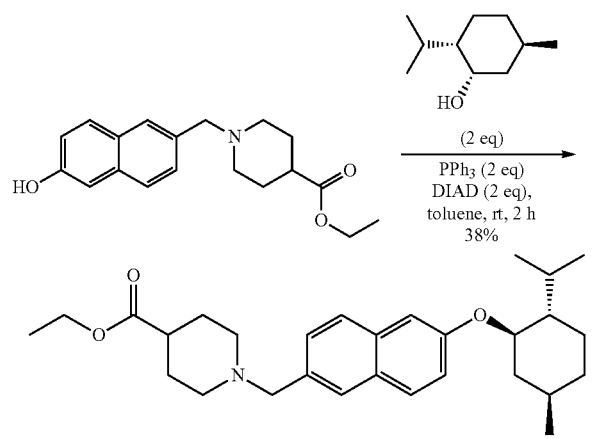

The preparation of ethyl 1-((6-(((1R,2S,5R)-2-isopropyl-5-ethylcyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 82 mg, slight yellow oil, yield: 38%. ESI-MS (M+1)⁺: 452.2. ¹H NMR (400 MHz, CDCl₃) δ: 7.66-7.63 (m, 3H), 7.40-7.39 (m, 1H), 7.08-7.05 (m, 2H), 4.12-4.03 (m, 3H), 3.54 (s, 2H), 2.84-2.80 (m, 1H), 2.25-2.15 (m, 2H), 1.81-1.69 (m, 1H), 1.70-1.66 (m, 2H), 1.25-1.15 (m, 11H), 1.10-0.91 (m, 4H), 0.87 (d, J=6.8 Hz, 6H), 0.71 (d, J=6.8 Hz, 3H).

Example 102

1-((6-(((1R,2S,5R)-2-isopropyl-5-methylcyclohexyl)oxy)naphthalen-2-yl)methyl)piperidine-4-carboxylic acid

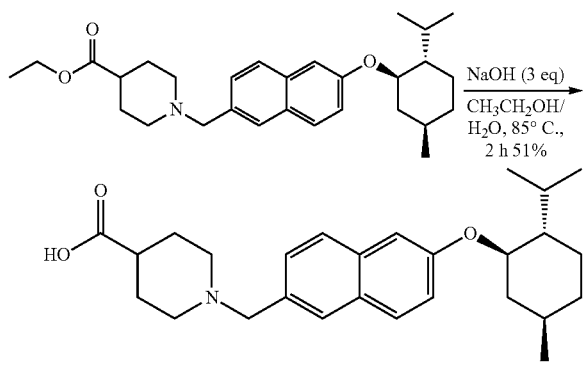

The preparation of 1-((6-(((1R,2S,5R)-2-isopropyl-5-methylcyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 62 mg, slight yellow solid, yield: 51%. ESI-MS (M+1)+: 424.4, HPLC: 98.67%. ¹H NMR (400 MHz, DMSO-d₆) δ: 7.80-7.73 (m, 3H), 7.44-7.37 (m, 2H), 7.14 (d, J=7.6 Hz, 1H), 4.30 (t, J=6.4 Hz, 1H), 3.44 (s, 2H), 2.86-2.81 (m, 2H), 2.19-2.12 (m, 3H), 1.84-1.81 (m, 2H), 1.73-1.47 (m, 6H), 1.26-1.12 (m, 3H), 1.02-0.96 (m, 2H), 0.90 (d, J=6.8 Hz, 6H), 0.75 (d, J=7.2 Hz, 3H).

Example 103 ethyl 1-((6-((4,4-dimethylcyclohexyl)oxy)naphthalen-2-yl)methyl)piperidine-4-carboxylate

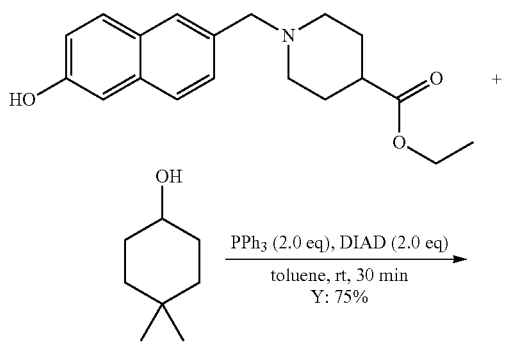

-continued

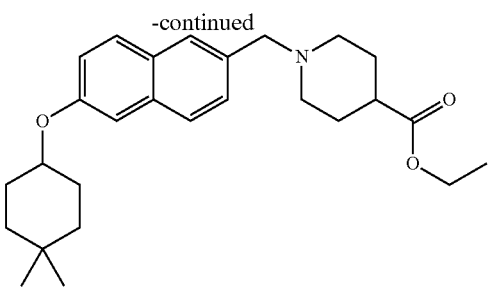

The preparation of ethyl 1-((6-((4,4-dimethylcyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 400 mg, yellow oil, Y: 75%. ESI-MS (M+H)$^+$: 424.1. $^1$H NMR (400 MHz, CDCl$_3$) δ: 7.45-7.38 (m, 3H), 7.18 (d, J=8.4 Hz, 1H), 6.89-6.82 (m, 2H), 4.14-4.09 (m, 1H), 3.87 (q, J=7.6 Hz, 2H), 3.35-3.25 (m, 3H), 2.63-2.57 (m, 2H), 2.58-2.54 (m, 1H), 2.09-1.72 (m, 7H), 1.00-0.93 (m, 6H), 0.74-0.72 (m, 6H), 0.68-0.65 (m, 3H).

Example 104

1-((6-((4-dimethylcyclohexyl)oxy)naphthalen-2-yl)methyl)piperidine-4-carboxylic acid

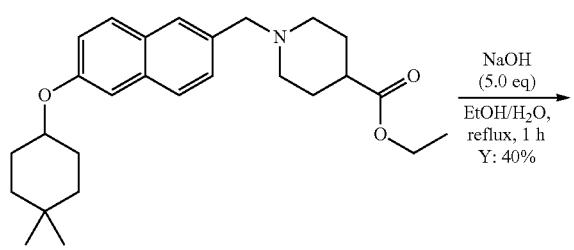

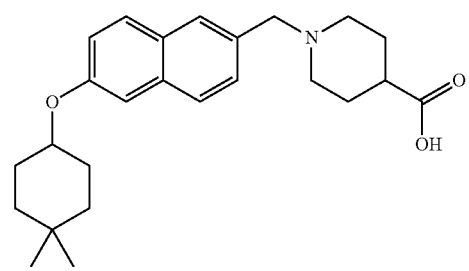

The preparation of 1-((6-((4,4-dimethylcyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 150 mg, a slight yellow solid, Y: 40%. ESI-MS (M+H)$^+$: 396.3, HPLC: 100.00%. $^1$H NMR (400 MHz, CD$_3$OD) δ: 7.94 (s, 1H), 7.87 (d, J=8.4 Hz, 1H), 7.84 (d, J=9.2 Hz, 1H), 7.51 (dd, J=8.8, 1.6 Hz, 1H), 7.30 (d, J=2.0 Hz, 1H), 7.22 (dd, J=9.2, 2.4 Hz, 1H), 4.56-4.51 (m, 1H), 4.44 (s, 2H), 3.58-3.55 (m, 2H), 3.09-3.04 (m, 2H), 2.63-2.60 (m, 1H), 2.23-2.21 (m, 2H), 1.98-1.74 (m, 6H), 1.59-1.54 (m, 2H), 1.41-1.37 (m, 2H), 1.01 (d, J=3.6 Hz, 6H).

Example 105 ethyl 1-((6-((4-propylcyclohexyl)oxy)naphthalen-2-yl)methyl)piperidine-4-carboxylate

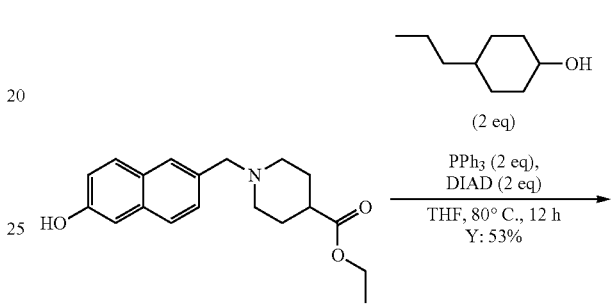

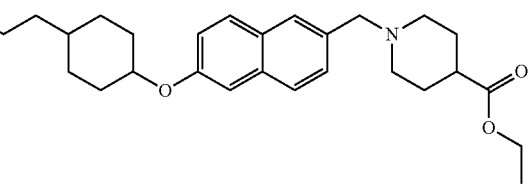

The preparation of ethyl 1-((6-((4-propylcyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 370 mg, a yellow solid, yield: 53%, ESI-MS (M+1)$^+$: 438.2. $^1$HNMR (400 MHz, CDCl$_3$) (mixture of cis and trans isomers) δ: 7.92 (s, 1H), 7.88-7.82 (m, 2H), 7.50 (d, J=8.8 Hz, 1H), 7.31 (s, 1H), 7.20 (d, J=8.8 Hz, 1H), 4.58-4.55 (m, 0.4H), 4.22-4.20 (m, 0.4H), 4.13 (q, J=7.2 Hz, 2H), 3.55-3.54 (m, 1H), 3.12-3.00 (m, 2H), 2.66-2.60 (m, 2H), 2.25-2.23 (m, 3H), 2.08-2.01 (m, 2H), 1.93-1.90 (m, 3H), 1.57-1.52 (m, 1H), 1.44-1.15 (m, 13H), 0.94 (t, J=7.2 Hz, 3H).

Example 106

1-((6-((4-propylcyclohexyl)oxy)naphthalen-2-yl)methyl)piperidine-4-carboxylic acid

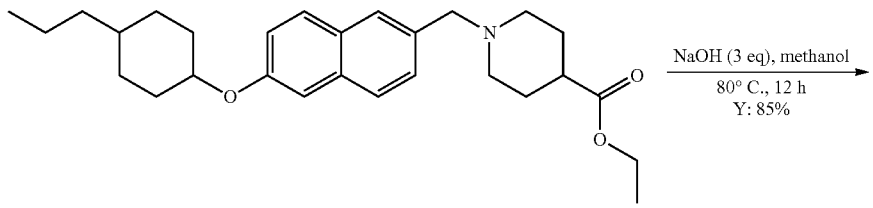

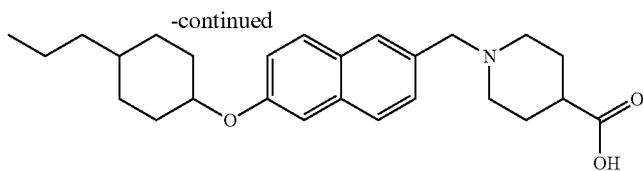

The preparation of 1-((6-(((4-propylcyclohexyl)oxy)naphthalen-2-yl)methyl)piperidine-4-carboxylic acid was the same as that of 1-((6-(((cis-4-phenylcyclohexyl)oxy)naphthalen-2-yl)methyl)piperidine-4-carboxylic acid. 120 mg, yield: 85%. ESI-MS (M+1)⁺: 410.3. HPLC: 100%. ¹H NMR (400 MHz, CD₃OD) (mixture of cis and trans isomers) δ: 7.92 (s, 1H), 7.89-7.81 (m, 2H), 7.50 (dd, J=8.8, 2.0 Hz, 1H), 7.30 (s, 1H), 7.19 (d, J=8.8 Hz, 1H), 4.82-4.80 (m, 0.4H), 4.44 (s, 2H), 4.43-4.40 (m, 0.6H), 3.55-3.52 (m, 1H), 3.10-3.09 (m, 2H), 2.64-2.62 (m, 1H), 2.24-2.22 (m, 3H), 2.08-2.02 (m, 1H), 1.91-1.88 (m, 3H), 1.59-1.50 (m, 1H), 1.44-1.13 (m, 10H), 0.93 (t, J=7.2 Hz, 3H).

Example 107 ethyl 1-((6-cyclobutoxynaphthalen-2-yl)methyl)piperidine-4-carboxylate

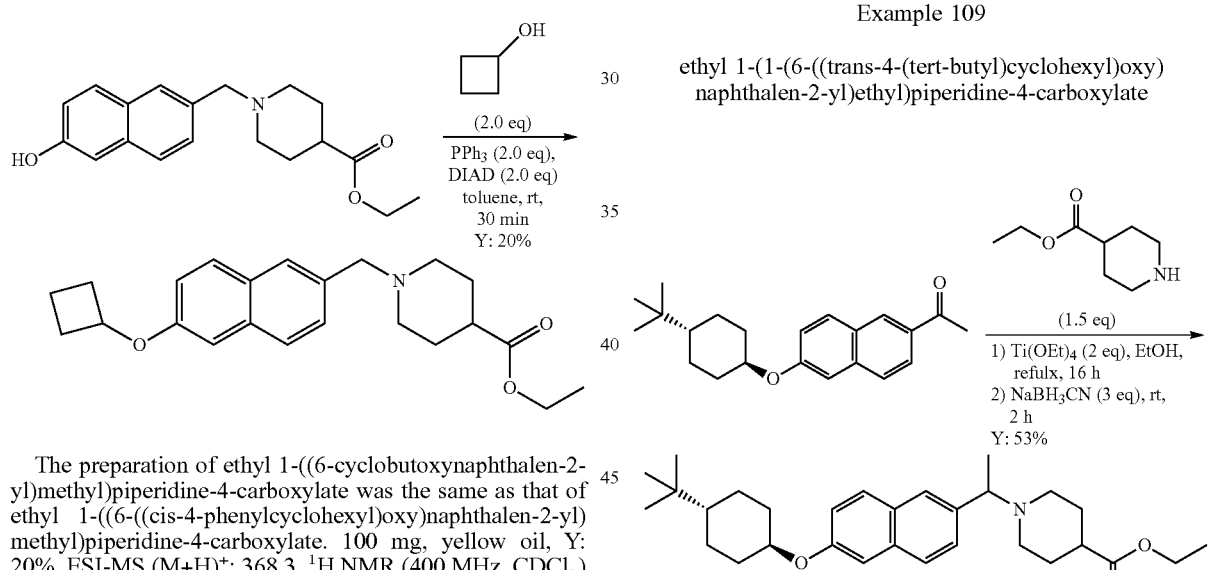

The preparation of ethyl 1-((6-cyclobutoxynaphthalen-2-yl)methyl)piperidine-4-carboxylate was the same as that of ethyl 1-((6-(((cis-4-phenylcyclohexyl)oxy)naphthalen-2-yl)methyl)piperidine-4-carboxylate. 100 mg, yellow oil, Y: 20%. ESI-MS (M+H)⁺: 368.3. ¹H NMR (400 MHz, CDCl₃) δ: 7.71-7.67 (m, 3H), 7.43 (d, J=10 Hz, 1H), 7.09 (d, J=8.8 Hz, 1H), 6.99 (s, 1H), 4.81-4.76 (m, 1H), 4.14 (q, J=7.2 Hz, 2H), 3.92 (t, J=6.4 Hz, 1H), 3.61 (s, 2H), 2.90-2.87 (m, 2H), 2.55-2.52 (m, 1H), 2.27-2.20 (m, 2H), 2.05-2.02 (m, 3H), 1.80-1.76 (m, 5H), 1.26-1.23 (m, 5H).

Example 108

1-((6-cyclobutoxynaphthalen-2-yl)methyl)piperidine-4-carboxylic acid

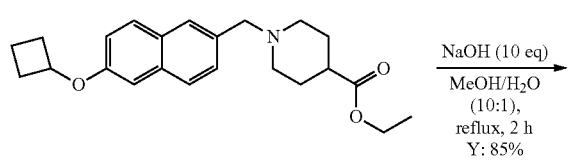

The preparation of 1-((6-cyclobutoxynaphthalen-2-yl)methyl)piperidine-4-carboxylic acid was the same as that of 1-((6-(((cis-4-phenylcyclohexyl)oxy)naphthalen-2-yl)methyl)piperidine-4-carboxylic acid. 80 mg, yellow oil, Y: 85%. ESI-MS (M+H)⁺: 340.3, HPLC: 97.37%. ¹H NMR (400 MHz, CDCl₃) δ: 7.93 (s, 1H), 7.87-7.81 (m, 2H), 7.51 (dd, J=8.0, 1.2 Hz, 1H), 7.19-7.15 (m, 2H), 4.86-4.83 (m, 1H), 4.42 (s, 2H), 3.48 (br, 2H), 3.15 (br, 2H), 2.58-2.55 (m, 3H), 2.21-2.16 (m, 4H), 1.81-1.78 (m, 4H).

Example 109 ethyl 1-(1-(6-(((trans-4-(tert-butyl)cyclohexyl)oxy)naphthalen-2-yl)ethyl)piperidine-4-carboxylate A mixture of 1-(6-(((trans-4-(tert-butyl)cyclohexyl)oxy)naphthalen-2-yl)ethanone (200 mg, 0.62 mmol) and ethyl 4-piperidinecarboxylate (146 mg, 0.93 mmol, 1.5 eq) in anhydrous EtOH (5 mL) was stirred at room temperature for 15 min, then Ti(OEt)₄ (356 mg, 1.23 mmol, 2 eq) was added. The reaction mixture was stirred at reflux for 16 h under N₂. After cooling to room temperature, the mixture was concentrated and the residue was dissolved in EtOH (3 mL) and NaBH₃CN (125 mg, 1.85 mmol, 3 eq) was added. The reaction mixture was stirred at room temperature for 2 h. The mixture was concentrated and purified by silica gel (PE/EA=4/1) to give ethyl 1-(1-(6-(((trans-4-(tert-butyl)cyclohexyl)oxy)naphthalen-2-yl)ethyl)piperidine-4-carboxylate as yellow oil (140 mg, yield: 53%). ESI-MS (M+H⁺): 466.4. ¹H NMR (400 MHz, CDCl₃) δ: 7.71-7.65 (m, 2H), 7.60 (s, 1H), 7.44 (d, J=8.0 Hz, 1H), 7.14-7.11 (m, 2H), 4.29-4.24

(m, 1H), 4.11 (q, J=7.2 Hz, 2H), 3.56 (br, 1H), 3.07 (br, 1H), 2.84 (br, 1H), 2.29-2.20 (m, 3H), 2.08-2.01 (m, 4H), 1.90-1.81 (m, 5H), 1.45-1.38 (m, 5H), 1.26-1.09 (m, 6H), 0.89 (s, 9H).

Example 110

1-(1-(6-((trans-4-(tert-butyl)cyclohexyl)oxy)naphthalen-2-yl)ethyl)piperidine-4-carboxylic acid

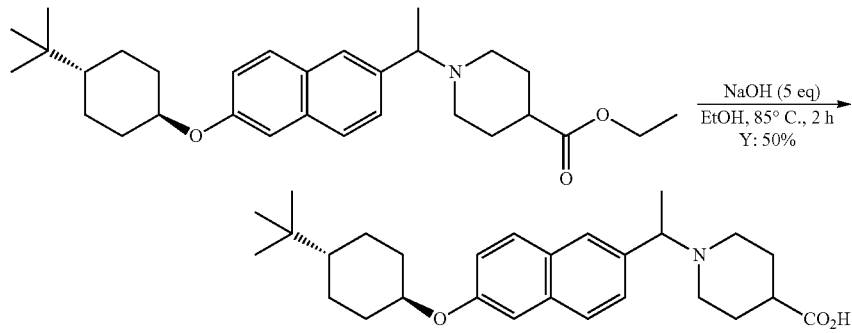

Ethyl 1-(1-(6-((trans-4-(tert-butyl)cyclohexyl)oxy)naphthalen-2-yl)ethyl)piperidine-4-carboxylate (100 mg, 0.22 mmol) was dissolved in EtOH (5 mL). Then sodium hydroxide (44 mg, 1.1 mmol, 5.0 eq) in water (0.5 mL) was added. The mixture was stirred at 85 ° C. for 2 h. Solvent was removed and the residue was dissolved in H₂O (3 mL). 1M aqueous HCl was added to adjust pH=7. The mixture was filtrated to give 1-(1-(6-((trans-4-(tert-butyl)cyclohexyl)oxy)naphthalen-2-yl)ethyl)piperidine-4-carboxylic acid as white solid (50 mg, 50%). ESI-MS (M+H⁺): 438.3. HPLC: 100%. ¹H NMR (400 MHz, CD₃OD) δ: 7.80-7.78 (m, 2H), 7.34 (d, J=8.8 Hz, 1H), 7.42 (dd, J=8.4, 1.6 Hz, 1H), 7.22 (d, J=2.0 Hz, 1H), 7.11 (dd, J=8.8, 2.0 Hz, 1H), 4.37-4.28 (m, 2H), 3.24-3.17 (m, 2H), 2.82-2.76 (m, 2H), 2.23-2.19 (m, 3H), 1.97-1.84 (m, 5H), 1.71 (d, J=6.8 Hz, 3H), 1.41-1.32 (m, 2H), 1.26-1.16 (m, 3H), 1.10-1.04 (m, 1H), 0.86 (s, 9H).

Example 111

1-(tert-butyl)-4-methylenecyclohexane

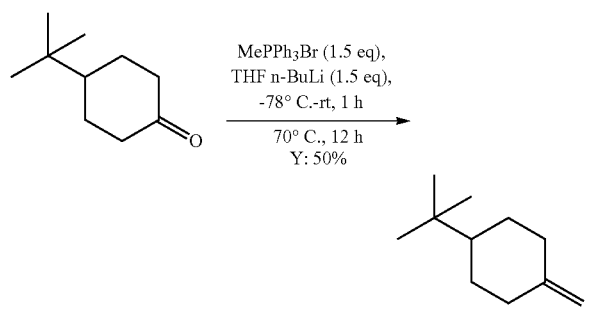

To a solution of methyltriphenylphosphonium bromide (5.36 g, 15 mmol, 1.5 eq) in dried THF (40 mL) was added n-BuLi (2.5 M) (6 mL, 15 mmol, 1.5 eq) at −78° C. The mixture was stirred at room temperature for 1 h. The solution of 4-(tert-butyl)cyclohexanone (1.54 g, 10 mmol) in THF (10 mL) was added to the reaction mixture at −78° C. The mixture was stirred at 70° C. for 12 h. The solvent was removed and the residue was suspended in hexane. The mixture was filtered, and the filtrate was concentrated to give 1-(tert-butyl)-4-methylenecyclohexane as yellow oil (0.80 g, yield: 50%). ¹HNMR (400 MHz, CDCl₃) δ: 4.58 (s, 2H), 2.34-2.31 (m, 2H), 2.01-1.95 (m, 2H), 1.88-1.84 (m, 2H), 1.14-1.06 (m, 3H), 0.86 (s, 9H).

Example 112 ethyl 1-((6-(((trifluoromethyl)sulfonyl)oxy)naphthalen-2-yl)methyl)piperidine-4-carboxylate

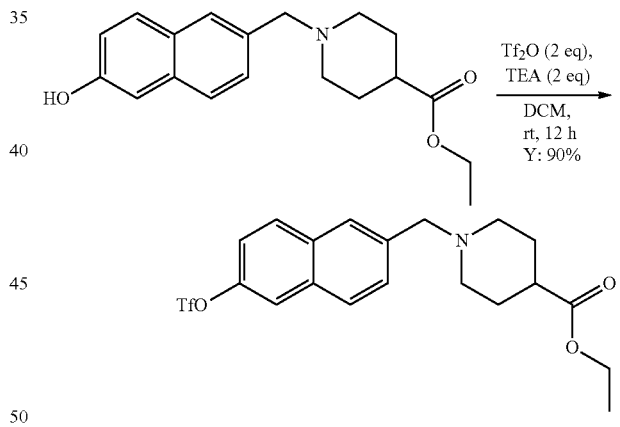

To a solution of ethyl 1-((6-hydroxynaphthalen-2-yl)methyl)piperidine-4-carboxylate (1 g, 3.19 mmol) and TEA (0.64 g, 6.38 mmol, 2 eq) in DCM (20 mL) was added Tf₂O (1.8 g, 6.38 mmol, 2 eq) dropwise at 0° C. The mixture was stirred at room temperature for 12 h. The reaction was quenched with water at 0° C., washed with sat. NaHCO₃ (10 mL) and brine (5 mL×3). The organic layer was dried over Na₂SO₄ and concentrated to afford ethyl 1-((6-(((trifluoromethyl)sulfonyl)oxy)naphthalen-2-yl)methyl)piperidine-4-carboxylate as a brown solid (350 mg, yield: 90%). ESI-MS: 446.1 (M+H)⁺. ¹HNMR (400 MHz, CDCl₃) δ: 7.88 (d, J=9.2 Hz, 1H), 7.84-7.82 (m, 2H), 7.79 (s, 1H), 7.60 (d, J=7.6 Hz, 1H), 7.35 (d, J=9.2 Hz , 1H), 4.13 (q, J=7.6 Hz, 2H), 3.66 (s, 2H), 2.89-2.86 (m, 2H), 2.32-2.28 (m, 1H), 2.11-2.07 (m, 2H), 1.88-1.78 (m, 4H), 1.26 (t, J=7.6 Hz, 3H).

Example 113 ethyl 1-((6-(((4-(tert-butyl)cyclohexylidene)methyl)naphthalen-2-yl)methyl)piperidine-4-carboxylate

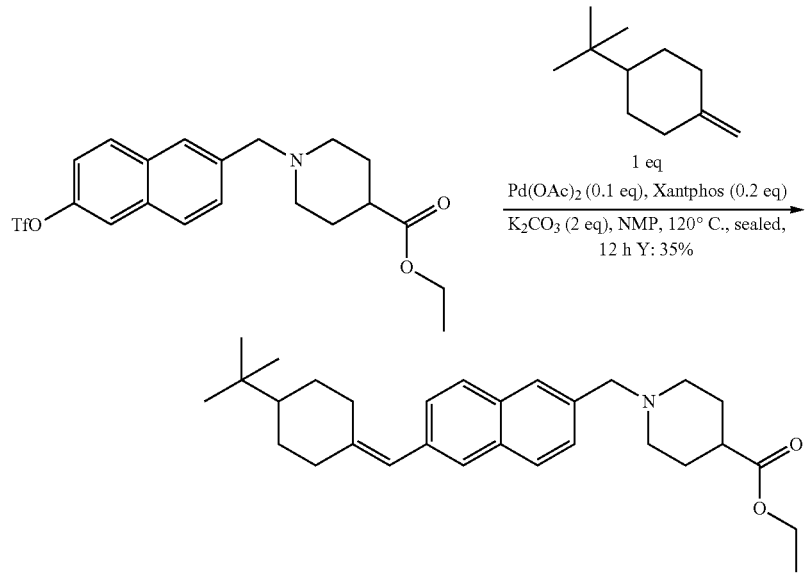

Into a sealed tube were added ethyl 1-((6-((((trifluoromethyl)sulfonyl)oxy)naphthalen-2-yl)methyl)piperidine-4-carboxylate (500 mg, 1.12 mmol), 1-(tert-butyl)-4-methylenecyclohexane (340 mg, 2.24 mmol, 2 eq), K$_2$CO$_3$ (309 mg, 2.24 mmol, 2 eq), Xantphos (130 mg, 0.22 mmol, 0.2 eq), Pd(OAc)$_2$ (25 mg, 0.11 mmol, 0.1 eq) and NMP (2 mL). The mixture was flushed with N$_2$ for 5 min. Then the reaction was stirred at 120° C. for 12 h. The reaction mixture was diluted with ethyl acetate (20 mL) and washed with water (5 mL×3). The organic solvent was removed in vacuum and the residue was purified by silica gel chromatography (petroleum ether: ethyl acetate=2:1) to give ethyl 1-((6-((4-(tert-butyl)cyclohexylidene)methyl)naphthalen-2-yl)methyl)piperidine-4-carboxylate (180 mg, yield: 35%) as a yellow solid. ESI-MS (M+1)$^+$: 448.3. $^1$H NMR (400 MHz, CDCl$_3$) δ: 7.76-7.73 (m, 2H), 7.68 (s, 1H), 7.61 (s, 1H), 7.46 (d, J=8.0 Hz, 1H), 7.34 (d, J=8.8 Hz, 1H), 6.34 (s, 1H), 4.13 (q, J=8.8 Hz, 2H), 3.64 (s, 2H), 2.92-2.89 (m, 2H), 2.30-2.25 (m, 2H), 2.08-2.05 (m, 2H), 1.94-1.77 (m, 8H), 1.60 (br, 2H), 1.26-1.23 (m, 5H), 0.87 (s, 9H).

Example 114 ethyl 1-((6-((4-(tert-butyl)cyclohexyl)methyl)naphthalen-2-yl)methyl)piperidine-4-carboxylate

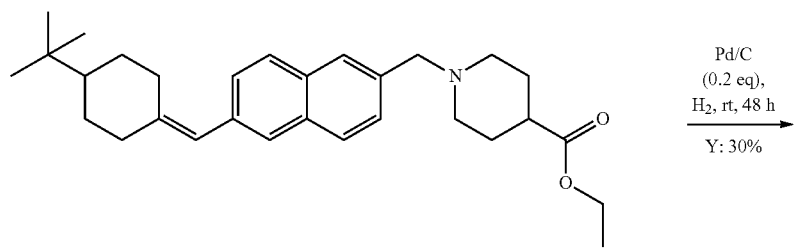

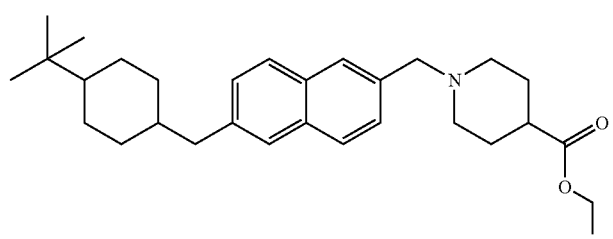

Into a 100 mL round bottom flask was added ethyl 1-((6-((4-(tert-butyl)cyclohexylidene)methyl)naphthalen-2-yl)methyl)piperidine-4-carboxylate (200 mg, 0.45 mmol), Pd/C (20%, 20 mg) and THF (30 mL). The reaction mixture was flushed 3 times with hydrogen gas and stirred for 48 h under H₂ atmosphere. The reaction mixture was filtered and the filtrate was concentrated in vacuum to afford the desired compound ethyl 1-((6-((4-(tert-butyl)cyclohexyl)methyl)naphthalen-2-yl)methyl)piperidine-4-carboxylate as purple oil (150 mg, yield: 30%). ESI-MS (M+1)⁺: 450.3.

Example 115

1-((6-((4-(tert-butyl)cyclohexyl)methyl)naphthalen-2-yl)methyl)piperidine-4-carboxylic acid

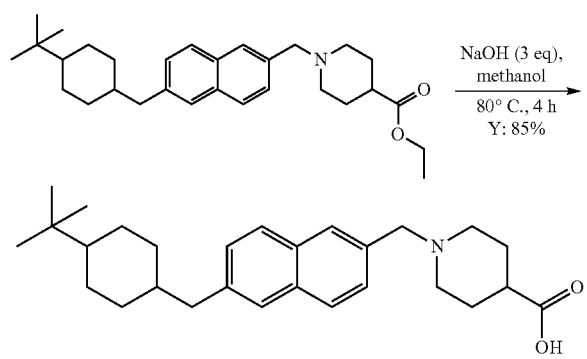

To a solution of ethyl 1-((6-((4-(tert-butyl)cyclohexyl)methyl)naphthalen-2-yl)methyl)piperidine-4-carboxylate (150 mg, 0.33 mmol) in MeOH (5 mL) was added NaOH (68 mg, 1.7 mmol, 5.0 eq) and H₂O (0.5 mL). The reaction mixture was stirred at 80° C. for 4 h. The pH of the solution was adjusted to 6 with 3 N HCl. The mixture was filtered and the yellow solid was purified by prep-HPLC (CH₃CN:H₂O/0.05% TFA=0-95%) to afford the desired product 1-((6-((4-(tert-butyl)cyclohexyl)methyl)naphthalen-2-yl)methyl)piperidine-4-carboxylic acid (120 mg, 85%). ESI-MS (M+1)⁺: 422.3. ¹H NMR (400 MHz, CD₃OD) δ: 7.89 (s, 1H), 7.84~7.81 (m, 1H), 7.77-7.74 (m, 1H), 7.58 (d, J=10 Hz, 1H), 7.43 (d, J=8.8 Hz, 1H), 7.35~7.32 (m, 1H), 4.36 (s, 2H), 3.50~3.46 (m, 2H), 3.22-3.20 (m, 2H), 2.77-2.75 (m, 1H), 2.58-2.56 (m, 2H), 2.15-2.11 (m, 2H), 1.91 (br, 1H), 1.75-1.66 (m, 3H), 1.56-1.25 (m, 6H), 1.00-0.88 (m, 2H), 0.81 (s, 9H). HPLC: 96.20%

Example 116 ethyl 1-((6-((tetrahydrofuran-3-yl)oxy)naphthalen-2-yl)methyl)piperidine-4-carboxylate

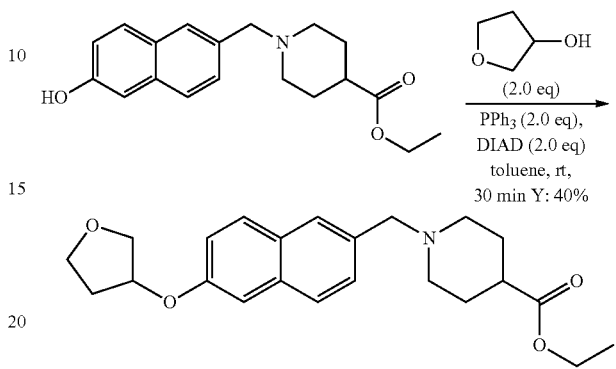

The preparation of ethyl 1-((6-((tetrahydrofuran-3-yl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 150 mg, yellow oil, Y: 40%. ESI-MS (M+H)⁺: 384.2. ¹H NMR (400 MHz, CDCl₃) δ: 7.65-7.60 (m, 3H), 7.38 (d, J=8.4 Hz, 1H), 7.06 (dd, J=8.8, 2.4 Hz, 1H), 6.97 (s, 1H), 4.93-4.91 (m, 1H), 4.89-4.85 (m, 2H), 4.03-3.98 (m, 5H), 3.87-3.84 (m, 1H), 3.55 (s, 2H), 2.84-2.81 (m, 2H), 2.22-2.15 (m, 3H), 2.02-1.98 (m, 3H), 1.80-1.70 (m, 4H).

Example 117

1-((6-((tetrahydrofuran-3-yl)oxy)naphthalen-2-yl)methyl)piperidine-4-carboxylic acid

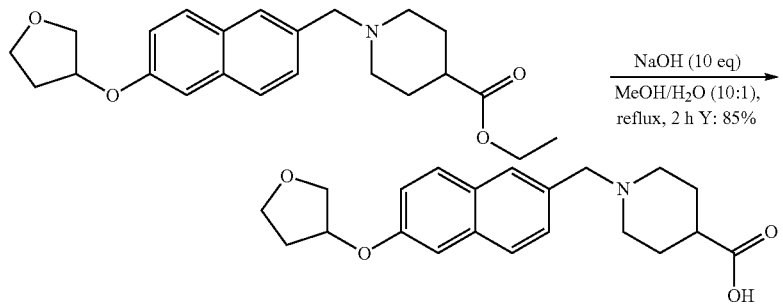

The preparation of 1-((6-((tetrahydrofuran-3-yl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 100 mg, a slight yellow solid, Y: 85%. ESI-MS (M+H)⁺: 356.1, HPLC: 100.0%. ¹H NMR (400 MHz, CD₃OD) δ: 7.94 (s, 1H), 7.89-7.83 (m, 2H), 7.43 (dd, J=8.4, 1.6 Hz, 1H), 7.25 (s, 1H), 7.20 (dd, J=8.8, 2.4 Hz, 1H), 5.17-5.14 (m, 1H), 4.43 (s, 2H), 4.04-3.99 (m, 3H), 3.92-3.89 (m, 1H), 3.52-3.50 (m, 2H), 3.15-3.12 (m, 2H), 2.68-2.65 (m, 1H), 2.34-2.30 (m, 1H), 2.18-2.14 (m, 3H), 2.00-1.94 (m, 2H).

Example 118 ethyl 1-((6-(cyclohexyloxy)naphthalen-2-yl)methyl)piperidine-4-carboxylate

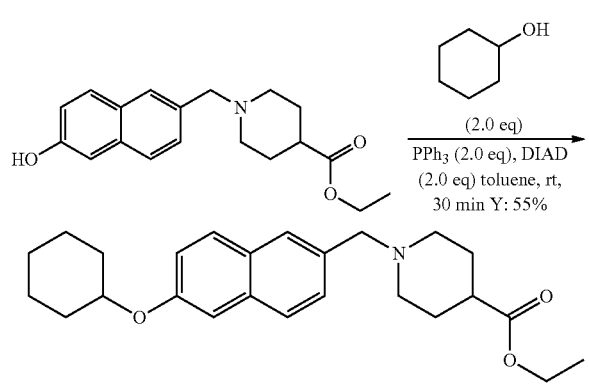

The preparation of ethyl 1-((6-(cyclohexyloxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 200 mg, a yellow solid, Y: 55%. ESI-MS (M+H)$^+$: 396.1. $^1$H NMR (400 MHz, CDCl$_3$) δ: 7.72-7.65 (m, 3H), 7.44 (d, J=8.4 Hz, 1H), 7.16-7.13 (m, 2H), 4.41-4.39 (m, 1H), 4.13 (q, J=7.2 Hz, 2H), 3.62 (s, 2H), 2.92-2.89 (m, 2H), 2.31-2.29 (m, 2H), 2.09-2.06 (m, 4H), 1.91-1.78 (m, 7H), 1.64-1.56 (m, 4H), 1.27-1.25 (m, 3H).

Example 119

1-((6-(cyclohexyloxy)naphthalen-2-yl)methyl)piperidine-4-carboxylic acid

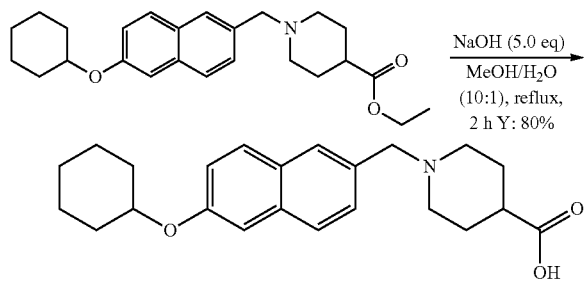

The preparation of 1-((6-(cyclohexyloxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 130 mg, a slight yellow solid, Y: 80%. ESI-MS (M+H)$^+$: 368.3, HPLC: 99.06%. $^1$H NMR (400 MHz, CD$_3$OD) δ: 7.92 (s, 1H), 7.88-7.82 (m, 2H), 7.50 (dd, J=8.8, 1.6 Hz, 1H), 7.30 (s, 1H), 7.21 (dd, J=8.8, 2.4 Hz, 1H), 4.52-4.51 (m, 1H), 4.43 (s, 2H), 3.57-3.55 (m, 2H), 3.12-3.09 (m, 2H), 2.67-2.64 (m, 1H), 2.22-2.19 (m, 2H), 2.08-2.04 (m, 2H), 1.86-1.84 (m, 3H), 1.57-1.37 (m, 7H).

Example 120

6-((tert-butyldimethylsilyl)oxy)-2-methylquinoline

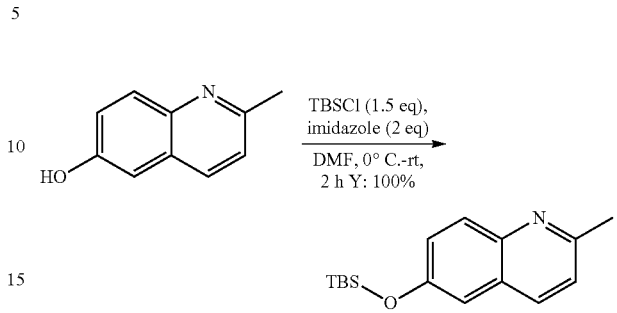

To a solution of 2-methylquinolin-6-ol (6.36 g, 40 mmol) and imidazole (5.44 g, 80 mmol, 2 eq) in DMF (100 mL) was added TBSCl (9 g, 60 mmol, 1.5 eq) at 0° C. Then the reaction mixture was warmed to room temperature and stirred for 1 h. The reaction mixture was diluted with ethyl acetate (200 mL), washed with H$_2$O (2×200 mL) and brine (200 mL). The combined organic layer was dried (Na$_2$SO$_4$) and concentrated to give the crude 6-((tert-butyldimethylsilyl)oxy)-2-methylquinoline as yellow solid (14 g, yield: 100%). ESI-MS (M+H)$^+$: 274.2. $^1$H NMR (400 MHz, CDCl$_3$) δ: 7.94-7.92 (m, 2H), 7.26 (dd, J=8.8, 2.0 Hz, 1H), 7.21 (d, J=8.4 Hz, 1H), 7.13 (d, J=2.4 Hz, 1H), 2.73 (s, 3H), 1.05 (s, 9H), 0.28 (s, 6H).

Example 121

6-((tert-butyldimethylsilyl)oxy)quinoline-2-carbaldehyde

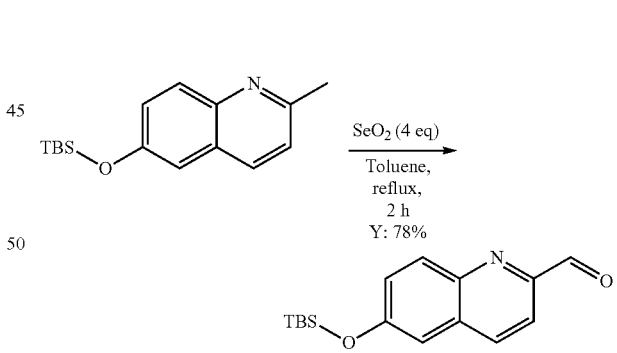

A mixture of 6-((tert-butyldimethylsilyl)oxy)-2-methylquinoline (6.5 g, 23.8 mmol) and SeO$_2$ (11 g, 95.2 mmol, 4 eq) in toluene (100 mL) was stirred at reflux for 2 h under N$_2$. After cooling down to room temperature, the mixture was filtered and the filtrate was concentrated to give 6-((tert-butyldimethylsilyl)oxy)quinoline-2-carbaldehyde as yellow solid (5.3 g, yield: 78%) which was used to the next step without further purification. ESI-MS (M+H)$^+$: 288.2. $^1$H NMR (400 MHz, CDCl$_3$) δ: 10.19 (s, 1H), 8.15-8.13 (m, 2H), 7.98 (d, J=8.4 Hz, 1H), 7.40 (dd, J=9.2, 2.8 Hz, 1H), 7.20 (d, J=2.8 Hz, 1H), 1.03 (s, 9H), 0.30 (s, 6H).

Example 122 ethyl 1-((6-((tert-butyldimethylsilyl)oxy)quinolin-2-yl)methyl)piperidine-4-carboxylate

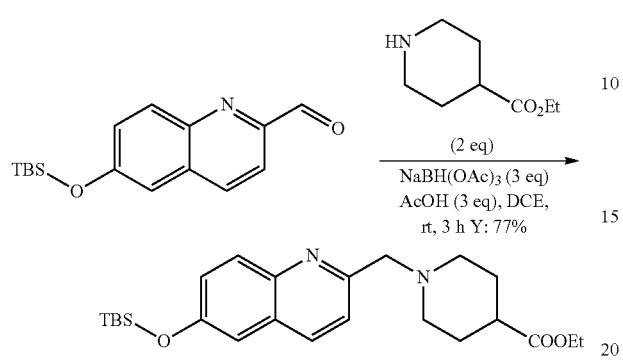

6-((tert-butyldimethylsilyl)oxy)quinoline-2-carbaldehyde (5.74 g, 20 mmol), AcOH (3.6 g, 60 mmol, 3 eq) and ethyl 4-piperidinecarboxylate (6.28 g, 40 mmol, 2 eq) in DCE (100 mL) were stirred at room temperature for 30 min. Then NaBH(OAc)$_3$ (12.7 g, 60 mmol, 3 eq) was added to the mixture at room temperature and stirred for 3 h. The reaction mixture was quenched with water (300 mL), and adjusted to pH=8 with conc. aq. NH$_3$ solution. Then the mixture was extracted with DCM (3×400 mL). The combined organic layer was washed by brine (300 mL), dried (Na$_2$SO$_4$) and concentrated. The crude product was purified by silica gel chromatography (PE: EA=4:1) to give ethyl 1-((6-((tert-butyldimethylsilyl)oxy)quinolin-2-yl)methyl)piperidine-4-carboxylate as yellow oil (6.65 g, yield: 77%). ESI-MS (M+H)$^+$: 429.3. $^1$H NMR (400 MHz, CDCl$_3$) δ: 7.97 (d, J=8.4 Hz, 1H), 7.94 (d, J=9.2 Hz, 1H), 7.57 (d, J=8.4 Hz, 1H), 7.27 (dd, J=9.2, 2.4 Hz, 1H), 7.12 (d, J=2.8 Hz, 1H), 4.12 (q, J=7.2 Hz, 2H), 3.78 (s, 2H), 2.92-2.89 (m, 2H), 2.30-2.25 (m, 1H), 2.20-2.15 (m, 2H), 1.91-1.79 (m, 4H), 1.25 (t, J=7.2 Hz, 3H), 1.02 (s, 9H), 0.25 (s, 6H).

Example 123 ethyl 1-((6-hydroxyquinolin-2-yl)methyl)piperidine-4-carboxylate

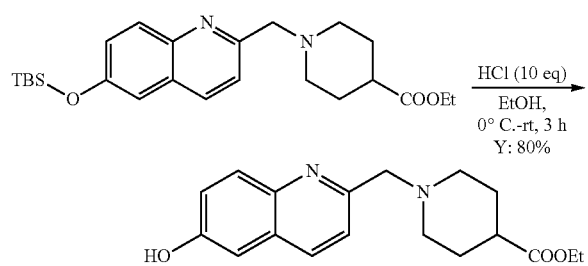

To a solution of ethyl 1-((6-((tert-butyldimethylsilyl)oxy)quinolin-2-yl)methyl)piperidine-4-carboxylate (6.5 g, 15.2 mmol) in ethanol (100 mL) was added concentrated HCl (13 mL) dropwise at 0° C. The reaction mixture was stirred at room temperature for 3 h. The mixture was neutralized by sat. NaHCO$_3$ and the solvent was removed. Then the mixture was extracted with DCM (3×30 mL). The combined organic layers were washed by brine (30 mL), dried over Na$_2$SO$_4$ and concentrated to give crude product ethyl 1-((6-hydroxyquinolin-2-yl)methyl)piperidine-4-carboxylate as a white solid (3.9 g, yield: 80%). ESI-MS (M+H)$^+$: 315.2. $^1$H NMR (400 MHz, CDCl$_3$) δ: 7.88 (d, J=8.8 Hz, 1H), 7.83 (d, J=8.8 Hz, 1H), 7.53 (d, J=8.4 Hz, 1H), 7.22 (dd, J=9.2, 2.4 Hz, 1H), 7.04 (s, 1H), 4.11 (q, J=7.2 Hz, 2H), 3.80 (s, 2H), 2.93-2.90 (m, 2H), 2.28-2.16 (m, 3H), 1.89-1.76 (m, 4H), 1.22 (t, J=7.2 Hz, 3H).

Example 124

Synthesis of ethyl 1-((6-(cyclohexyloxy)quinolin-2-yl)methyl)piperidine-4-carboxylate

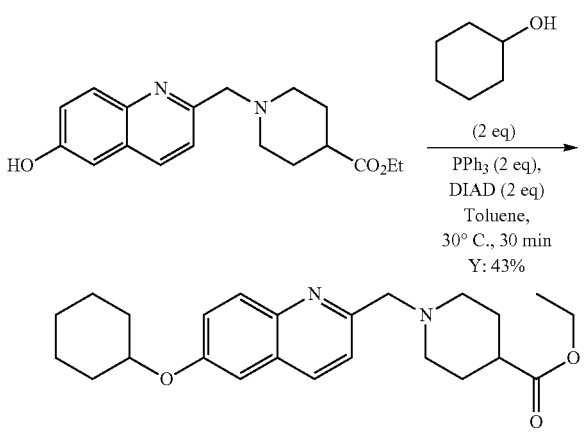

Into a 25 mL round bottom flask was added ethyl 1-((6-hydroxyquinolin-2-yl)methyl)piperidine-4-carboxylate (314 mg, 0.1 mmol), cyclohexanol (200 mg, 0.2 mmol, 2 eq), PPh$_3$ (562 mg, 0.2 mmol, 2 eq) and dry toluene (0.5 mL) under N$_2$. Then DIAD (404 mg, 0.2 mmol, 2 eq) was quickly added in one portion at room temperature. The reaction mixture was stirred at 30° C. for 30 min. The solvent was removed under reduced pressure and the residue was purified by silica gel column chromatography (PE: EA=4:1) to give ethyl 1-((6-(cyclohexyloxy)quinolin-2-yl)methyl)piperidine-4-carboxylate (168 mg, yield: 43%) as slight yellow oil. ESI-MS (M+H)$^+$: 397.2. $^1$H NMR (400 MHz, CDCl$_3$) δ: 7.99 (d, J=8.4 Hz, 1H), 7.94 (d, J=9.6 Hz, 1H), 7.69-7.64 (m, 1H), 7.33 (dd, J=8.8, 2.4 Hz, 1H), 7.07 (d, J=2.0 Hz, 1H), 4.43-4.37 (m, 1H), 4.13 (q, J=7.2 Hz, 2H), 3.78 (s, 2H), 2.93-2.89 (m, 2H), 2.08-2.03 (m, 3H), 1.87-1.82 (m, 4H), 1.63-1.55 (m, 5H), 1.46-1.26 (m, 5H), 1.23 (t, J=7.2 Hz, 3H).

Example 125

1-((6-(cyclohexyloxy)quinolin-2-yl)methyl)piperidine-4-carboxylic acid

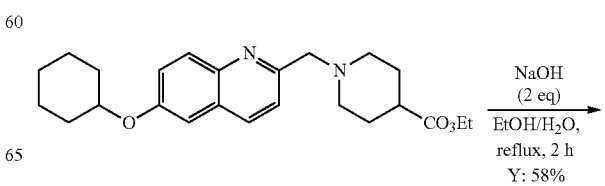

-continued

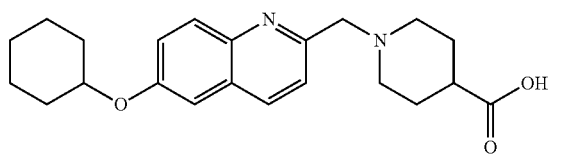

Ethyl 1-((6-(cyclohexyloxy)quinolin-2-yl)methyl)piperidine-4-carboxylate (117 mg, 0.30 mmol) was dissolved in EtOH (5 mL). NaOH (24 mg, 0.60 mmol, 2 eq) was added in one portion at room temperature. The mixture was stirred at reflux for 2 h. The solvent was removed and the residue was dissolved in H$_2$O (3 mL) and adjusted to pH=7 with HCl (1 M). The precipitate was collected and dried under vacuum to give 1-((6-(cyclohexyloxy)quinolin-2-yl)methyl)piperidine-4-carboxylic acid (40 mg, yield: 58%) as white solid. ESI-MS (M+H)$^+$: 369.2, HPLC: 97.89%. $^1$H NMR (400 MHz, CD$_3$OD) δ: 8.18 (d, J=8.8 Hz, 1H), 7.89 (d, J=9.2 Hz, 1H), 7.37 (d, J=8.4 Hz, 1H), 7.33 (dd, J=8.8, 2.4 Hz, 1H), 7.21 (d, J=2.4 Hz, 1H), 4.51 (s, 2H), 4.45-4.40 (m, 1H), 3.56-3.52 (m, 2H), 3.23-3.20 (m, 2H), 2.65-2.62 (m, 1H), 2.16-2.11 (m, 2H), 2.00-1.93 (m, 4H), 1.75-1.71 (m, 2H), 1.53-1.23 (m, 6H).

Example 126 ethyl 1-((6-((trans-4-methylcyclohexyl)oxy)quinolin-2-yl)methyl)piperidine-4-carboxylate

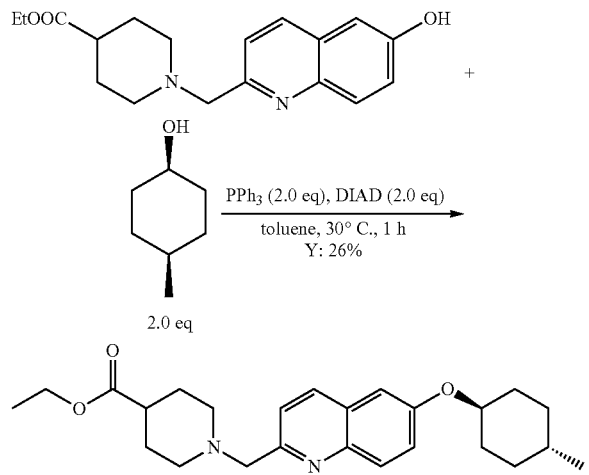

The preparation of ethyl 1-((6-((trans-4-methylcyclohexyl)oxy)quinolin-2-yl)methyl)piperidine-4-carboxylate was the same as that of ethyl 1-((6-(cyclohexyloxy)quinolin-2-yl)methyl)piperidine-4-carboxylate, 175 mg, a white solid. Yield: 26%, ESI-MS (M+H+): 411.2. $^1$H NMR (400 MHz, CDCl$_3$) δ: 7.73 (d, J=8.8 Hz, 1H), 7.70 (d, J=9.2 Hz, 1H), 7.31 (d, J=8.0 Hz, 1H), 7.07 (dd, J=9.2, 2.8 Hz, 1H), 6.83 (d, J=2.8 Hz, 1H), 4.09-4.01 (m, 1H), 3.87 (q, J=7.2 Hz, 2H), 3.51 (s, 2H), 2.65-2.63 (m, 2H), 2.09-2.02 (m, 1H), 1.96-1.88 (m, 4H), 1.65-1.54 (m, 6H), 1.25-1.19 (m, 3H), 0.99 (t, J=7.2 Hz, 3H), 0.86-0.83 (m, 2H), 0.68 (d, J=6.4 Hz, 3H).

Example 127

1-((6-((trans-4-methylcyclohexyl)oxy)quinolin-2-yl)methyl)piperidine-4-carboxylic acid

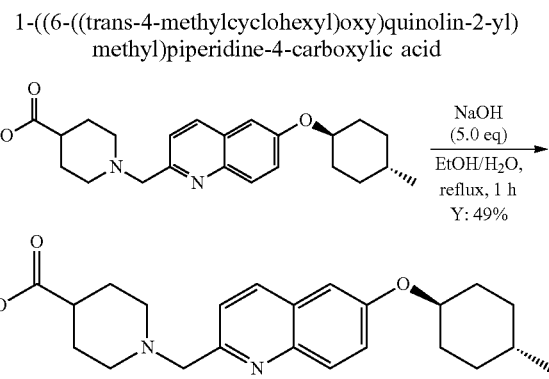

The preparation of 1-((6-((trans-4-methylcyclohexyl)oxy)quinolin-2-yl)methyl)piperidine-4-carboxylic acid was the same as that of 1-((6-(cyclohexyloxy)quinolin-2-yl)methyl)piperidine-4-carboxylic acid, 80 mg, a yellow solid. Yield: 49%, ESI-MS (M+H)$^+$: 383.2, HPLC: 100%. $^1$H NMR (400 MHz, CD$_3$OD) δ: 8.30 (d, J=8.4 Hz, 1H), 8.00 (d, J=9.2 Hz, 1H), 7.49 (d, J=8.4 Hz, 1H), 7.42 (dd, J=9.2, 2.8 Hz, 1H), 7.33 (d, J=2.4 Hz, 1H), 4.62 (s, 2H), 4.47-4.39 (m, 1H), 3.66-3.63 (m, 2H), 3.34-3.28 (m, 2H), 2.77-2.72 (m, 1H), 2.27-2.20 (m, 4H), 2.11-2.08 (m, 2H), 1.85-1.82 (m, 2H), 1.51-1.44 (m, 3H), 1.24-1.14 (m, 2H), 0.97 (d, J=6.4 Hz, 3H).

Example 128 ethyl 1-((6-((trans-4-ethylcyclohexyl)oxy)quinolin-2-yl)methyl)piperidine-4-carboxylate

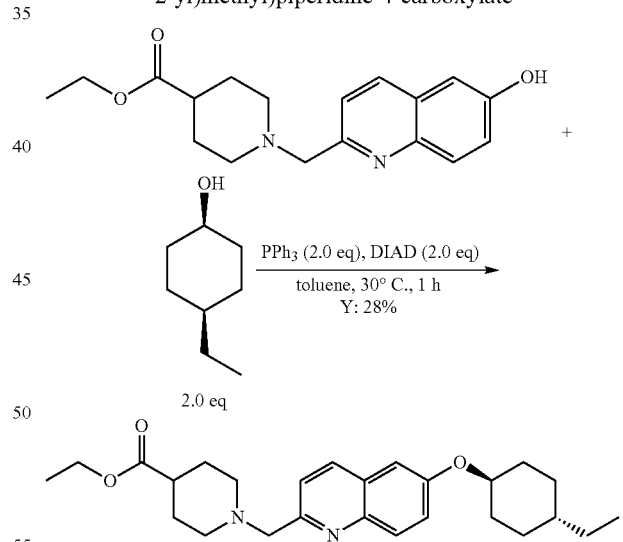

The preparation of ethyl 1-((6-((trans-4-ethylcyclohexyl)oxy)quinolin-2-yl)methyl)piperidine-4-carboxylate was the same as that of ethyl 1-((6-(cyclohexyloxy)quinolin-2-yl)methyl)piperidine-4-carboxylate, 270 mg, a yellow oil. Yield: 28%, ESI-MS (M+H+): 425.2. $^1$H NMR (400 MHz, CDCl$_3$) δ: 7.73 (d, J=8.8 Hz, 1H), 7.70 (d, J=9.6 Hz, 1H), 7.31 (d, J=8.4 Hz, 1H), 7.07 (dd, J=9.2, 3.2 Hz, 1H), 6.83 (d, J=2.8 Hz, 1H), 4.06-3.99 (m, 1H), 3.87 (q, J=7.2 Hz, 2H), 3.51 (s, 2H), 2.66-2.63 (m, 2H), 2.09-1.87 (m, 5H), 1.65-1.50 (m, 6H), 1.26-1.16 (m, 2H), 1.04-0.96 (m, 6H), 0.85-0.75 (m, 2H), 0.65 (t, J=7.2 Hz, 3H).

Example 129

1-((6-((trans-4-ethylcyclohexyl)oxy)quinolin-2-yl)methyl)piperidine-4-carboxylic acid

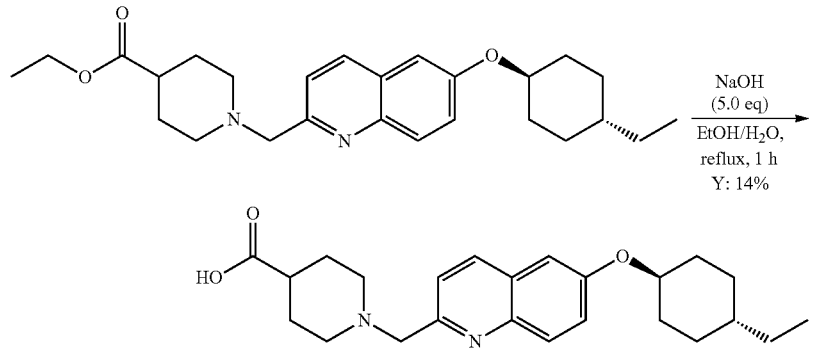

The preparation of 1-((6-((trans-4-ethylcyclohexyl)oxy)quinolin-2-yl)methyl)piperidine-4-carboxylic acid was the same as that of 1-((6-(cyclohexyloxy)quinolin-2-yl)methyl)piperidine-4-carboxylic acid, 19 mg, a white solid. Yield: 14%, ESI-MS (M+H)$^+$: 397.2, HPLC: 100%. $^1$H NMR (400 MHz, CD$_3$OD) δ: 8.27 (d, J=8.8 Hz, 1H), 8.00 (d, J=9.2 Hz, 1H), 7.50-7.45 (m, 2H), 7.31 (d, J=2.4 Hz, 1H), 4.78-4.76 (m, 1H), 4.63 (s, 2H), 3.66-3.63 (m, 2H), 3.34-3.31 (m, 2H), 2.76-2.74 (m, 1H), 2.27-2.22 (m, 2H), 2.10-2.06 (m, 4H), 1.71-1.59 (m, 4H), 1.43-1.40 (m, 2H), 1.32-1.30 (m, 3H), 0.93 (t, J=6.8 Hz, 3H).

Example 130 ethyl 1-46-((trans-4-(tert-pentyl)cyclohexyl)oxy)quinolin-2-yl)methyl)piperidine-4-carboxylate

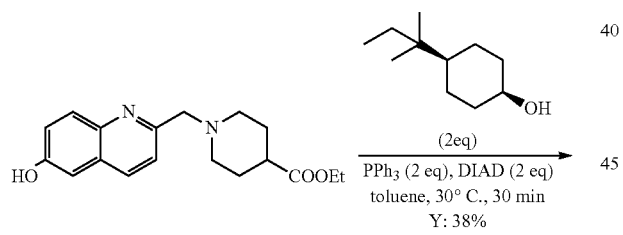

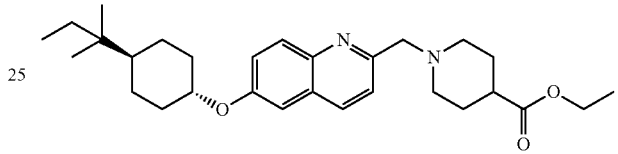

The preparation of ethyl 1-((6-((trans-4-(tert-pentyl)cyclohexyl)oxy)quinolin-2-yl)methyl)piperidine-4-carboxylate was the same as that of ethyl 1-((6-(cyclohexyloxy)quinolin-2-yl)methyl)piperidine-4-carboxylate, 180 mg, as yellow oil. Yield: 38%. ESI-MS (M+H)$^+$: 467.3. $^1$H NMR (400 MHz, CDCl$_3$) δ: 7.92 (d, J=8.4Hz, 1H), 7.87 (d, J=9.2 Hz, 1H), 7.50 (s, 1H), 7.25 (dd, J=9.2, 2.4 Hz, 1H), 7.01 (d, J=2.8 Hz, 1H), 4.23-4.15 (m, 1H), 4.06 (q, J=7.2 Hz, 2H), 3.70 (s, 2H), 2.85-2.82 (m, 2H), 2.22-2.19 (m, 3H), 2.10-2.06 (m, 1H), 1.79-1.75 (m, 5H), 1.58-1.55 (m, 1H), 1.39-1.36 (m, 2H), 1.22-1.17 (m, 9H), 0.77-0.75 (m, 9H).

Example 131

1-((6-((trans-4-(tert-pentyl)cyclohexyl)oxy)quinolin-2-yl)methyl)piperidine-4-carboxylic acid

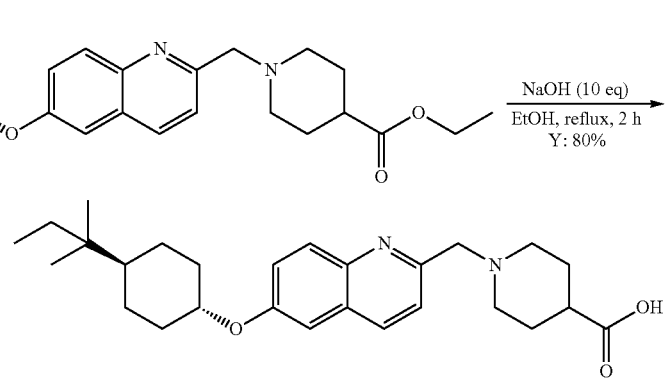

The preparation of 1-((6-(((trans-4-(tert-pentyl)cyclohexyl)oxy)quinolin-2-yl)methyl)piperidine-4-carboxylic acid was the same as that of 1-((6-(cyclohexyloxy)quinolin-2-yl)methyl)piperidine-4-carboxylic acid, 130 mg, as yellow solid. Yield: 80%. ESI-MS (M+H)⁺: 439.4, HPLC: 99.08%. ¹H NMR (400 MHz, CD₃OD) δ: 8.22 (d, J=8.4 Hz, 1H), 7.92 (d, J=9.2 Hz, 1H), 7.53 (d, J=8.4 Hz, 1H), 7.36 (d, J=9.2 Hz, 1H), 7.29 (s, 1H), 4.39-4.36 (m, 1H), 4.15 (s, 2H), 3.25-3.22 (m, 2H), 2.71-2.66 (m, 2H), 2.32-2.26 (m, 3H), 2.01-1.96 (m, 2H), 1.91-1.84 (m, 5H), 1.31-1.24 (m, 6H), 0.85-0.84 (m, 9H).

Example 132 ethyl 1-((6-(((trans-4-(trifluoromethyl)cyclohexyl)oxy)quinolin-2-yl)methyl)piperidine-4-carboxylate

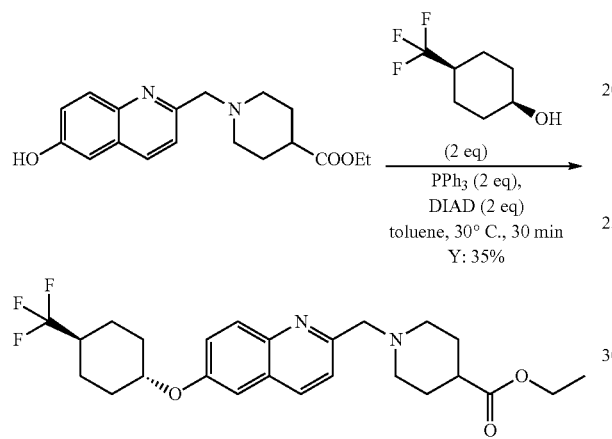

The preparation of ethyl 1-((6-(((trans-4-(trifluoromethyl)cyclohexyl)oxy)quinolin-2-yl)methyl)piperidine-4-carboxylate was the same as that of ethyl 1-((6-(cyclohexyloxy)quinolin-2-yl)methyl)piperidine-4-carboxylate, 150 mg, a yellow oil. Yield: 35%, ESI-MS (M+H)⁺: 465.2. ¹H NMR (400 MHz, CDCl₃) δ: 7.93 (d, J=8.4 Hz, 1H), 7.89 (d, J=9.2 Hz, 1H), 7.52 (d, J=7.2 Hz, 1H), 7.24 (dd, J=9.2, 2.8 Hz, 1H), 7.02 (d, J=2.8 Hz, 1H), 4.26-4.25 (m, 1H), 4.06 (q, J=7.2 Hz, 2H), 3.71 (s, 2H), 2.84-2.83 (m, 2H), 2.28-2.27 (m, 3H), 2.10-2.04 (m, 6H), 1.81-1.74 (m, 4H), 1.47-1.43 (m, 3H), 1.18 (t, J=7.2 Hz, 3H).

Example 133

1-((6-(((trans-4-(trifluoromethyl)cyclohexyl)oxy)quinolin-2-yl)methyl)piperidine-4-carboxylic acid

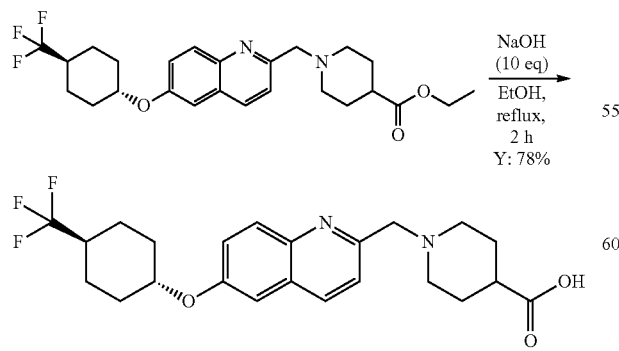

The preparation of 1-((6-(((trans-4-(trifluoromethyl)cyclohexyl)oxy)quinolin-2-yl)methyl)piperidine-4-carboxylic acid was the same as that of 1-((6-(cyclohexyloxy)quinolin-2-yl)methyl)piperidine-4-carboxylic acid, 100 mg, as yellow solid. Yield: 78%, ESI-MS (M+H)⁺: 437.3, HPLC: 98.94%. ¹H NMR (400 MHz, CD₃OD) δ: 8.22 (d, J=8.4 Hz, 1H), 7.92 (d, J=9.2 Hz, 1H), 7.56 (d, J=8.4 Hz, 1H), 7.37 (dd, J=8.8, 2.4 Hz, 1H), 7.32 (d, J=2.4 Hz, 1H), 4.48-4.44 (m, 1H), 4.07 (s, 2H), 3.18-3.15 (m, 2H), 2.60-2.55 (m, 2H), 2.33-2.29 (m, 4H), 2.06-2.02 (m, 4H), 1.90-1.85 (m, 2H), 1.59-1.48 (m, 4H).

Example 134 ethyl 1-((6-((4,4-dimethylcyclohexyl)oxy)quinolin-2-yl)methyl)piperidine-4-carboxylate

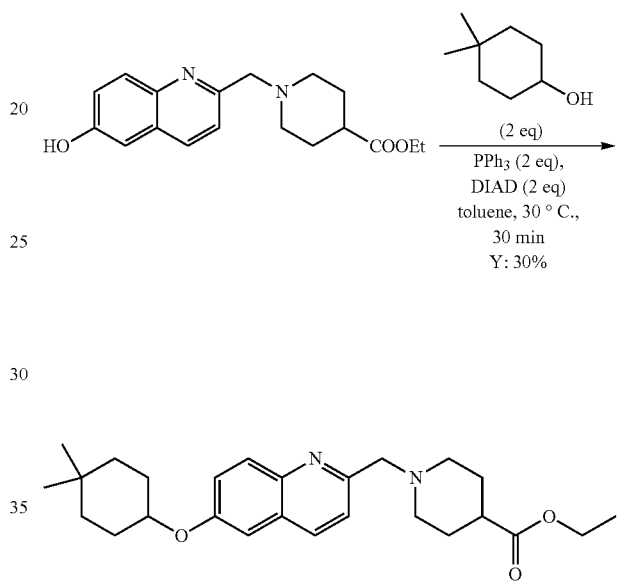

The preparation of ethyl 1-((6-((4,4-dimethylcyclohexyl)oxy)quinolin-2-yl)methyl)piperidine-4-carboxylate was the same as that of ethyl 1-((6-(cyclohexyloxy)quinolin-2-yl)methyl)piperidine-4-carboxylate, 170 mg, a yellow solid. Yield: 30%, ESI-MS (M+H)⁺: 425.3. ¹H NMR (400 MHz, CDCl₃) δ: 7.91 (d, J=8.4 Hz, 1H), 7.88 (d, J=9.2 Hz, 1H), 7.51 (d, J=7.6 Hz, 1H), 7.24 (dd, J=8.8, 2.4 Hz, 1H), 7.01 (d, J=2.8 Hz, 1H), 4.33-4.29 (m, 1H), 4.06 (q, J=7.2 Hz, 2H), 3.71 (s, 2H), 2.85-2.82 (m, 2H), 2.24-2.22 (m, 1H), 2.11-2.09 (m, 2H), 1.85-1.66 (m, 8H), 1.50-1.47 (m, 2H), 1.28-1.24 (m, 2H), 1.18 (t, J=7.2 Hz, 3H), 0.93 (s, 3H), 0.90 (s, 3H).

Example 135

1-((6-((4,4-dimethylcyclohexyl)oxy)quinolin-2-yl)methyl)piperidine-4-carboxylic acid

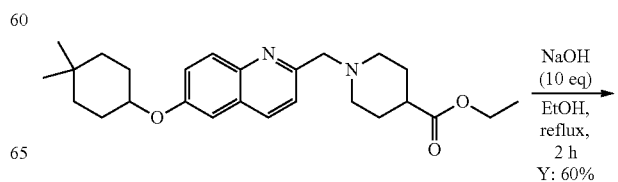

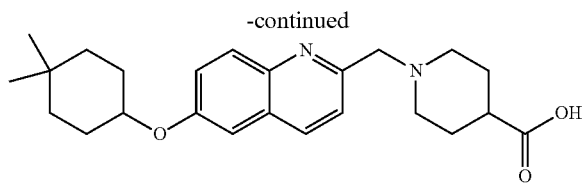

The preparation of 1-((6-((4,4-dimethylcyclohexyl)oxy)quinolin-2-yl)methyl)piperidine-4-carboxylic acid was the same as that of 1-((6-(cyclohexyloxy)quinolin-2-yl)methyl)piperidine-4-carboxylic acid, 100 mg, a yellow oil. Yield: 60%, ESI-MS (M+H)$^+$: 397.3, HPLC: 98.99%. $^1$H NMR (400 MHz, CD$_3$OD) δ: 8.19 (d, J=8.4 Hz, 1H), 7.90 (d, J=8.8 Hz, 1H), 7.37 (d, J=8.4 Hz, 1H), 7.35 (dd, J=9.2, 2.4 Hz, 1H), 7.23 (d, J=2.4 Hz, 1H), 4.52 (s, 2H), 4.52-4.40 (m, 1H), 3.57-3.54 (m, 2H), 3.22-3.18 (m, 2H), 2.67-2.61 (m, 1H), 2.17-2.12 (m, 2H), 2.03-1.98 (m, 2H), 1.89-1.85 (m, 2H), 1.67-1.62 (m, 2H), 1.49-1.45 (m, 2H), 1.31-1.28 (m, 2H), 0.91 (s, 3H), 0.90 (s, 3H).

Example 136 ethyl 1-((6-(spiro[3.5]nonan-7-yloxy)quinolin-2-yl)methyl)piperidine-4-carboxylate

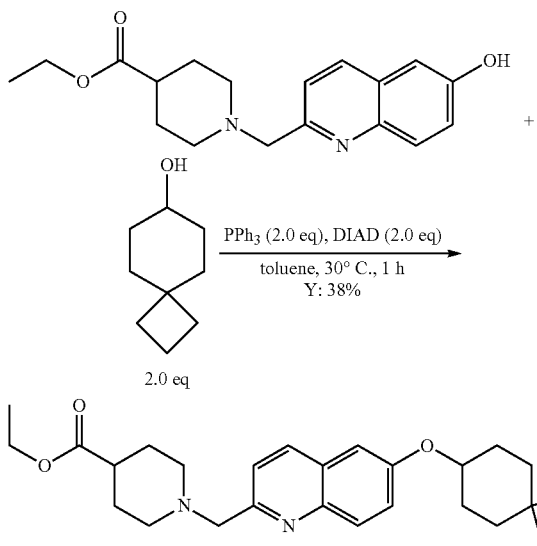

The preparation of ethyl 1-((6-(spiro[3.5]nonan-7-yloxy)quinolin-2-yl)methyl)piperidine-4-carboxylate was the same as that of ethyl 1-((6-(cyclohexyloxy)quinolin-2-yl)methyl)piperidine-4-carboxylate, 200 mg, a white solid. Yield: 38%. ESI-MS (M+H)$^+$: 437.2.

Example 137

1-((6-(spiro[3.5]nonan-7-yloxy)quinolin-2-yl)methyl)piperidine-4-carboxylic acid The preparation of 1-((6-(spiro[3.5]nonan-7-yloxy)quinolin-2-yl)methyl)piperidine-4-carboxylic acid was the same as that of 1-((6-(cyclohexyloxy)quinolin-2-yl)methyl)piperidine-4-carboxylic acid, 75 mg, a slight yellow solid, Yield: 40%. ESI-MS (M+H)$^+$: 409.3, HPLC: 100%. $^1$H NMR (400 MHz, CD$_3$OD) δ: 8.29 (d, J=8.4 Hz, 1H), 8.00 (d, J=9.2 Hz, 1H), 7.48 (d, J=8.4 Hz, 1H), 7.43 (dd, J=9.2, 2.4 Hz, 1H), 7.32 (d, J=2.4 Hz, 1H), 4.61 (s, 2H), 4.51-4.49 (m, 1H), 3.65-3.62 (m, 2H), 3.31-3.28 (m, 2H), 2.73-2.71 (m, 1H), 2.25-2.07 (m, 4H), 1.91-1.80 (m, 10H), 1.64-1.54 (m, 2H), 1.52-1.49 (m, 2H).

Example 138 ethyl 1-46-(spiro[5.5]undecan-3-yloxy)quinolin-2-yl)methyl)piperidine-4-carboxylate

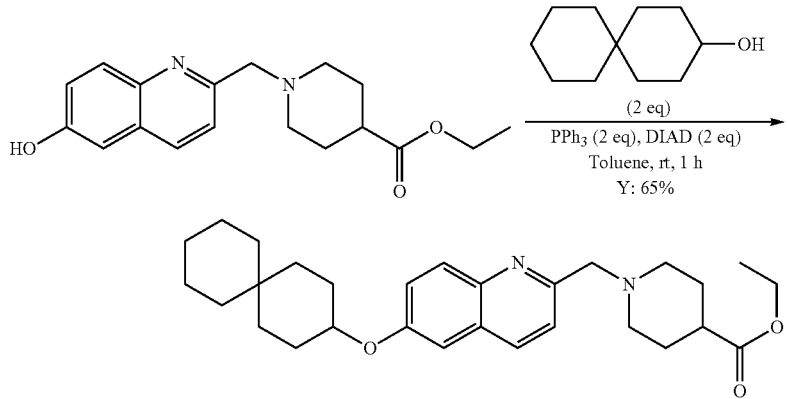

The preparation of ethyl 1-((6-(spiro[5.5]undecan-3-yloxy)quinolin-2-yl)methyl)piperidine-4-carboxylate was the same as that of ethyl 1-((6-(cyclohexyloxy)quinolin-2-yl)methyl)piperidine-4-carboxylate, 300 mg, slight yellow oil. Yield: 65%. ESI-MS (M+1)+: 464.3.

Example 139

1-((6-(spiro[5.5]undecan-3-yloxy)quinolin-2-yl)methyl)piperidine-4-carboxylic acid

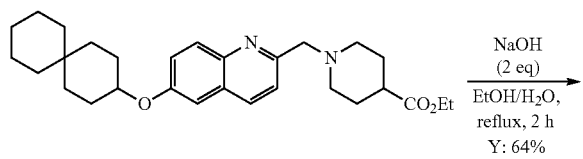

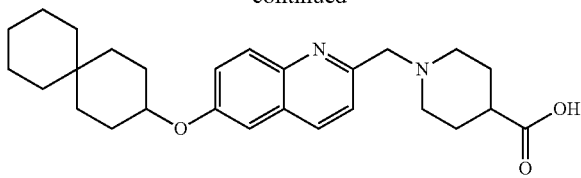

The preparation of 1-((6-(spiro[5.5]undecan-3-yloxy)quinolin-2-yl)methyl)piperidine-4-carboxylic acid was the same as that of 1-((6-(cyclohexyloxy)quinolin-2-yl)methyl)piperidine-4-carboxylic acid, 60 mg, a white solid. Yield: 64%. ESI-MS (M+H)+: 437.2, HPLC: 98.17%. $^1$H NMR (400 MHz, CD$_3$OD) δ: 8.36 (d, J=8.4 Hz, 1H), 8.11 (d, J=9.2 Hz, 1H), 7.62 (d, J=8.4 Hz, 1H), 7.57 (dd, J=9.2, 2.4 Hz, 1H), 7.36 (d, J=2.0 Hz, 1H), 4.70 (s, 2H), 4.65-4.60 (m, 1H), 3.75-3.71 (m, 2H), 3.46-3.42 (m, 2H), 2.89-2.84 (m, 1H), 2.41-2.37 (m, 2H), 2.29-2.21 (m, 2H), 2.10-2.04 (m, 2H), 1.90-1.83 (m, 4H), 1.60-1.56 (m, 8H), 1.48-1.42 (m, 4H).

Example 140 ethyl 1-((6-((cis-4-ethylcyclohexyl)oxy)quinolin-2-yl)methyl)piperidine-4-carboxylate

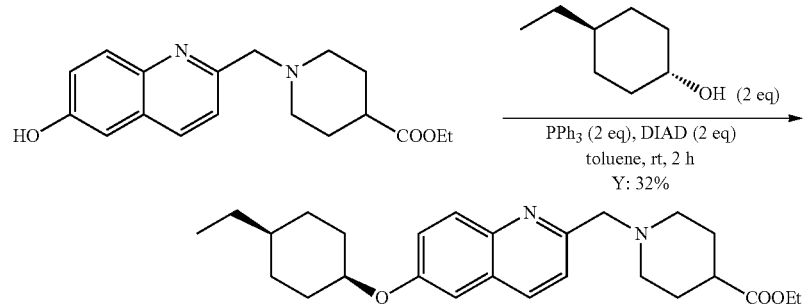

The preparation of ethyl 1-((6-((cis-4-ethylcyclohexyl)oxy)quinolin-2-yl)methyl)piperidine-4-carboxylate was the same as that of ethyl 1-((6-(cyclohexyloxy)quinolin-2-yl)methyl)piperidine-4-carboxylate, 129 mg, a slight yellow oil. Yield: 32%. ESI-MS (M+1)+: 425.3. $^1$H NMR (400 MHz, CDCl$_3$) δ: 7.93-7.86 (m, 2H), 7.50-7.49 (m, 1H), 7.31-7.28 (m, 1H), 7.02 (d, J=2.4 Hz, 1H), 4.60-4.58 (m, 1H), 4.06 (q, J=7.2 Hz, 2H), 3.70 (s, 2H), 2.84-2.82 (m, 2H), 2.24-2.23 (m, 1H), 2.10-1.97 (m, 4H), 1.81-1.72 (m, 3H), 1.58-1.47 (m, 5H), 1.40-1.33 (m, 2H), 1.30-1.20 (m, 3H), 1.18 (t, J=7.2 Hz, 3H), 0.84 (t, J=7.2 Hz, 3H).

Example 141

1-((6-((cis-4-ethylcyclohexyl)oxy)quinolin-2-yl)methyl)piperidine-4-carboxylic acid

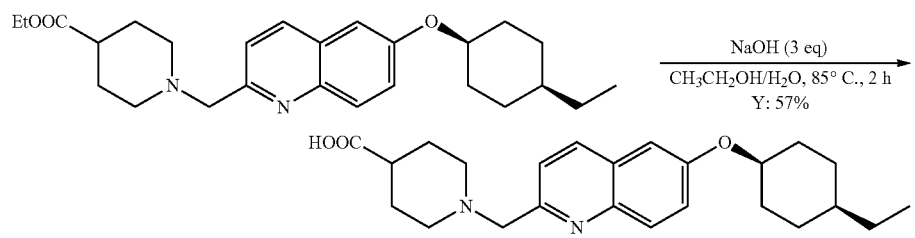

The preparation of 1-((6-((cis-4-ethylcyclohexyl)oxy)quinolin-2-yl)methyl)piperidine-4-carboxylic acid was the same as that of 1-((6-(cyclohexyloxy)quinolin-2-yl)methyl)piperidine-4-carboxylic acid, 69 mg, a white solid. Yield: 57%. ESI-MS (M+H)⁺: 397.2, HPLC: 99.65%. $^1$H NMR (400 MHz, CD$_3$OD) δ: 8.25 (d, J=8.0 Hz, 1H), 7.98 (d, J=9.2 Hz, 1H), 7.53 (d, J=8.4 Hz, 1H), 7.45 (dd, J=9.2, 2.8 Hz, 1H), 7.31 (d, J=2.4 Hz, 1H), 4.78-4.76 (m, 1H), 4.30 (s, 2H), 3.39-3.35 (m, 2H), 2.89-2.87 (m, 2H), 2.44-2.38 (m, 1H), 2.11-2.04 (m, 4H), 1.99-1.91 (m, 2H), 1.72-1.60 (m, 4H), 1.47-1.42 (m, 2H), 1.39-1.30 (m, 3H), 0.94 (t, J=7.2 Hz, 3H).

Example 142 ethyl 1-((6-(spiro[2.5]octan-6-yloxy)naphthalen-2-yl)methyl)piperidine-4-carboxylate

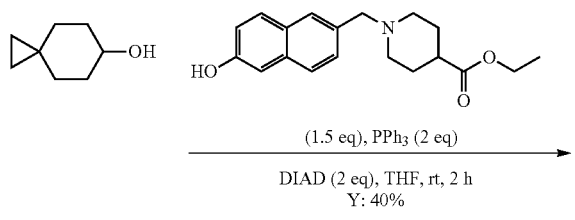

(1.5 eq), PPh$_3$ (2 eq)
DIAD (2 eq), THF, rt, 2 h
Y: 40%

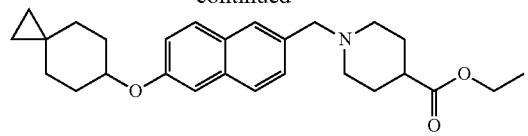

The preparation of ethyl 1-((6-(spiro[2.5]octan-6-yloxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate, yellow oil, 550 mg, yield: 40%. ESI-MS (M+1)⁺: 422.2. $^1$H NMR (400 MHz, DMSO-d6): δ 7.73-7.61 (m, 3H), 7.34-7.28 (m, 2H), 7.09 (d, J=11.2 Hz, 1H), 4.55-4.51 (m, 1H), 3.99 (q, J=7.2 Hz, 2H), 3.48 (s, 2H), 2.73-2.70 (m, 2H), 2.27-2.20 (m, 1H), 1.98-1.92 (m, 4H), 1.74-1.71 (m, 2H), 1.63-1.45 (m, 6H), 1.30-1.21 (m, 5H), 0.28-0.18 (m, 4H).

Example 143

1-((6-(spiro[2.5]octan-6-yloxy)naphthalen-2-yl)methyl)piperidine-4-carboxylic acid

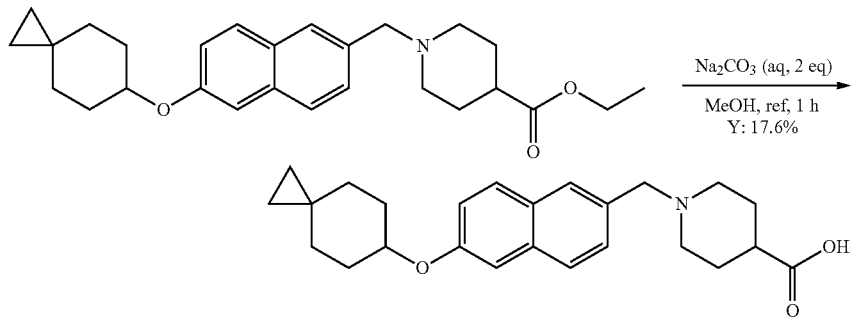

Na$_2$CO$_3$ (aq, 2 eq)
MeOH, ref, 1 h
Y: 17.6%

The preparation of 1-((6-(spiro[2.5]octan-6-yloxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid, yellow oil, 550 mg, yield: 17.6%. ESI-MS (M+1)⁺: 394.1, HPLC: 100%. $^1$H NMR (400 MHz, DMSO-d6): δ 7.77-7.72 (m, 2H), 7.66 (s, 1H), 7.39 (dd, J=8.8, 1.6 Hz, 1H), 7.33 (d, J=2.4 Hz, 1H), 7.14 (dd, J=8.4, 2.0 Hz, 1H), 4.61-4.57 (m, 1H), 3.52 (s, 2H), 2.76-2.73 (m, 2H), 2.01-1.92 (m, 5H), 1.73-1.50 (m, 8H), 1.30-1.27 (m, 2H), 0.34-0.23 (m, 4H).

Example 144 ethyl 1-((6-(spiro[4.5]decan-8-yloxy)quinolin-2-yl)methyl)piperidine-4-carboxylate

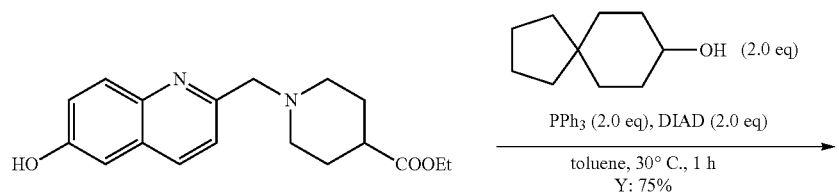

PPh$_3$ (2.0 eq), DIAD (2.0 eq)
toluene, 30° C., 1 h
Y: 75%

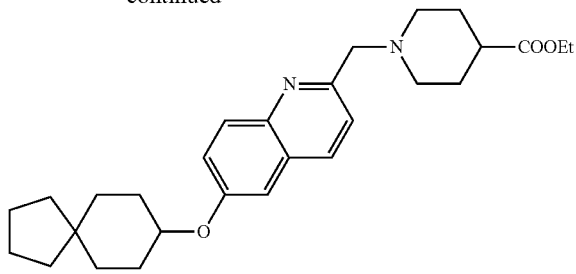

The preparation of ethyl 1-((6-(spiro[4.5]decan-8-yloxy)quinolin-2-yl)methyl)piperidine-4-carboxylate was the same as that of ethyl 1-((6-(cyclohexyloxy)quinolin-2-yl)methyl)piperidine-4-carboxylate, 380 mg, a white solid. Yield: 75%. ESI-MS (M+H)$^+$: 451.1. $^1$H NMR (400 MHz, CDCl$_3$) δ: 7.98 (d, J=8.4 Hz, 1H), 7.95 (d, J=9.2 Hz, 1H), 7.56 (d, J=8.4 Hz, 1H), 7.33 (dd, J=9.6, 3.2 Hz, 1H), 7.09 (d, J=2.8 Hz, 1H), 4.42-4.37 (m, 1H), 4.13 (q, J=7.2 Hz, 2H), 3.77 (s, 2H), 2.91-2.88 (m, 2H), 2.33-2.28 (m, 1H), 2.19-2.14 (m, 2H), 2.00-1.79 (m, 6H), 1.71-1.60 (m, 7H), 1.50-1.38 (m, 6H), 1.26-1.24 (m, 4H).

Example 145

1-((6-(spiro[4.5]decan-8-yloxy)quinolin-2-yl)methyl)piperidine-4-carboxylic acid The preparation of 1-((6-(spiro[4.5]decan-8-yloxy)quinolin-2-yl)methyl)piperidine-4-carboxylic acid was the same as that of 1-((6-(cyclohexyloxy)quinolin-2-yl)methyl)piperidine-4-carboxylic acid, 138 mg, a white solid. Yield: 39%. ESI-MS (M+H)$^+$: 423.1. $^1$H NMR (400 MHz, CD$_3$OD) δ: 8.14 (d, J=8.4 Hz, 1H), 7.86 (d, J=9.2 Hz, 1H), 7.42 (d, J=8.4 Hz, 1H), 7.31 (dd, J=9.2, 2.8 Hz, 1H), 7.21 (d, J=2.8 Hz, 1H), 4.45-4.40 (m, 1H), 4.16 (s, 2H), 3.24-3.21 (m, 2H), 2.73 (m, 2H), 2.32-2.25 (m, 1H), 1.97-1.79 (m, 6H), 1.65-1.51 (m, 8H), 1.44-1.32 (m, 6H).

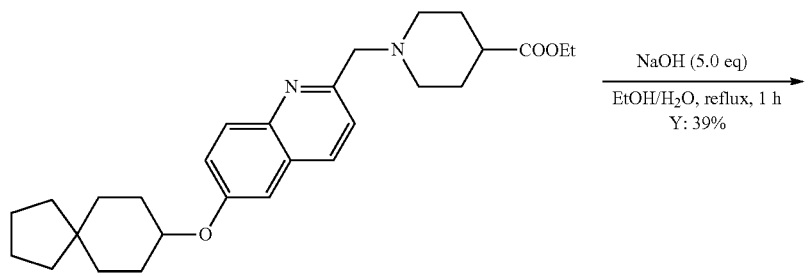

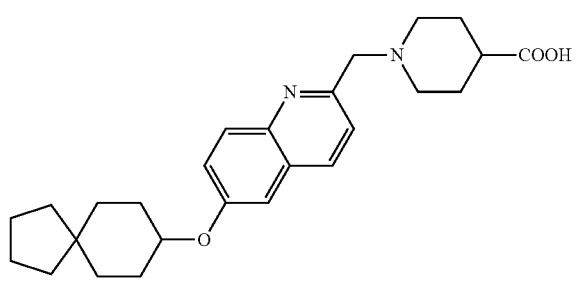

Example 146 ethyl 1-((6-((3,3,5-trimethylcyclohexyl)oxy)naphthalen-2-yl)methyl)piperidine-4-carboxylate

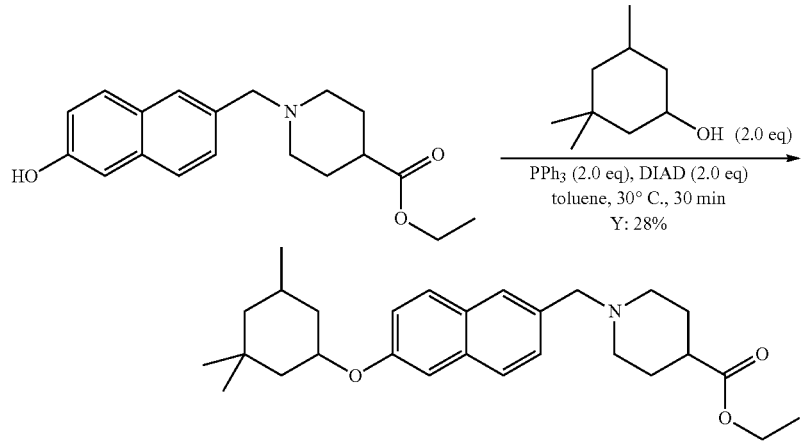

The preparation of ethyl 1-((6-((3,3,5-trimethylcyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate, 122 mg, as yellow oil, Y: 28%. ESI-MS (M+H)$^+$: 438.3. $^1$H NMR (400 MHz, CDCl$_3$) δ: 7.72-7.67 (m, 3H), 7.45 (d, J=8.4 Hz, 1H), 7.14-7.10 (m, 2H), 4.56-4.51 (m, 1H), 4.13 (q, J=7.2 Hz, 2H), 3.63 (s, 2H), 2.92-2.90 (m, 2H), 2.30-2.20 (m, 2H), 2.07-1.79 (m, 8H), 1.64-1.61 (m, 3H), 1.44-1.40 (m, 3H), 1.05 (s, 3H), 1.00 (s, 3H), 0.96 (d, J=6.4 Hz, 3H), 0.96-0.86 (m, 1H).

Example 147

1-((6-((3,3,5-trimethylcyclohexyl)oxy)naphthalen-2-yl)methyl)piperidine-4-carboxylic acid

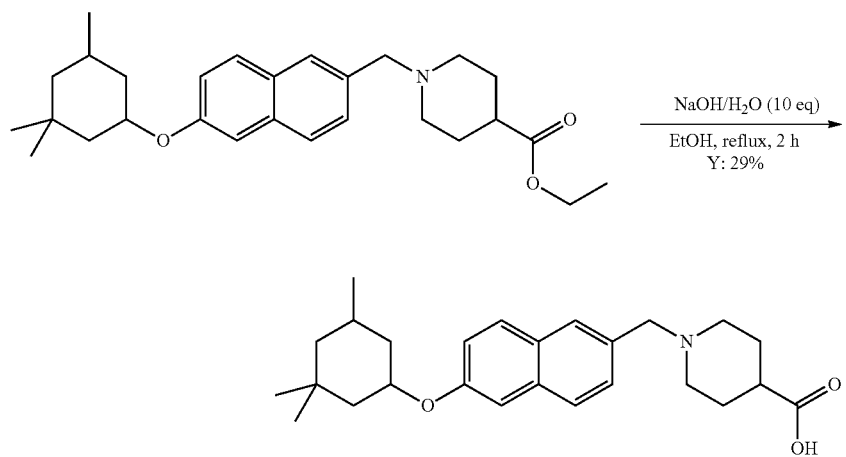

The preparation of 1-((6-((3,3,5-trimethylcyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid, 32 mg, as a yellow solid, Y: 29%. ESI-MS (M+H)$^+$: 410.3, HPLC: 98.56%. $^1$H NMR (400 MHz, CD$_3$OD) δ: 7.90 (s, 1H), 7.85-7.79 (m, 2H), 7.48 (dd, J=8.8, 1.6 Hz, 1H), 7.26 (d, J=2.4 Hz, 1H), 7.17 (dd, J=8.8, 2.4 Hz, 1H), 4.65-4.60 (m, 1H), 4.39 (s, 2H), 3.47-3.44 (m, 2H), 3.14-3.10 (m, 2H), 2.63-2.61 (m, 1H), 2.21-2.13 (m, 3H), 1.95-1.82 (m, 4H), 1.43-1.40 (m, 1H), 1.23-1.20 (m, 1H), 1.06 (s, 3H), 0.98(s, 3H), 0.95 (d, J=6.4 Hz, 3H), 0.93-0.84 (m, 2H).

Example 148 ethyl 1-((6-((cis-4-isopropylcyclohexyl)oxy)quinolin-2-yl)methyl)piperidine-4-carboxylate

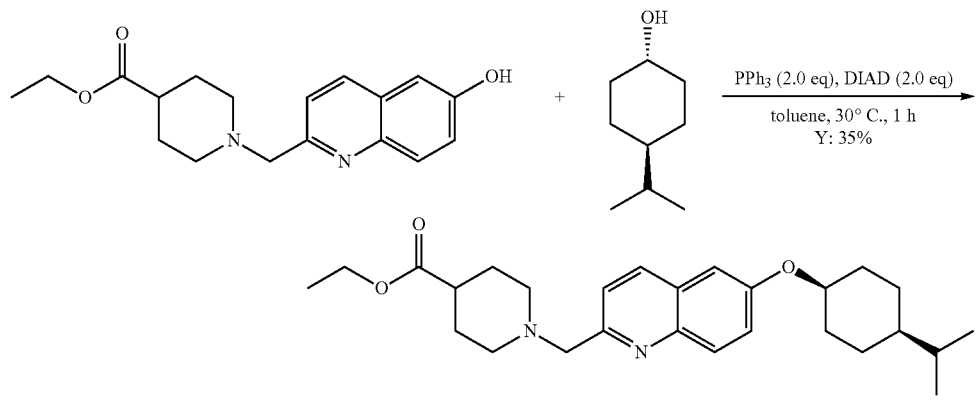

The preparation of ethyl 1-((6-((cis-4-isopropylcyclohexyl)oxy)quinolin-2-yl)methyl)piperidine-4-carboxylate was the same as that of ethyl 1-((6-(cyclohexyloxy)quinolin-2-yl)methyl)piperidine-4-carboxylate, 180 mg, a white solid. Yield: 35%, ESI-MS (M+H)+: 439.2. $^1$H NMR (400 MHz, CDCl$_3$) δ: 7.72 (d, J=8.0 Hz, 1H), 7.71 (d, J=8.8 Hz, 1H), 7.30 (d, J=8.4 Hz, 1H), 7.11 (dd, J=9.2, 2.8 Hz, 1H), 6.83 (d, J=2.8 Hz, 1H), 4.42-4.38 (m, 1H), 3.87 (q, J=7.2 Hz, 2H), 3.51 (s, 2H), 2.65-2.62 (m, 2H), 2.09-2.02 (m, 1H), 1.93-1.88 (m, 4H), 1.62-1.53 (m, 4H), 1.31-1.21 (m, 7H), 0.99 (t, J=7.6 Hz, 3H), 0.89-0.77 (m, 1H), 0.64 (d, J=6.8 Hz, 6H).

Example 149

1-((6-((cis-4-isopropylcyclohexyl)oxy)quinolin-2-yl)methyl)piperidine-4-carboxylic acid

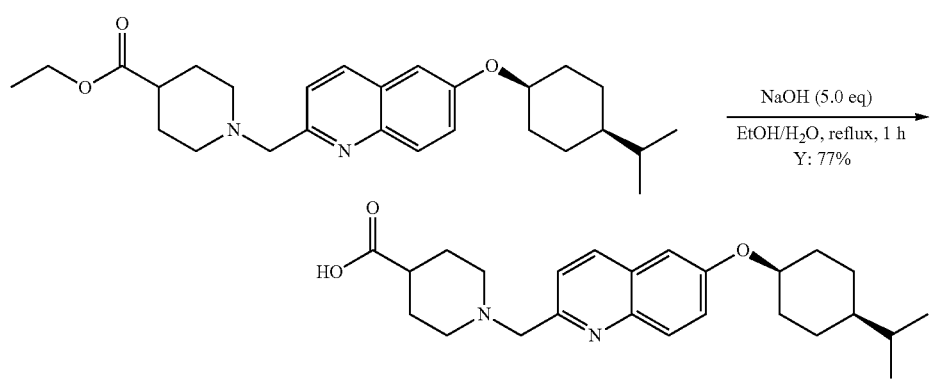

The preparation of 1-((6-((cis-4-isopropylcyclohexyl)oxy)quinolin-2-yl)methyl)piperidine-4-carboxylic acid was the same as that of 1-((6-(cyclohexyloxy)quinolin-2-yl)methyl)piperidine-4-carboxylic acid, 130 mg, a white solid. Yield: 77%, ESI-MS (M+H)+: 411.3, HPLC: 100%. $^1$H NMR (400 MHz, CD$_3$OD) δ: 8.27 (d, J=8.4 Hz, 1H), 8.00 (d, J=9.2 Hz, 1H), 7.47-7.45 (m, 2H), 7.31 (d, J=2.8 Hz, 1H), 4.77-4.76 (m, 1H), 4.58 (s, 2H), 3.63-3.60 (m, 2H), 3.28-3.20 (m, 2H), 2.74-2.67 (m, 1H), 2.24-2.06 (m, 6H), 1.69-1.44 (m, 7H), 1.24-1.16 (m, 1H), 0.91 (d, J=6.8 Hz, 6H).

Example 150 ethyl 1-((6-((3-methylcyclohexyl)oxy)naphthalen-2-yl)methyl)piperidine-4-carboxylate

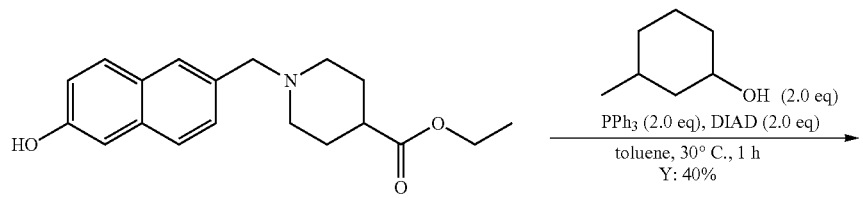

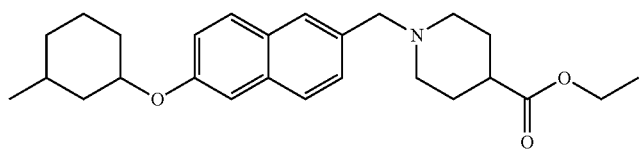

The preparation of ethyl 1-((6-((3-methylcyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate, 30 mg, buff solid, Y: 40%. ESI-MS (M+H)$^+$: 410.3. $^1$H NMR (400 MHz, CDCl$_3$) (mixture of isomers) δ: 7.70-7.62 (m, 3H), 7.41 (d, J=8.0 Hz, 1H), 7.15-7.13 (m, 2H), 4.79-4.76 (m, 0.6H), 4.46-4.38 (m, 0.4H), 4.11 (q, J=7.2 Hz, 2H), 3.59 (s, 2H), 2.90-2.87 (m, 2H), 2.30-2.18 (m, 2H), 2.06-2.01 (m, 3H), 1.89-1.67 (m, 7H), 1.57-1.34 (m, 3H), 1.25-1.23 (m, 4H), 0.97-0.88 (m, 3H).

Example 151

1-((6-((3-methylcyclohexyl)oxy)naphthalen-2-yl)methyl)piperidine-4-carboxylic acid

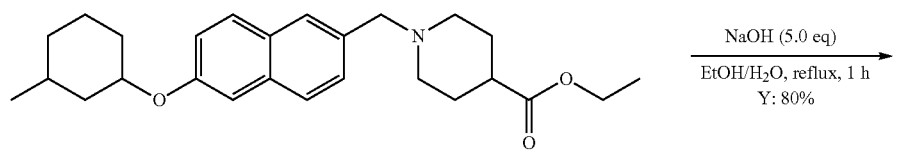

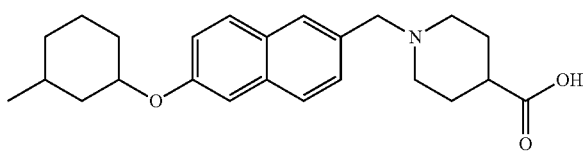

The preparation of 1-((6-((3-methylcyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid, 10 mg, white solid, Y: 80%. ESI-MS (M+H)$^+$: 382.3, HPLC: 100%. $^1$H NMR (400 MHz, DMSO-d$_6$) (mixture of isomers) δ: 7.79-7.70 (m, 2H), 7.66 (s, 1H), 7.39 (d, J=8.4 Hz, 1H), 7.32-7.29 (m, 1H), 7.15-7.09 (m, 1H), 4.82-4.76 (m, 0.6H), 4.45-4.38 (m, 0.4H), 3.53 (s, 2H), 2.77-2.74 (m, 2H), 2.16-2.11 (m, 2H), 2.01-1.90 (m, 3H), 1.85-1.39 (m, 9H), 1.30-1.23 (m, 1H), 1.06-0.97 (m, 1H), 0.94-0.86 (m, 3H).

Example 152 ethyl 1-((6-((4-(tert-pentyl)cyclohexyl)oxy)naphthalen-2-yl)methyl)piperidine-4-carboxylate

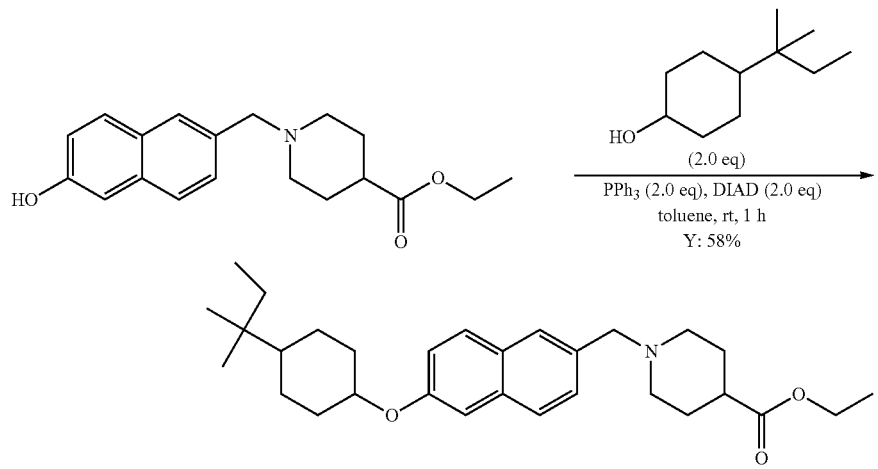

The preparation of ethyl 1-((6-((4-(tert-pentyl)cyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate, 45 mg, as yellow oil, Y: 58%. ESI-MS (M+H)$^+$: 466.3. $^1$H NMR (400 MHz, CDCl$_3$) δ: 7.75-7.65 (m, 3H), 7.45-7.42 (m, 1H), 7.18-7.11 (m, 2H), 4.70-4.68 (m, 0.6H), 4.30-4.23 (m, 0.4H), 4.13 (q, J=7.2 Hz, 2H), 3.63 (s, 2H), 2.92-2.89 (m, 2H), 2.30-2.20 (m, 3H), 2.03-2.00 (m, 2H), 1.74-1.71 (m, 2H), 1.52-1.50 (m, 2H), 1.28-1.20 (m, 9H), 0.83-0.77 (m, 12H).

Example 153

1-((6-((4-(tert-pentyl)cyclohexyl)oxy)naphthalen-2-yl)methyl)piperidine-4-carboxylic acid

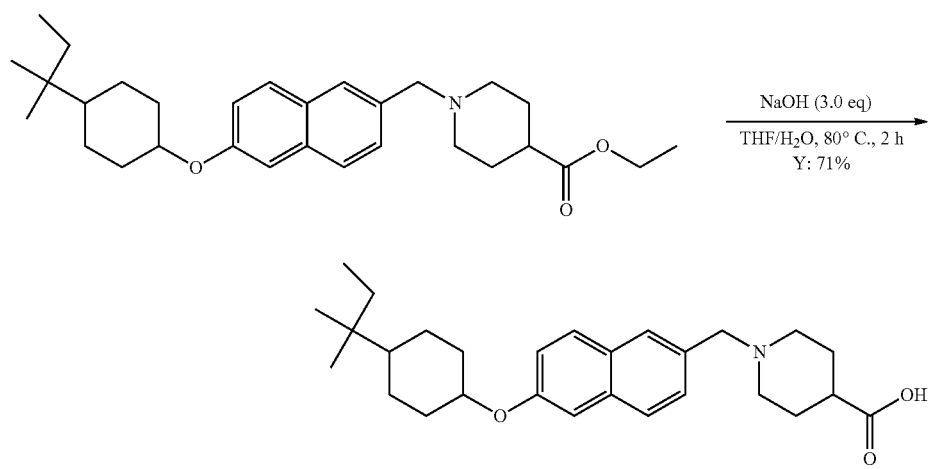

The preparation of 1-((6-((4-(tert-pentyl)cyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid, 30 mg, as a white solid, Y: 71%. ESI-MS (M+H)$^+$: 438.2. HPLC: 100%. $^1$H NMR (400 MHz, DMSO-d$_6$) (mixture of isomers) δ: 12.17 (s, 1H), 7.78-7.66 (m, 3H), 7.39-7.28 (m, 2H), 7.16-7.08 (m, 1H), 4.74-4.72 (m, 0.7H), 4.37-4.35 (m, 0.3H), 3.53 (s, 2H), 2.77-2.75 (m, 2H), 2.21-1.97 (m, 5H), 1.78-1.75 (m, 2H), 1.59-1.18 (m, 11H), 0.81-0.78 (m, 9H).

Example 154 ethyl 1-((6-((cis-4-(ethoxymethyl)cyclohexyl)oxy)naphthalen-2-yl)methyl)piperidine-4-carboxylate

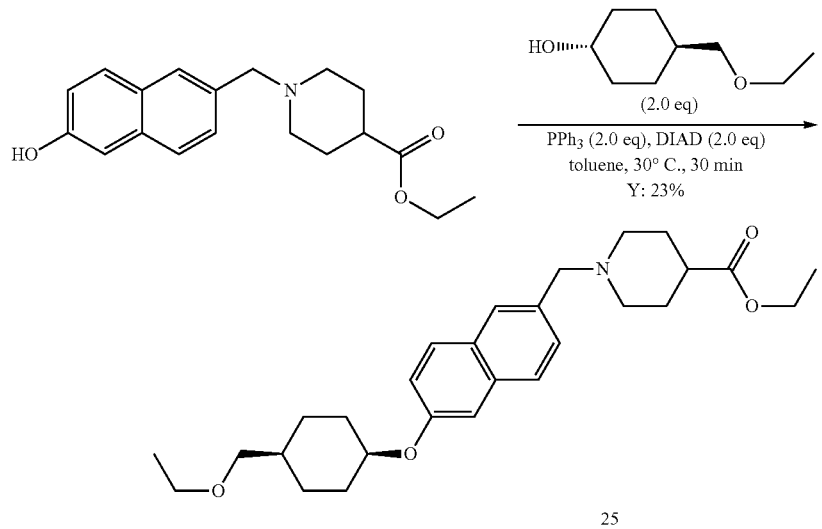

The preparation of ethyl 1-((6-((cis-4-(ethoxymethyl)cyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate, 110 mg, as yellow oil, yield: 23%. ESI-MS (M+H)$^+$: 454.3. $^1$H NMR (400 MHz, CDCl$_3$) δ: 7.72-7.64 (m, 3H), 7.43 (d, J=8.4 Hz, 1H), 7.17-7.14 (m, 2H), 4.69-4.67 (m, 1H), 4.12 (q, J=6.8 Hz, 2H), 3.62 (s, 2H), 3.49 (q, J=6.8 Hz, 2H), 3.30 (d, J=6.0 Hz, 2H), 2.91-2.89 (m, 2H), 2.11-2.07 (m, 4H), 1.86-1.65 (m, 6H), 1.59-1.49 (m, 4H), 1.48-1.43 (m, 2H), 1.23-1.18 (m, 6H).

Example 155

1-((6-((cis-4-(ethoxymethyl)cyclohexyl)oxy)naphthalen-2-yl)methyl)piperidine-4-carboxylic acid

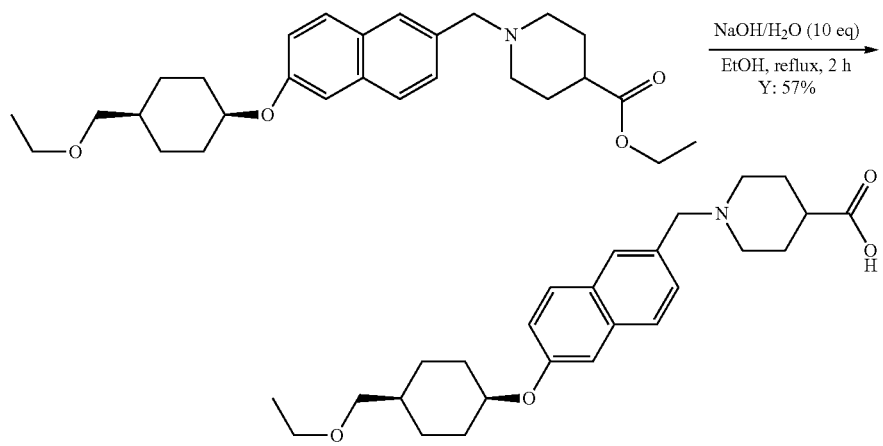

The preparation of 1-((6-((cis-4-(ethoxymethyl)cyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid, 45 mg, yellow solid, yield: 57%. ESI-MS (M+H)$^+$: 426.2, HPLC: 95.42%. $^1$H NMR (400 MHz, DMSO-d$_6$) δ: 12.20 (s, 1H), 7.78 (d, J=9.2 Hz, 1H), 7.72 (d, J=8.4 Hz, 1H), 7.66 (s, 1H), 7.39 (dd, J=8.8, 1.6 Hz, 1H), 7.30 (d, J=2.4 Hz, 1H), 7.15 (dd, J=8.8, 2.4 Hz, 1H), 4.73-4.72 (m, 1H), 3.54 (s, 2H), 3.41 (q, J=6.8 Hz, 2H), 3.23 (d, J=6.4 Hz, 2H), 2.78-2.75 (m, 2H), 2.21-2.16 (m, 1H), 2.02-1.94 (m, 4H), 1.78-1.76 (m, 2H), 1.65-1.53 (m, 7H), 1.41-1.32 (m, 2H), 1.10 (t, J=7.2 Hz, 3H).

Example 156 ethyl 1-((6-((octahydro-1H-inden-5-yl)oxy)naphthalen-2-yl)methyl)piperidine-4-carboxylate

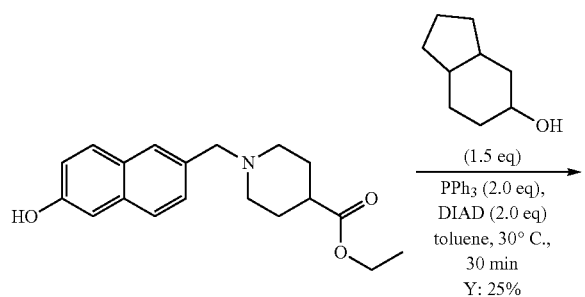

The preparation of ethyl 1-((6-((octahydro-1H-inden-5-yl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 170 mg, yellow oil, Y: 25%. ESI-MS (M+H)$^+$: 436.3. $^1$H NMR (400 MHz, CDCl$_3$) δ: 7.72-7.65 (m, 3H), 7.44 (d, J=8.0 Hz, 1H), 7.15-7.11 (m, 2H), 4.61-4.55 (m, 0.4H), 4.37-4.30 (m, 0.6H), 4.13 (q, J=6.8 Hz, 2H), 3.63 (s, 2H), 2.92-2.90 (m, 2H), 2.29-2.23 (m, 1H), 2.05-1.88 (m, 8H), 1.82-1.58 (m, 12H), 1.25 (t, J=6.8 Hz, 3H).

Example 157

1-((6-((octahydro-1H-inden-5-yl)oxy)naphthalen-2-yl)methyl)piperidine-4-carboxylic acid

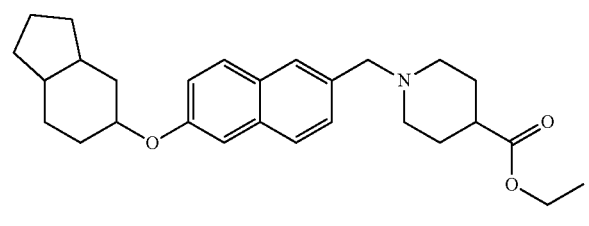

The preparation of 1-((6-((octahydro-1H-inden-5-yl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 80 mg, a slight yellow solid, Y: 50%. ESI-MS (M+H)$^+$: 408.3, HPLC: 100.00%. $^1$H NMR (400 MHz, MeOD-d$_4$) δ: 7.81 (s, 1H), 7.77-7.71 (m, 2H), 7.39 (d, J=7.2 Hz, 1H), 7.18 (d, J=2.0 Hz, 1H), 7.12-7.07 (m, 1H), 4.61-4.57 (m, 0.4H), 4.38-4.36 (0.6H), 4.32 (s, 2H), 3.43-3.38 (m, 2H), 3.07-3.00 (m, 2H), 2.57-2.53 (m, 1H), 2.07-1.82 (m, 8H), 1.71-1.53 (m, 4H), 1.42-1.26 (m, 6H).

Example 158 ethyl 1-((6-(spiro[2.5]octan-6-yloxy)quinolin-2-yl)methyl)piperidine-4-carboxylate

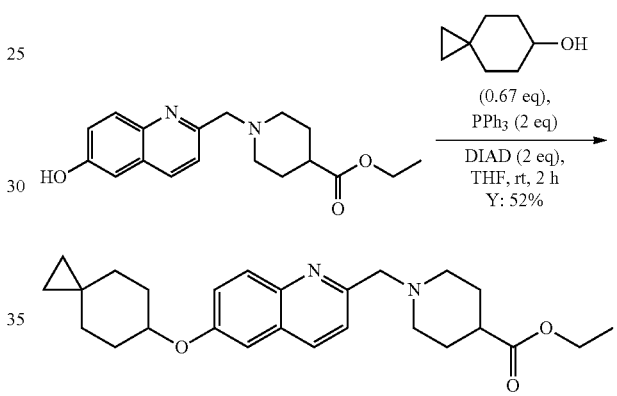

The preparation of ethyl 1-((6-(spiro[2.5]octan-6-yloxy)quinolin-2-yl)methyl)piperidine-4-carboxylate was the same as that of ethyl 1-((6-(cyclohexyloxy)quinolin-2-yl)methyl)piperidine-4-carboxylate, 330 mg, a white solid. Yield: 52%. ESI-MS (M+H)$^+$: 423.3. $^1$H NMR (400 MHz, CDCl$_3$) δ: 7.92 (d, J=8.4 Hz, 1H), 7.88 (d, J=9.2 Hz, 1H), 7.51 (d, J=8.4 Hz, 1H), 7.29 (dd, J=9.2, 2.4 Hz, 1H), 7.04 (d, J=2.4 Hz, 1H), 4.45-4.41 (m, 1H), 4.06 (q, J=7.2 Hz, 2H), 3.71 (s, 2H), 2.85-2.82 (m, 2H), 2.27-1.95 (m, 5H), 1.84-1.68 (m, 6H), 1.48-1.29 (m, 4H), 1.21-1.19 (m, 3H), 0.29-0.20 (m, 4H).

Example 159

1-((6-(spiro[2.5]octan-6-yloxy)quinolin-2-yl)methyl)piperidine-4-carboxylic acid

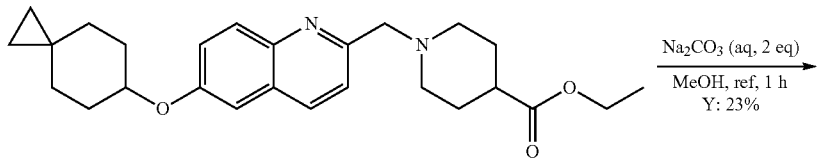

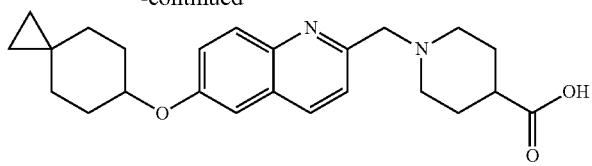

The preparation of 1-((6-(spiro[2.5]octan-6-yloxy)quinolin-2-yl)methyl)piperidine-4-carboxylic acid was the same as that of 1-((6-(cyclohexyloxy)quinolin-2-yl)methyl)piperidine-4-carboxylic acid, 22 mg, a white solid. Yield: 23%. ESI-MS (M+H)+: 395.2. HPLC: 100%. $^1$H NMR (400 MHz, DMSO-d$_6$) δ: 11.91 (s, 1H), 8.09 (d, J=8.4 Hz, 1H), 7.85 (d, J=9.2 Hz, 1H), 7.55 (d, J=8.0 Hz, 1H), 7.32 (dd, J=9.2, 2.4 Hz, 1H), 7.24 (d, J=2.0 Hz, 1H), 4.58-4.54 (m, 1H), 3.71 (s, 2H), 2.85-2.82 (m, 2H), 2.22-2.01 (m, 5H), 1.85-1.62 (m, 6H), 1.55-1.50 (m, 2H), 1.38-1.34 (m, 2H), 0.35-0.27 (m, 4H).

Example 160 ethyl 1-((6-((3,4-dimethylcyclohexyl)oxy)naphthalen-2-yl)methyl)piperidine-4-carboxylate

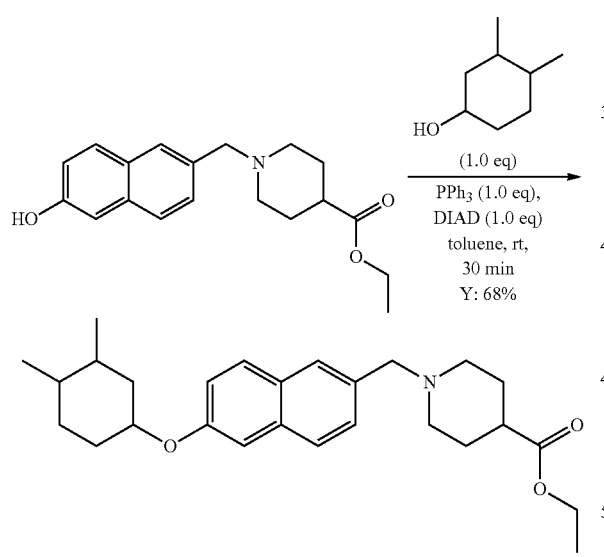

The preparation of ethyl 1-((6-((3,4-dimethylcyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate, 144 mg, as yellow oil, Y: 68%. ESI-MS (M+H)+: 424.3.

Example 161

1-((6-((3,4-dimethylcyclohexyl)oxy)naphthalen-2-yl)methyl)piperidine-4-carboxylic acid

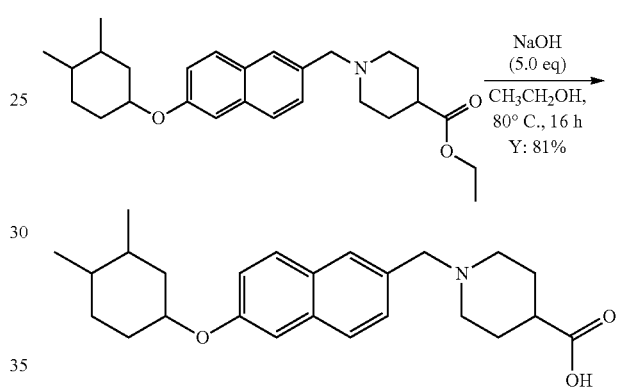

The preparation of 1-((6-((3,4-dimethylcyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid, 75 mg, as a yellow solid, yield: 81%. ESI-MS (M+H)+: 396.3, HPLC: 100%. $^1$H NMR (400 MHz, DMSO-d$_6$) (mixture of isomers) δ: 12.05 (s, 1H), 7.89-7.71 (m, 2H), 7.66 (s, 1H), 7.39 (d, J=8.4 Hz, 1H), 7.31-7.29 (m, 1H), 7.16-7.10 (m, 1H), 4.80-4.76 (m, 0.6H), 4.66-4.62 (m, 0.1H), 4.44-4.40 (m, 0.3H), 3.54 (s, 2H), 2.78-2.75 (m, 2H), 2.22-2.16 (m, 1H), 2.02-1.95 (m, 3H), 1.79-1.76 (m, 3H), 1.61-1.25 (m, 7H), 1.12-1.04 (m, 1H), 0.93-0.85 (m, 6H).

Example 162 ethyl 1-((6-((cis-4-(methoxymethyl)cyclohexyl)oxy)naphthalen-2-yl)methyl)piperidine-4-carboxylate

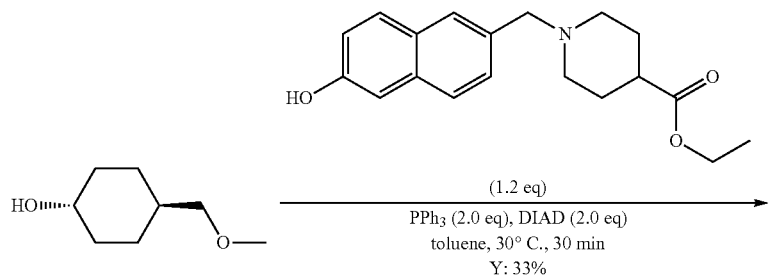

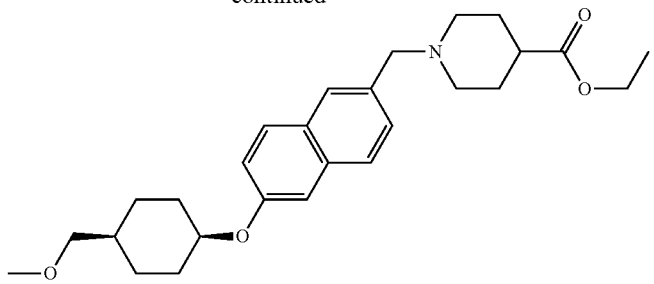

The preparation of ethyl 1-((6-((cis-4-(methoxymethyl)cyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate, 110 mg, as a yellow solid, yield: 33%. ESI-MS (M+H)$^+$: 440.3. $^1$H NMR (400 MHz, CDCl$_3$) δ: 7.65-7.62 (m, 3H), 7.36 (d, J=8.0 Hz, 1H), 7.10-7.07 (m, 2H), 4.62-4.60 (m, 1H), 4.05 (q, J=7.2 Hz, 2H), 3.57 (s, 2H), 3.28 (s, 3H), 3.20 (d, J=6.8 Hz, 2H), 2.84-2.82 (m, 2H), 2.24-2.22 (m, 1H), 2.04-2.01 (m, 3H), 1.94-1.91 (m, 1H), 1.81-1.73 (m, 4H), 1.57-1.39 (m, 7H), 1.17 (t, J=7.6 Hz, 3H).

Example 163

1-((6-((cis-4-(methoxymethyl)cyclohexyl)oxy)naphthalen-2-yl)methyl)piperidine-4-carboxylic acid

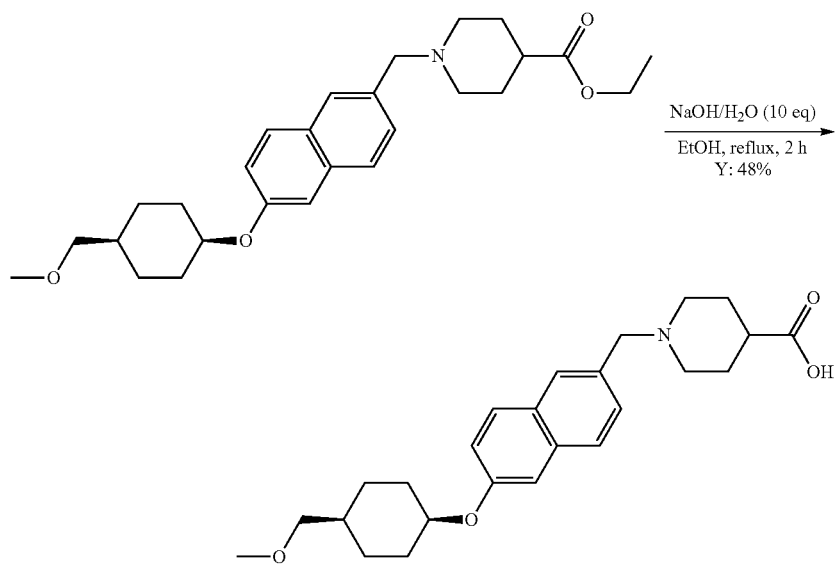

The preparation of 1-((6-((cis-4-(methoxymethyl)cyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid, 50 mg as a yellow solid, yield: 50%. ESI-MS (M+H)$^+$: 412.2, HPLC: 100.00%. $^1$H NMR (400 MHz, CD$_3$OD) δ: 7.67-7.63 (m, 3H), 7.35 (dd, J=8.4, 2.0 Hz, 1H), 7.14 (d, J=2.0 Hz, 1H), 7.07 (dd, J=8.8, 2.4 Hz, 1H), 4.66-4.65 (m, 1H), 3.84 (s, 2H), 3.23 (s, 3H), 3.17 (d, J=6.4 Hz, 2H), 3.04-3.01 (m, 2H), 2.43-2.38 (m, 2H), 2.15-2.09 (m, 1H), 2.00-1.96 (m, 2H), 1.87-1.83 (m, 2H), 1.76-1.70 (m, 2H), 1.59-1.48 (m, 5H), 1.42-1.36 (m, 2H).

Example 164 ethyl 1-((6-((cis-4-(tert-butoxymethyl)cyclohexyl)oxy)naphthalen-2-yl)methyl)piperidine-4-carboxylate

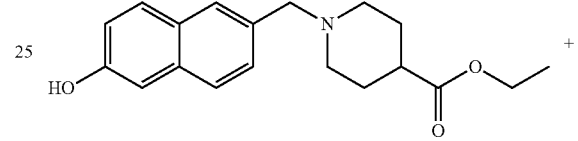

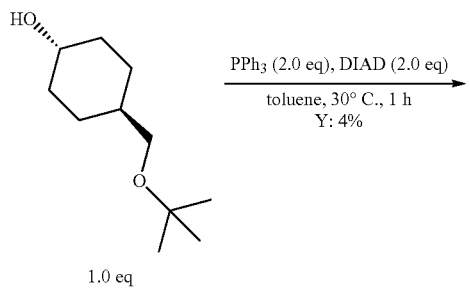

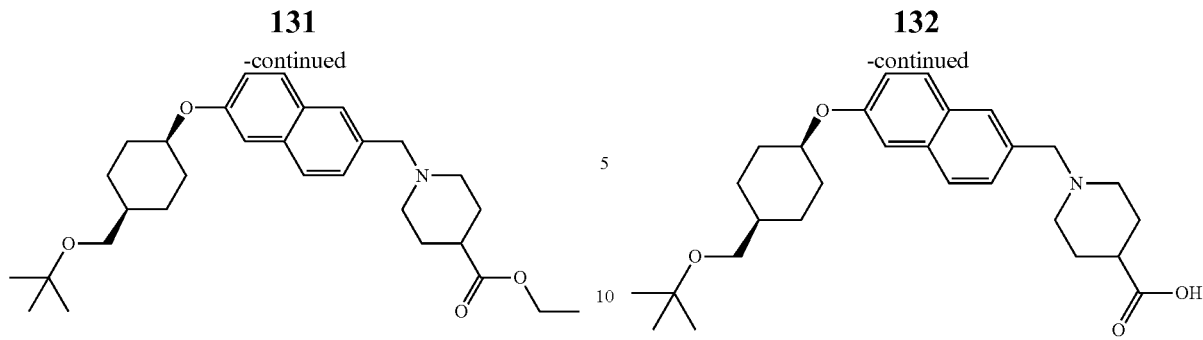

The preparation of ethyl 1-((6-((cis-4-(tert-butoxymethyl)cyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate, 20 mg, a white solid, yield: 4%, ESI-MS (M+H)⁺: 482.3. $^1$H NMR (400 MHz, CDCl₃) δ: 7.64-7.56 (m, 3H), 7.35 (d, J=8.4 Hz, 1H), 7.09-7.07 (m, 2H), 4.62-4.57 (m, 1H), 4.05 (q, J=7.2 Hz, 2H), 3.53 (s, 2H), 3.14 (d, J=6.4 Hz, 2H), 2.83-2.80 (m, 2H), 2.23-2.18 (m, 1H), 2.01-1.97 (m, 4H), 1.82-1.69 (m, 4H), 1.58-1.52 (m, 5H), 1.41-1.35 (m, 2H), 1.16 (t, J=7.2 Hz, 3H), 1.11 (s, 9H).

Example 165

1-((6-((cis-4-(tert-butoxymethyl)cyclohexyl)oxy)naphthalen-2-yl)methyl)piperidine-4-carboxylic acid

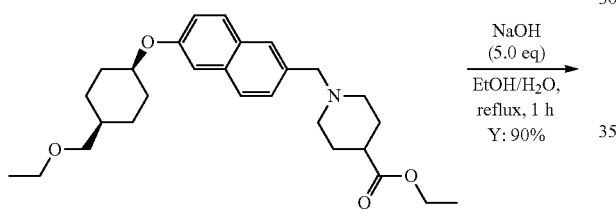

The preparation of 1-((6-((cis-4-(tert-butoxymethyl)cyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 17 mg, a white solid, yield: 90%, ESI-MS (M+H)⁺: 454.2, HPLC: 100%. $^1$H NMR (400 MHz, CD₃OD) δ: 7.85 (s, 1H), 7.74 (d, J=8.8 Hz, 2H), 7.44 (d, J=8.4 Hz, 1H), 7.19 (d, J=2.0 Hz, 1H), 7.13 (dd, J=8.8, 2.0 Hz, 1H), 4.67-4.65 (m, 1H), 4.33 (s, 2H), 3.38-3.35 (m, 2H), 3.15 (d, J=6.4 Hz, 2H), 3.06-3.04 (m, 2H), 2.57-2.54 (m, 1H), 2.09-2.05 (m, 2H), 1.98-1.88 (m, 4H), 1.60-1.48 (m, 5H), 1.39-1.18 (m, 2H), 1.09 (s, 9H).

Example 166 ethyl 1-((6-((cis-4-(isobutoxymethyl)cyclohexyl)oxy)naphthalen-2-yl)methyl)piperidine-4-carboxylate

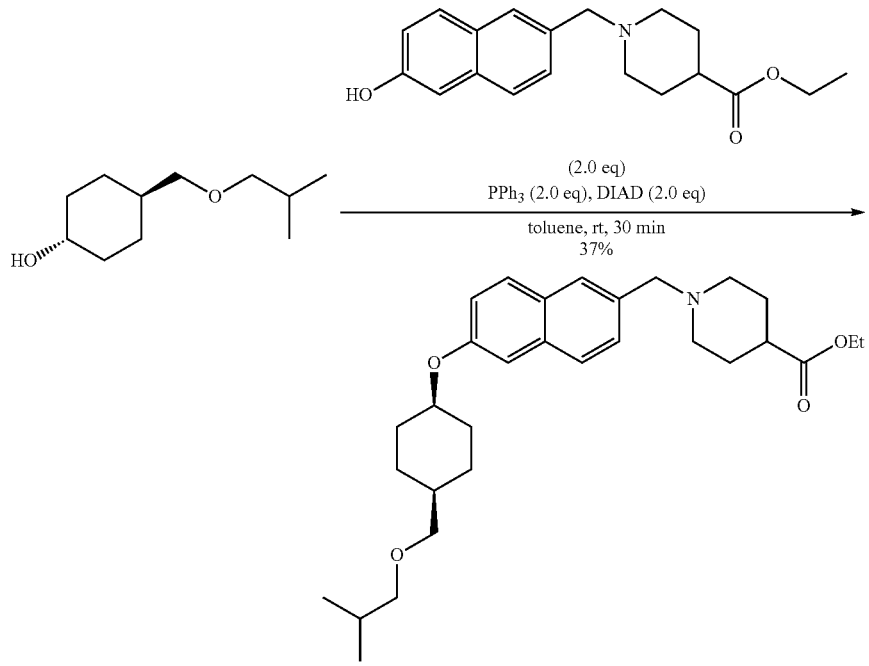

The preparation of ethyl 1-((6-(((cis-4-(isobutoxymethyl)cyclohexyl)oxy)naphthalen-2-yl)methyl)piperidine-4-carboxylate was the same as that of ethyl 1-((6-(((cis-4-phenylcyclohexyl)oxy)naphthalen-2-yl)methyl)piperidine-4-carboxylate. 190 mg, white solid, yield: 37%. ESI-MS (M+H)$^+$: 482.1. $^1$H NMR (400 MHz, CDCl$_3$) δ: 7.71-7.64 (m, 3H), 7.42 (d, J=8.4 Hz, 1H), 7.16-7.14 (m, 2H), 4.68-4.65 (m, 1H), 4.12 (q, J=7.2 Hz, 2H), 3.61 (s, 2H), 3.28 (d, J=6.8 Hz, 2H), 3.18 (d, J=6.8 Hz, 2H), 2.91-2.87 (m, 2H), 2.31-2.25 (m, 1H), 2.11-2.02 (m, 4H), 1.88-1.78 (m, 6H), 1.71-1.61 (m, 3H), 1.31-1.22 (m, 6H), 0.90 (d, J=6.8 Hz, 6H).

Example 167

1-((6-(((cis-4-(isobutoxymethyl)cyclohexyl)oxy)naphthalen-2-yl)methyl)piperidine-4-carboxylic acid

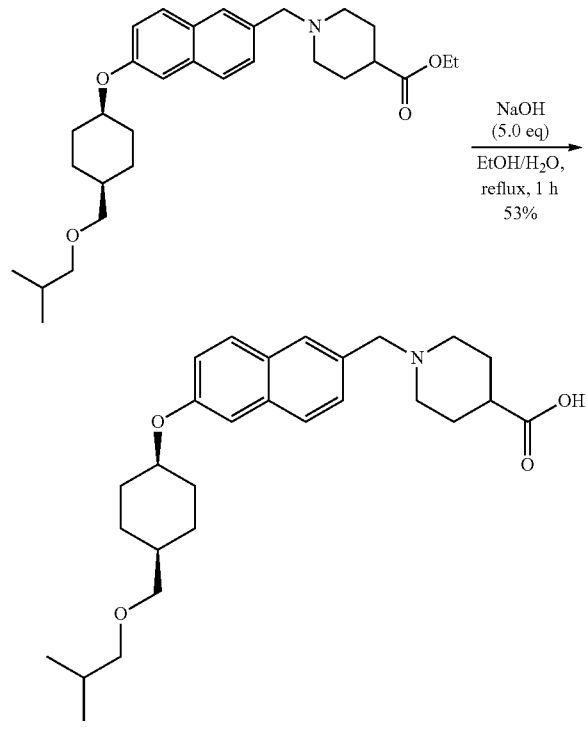

The preparation of 1-((6-(((cis-4-(isobutoxymethyl)cyclohexyl)oxy)naphthalen-2-yl)methyl)piperidine-4-carboxylic acid was the same as that of 1-((6-(((cis-4-phenylcyclohexyl)oxy)naphthalen-2-yl)methyl)piperidine-4-carboxylic acid. 94 mg, white solid, yield: 53%. ESI-MS (M+H)$^+$: 454.1, HPLC: 98.62%. $^1$H NMR (400 MHz, CD$_3$OD) δ: 7.77 (s, 1H), 7.73 (d, J=8.4 Hz, 1H), 7.71 (d, J=9.2 Hz, 1H), 7.37 (dd, J=8.4, 2.0 Hz, 1H), 7.19 (d, J=2.0 Hz, 1H), 7.12 (dd, J=8.8, 2.4 Hz, 1H), 4.68-4.66 (m, 1H), 4.17 (s, 2H), 3.27-3.20 (m, 3H), 3.10 (d, J=6.4 Hz, 2H), 2.84-2.82 (m, 2H), 2.29-2.22 (m, 1H), 2.01-1.93 (m, 4H), 1.84-1.70 (m, 3H), 1.67-1.51 (m, 6H), 1.44-1.34 (m, 2H), 0.81 (d, J=6.8 Hz, 6H).

Example 168 ethyl 1-((6-(((trans-4-(tert-butoxymethyl)cyclohexyl)oxy)naphthalen-2-yl)methyl)piperidine-4-carboxylate

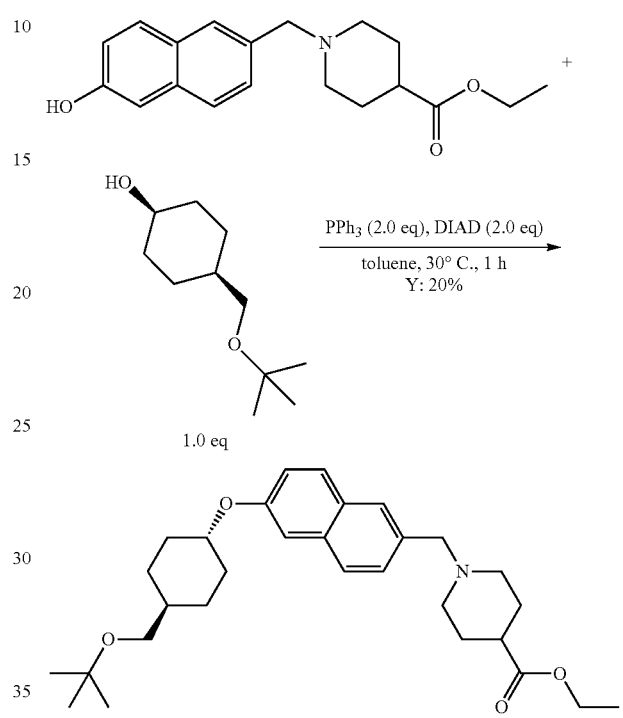

The preparation of ethyl 1-((6-(((trans-4-(tert-butoxymethyl)cyclohexyl)oxy)naphthalen-2-yl)methyl)piperidine-4-carboxylate was the same as that of ethyl 1-((6-(((cis-4-phenylcyclohexyl)oxy)naphthalen-2-yl)methyl)piperidine-4-carboxylate. 110 mg, a white solid, Y: 20%. ESI-MS (M+H)$^+$: 482.1. $^1$H NMR (400 MHz, CDCl$_3$) δ: 7.65-7.57 (m, 3H), 7.37 (d, J=8.8 Hz, 1H), 7.09-7.05 (m, 2H), 4.26-4.22 (m, 1H), 4.07 (q, J=7.2 Hz, 2H), 3.54 (s, 2H), 3.14 (d, J=6.4 Hz, 2H), 2.85-2.82 (m, 2H), 2.21-2.19 (m, 3H), 2.04-2.01 (m, 4H), 1.99-1.71 (m, 6H), 1.51-1.39 (m, 3H), 1.22-1.17 (m, 3H), 1.14 (s, 9H).

Example 169

1-((6-(((trans-4-(tert-butoxymethyl)cyclohexyl)oxy)naphthalen-2-yl)methyl)piperidine-4-carboxylic acid

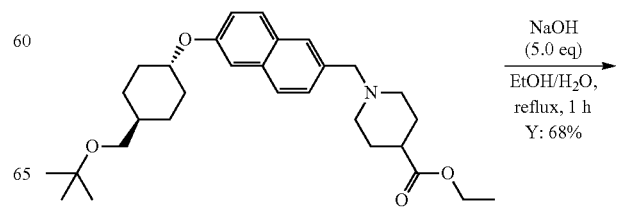

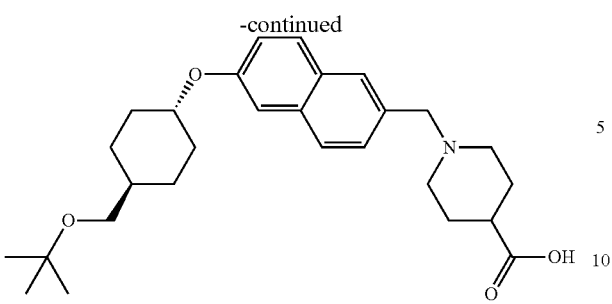

The preparation of 1-((6-((trans-4-(tert-butoxymethyl)cyclohexyl)oxy)naphthalen-2-yl)methyl)pipefidine-4-carboxylic acid was the same as that of 1-((6-((cis-4-phenylcyclohexyl)oxy)naphthalen-2-yl)methyl)piperidine-4-carboxylic acid. 70 mg, a slight yellow solid, yield: 68%. ESI-MS (M+H)$^+$: 454.3, HPLC: 100%. $^1$H NMR (400 MHz, CD$_3$OD) δ: 7.86 (s, 1H), 7.80-7.74 (m, 2H), 7.44 (d, J=8.4 Hz, 1H), 7.23 (s, 1H), 7.12 (dd, J=8.8, 2.0 Hz, 1H), 4.37-4.32 (m, 3H), 3.48-3.41 (m, 2H), 3.18 (d, J=6.4 Hz, 2H), 3.08-3.04 (m, 2H), 2.71-2.58 (m, 1H), 2.18-2.12 (m, 4H), 1.87-1.84 (m, 4H), 1.46-1.34 (m, 3H), 1.18-0.84 (m, 11H).

Example 170

Synthesis of ethyl 1-((6-((trans-4-(isobutoxymethyl)cyclohexyl)oxy)naphthalen-2-yl)methyl)piperidine-4-carboxylate 2.30-2.24 (m, 2H), 2.07-2.02 (m, 2H), 1.95-1.76 (m, 6H), 1.67-1.62 (m, 2H), 1.54-1.44 (m, 2H), 1.32-1.27 (m, 6H), 0.91 (d, J=6.4 Hz, 6H).

Example 171

1-((6-((trans-4-(isobutoxymethyl)cyclohexyl)oxy)naphthalen-2-yl)methyl)piperidine-4-carboxylic acid

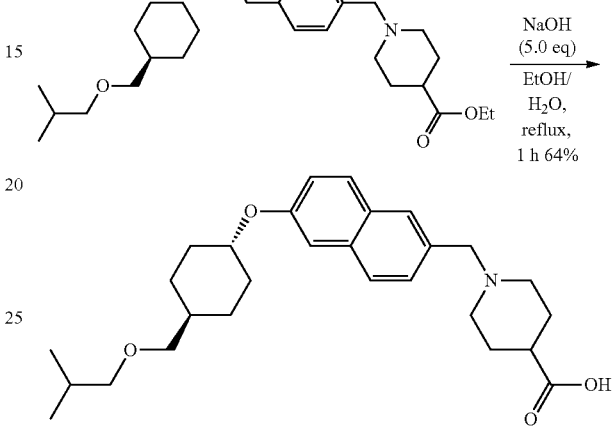

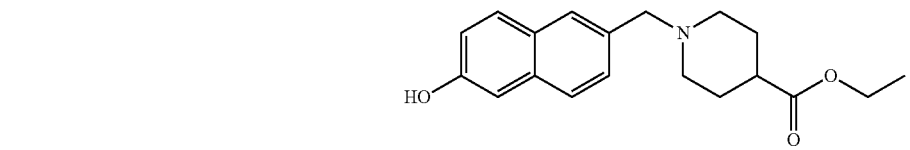

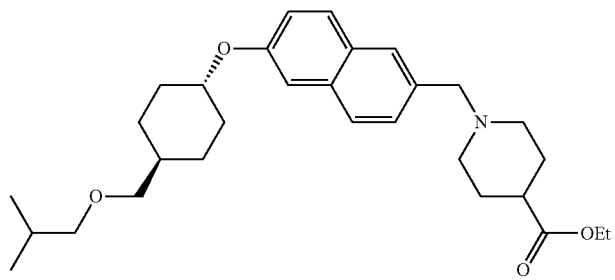

The preparation of ethyl 1-((6-((trans-4-(isobutoxymethyl)cyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 50 mg, white solid, yield: 10%. ESI-MS (M+H)$^+$: 482.1. $^1$H NMR (400 MHz, CDCl$_3$) δ: 7.70-7.63 (m, 3H), 7.42 (d, J=8.0 Hz, 1H), 7.14-7.10 (m, 2H), 4.32-4.27 (m, 1H), 4.12 (q, J=7.2 Hz, 2H), 3.60 (s, 2H), 3.28 (d, J=6.4 Hz, 2H), 3.17 (d, J=6.8 Hz, 2H), 2.90-2.87 (m, 2H), The preparation of 1-((6-((trans-4-(isobutoxymethyl)cyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 30 mg, white solid, yield: 64%. ESI-MS (M+H)$^+$: 454.1, HPLC: 99.28%. $^1$H NMR (400 MHz, CD$_3$OD) δ: 7.78-7.71 (m, 3H), 7.40 (dd, J=8.4, 1.2 Hz, 1H), 7.21 (d, J=2.0 Hz, 1H), 7.09 (dd, J=8.8, 2.4 Hz, 1H), 4.37-4.30 (m, 1H), 4.15 (s, 2H), 3.27-3.21 (m, 3H), 3.12 (d, J=6.4 Hz, 2H), 2.82-2.80 (m, 2H), 2.29-2.24 (m, 1H), 2.18-2.15 (m, 2H), 1.98-1.94 (m, 2H), 1.86-1.79 (m, 6H), 1.64-1.53 (m, 1H), 1.44-1.34 (m, 2H), 1.21-1.09 (m, 2H), 0.84 (d, J=6.8 Hz, 6H).

Example 172 ethyl 1-((6-((trans-4-(propoxymethyl)cyclohexyl)oxy)naphthalen-2-yl)methyl)piperidine-4-carboxylate The preparation of 1-((6-((trans-4-(propoxymethyl)cyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 30 mg, white solid, yield: 17%. ESI-MS (M+H)$^+$: 440.1, HPLC: 97.18%. $^1$H NMR (400 MHz, CD$_3$OD) δ: 7.81 (s, 1H), 7.74-7.69 (m, 2H), 7.42 (dd, J=8.4, 1.2 Hz, 1H), 7.17 (d, J=2.0 Hz, 1H), 7.06 (dd, J=8.4, 2.0 Hz, 1H), 4.32-4.27 (m, 1H), 4.26 (s, 2H), 3.32-3.27 (m, 3H), 3.21-3.17 (m, 3H),

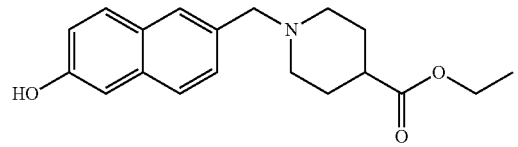

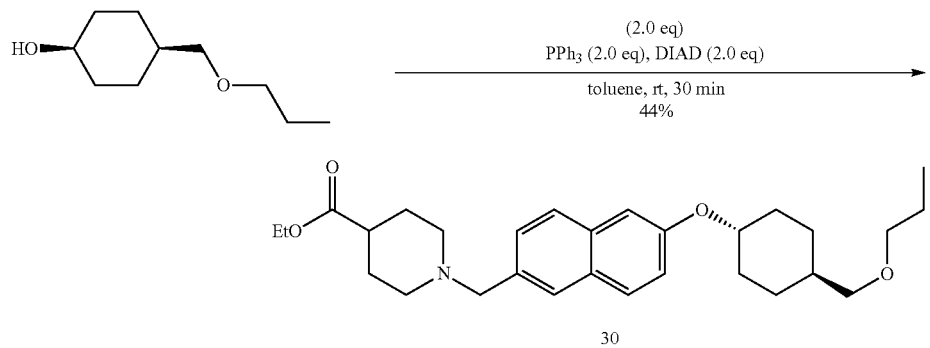

The preparation of ethyl 1-((6-((trans-4-(propoxymethyl)cyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 190 mg, white solid, yield: 44%. ESI-MS (M+H)$^+$: 468.1. $^1$H NMR (400 MHz, CDCl$_3$) δ: 7.70-7.64 (m, 3H), 7.42 (dd, J=8.0, 1.2 Hz, 1H), 7.17-7.09 (m, 2H), 4.34-4.26 (m, 1H), 4.12 (q, J=7.2 Hz, 2H), 3.63 (s, 2H), 3.38 (t, J=6.8 Hz, 2H), 3.27 (d, J=6.4 Hz, 2H), 2.90-2.87 (m, 2H), 2.32-2.25 (m, 3H), 2.07-2.02 (m, 2H), 1.95-1.78 (m, 4H), 1.50-1.32 (m, 2H), 1.31-1.17 (m, 10H), 0.93 (t, J=7.2 Hz, 3H).

Example 173

1-((6-((trans-4-(propoxymethyl)cyclohexyl)oxy)naphthalen-2-yl)methyl)piperidine-4-carboxylic acid 2.97-2.90 (m, 2H), 2.41-2.39 (m, 1H), 2.14-2.10 (m, 2H), 2.02-1.98 (m, 2H), 1.89-1.78 (m, 4H), 1.54-1.45 (m, 3H), 1.38-1.29 (m, 2H), 1.15-1.07 (m, 2H), 0.83 (t, J=7.2 Hz, 3H).

Example 174 ethyl 1-((6-((2-methylcyclohexyl)oxy)naphthalen-2-yl)methyl)piperidine-4-carboxylate

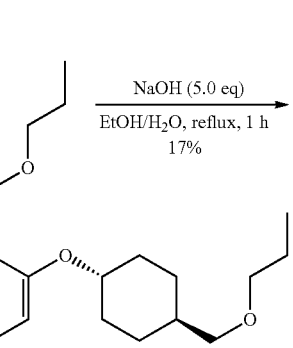

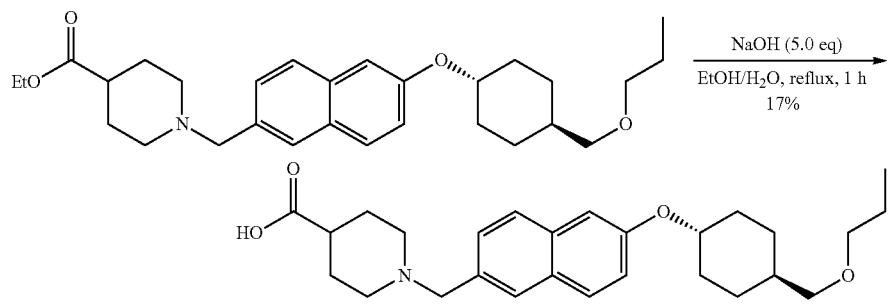

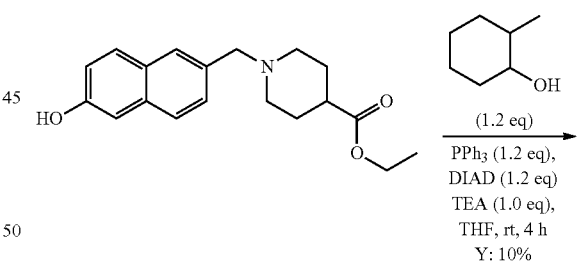

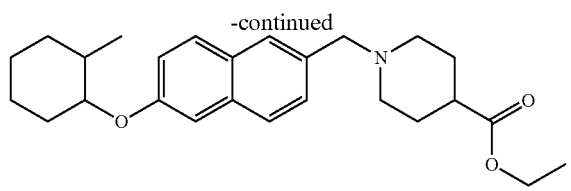

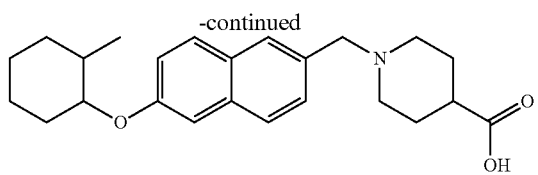

The preparation of ethyl 1-((6-((2-methylcyclohexyl)oxy) naphthalen-2-yl)methyl)piperidine-4-carboxylate was the same as that of ethyl 1-((6-((cis-4-phenylcyclohexyl)oxy) naphthalen-2-yl)methyl)piperidine-4-carboxylate, 61 mg, as yellow oil, Y: 10%. ESI-MS (M+H)$^+$: 410.1. $^1$H NMR (400 MHz, CDCl$_3$) (mixture of isomers) δ: 7.76 (s, 1H), 7.72-7.69 (m, 2H), 7.40-7.38 (m, 1H), 7.20-7.15 (m, 1H), 7.13 (s, 1H), 4.48-4.46 (m, 0.6H), 4.28-4.25 (m, 2H), 4.18-4.06 (m, 2H), 3.69-3.58 (m, 0.4H), 3.44-3.31 (m, 2H), 2.91-2.65 (m, 2H), 2.24-2.03 (m, 5H), 1.88-1.32 (m, 7H), 1.24-1.17 (m, 5H), 0.99-0.88 (m, 3H).

The preparation of 1-((6-((2-methylcyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid, 45 mg, as a white solid, Y: 79%. ESI-MS: 382.2 (M+H)$^+$. $^1$H NMR (400 MHz, CD$_3$OD) (mixture of isomers) δ: 7.82 (s, 1H), 7.72-7.69 (m, 2H), 7.42 (d, J=8.8 Hz, 1H), 7.16 (s, 1H), 7.11-7.06 (m, 1H), 4.46-4.44 (m, 0.6H), 3.93-3.87 (m, 0.4H), 3.30-3.25 (m, 2H), 2.96-2.91 (m, 2H), 2.39-2.31 (m, 1H), 2.18-1.90 (m, 3H), 1.80-1.15 (m, 12H), 0.92-0.88 (m, 3H).

Example 176 ethyl 1-((6-((trans-4-phenylcyclohexyl)oxy)quinolin-2-yl)methyl)piperidine-4-carboxylate

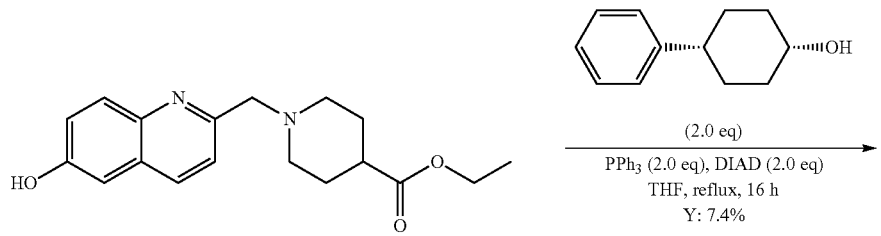

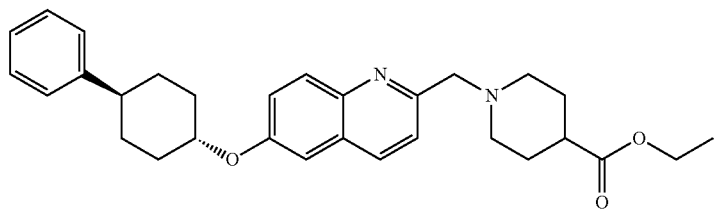

Example 175

1-((6-((2-methylcyclohexyl)oxy)naphthalen-2-yl) methyl)piperidine-4-carboxylic acid

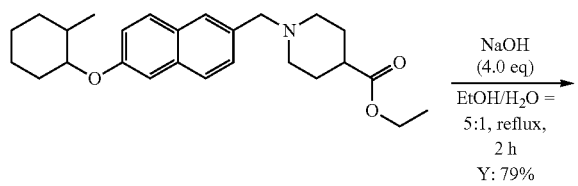

The preparation of ethyl 1-((6-((trans-4-phenylcyclohexyl)oxy)quinolin-2-yl)methyl)piperidine-4-carboxylate was the same as that of ethyl 1-((6-(cyclohexyloxy)quinolin-2-yl)methyl)piperidine-4-carboxylate, 35 mg, a yellow oil. Yield: 7.4%, ESI-MS (M+H)$^+$: 473.3. $^1$H NMR (400 MHz, CDCl$_3$) δ: 8.00 (d, J=8.8 Hz, 1H), 7.97 (d, J=9.2 Hz, 1H), 7.58 (d, J=8.4 Hz, 1H), 7.37-7.31 (m, 3H), 7.25-7.22 (m, 3H), 7.13 (d, J=2.8 Hz, 1H), 4.46-4.38 (m, 1H), 4.13 (q, J=7.2 Hz, 2H), 3.78 (s, 2H), 2.92-2.89 (m, 2H), 2.65-2.59 (m, 1H), 2.37-2.31 (m, 3H), 2.19-2.16 (m, 2H), 2.08-2.03 (m, 2H), 1.90-1.79 (m, 5H), 1.69-1.64 (m, 3H), 1.25 (t, J=7.2 Hz, 3H).

Example 177

1-((6-((trans-4-phenylcyclohexyl)oxy)quinolin-2-yl)methyl)piperidine-4-carboxylic acid

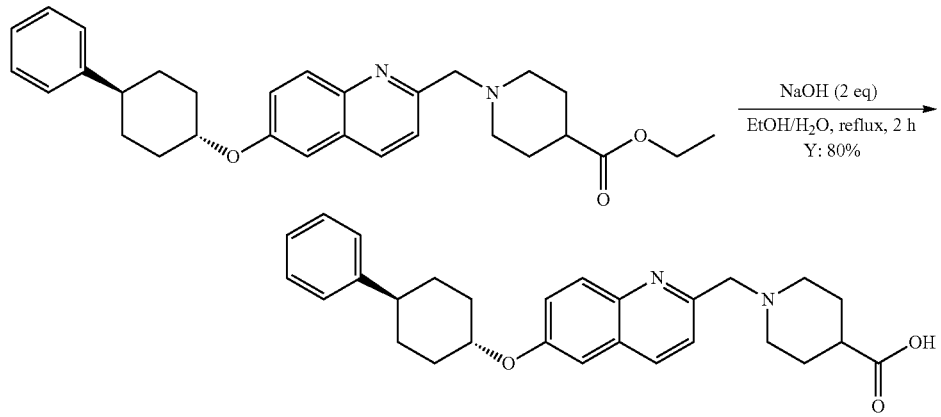

The preparation of 1-((6-((trans-4-phenylcyclohexyl)oxy)quinolin-2-yl)methyl)piperidine-4-carboxylic acid was the same as that of 1-((6-(cyclohexyloxy)quinolin-2-yl)methyl)piperidine-4-carboxylic acid, 20 mg, a yellow oil. Yield: 80%, ESI-MS (M+H)+: 445.2, HPLC: 100.00%. 1H NMR (400 MHz, CD3OD) δ: 8.26 (d, J=8.4 Hz, 1H), 7.97 (d, J=9.2 Hz, 1H), 7.61 (d, J=8.8 Hz, 1H), 7.43 (dd, J=9.2, 2.8 Hz, 1H), 7.34 (d, J=2.8 Hz, 1H), 7.33-7.28 (m, 4H), 7.21-7.17 (m, 1H), 4.61-4.54 (m, 1H), 4.07 (s, 2H), 3.19-3.16 (m, 2H), 2.68-2.54 (m, 3H), 2.40-2.27 (m, 3H), 2.03-1.97 (m, 4H), 1.94-1.87 (m, 2H), 1.83-1.68 (m, 4H).

Example 178 ethyl 1-((6-((trans-4-(isopropoxymethyl)cyclohexyl)oxy)naphthalen-2-yl)methyl)piperidine-4-carboxylate

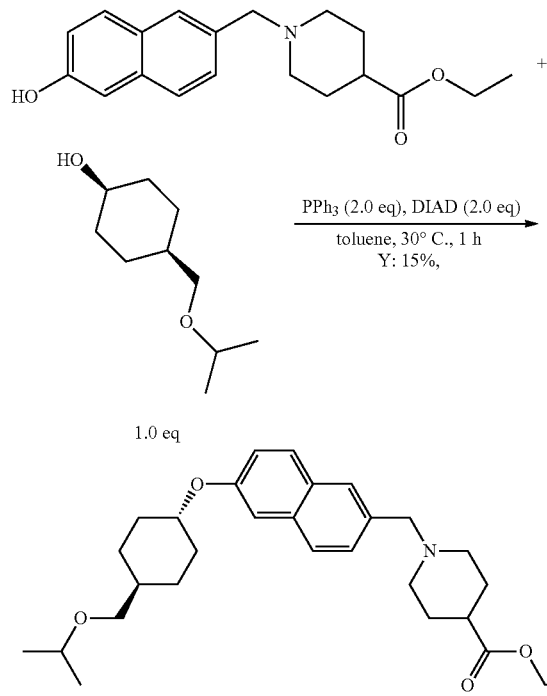

The preparation of ethyl 1-((6-((trans-4-(isopropoxymethyl)cyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 80 mg, yellow oil, Y: 15%, ESI-MS (M+H)+: 468.3. 1H NMR (400 MHz, CDCl3) δ: 7.71-7.64 (m, 3H), 7.44 (d, J=6.8 Hz, 1H), 7.15-7.11 (m, 2H), 4.34-4.28 (m, 1H), 4.14 (q, J=6.8 Hz, 2H), 3.61 (s, 2H), 3.58-3.52 (m, 1H), 3.28 (d, J=6.4 Hz, 2H), 2.91-2.89 (m, 2H), 2.28-2.25 (m, 3H), 2.09-2.04 (m, 2H), 1.97-1.74 (m, 8H), 1.64-1.61 (m, 1H), 1.55-1.45 (m, 2H), 1.25 (t, J=7.2 Hz, 3H), 1.17 (d, J=6.4 Hz, 6H).

Example 179

1-((6-((trans-4-(isopropoxymethyl)cyclohexyl)oxy)naphthalen-2-yl)methyl)piperidine-4-carboxylic acid

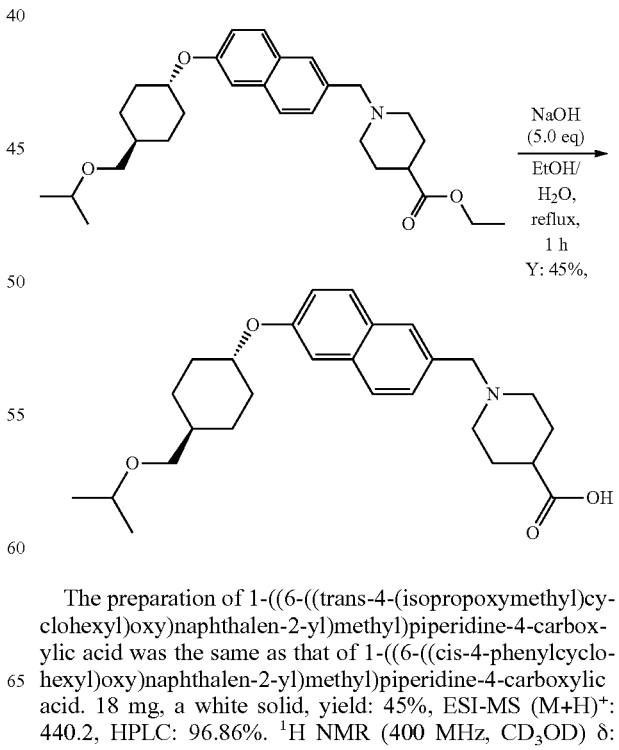

The preparation of 1-((6-((trans-4-(isopropoxymethyl)cyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 18 mg, a white solid, yield: 45%, ESI-MS (M+H)+: 440.2, HPLC: 96.86%. 1H NMR (400 MHz, CD3OD) δ:

7.82 (s, 1H), 7.77-7.71 (m, 2H), 7.40 (d, J=8.8 Hz, 1H), 7.20 (d, J=2.4 Hz, 1H), 7.09 (dd, J=8.8, 2.8 Hz, 1H), 4.35-4.29 (m, 1H), 4.28 (s, 2H), 3.51-3.45 (m, 1H), 3.39-3.35 (m, 2H), 3.05-3.01 (m, 2H), 2.59-2.50 (m, 1H), 2.15-2.04 (m, 4H), 1.84-1.81 (m, 4H), 1.52-1.46 (m, 1H), 1.41-1.31 (m, 2H), 1.18-1.06 (m, 3H), 0.93 (d, J=6.4 Hz, 6H), 0.81-0.75 (m, 1H).

Example 180 ethyl 1-((6-((cis-4-(propoxymethyl)cyclohexyl)oxy) naphthalen-2-yl)methyl)piperidine-4-carboxylate

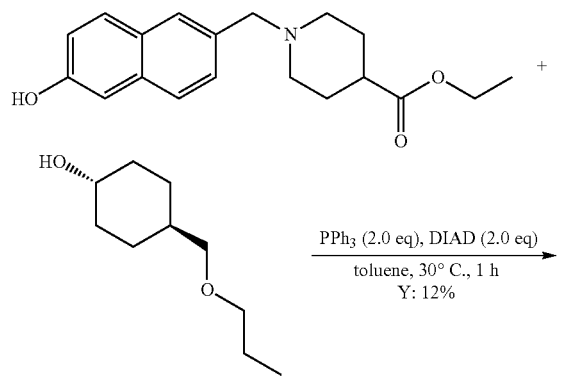

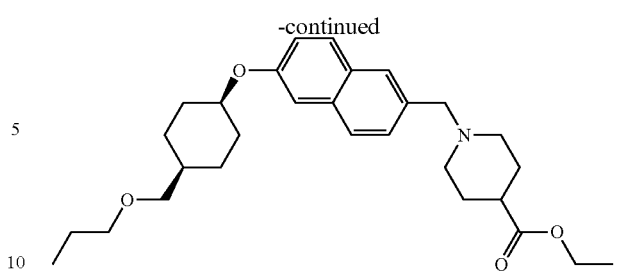

The preparation of ethyl 1-((6-((cis-4-(propoxymethyl) cyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate, 80 mg, white solid, yield: 12%, ESI-MS (M+H)$^+$: 468.3. $^1$H NMR (400 MHz, CDCl$_3$) δ: 7.64-7.58 (m, 3H), 7.36 (d, J=8.4 Hz, 1H), 7.10-7.08 (m, 2H), 4.56-4.54 (m, 1H), 3.99 (q, J=7.2 Hz, 2H), 3.48 (s, 2H), 3.26 (t, J=6.4 Hz, 2H), 3.17 (d, J=6.4 Hz, 2H), 2.78-2.75 (m, 2H), 2.17-2.15 (m, 1H), 1.99-1.90 (m, 4H), 1.77-1.58 (m, 6H), 1.53-1.45 (m, 5H), 1.39-1.33 (m, 2H), 1.11 (t, J=7.2 Hz, 3H), 0.87 (t, J=7.6 Hz, 3H).

Example 181

1-((6-((cis-4-(propoxymethyl)cyclohexyl)oxy)naphthalen-2-yl)methyl)piperidine-4-carboxylic acid

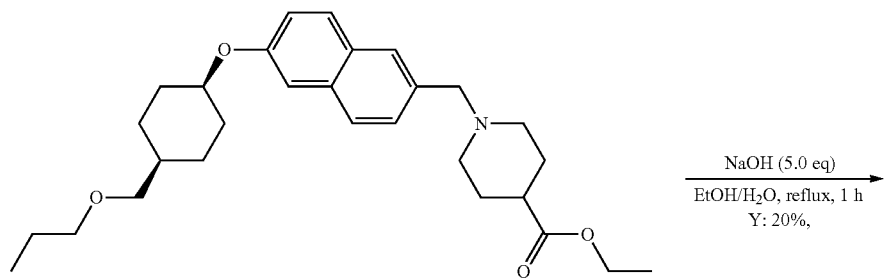

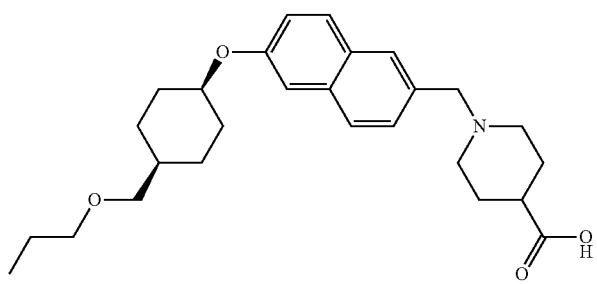

The preparation of 1-((6-((cis-4-(propoxymethyl)cyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 15 mg, a yellow solid, yield: 20%, ESI-MS (M+H)+: 440.2, HPLC: 100.00%. $^1$H NMR (400 MHz, CD$_3$OD) δ: 7.83 (s, 1H), 7.76-7.73 (m, 2H), 7.42 (d, J=8.4 Hz, 1H), 7.19 (s, 1H), 7.13 (d, J=9.2 Hz, 1H), 4.67-4.65 (m, 1H), 4.32 (s, 2H), 3.36 (d, J=7.2 Hz, 2H), 3.28 (t, J=7.6 Hz, 2H), 3.04-3.02 (m, 2H), 2.59-2.53 (m, 1H), 2.08-1.87 (m, 6H), 1.65-1.35 (m, 10H), 1.19-1.17 (m, 1H), 0.83 (t, J=7.6 Hz, 3H).

acid was the same as that of 1-((2-(trans-4-tert-Butylcyclohexyloxy)quinolin-6-yl)methyl)piperidine-4-carboxylic acid. 30 mg, as a white solid, Y: 28%. ESI-MS (M+H)+: 438.1. HPLC: 100.00%. $^1$H NMR (400 MHz, CD$_3$OD) δ: 7.82 (s, 1H), 7.77 (d, J=8.8 Hz, 1H), 7.72 (d, J=8.4 Hz, 1H), 7.40 (dd, J=8.4, 1.6 Hz, 1H), 7.20 (d, J=2.4 Hz, 1H), 7.09 (dd, J=8.8, 2.4 Hz, 1H), 4.33 (s, 2H), 4.32-4.25 (m, 1H), 3.51-3.39 (m, 2H), 2.88-2.79 (m, 1H), 2.71-2.65 (m, 1H), 2.29-2.17 (m, 5H), 1.90-1.81 (m, 4H), 1.73-1.63 (m, 1H), 1.39-1.29 (m, 2H), 1.23-1.13 (m, 3H), 1.04-0.98 (m, 1H), 0.83 (s, 9H).

Example 182

2-(piperidin-3-yl)acetic acid

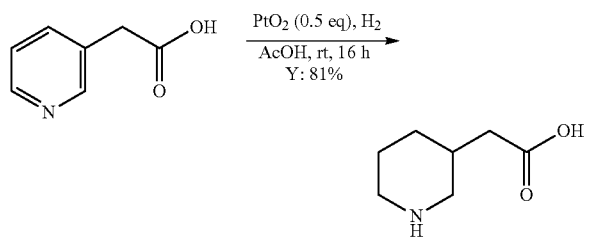

To a solution of 2-(pyridin-3-yl)acetic acid (274 mg, 2.0 mmol, 1.0 eq) in AcOH (2 mL) was added PtO$_2$ (226 mg, 1.0 mmol, 0.5 eq). The mixture was stirred at room temperature for 16 h under H$_2$. The catalyst was filtered out and the filtrate was concentrated to give 2-(piperidin-3-yl)acetic acid as a slight yellow solid (300 mg, Y: 81%). ESI-MS (M+H)+: 143.1. $^1$H NMR (400 MHz, CD$_3$OD) δ: 3.34-3.31 (m, 1H), 2.84-2.77 (m, 1H), 2.64-2.57 (m, 3H), 2.18-2.10 (m, 3H), 1.86-1.83 (m, 2H), 1.71-1.67 (m, 1H), 1.24-1.22 (m, 1H).

Example 183

2-(1-((6-((trans-4-(tert-butyl)cyclohexyl)oxy)naphthalen-2-yl)methyl)piperidin-3-yl)acetic acid Example 184 ethyl 1-((6-((tert-butyldimethylsilyl)oxy)quinolin-2-yl)methyl)piperidine-3-carboxylate

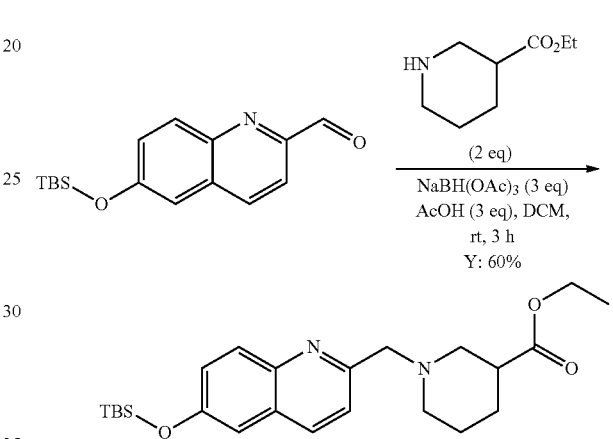

The preparation of ethyl 1-((6-((tert-butyldimethylsilyl)oxy)quinolin-2-yl)methyl)piperidine-3-carboxylate was the same as that of ethyl 1-((6-((trans-4-(tert-butyl)cyclohexyl)oxy)naphthalen-2-yl)methyl)-3-methylpiperidine-4-carboxylate, 270 mg, as yellow oil, Y: 60%, ESI-MS (M+H)+: 429.3. $^1$H NMR (400 MHz, CDCl$_3$) δ: 7.97 (d, J=8.4 Hz, 1H), 7.94 (d, J=9.2 Hz, 1H), 7.57 (d, J=8.0 Hz, 1H), 7.27

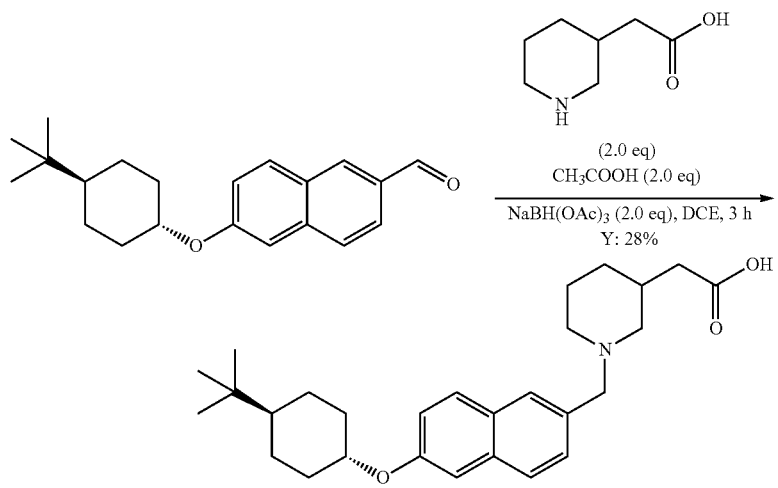

The preparation of 2-(1-((6-((trans-4-(tert-butyl)cyclohexyl)oxy)naphthalen-2-yl)methyl)piperidin-3-yl)acetic (dd, J=9.2, 2.4 Hz, 1H), 7.12 (d, J=2.8 Hz, 1H), 4.11 (q, J=7.2 Hz, 2H), 3.83-3.80 (m, 2H), 3.01-3.00 (m, 1H), 2.77-2.64 (m, 2H), 2.43-2.39 (m, 1H), 2.22-2.20 (m, 1H), 1.95-1.92 (m, 1H), 1.74-1.51 (m, 3H), 1.22 (t, J=7.2 Hz, 3H), 1.02 (s, 9H), 0.25 (s, 6H).

Example 185 ethyl 1-((6-hydroxyquinolin-2-yl)methyl)piperidine-3-carboxylate

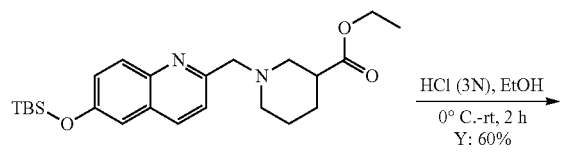

To a solution of ethyl 1-((6-((tert-butyldimethylsilyl)oxy)quinolin-2-yl)methyl)piperidine-3-carboxylate (240 mg, 0.56 mmol,) in EtOH (30 mL) was added HCl (3 N, 1 mL) dropwise at 0° C. The reaction mixture was stirred at room temperature for 2 h. The mixture was neutralized with sat. NaHCO₃ and the organic solvent were removed. Then the mixture was extracted with DCM (3×10 mL). The combined

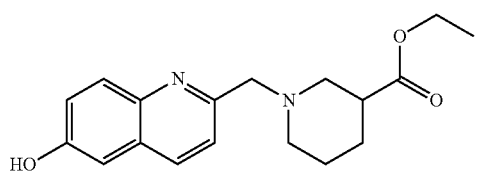

organic layer was washed with brine (10 mL), dried (Na₂SO₄) and concentrated to give ethyl 1-((6-hydroxyquinolin-2-yl)methyl)pipefidine-3-carboxylate as a white solid, 120 mg, Y: 60%, ESI-MS (M+H)⁺: 315.2. ¹H NMR (400 MHz, CDCl₃) δ: 7.86 (d, J=8.8 Hz, 2H), 7.54 (d, J=8.8 Hz, 1H), 7.29 (dd, J=9.2, 2.4 Hz, 1H), 7.05 (d, J=2.0 Hz, 1H), 4.09 (q, J=6.4 Hz, 2H), 3.90 (ABq, J=21.6, 13.6 Hz, 2H), 3.12-3.09 (m, 1H), 2.89-2.86 (m, 1H), 2.70-2.68 (m, 1H), 2.49-2.44 (m, 1H), 2.31-2.26 (m, 1H), 1.95-1.92 (m, 1H), 1.75-1.70 (m, 2H), 1.50-1.48 (m, 1H), 1.20 (t, J=7.2 Hz, 3H).

Example 186 ethyl 1-((6-((trans-4-(tert-butyl)cyclohexyl)oxy)quinolin-2-yl)methyl)piperidine-3-carboxylate

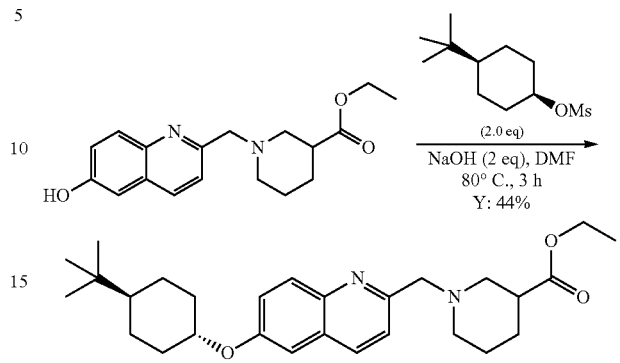

The preparation of ethyl 1-((6-((trans-4-(tert-butyl)cyclohexyl)oxy)quinolin-2-yl)methyl)piperidine-3-carboxylate was the same as that of 2-Bromo-6-(trans-4-tert-butylcyclohexyloxy)naphthalene, 58 mg as yellow oil, Y: 44%. ESI-MS (M+H)⁺: 453.3. ¹H NMR (400 MHz, CDCl₃) δ: 8.38-8.35 (m, 1H), 8.15-8.11 (m, 1H), 7.84 (d, J=8.4 Hz, 1H), 7.52-7.48 (m, 1H), 7.18 (d, J=2.4 Hz, 1H), 4.77 (s, 2H), 4.36-4.29 (m, 1H), 4.14 (q, J=7.2 Hz, 2H), 3.71-3.69 (m, 1H), 3.50-3.39 (m, 1H), 3.15-3.06 (m, 3H), 2.29-1.91 (m, 7H), 1.63-1.46 (m, 3H), 1.23 (t, J=7.2 Hz, 3H), 1.17-1.09 (m, 3H), 0.91 (s, 9H).

Example 187

1-((6-((trans-4-(tert-butyl)cyclohexyl)oxy)quinolin-2-yl)methyl)piperidine-3-carboxylic acid

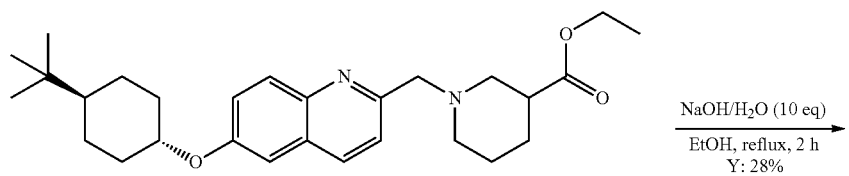

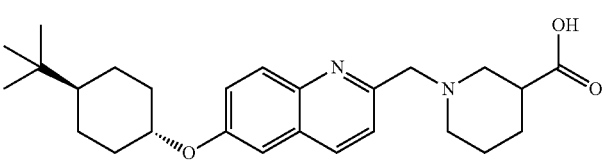

The preparation of 1-((6-((trans-4-(tert-butyl)cyclohexyl)oxy)quinolin-2-yl)methyl)piperidine-3-carboxylic acid was the same as that of 1-((6-((cis-4-phenylcyclohexyl)oxy)naphthalen-2-yl)methyl)piperidine-4-carboxylic acid, 20 mg, as a yellow solid, Y: 28%. ESI-MS (M+H)⁺: 425.3, HPLC: 100.00%. ¹H NMR (400 MHz, CD₃OD) δ: 8.15 (d, J=8.8 Hz, 1H), 7.89 (d, J=8.8 Hz, 1H), 7.39 (d, J=8.4 Hz, 1H), 7.49 (dd, J=9.2, 2.8 Hz, 1H), 7.20 (d, J=2.4 Hz, 1H), 4.32 (s, 2H), 4.29-4.24 (m, 1H), 3.07-3.05 (m, 2H), 2.63-2.61 (m, 1H), 2.19-2.16 (m, 2H), 1.90-1.71 (m, 6H), 1.38-1.28 (m, 1H), 1.24-1.12 (m, 4H), 1.06-1.00 (m, 1H), 0.82 (s, 9H).

Example 188 ethyl 1-((6-((4,4-difluorocyclohexyl)oxy)naphthalen-2-yl)methyl)piperidine-4-carboxylate

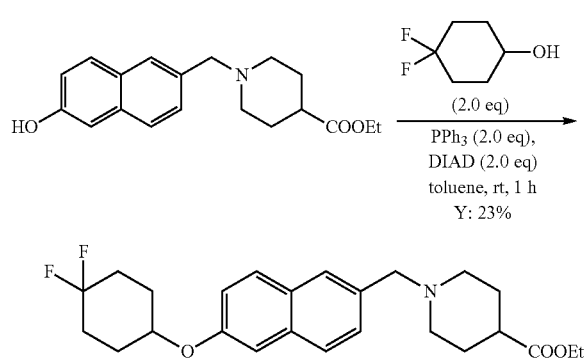

The preparation of ethyl 1-((6-((4,4-difluorocyclohexyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 50 mg, as a white solid, Y: 23%. ESI-MS (M+H)$^+$: 432.1.

Example 189

1-((6-((4,4-difluorocyclohexyl)oxy)naphthalen-2-yl)methyl)piperidine-4-carboxylic acid

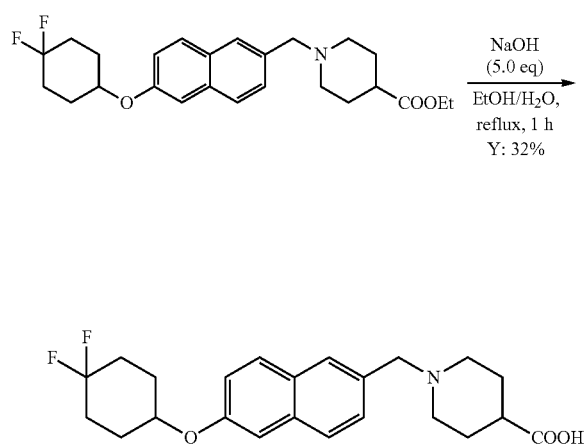

The preparation of 1-((64(4,4-difluorocyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 15 mg, as a white solid, Y: 32%. ESI-MS (M+H)$^+$: 404.1, HPLC: 100%. $^1$H NMR (400 MHz, CD$_3$OD) δ: 7.94 (s, 1H), 7.89 (d, J=8.4 Hz, 1H), 7.86 (d, J=9.2 Hz, 1H), 7.52 (dd, J=8.4, 1.6 Hz, 1H), 7.38 (d, J=1.6 Hz, 1H), 7.26 (dd, J=8.8, 2.4 Hz, 1H), 4.79-4.76 (m, 1H), 4.43 (s, 2H), 3.49-3.46 (m, 2H), 3.16-3.13 (m, 2H), 2.65-2.60 (m, 1H), 2.20-2.12 (m, 4H), 2.06-1.94 (m, 8H).

Example 190 ethyl 1-((6-((2-methylcyclopentyl)oxy)naphthalen-2-yl)methyl)piperidine-4-carboxylate

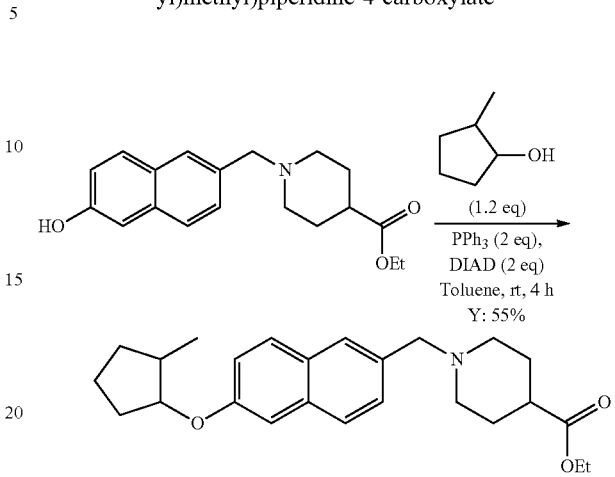

The preparation of ethyl 1-((6-((2-methylcyclopentyl)oxy)naphthalen-2-yl)methyl)piperidine-4-carboxylate was the same as that of ethyl 1-((6-((cis-4-phenylcyclohexyl)oxy)naphthalen-2-yl)methyl)piperidine-4-carboxylate. 220 mg, as a colorless oil, Y: 55%. ESI-MS (M+H)$^+$: 396.2. $^1$H NMR (400 MHz, CDCl$_3$) δ: 7.69-7.63 (m, 3H), 7.43-7.41 (m, 1H), 7.13-7.07 (m, 2H), 4.68-4.65 (m, 0.6H), 4.40-4.36 (m, 0.4H), 4.12 (q, J=6.8 Hz, 2H), 3.60 (s, 2H), 2.31-2.24 (m, 1H), 2.15-1.98 (m, 4H), 1.93-1.76 (m, 7H), 1.66-1.57 (m, 2H), 1.29-1.22 (m, 5H), 1.11-1.08 (m, 3H).

Example 191

1-((6-((2-methylcyclopentyl)oxy)naphthalen-2-yl)methyl)piperidine-4-carboxylic acid

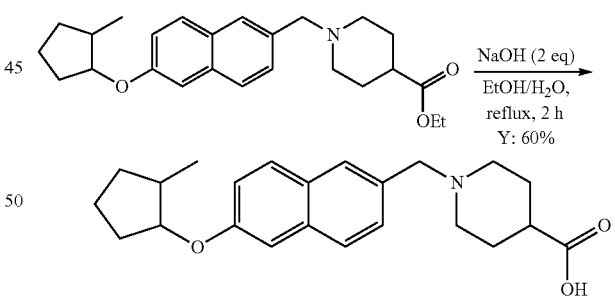

The preparation of 1-((6-((2-methylcyclopentyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 80 mg, as a white solid, Y: 60%. ESI-MS (M+H)$^+$: 368.2, HPLC: 97.19%. $^1$H NMR (400 MHz, CD$_3$OD) δ: 7.93 (s, 1H), 7.87 (d, J=8.8 Hz, 1H), 7.83 (d, J=9.2 Hz, 1H), 7.50 (d, J=8.4 Hz, 1H), 7.27(s, 1H), 7.23-7.19 (m, 1H), 4.91-4.89 (m, 0.6H), 4.49-4.47 (m, 0.4H), 4.44 (s, 2H), 3.60-3.43 (m, 2H), 3.22-3.05 (m, 2H), 2.86-2.43 (m, 1H), 2.26-1.99 (m, 5H), 1.90-1.58 (m, 5.5H), 1.35-1.30 (m, 0.5H), 1.12 (d, J=6.8 Hz, 3H).

Example 192 ethyl 1-((6-(4-((2-hydroxypropan-2-yl)cyclohexyl)oxy)naphthalen-2-yl)methyl)piperidine-4-carboxylate

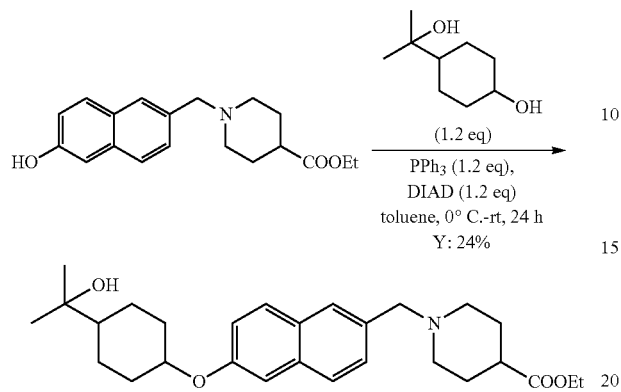

The preparation of ethyl 1-((6-((4-(2-hydroxypropan-2-yl)cyclohexyl)oxy)naphthalen-2-yl)methyl)piperidine-4-carboxylate was the same as that of ethyl 1-((6-((trans-4-(tert-butyl)cyclohexyl)oxy)naphthalen-2-yl)methyl)-3-methylpiperidine-4-carboxylate. 170 mg, as a white solid, Y: 24%. ESI-MS (M+H)+: 454.2. $^1$HNMR (400 MHz, DMSO-d$_6$) δ: 7.69 (d, J=9.2 Hz, 1H), 7.65 (d, J=8.4 Hz, 1H), 7.63 (s, 1H), 7.42 (dd, J=8.8 Hz, J=2.0 Hz, 1H), 7.14 (d, J=2.4 Hz, 1H), 7.12 (d, J=8.4 Hz, 1H), 4.33-4.24 (m, 1H), 4.12 (q, J=6.8 Hz, 2H), 3.60 (s, 2H), 2.90-2.88 (m, 2H), 2.32-2.28 (m, 3H), 2.08-1.96 (m, 4H), 1.86-1.76 (m, 5H), 1.49-1.29 (m, 3H), 1.27-1.22 (m, 4H), 1.20 (s, 6H).

Example 193

1-((6-((4-(2-hydroxypropan-2-yl)cyclohexyl)oxy)naphthalen-2-yl)methyl)piperidine-4-carboxylic acid

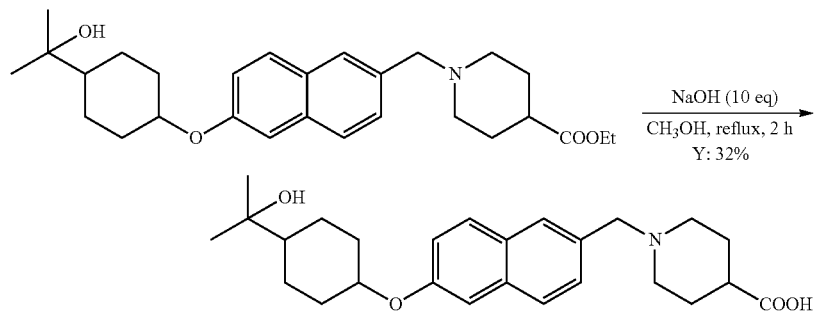

The preparation of 1-((6-((4-(2-hydroxypropan-2-yl)cyclohexyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid, 40 mg, as a white solid, Y: 32%. ESI-MS (M+H)+: 426.2, HPLC: 98.86%. $^1$HNMR (400 MHz, DMSO-d$_6$) δ: 7.77 (s, 1H), 7.73 (d, J=8.4 Hz, 1H), 7.69 (d, J=8.8 Hz, 1H), 7.37 (dd, J=8.8, 1.6 Hz, 1H), 7.18 (d, J=2.0 Hz, 1H), 7.07 (dd, J=8.8, 2.0 Hz, 1H), 4.31-4.28 (m, 1H), 4.17 (s, 2H), 3.26-3.23 (m, 1H), 2.85-2.82 (m, 2H), 2.25-2.17 (m, 3H), 1.93-1.79 (m, 6H), 1.33-1.21 (m, 6H), 1.18 (s, 6H).

Example 194 ethyl 1-((6-((3-methylcyclopentyl)oxy)naphthalen-2-yl)methyl)piperidine-4-carboxylate

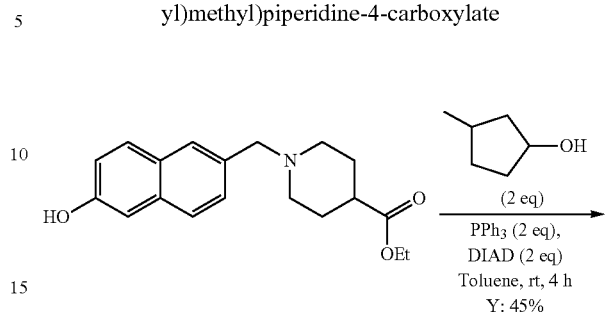

The preparation of ethyl 1-((6-((3-methylcyclopentyl)oxy)naphthalen-2-yl)methyl)piperidine-4-carboxylate was the same as that of ethyl 1-((6-((trans-4-(tert-butyl)cyclohexyl)oxy)naphthalen-2-yl)methyl)-3-methylpiperidine-4-carboxylate. 180 mg, as yellow oil, Y: 45%. ESI-MS (M+H)+: 396.2.

Example 195

1-((6-((3-methylcyclopentyl)oxy)naphthalen-2-yl)methyl)piperidine-4-carboxylic acid

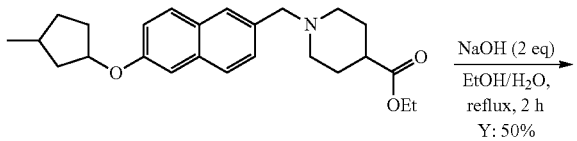

153

-continued

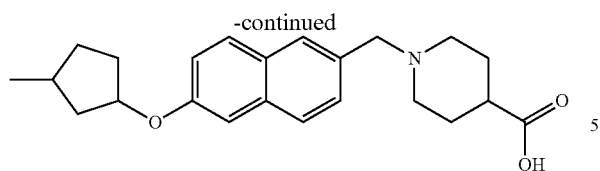

The preparation of 1-((6-((3-methylcyclopentyl)oxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 60 mg, as a white solid, Y: 50%. ESI-MS (M+H)⁺: 368.2, HPLC: 95.36%. ¹H NMR (400 MHz, CD₃OD) δ: 7.88 (s, 1H), 7.84 (d, J=8.8 Hz, 1H), 7.81 (d, J=9.2 Hz, 1H), 7.49 (dd, J =8.8, 2.0 Hz, 1H), 7.21 (d, J=2.0 Hz, 1H), 7.18-7.14 (m, 1H), 4.99-4.97 (m, 1H), 4.29 (s, 2H), 3.39-3.36 (m, 2H), 2.98-2.93 (m, 2H), 2.41-2.37 (m, 1H), 2.30-2.24 (m, 1H), 2.10-1.82 (m, 7H), 1.59-1.53 (m, 1H), 1.45-1.38 (m, 1H), 1.28-1.21 (m, 1H), 1.12-1.06 (m, 3H).

Example 196 ethyl 1-((6-(bicyclo[3.1.0]hexan-3-yloxy)naphthalen-2-yl)methyl)piperidine-4-carboxylate

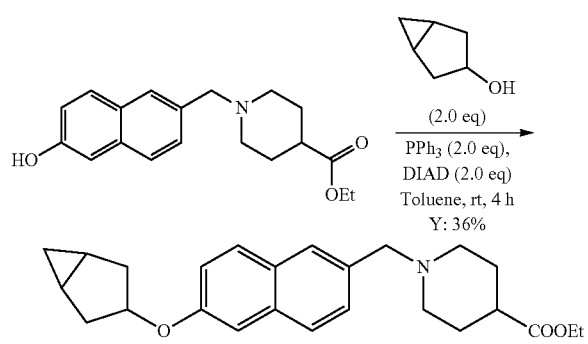

The preparation of ethyl 1-((6-(bicyclo[3.1.0]hexan-3-yloxy)naphthalen-2-yl)methyl)piperidine-4-carboxylate was the same as that of ethyl 1-((6-((trans-4-(tert-butyl)cyclohexyl)oxy)naphthalen-2-yl)methyl)-3-methylpiperidine-4-carboxylate. 90 mg, as yellow oil, Y: 36%. ESI-MS (M+H)⁺: 394.2. ¹H MR (400 MHz, CDCl₃) δ: 7.68-7.63 (m, 3H), 7.44-7.42 (m, 1H), 7.09-7.07(m, 2H), 4.58-4.51 (m, 1H), 4.12 (q, J=7.2 Hz, 2H), 3.61 (s, 2H), 2.90-2.88 (m, 2H) 2.46-2.41 (m, 2H), 2.32-2.23 (m, 1H), 2.08-2.03 (m, 2H), 2.01-1.95 (m, 2H), 1.89-1.86 (m, 2H), 1.82-1.76 (m, 2H), 1.40-1.38 (m, 2H), 1.24 (t, J=7.2 Hz, 3H), 0.51-0.46 (m, 1H), 0.13-0.10 (m, 1H).

Example 197

1-((6-(bicyclo[3.1.0]hexan-3-yloxy)naphthalen-2-yl)methyl)piperidine-4-carboxylic acid

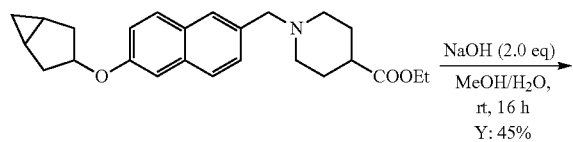

154

-continued

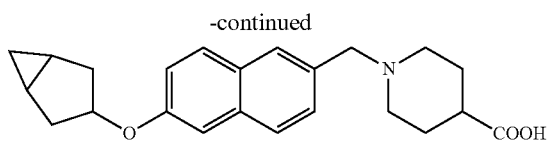

The preparation of 1-((6-(bicyclo[3.1.0]hexan-3-yloxy)naphthalen-2-yl)methyl)piperidine-4-carboxylic acid was the same as that of 1-((6-((cis-4-phenylcyclohexyl)oxy)naphthalen-2-yl)methyl)piperidine-4-carboxylic acid. 40 mg, as a white solid, Y: 45%. ESI-MS (M+H)⁺: 366.2. HPLC: 100.00%. ¹H NMR (400 MHz, CD₃OD) δ: 7.89 (s, 1H), 7.85 (d, J=8.8 Hz, 1H), 7.78 (d, J=8.8 Hz, 1H), 7.48 (dd, J=8.4 Hz, J=1.6 Hz, 1H), 7.23 (s, 1H), 7.16 (dd, J=9.2, 2.0 Hz, 1H), 4.68-4.61 (m, 4.41 (s, 2H), 3.57-3.41 (m, 2H), 3.19-3.03 (m, 2H), 2.84-2.58 (m, 1H), 2.47-2.42 (m, 2H), 2.32-2.20 (m, 2H), 2.01-1.85 (m, 4H), 1.40-1.39 (m, 2H), 0.51-0.46 (m, 1H), 0.20-0.17 (m, 1H).

Example 198 ethyl 1-46-((trans-4-isopropylcyclohexyl)oxy)naphthalen-2-yl)methyl)piperidine-4-carboxylate

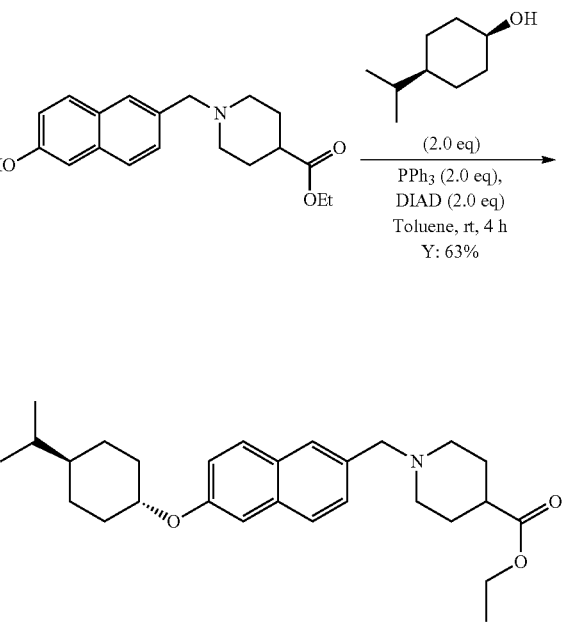

The preparation of ethyl 1-((6-((trans-4-isopropylcyclohexyl)oxy)naphthalen-2-yl)methyl)piperidine-4-carboxylate was the same as that of ethyl 1-((6-((trans-4-(tert-butyl)cyclohexyl)oxy)naphthalen-2-yl)methyl)-3-methylpiperidine-4-carboxylate. 275 mg, as yellow oil, Y: 63%. ESI-MS (M+H)⁺: 438.3.

Example 199

1-((6-(((trans-4-isopropylcyclohexyl)oxy)naphthalen-2-yl)methyl)piperidine-4-carboxylic acid

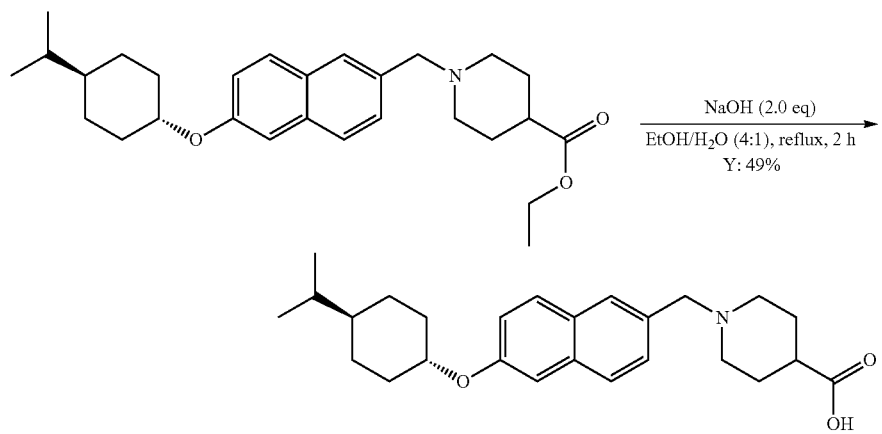

The preparation of 1-((6-(((trans-4-isopropylcyclohexyl)oxy)naphthalen-2-yl)methyl)piperidine-4-carboxylic acid was the same as that of 1-((6-(((cis-4-phenylcyclohexyl)oxy)naphthalen-2-yl)methyl)piperidine-4-carboxylic acid. 60 mg, as a yellow solid, Y: 49%. ESI-MS (M+H−56)$^+$: 410.3. $^1$H NMR (400 MHz, DMSO-$d_6$) δ: 9.98 (s, 1H), 7.94 (s, 1H), 7.87 (d, J=8.4 Hz, 1H), 7.83 (d, J=9.2 Hz, 1H), 7.55 (d, J=8.4 Hz, 1H), 7.42 (s, 1H), 7.20 (dd, J=8.8, 2.4 Hz, 1H), 4.42-4.39 (m, 3H), 3.45-3.42 (m, 2H), 3.00-2.98 (m, 2H), 2.51-2.46 (m, 1H), 2.26-1.64 (m, 8H), 1.53-1.06 (m, 6H), 0.88 (d, J=6.8 Hz, 6H).

Example 200

1-tert-butyl 4-methyl piperidine-1,4-dicarboxylate

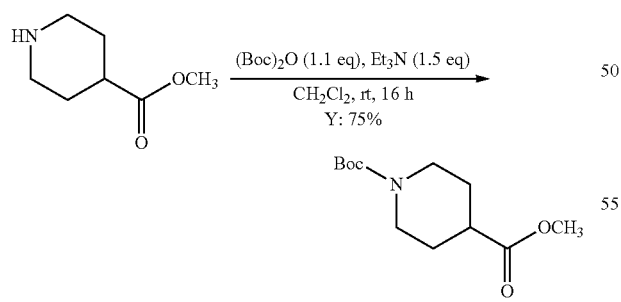

To a solution of methyl piperidine-4-carboxylate (3.0 g, 21.0 mmol, 1.0 eq) in CH$_2$Cl$_2$ (70 mL) were added Et$_3$N (3.18 g, 31.5 mmol, 1.5 eq) and (Boc)$_2$O (5.04 g, 23.1 mmol, 1.1 eq). Then the reaction mixture was stirred at room temperature for 16 h. After concentration, the residue was purified by silica gel column (PE: EA=3:1) to give 1-tert-butyl 4-methyl piperidine-1,4-dicarboxylate as colorless gum (3.8 g, Y: 75%). ESI-MS (M+H)$^+$: 244.1. $^1$H NMR (400 MHz, CDCl$_3$) δ: 4.03-4.00 (m, 2H), 3.67 (s, 3H), 2.86-2.79 (m, 2H), 2.48-2.42 (m, 1H), 1.89-1.85 (m, 2H), 1.67-1.57 (m, 2H), 1.45 (s, 9H).

Example 201

1-tert-butyl 4,4-dimethyl piperidine-1,4,4-tricarboxylate

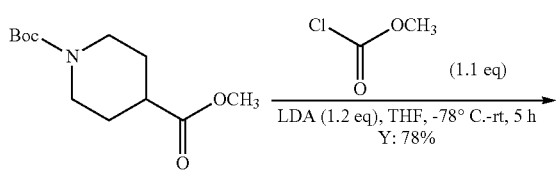

To a solution of 1-tert-butyl 4-methyl piperidine-1,4-dicarboxylate (1.3 g, 5.35 mmol, 1.0 eq) in dry THF (35 mL) was added LDA (2N, 3.25 mL, 6.42 mmol, 1.2 eq) dropwise at −78° C. under N$_2$. Then the mixture was stirred at −78° C. for 1 h. Then methyl carbonochloridate (0.55 g, 5.89 mmol, 1.1 eq) was added dropwise to this mixture. The resulting mixture was warmed to rt slowly for 4 h. Saturated NH$_4$Cl solution was added to this mixture, extracted with EtOAc (75 mL×2), washed with brine (20 mL), dried over Na$_2$SO$_4$, filtered, and concentrated in vacuo to give 1-tert-butyl 4,4-dimethyl piperidine-1,4,4-tricarboxylate as yellow oil (1.25 g, Y: 78%).

Example 202 dimethyl piperidine-4,4-dicarboxylate

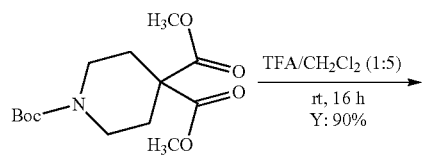

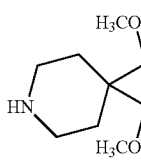

To a solution of dimethyl piperidine-4,4-dicarboxylate (1.2 g, 3.98 mmol, 1.0 eq) in CH$_2$Cl$_2$ (30.0 mL) was carefully added TFA (6.0 mL) at rt. The reaction solution was stirred at rt for 16 h. The solvent was removed to give crude product dimethyl piperidine-4,4-dicarboxylate as yellow oil (0.72 g, Y: 90%), which was directly used for the next step without further purification. ESI-MS (M+H)$^+$: 202.2. $^1$H NMR (400 MHz, CDCl$_3$) δ: 3.74 (s, 6H), 2.86-2.83 (m, 2H), 2.08-2.04 (m, 41-1), 1.26-1.19 (m, 2H).

Example 203 dimethyl 1-06-((trans-4-(tert-butyl)cyclohexyl)oxy) naphthalen-2-yl)methyl)piperidine-4,4-dicarboxylate

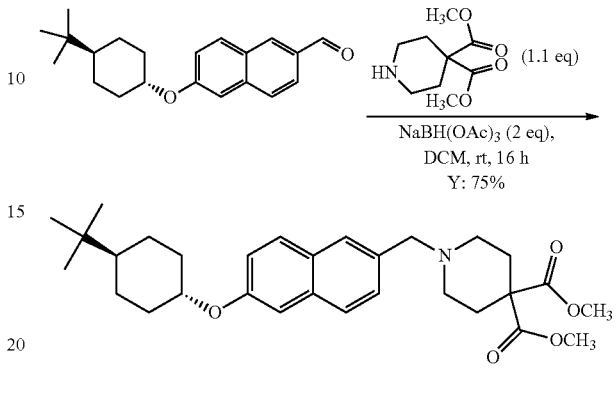

The preparation of dimethyl 1-((6-((trans-4-(tert-butyl) cyclohexyl)oxy)naphthalen-2-yl)methyl)piperidine-4,4-dicarboxylate was the same as that of ethyl 1-((6-((trans-4-(tert-butyl)cyclohexyl)oxy)naphthalen-2-yl)methyl)-3-methylpiperidine-4-carboxylate. 180 mg, as a yellow solid, Y: 75%. ESI-MS (M+H)$^+$: 496.3. $^1$H NMR (400 MHz, CDCl$_3$) δ: 7.68 (d, J=8.8 Hz, 114), 7.65 (d, J=8.4 Hz, 1H), 7.61 (s, 1H), 7.41 (d, J=8.4 Hz, 1H), 7.14-7.10 (m, 2H), 4.28-4.23 (m, 1H), 3.73 (s, 6H), 3.57 (s, 2H), 2.48-2.45 (m, 3H), 2.29-2.26 (m, 2H), 2.17-2.14 (m, 3H), 1.91-1.87 (m, 4H), 1.47-1.39 (m, 2H), 1.19-1.09 (m, 3H), 0.89 (s, 9H).

Example 204

1-((6-((trans-4-(tert-butyl)cyclohexyl)oxy)naphthalen-2-yl)methyl)piperidine-4,4-dicarboxylic acid

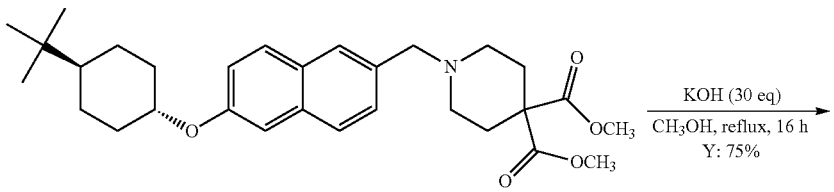

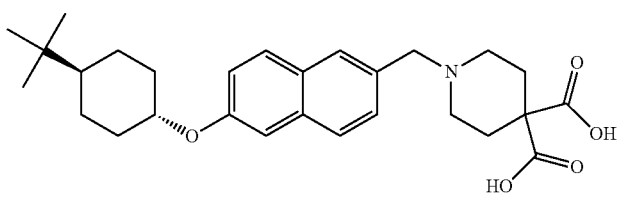

The preparation of 1-((6-(((trans-4-(tert-butyl)cyclohexyl)oxy)naphthalen-2-yl)methyl)piperidine-4,4-dicarboxylic acid was the same as that of 1-((6-(((cis-4-phenylcyclohexyl)oxy)naphthalen-2-yl)methyl)piperidine-4-carboxylic acid. 120 mg, as a white solid, Y: 75%. ESI-MS (M+H)+: 468.3, HPLC: 99.33%. $^1$H NMR (400 MHz, DMSO-d$_6$) δ: 7.82-7.77 (m, 3H), 7.51-7.48 (m, 1H), 7.36 (d, J=1.6 Hz, 1H), 7.14 (dd, J=8.4, 1.6 Hz, 1H), 4.39-4.36 (m, 1H), 3.94 (s, 2H), 3.11-2.79 (m, 4H), 2.22-2.18 (m, 2H), 2.02-2.00 (m, 4H), 1.83-1.80 (m, 2H), 1.36-1.07 (m, 5H), 0.88 (s, 9H).

Example 205 methyl 2-(1-((6-((trans-4-(tert-butyl)cyclohexyl)oxy)naphthalen-2-yl)methyl)piperidin-2-yl)acetate

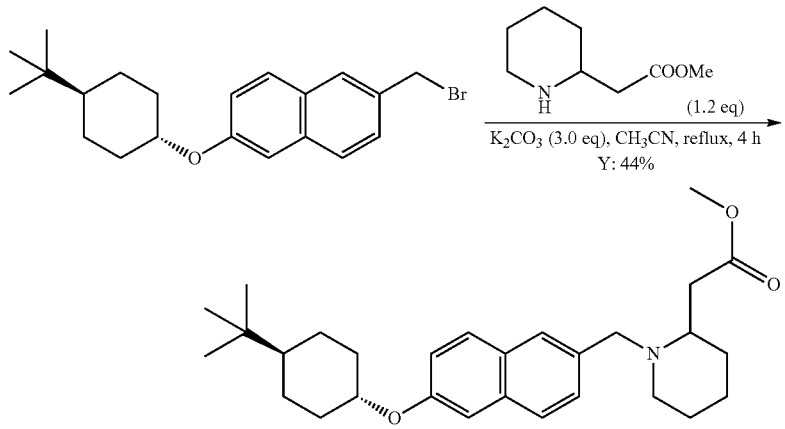

The preparation of methyl 2-(1-((6-((trans-4-(tert-butyl)cyclohexyl)oxy)naphthalen-2-yl)methyl)piperidin-2-yl)acetate was the same as that of methyl 2-(((6-((trans-4-(tert-butyl)cyclohexyl)oxy)naphthalen-2-yl)methyl)(methyl)amino)-2-methylpropanoate. 100 mg, as a white solid, Y: 44%. ESI-MS (M+H)+: 452.3. $^1$H NMR (400 MHz, CD$_3$OD) δ: 7.71 (d, J=9.2 Hz, 1H), 7.69 (d, J=8.0 Hz, 1H), 7.66 (s, 1H), 7.42 (dd, J=8.4, 1.2 Hz, 1H), 7.21 (d, J=2.4 Hz, 1H), 7.09 (dd, J=8.8, 2.4 Hz, 1H), 4.60 (s, 1H), 4.36-4.31 (m, 1H), 4.01-3.98 (m, 1H), 3.68 (s, 3H), 3.51-3.48 (m, 1H), 2.97-2.95 (m, 1H), 2.91-2.86 (m, 1H), 2.77-2.71 (m, 1H), 2.55-2.50 (m, 1H), 2.29-2.22 (m, 3H), 1.93-1.90 (m, 2H), 1.79-1.66 (m, 2H), 1.56-1.49 (m, 3H), 1.43-1.37 (m, 2H), 1.32-1.22 (m, 2H), 1.17-1.13 (m, 1H), 0.93 (s, 9H).

Example 206

2-(1-((6-((trans-4-(tert-butyl)cyclohexyl)oxy)naphthalen-2-yl)methyl)piperidin-2-yl)acetic acid

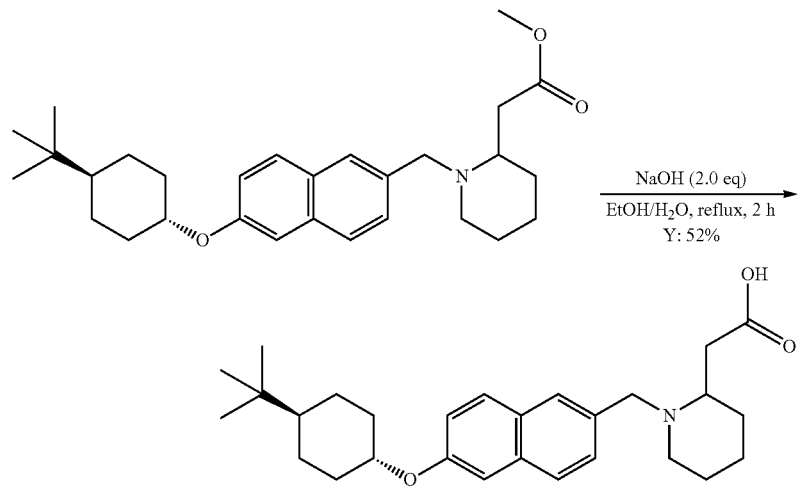

The preparation of 2-(1-((6-((trans-4-(tert-butyl)cyclohexyl)oxy)naphthalen-2-yl)methyl)piperidin-2-yl)acetic acid was the same as that of 2-(((6-((trans-4-(tert-butyl)cyclohexyl)oxy)naphthalen-2-yl)methyl)(methyl)amino)-2-methylpropanoic acid. 36 mg, as a white solid, Y: 52%. ESI-MS (M+H)⁺: 438.3, HPLC: 100.00%. ¹H NMR (400 MHz, CD₃OD) δ: 7.80 (s, 1H), 7.73 (d, J=8.4 Hz, 1H), 7.69 (d, J=9.2 Hz, 1H), 7.38 (dd, J=8.4, 1.2 Hz, 1H), 7.16 (d, J=2.4 Hz, 1H), 7.06 (dd, J=9.2, 2.4 Hz, 1H), 4.61-4.58 (m, 1H), 4.25-4.21 (m, 2H), 3.60-3.57 (m, 1H), 3.15-3.13 (m, 1H), 2.85-2.97 (m, 3H), 2.17-2.12 (m, 2H), 1.98-1.92 (m, 1H), 1.79-1.71 (m, 5H), 1.53-1.50 (m, 1H), 1.31-1.28 (m, 2H), 1.20-1.11 (m, 3H), 1.05-0.96 (m, 1H), 0.80 (s, 9H).

Example 207

2-bromo-6-((4,4-dimethylcyclohexyl)oxy)naphthalene

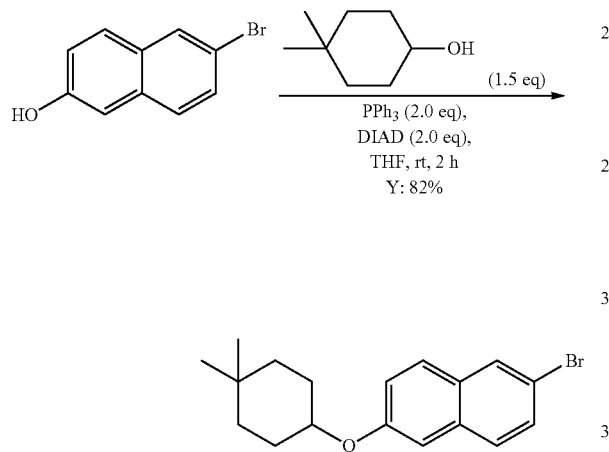

The preparation of 2-bromo-6-((4,4-dimethylcyclohexyl)oxy)naphthalene was the same as that of 2-bromo-6-((cis-4-ethylcyclohexyl)oxy)naphthalene. 6.27 g, as a white solid, Y: 82%. ESI-MS (M+H)⁺: 333.1. ¹H NMR (400 MHz, CD₃OD) δ: 7.93 (s, 1H), 7.69 (d, J=8.8 Hz, 1H), 7.68 (d, J=8.8 Hz, 1H), 7.47 (dd, J=8.8, 1.6 Hz, 1H), 7.22 (d, J=1.2 Hz, 1H), 7.15 (dd, J=8.8, 2.0 Hz, 1H), 4.48-4.44 (m, 1H), 1.98-1.91 (m, 2H), 1.78-1.69 (m, 2H), 1.59-1.53 (m, 2H), 1.39-1.32 (m, 2H), 1.00 (s, 3H), 0.99 (s, 3H).

Example 208

6-((4,4-dimethylcyclohexyl)oxy)-2-naphthaldehyde

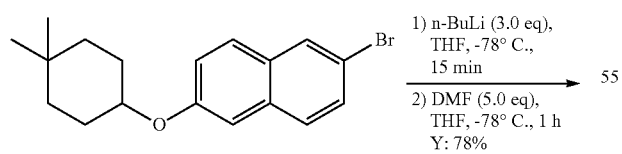

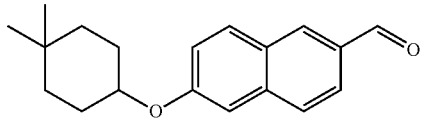

The preparation of 6-((4,4-dimethylcyclohexyl)oxy)-2-naphthaldehyde was the same as that of 2-(trans-4-tert-Butyl-cyclohexyloxy)-quinoline-6-carbaldehyde. 2.7 g, as a yellow solid, Y: 78%. ESI-MS (M+H)⁺: 283.2. ¹H NMR (400 MHz, CDCl₃) δ: 10.08 (s, 1H), 8.23 (s, 1H), 7.91-7.87 (m, 2H), 7.76 (d, J=8.8 Hz, 1H), 7.22 (dd, J=8.8, 2.4 Hz, 1H), 7.18 (d, J=2.0 Hz, 1H), 4.48-4.42 (m, 1H), 1.99-1.92 (m, 2H), 1.81-1.72 (m, 2H), 1.59-1.54 (m, 2H), 1.37-1.30 (m, 2H), 1.00 (s, 3H), 0.98 (s, 3H).

Example 209 ethyl 1-((6-((4,4-dimethylcyclohexyl)oxy)naphthalen-2-yl)methyl)piperidine-3-carboxylate

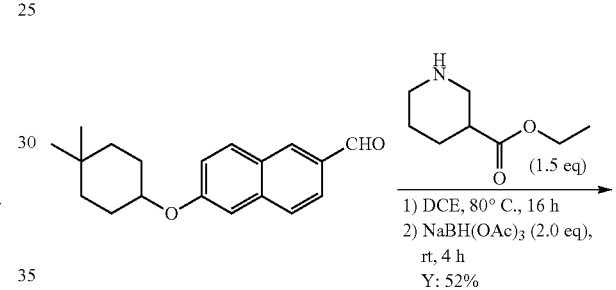

The preparation of ethyl 1-((6-((4,4-dimethylcyclohexyl)oxy)naphthalen-2-yl)methyl)piperidine-3-carboxylate was the same as that of ethyl 1-((6-((trans-4-(tert-butyl)cyclohexyl)oxy)naphthalen-2-yl)methyl)-3-methylpiperidine-4-carboxylate. 140 mg, as a white solid, Y: 52%. ESI-MS (M+H)⁺: 424.3.

Example 210

1-((6-((4,4-dimethylcyclohexyl)oxy)naphthalen-2-yl)methyl)piperidine-3-carboxylic acid

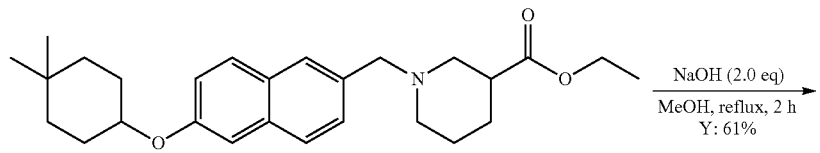

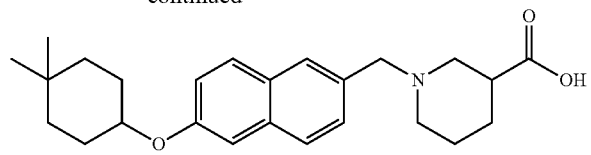

The preparation of 1-((6-((4,4-dimethylcyclohexyl)oxy)naphthalen-2-yl)methyl)piperidine-3-carboxylic acid was the same as that of 2-(((6-((trans-4-(tert-butyl)oxy)naphthalen-2-yl)methyl)(methyl)amino)-2-methylpropanoic acid. 80 mg, as a white solid, Y: 61%. ESI-MS (M+H)⁺: 396.2, HPLC: 100.00%. ¹H NMR (400 MHz, CD₃OD) δ7.82 (s, 1H), 7.75 (d, J=8.8 Hz, 1H), 7.11 (d, J=9.2 Hz, 1H), 7.40 (d, J=8.4 Hz, 1H), 7.18 (d, J=2.4 Hz, 1H), 7.10 (dd, J=8.8, 2.0 Hz, 1H), 4.41-4.35 (m, 3H), 3.59-3.38 (m, 2H), 2.96-2.73 (m, 3H), 2.10-2.06 (m, 1H), 1.90-1.58 (m, 7H), 1.47-1.41 (m, 2H), 1.29-1.21 (m, 2H), 0.88 (s, 3H), 0.87 (s, 3H).

Example 211 methyl 1-((6-((4,4-dimethylcyclohexyl)oxy)naphthalen-2-yl)methyl)-4-methylpiperidine-4-carboxylate

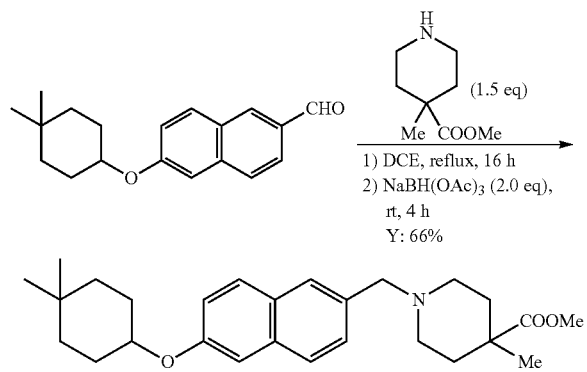

The preparation of methyl 1-((6-((4,4-dimethylcyclohexyl)oxy)naphthalen-2-yl)methyl)-4-methylpiperidine-4-carboxylate was the same as that of ethyl 1-((6-((trans-4-(tert-butyl)cyclohexyl)oxy)naphthalen-2-yl)methyl)-3-methylpiperidine-4-carboxylate. 187 mg, as a white solid, Y: 66%. ESI-MS (M+H)⁺: 424.2.

Example 212

1-((6-((4,4-dimethylcyclohexyl)oxy)naphthalen-2-yl)methyl)-4-methylpiperidine-4-carboxylic acid

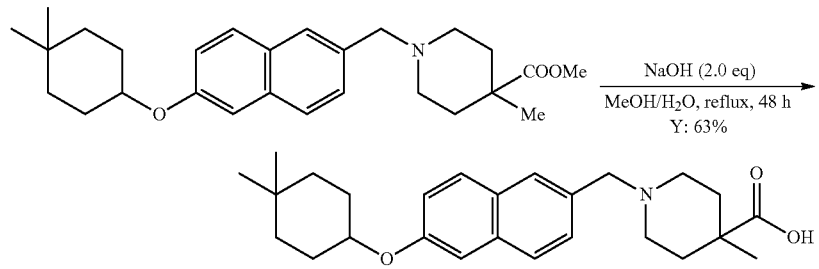

The preparation of 1-((6-((4,4-dimethylcyclohexyl)oxy)naphthalen-2-yl)methyl)-4-methylpiperidine-4-carboxylic acid was the same as that of 2-(((6-((trans-4-(tert-butyl)cyclohexyl)naphthalen-2-yl)methyl)(methyl)amino)-2-methylpropanoic acid. 90 mg, as a white solid, Y: 63%. ESI-MS (M+H)⁺: 410.2, HPLC: 100.00%. ¹H NMR (400 MHz, CD₃OD) δ: 7.80 (s, 1H), 7.74-7.69 (m, 2H), 7.38 (d, J=8.4Hz, 1H), 7.16 (d, J=1.2 Hz, 1H), 7.09 (dd, J=8.8, 2.4 Hz, 1H), 4.41-4.36 (m, 1H), 4.29 (s, 2H), 3.37-3.27 (m, 2H), 3.13-2.91 (m, 2H), 2.25-2.04 (m, 2H), 1.85-1.81 (m, 2H), 1.66-1.55 (m, 2H), 1.47-1.41 (m, 3H), 1.27-1.21 (m, 3H), 1.14 (s, 3H), 0.88 (s, 3H), 0.87 (s, 3H).

Example 213 methyl 1-((64(4,4-dimethylcyclohexyl)oxy)naphthalen-2-yl)methyl)-4-ethylpiperidine-4-carboxylate

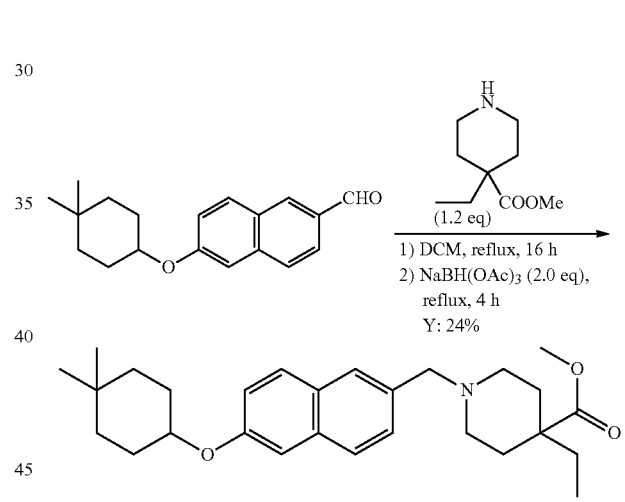

The preparation of methyl 1-((6-((4,4-dimethylcyclohexyl)oxy)naphthalen-2-yl)methyl)-4-ethylpiperidine-4-carboxylate was the same as that of ethyl 1-((6-((trans-4-(tert-butyl)cyclohexyl)oxy)naphthalen-2-yl)methyl)-3-methylpiperidine-4-carboxylate. 50 mg, as a white solid, Y: 24%. ESI-MS (M+H)⁺: 438.3.

Example 214

1-((6-((4,4-dimethylcyclohexyl)oxy)naphthalen-2-yl)methyl)-4-ethylpiperidine-4-carboxylic acid

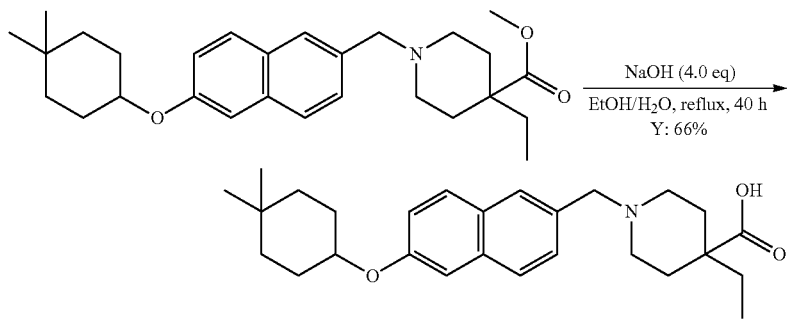

The preparation of 1-(((6-((4,4-dimethylcyclohexyl)oxy)naphthalen-2-yl)methyl)-4-ethylpiperidine-4-carboxylic acid was the same as that of 2-((((6-(((trans-4-(tert-butyl)cyclohexyl)oxy)naphthalen-2-yl)methyl)(methyl)amino)-2-methylpropanoic acid. 31 mg, as a white solid, Y: 66%. ESI-MS (M+H)+: 424.3, HPLC: 100.00%. $^1$H NMR (400 MHz, CD$_3$OD) δ: 7.80 (s, 1H), 7.74 (d, J=8.8 Hz, 1H), 7.71 (d, J=9.6 Hz, 1H), 7.38 (d, J=8.8, 1.6 Hz, 1H), 7.17 (d, J=2.0 Hz, 1H), 7.10 (dd, J=9.2, 2.4 Hz, 1H), 4.42-4.36 (m, 1H), 4.31 (s, 2H), 3.36-3.33 (m, 2H), 3.01-2.98 (m, 2H), 2.25-2.22 (m, 2H), 1.88-1.81 (m, 2H), 1.68-1.43 (m, 8H), 1.29-1.18 (m, 2H), 0.90 (s, 3H), 0.89 (s, 3H), 0.78 (t, J=7.2 Hz, 3H).

Example 215

1-[6-(Bicyclo[2.2.1]hept-5-en-2-yloxy)-naphthalen-2-ylmethyl]-piperidine-4-carboxylic acid ethyl ester

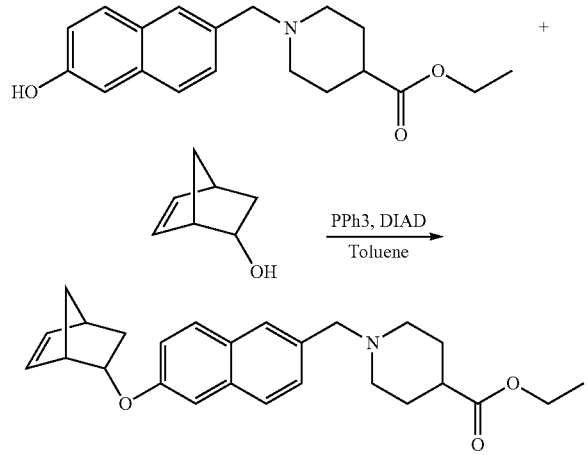

Triphenylphosphine was added to a solution of 1-(6-Hydroxy-naphthalen-2-ylmethyl)-piperidine-4-carboxylic acid ethyl ester (0.4319 g, 0.001378 mol) and bicyclo[2.2.1]hept-5-en-2-ol (0.243 g, 0.00220 mol) in toluene (0.881 mL, 0.00827 mol) and the mixture was stirred for several minutes. Diisopropyl azodicarboxylate (0.434 mL, 0.00220 mol) was then added dropwise and the mixture was stirred at room temperature for 72 hours. The reaction mixture was then diluted in ethylacetate and washed with water, then brine. The organic phase was dried over MgSO$_4$, filtered, concentrated under reduced pressure and purified by flash chromatography (0-40% EtOAc in heptanes) to give the title compound in 8% yield. ESI-MS (M+H+): 406.2.

Example 216

1-[6-(Bicyclo[2.2.1]hept-5-en-2-yloxy)-naphthalen-2-ylmethyl]-piperidine-4-carboxylic acid

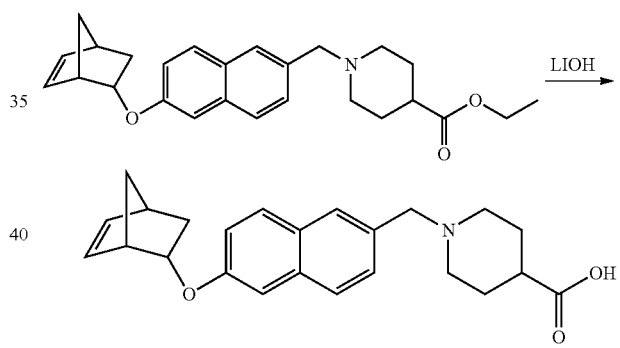

A solution of 2 M of lithium hydroxide, monohydrate in water (0.5 mL, 1 mmol) was added to a solution of 1-[6-(Bicyclo[2.2.1]hept-5-en-2-yloxy)-naphthalen-2-ylmethyl]-piperidine-4-carboxylic acid ethyl ester (0.047 g, 0.12 mmol) in THF and methanol (1.00 mL, 24.7 mmol) and the mixture was stirred at room temperature for 2 hours. The mixture was then concentrated to dryness under reduced pressure. The resulting residue was dissolved in methylene chloride and washed with 1 M of HCl in water (3 mL, 3 mmol). The layers were separated and the organic phase was concentrated to dryness and purified by preparative HPLC to give the desired product as a TFA salt. ESI-MS (M+H+): 378.3 $^1$H NMR (400 MHz, METHANOL-d$_4$) δ ppm 1.18-1.37 (m, 1 H) 1.53-1.60 (m, 1 H) 1.64-1.70 (m, 1 H) 1.79-1.96 (m, 4 H) 2.21-2.31 (m, 2 H) 2.60-2.69 (m, 1 H) 2.92-2.97 (m, 1 H) 3.05-3.12 (m, 2 H) 3.56-3.64 (m, 2 H) 4.44-4.50 (m, 3 H) 6.12-6.16 (m, 1 H) 6.36-6.41 (m, 1 H) 7.20-7.25 (m, 1 H) 7.26-7.29 (m, 1 H) 7.49-7.54 (m, 1 H) 7.83-7.87 (m, 1 H) 7.88-7.92 (m, 1 H) 7.93-7.96 (m, 1 H)

Example 217

1[6-(1,3,3-Trimethyl-bicyclo[2.2.1]hept-2-yloxy)-naphthalen-2-ylmethyl]-piperidine-4-carboxylic acid

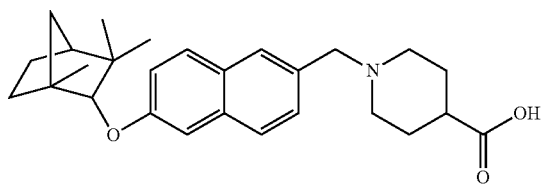 [SMILES: CC12CCC(C1)C(C)(C)C2Oc1ccc2cc(CN3CCC(C(=O)O)CC3)ccc2c1]

1-[6-(1,3,3-Trimethyl-bicyclo[2.2.1]hept-2-yloxy)-naphthalen-2-ylmethyl]-piperidine-4-carboxylic acid was synthesized as 1-[6-(Bicyclo[2.2.1]hept-5-en-2-yloxy)-naphthalen-2-ylmethyl]-piperidine-4-carboxylic acid using 1-(6-Hydroxy-naphthalen-2-ylmethyl)-piperidine-4-carboxylic acid ethyl ester (0.4510 g, 0.001439 mol). ESI-MS (M'H+): 422.4 $^1$H NMR (400 MHz, METHANOL-d$_4$) δ ppm 0.95 (s, 3 H) 1.06 (s, 3 H) 1.13 (s, 3 H) 1.21-1.34 (m, 2 H) 1.66-1.75 (m, 1 H) 1.78-1.92 (m, 5 H) 2.01-2.10 (m, 1 H) 2.21-2.30 (m, 2 H) 2.59-2.69 (m, 1 H) 3.04-3.15 (m, 2 H) 3.56-3.63 (m, 2 H) 4.28-4.32 (m, 1 H) 4.44 (s, 2 H) 5.50 (s, 1 H) 7.16-7.21 (m, 1 H) 7.23-7.26 (m, 1 H) 7.48-7.53 (m, 1 H) 7.81-7.86 (m, 1 H) 7.87-7.91 (m, 1 H) 7.92-7.94 (m, 1 H).

Example 218

6-Bromo-2-(4-tert-butyl-cyclohexyloxy)-quinoxaline

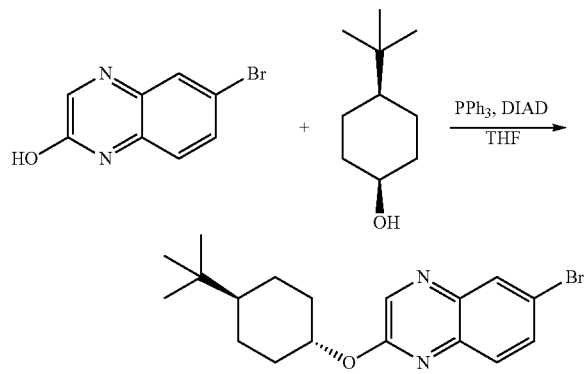

Triphenylphosphine (0.6988 g, 0.002664 mol) was added to a solution of 6-bromo-quinoxalin-2-ol (0.4283 g, 0.001903 mol) and (1s,4s)-4-(tert-butyl)cyclohexanol (0.4164 g, 0.002664 mol) in tetrahydrofuran (20 mL, 0.2 mol). The mixture was cooled in an ice/water bath and diisopropyl azodicarboxylate (0.5246 mL, 0.002664 mol) was slowly added. The mixture was stirred for 96 hours, allowing to reach room temperature. The reaction mixture was then diluted in ethylacetate and washed with water, then brine. The organic layer was dried over MgSO$_4$, filtered, concentrated under reduced pressure and purified by flash chromatography (24 g SiO$_2$ column; 0-20% ethylacetate in heptane eluent) to give the title compound. ESI-MS (M+H+): 365

Example 219

1-[2-(4-tert-Butyl-cyclohexyloxy)-quinoxalin-6-ylmethyl]-piperidine-4-carboxylic acid ethyl ester

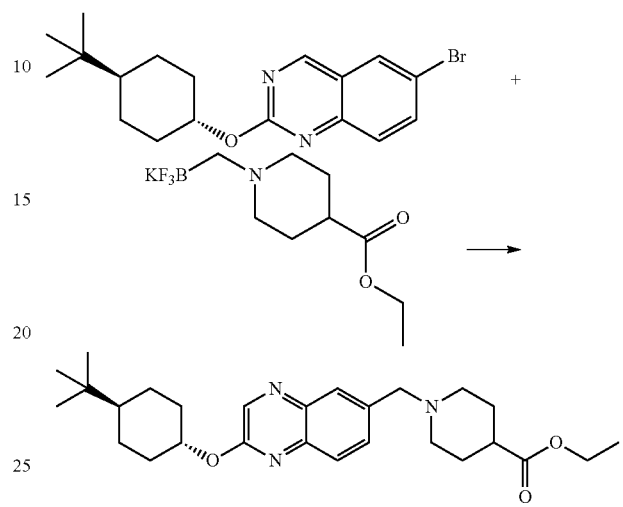

6-Bromo-2-(4 tert butyl-cyclohexyloxy)-quinoxaline (0.2879 g, 0.0007925 mol), potassium ((4-(ethoxycarbonyl)piperidin-1-yl)methyl) trifluoroborate (0.4392 g, 0.001585 mol), palladium acetate (0.01068 g, 4.755E-5 mol) 2-(Dicyclohexylphosphino)-2',4',6'-tri-isopropyl-1,1'-biphenyl (0.06800 g, 0.0001426 mol) and cesium carbonate (0.7746 g, 0.002377 mol) were added to a capped 40 mL vial equipped with a magnetic stir bar. The vial was degassed and purged with argon. Tetrahydrofuran (7.713 mL, 0.09510 mol) and water (1.142 mL, 0.06340 mol) were added and the reaction mixture was degassed, purged with argon then stirred at 60° C. for 24 hours. An additional 1 eq. of potassium ((4-(ethoxycarbonyl)piperidin-1-yl)methyl) trifluoroborate; 0.03 eq. of palladium acetate; 0.09 eq. of 2-(dicyclohexylphosphino)-2',4',6'-tri-isopropyl-1,1'-biphenyl and 1.5 eq. of cesium carbonate were added. The mixture was degassed, flushed with argon and heated at 60° C. overnight. The mixture was cooled to room temperature, diluted with ethyl acetate and washed with water, then brine. The layers were separated and the organic layer was dried over MgSO$_4$, filtered, concentrated under reduced pressure and purified by flash chromatography (24 g SiO$_2$ column; 0-10% MeOH in methylene chloride) to give the title compound. ESI-MS (M+H+): 454.1

Example 220

1-[2-(4-tert-Butyl-cyclohexyloxy)-quinoxalin-6-ylmethyl]-piperidine-4-carboxylic acid

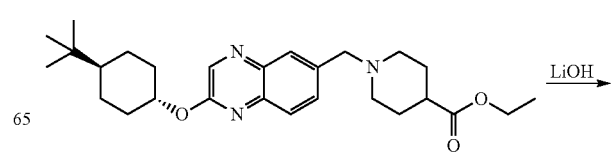

-continued

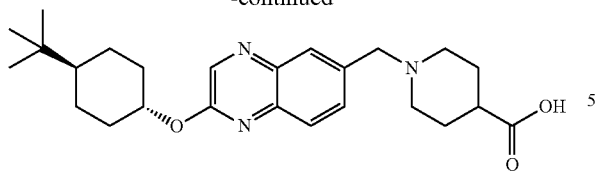

To a solution of 1-[2-(4-tert-Butyl-cyclohexyloxy)-quinoxalin-6-ylmethyl]-piperidine-4-carboxylic acid ethyl ester (0.2255 g, 0.4971 mmol) in tetrahydrofuran (6.00 mL, 74.0 mmol) and methanol (2.00 mL, 49.4 mmol) was added 2.00 mL of 2 M solution of lithium hydroxide monohydrate in water (4.00 mmol) and the mixture was stirred overnight. The mixture was concentrated to dryness under reduced pressure. The residue was dissolved in methylene chloride and washed with 1N HCl. The layers were separated and the organic layer was concentrated to dryness under reduced pressure. The crude product was dissolved in DMSO and purified by prep HPLC to give the title compound as a TFA salt. ESI-MS (M+H$^+$): 426.34. $^1$H NMR (400 MHz, METHANOL-d4) δ ppm 0.95 (s, 9 H) 1.12-1.23 (m, 1 H) 1.24-1.37 (m, 2 H) 1.47-1.61 (m, 2 H) 1.80-2.01 (m, 3 H) 2.22-2.38 (m, 4 H) 3.08-3.20 (m, 2 H) 3.58-3.66 (m, 1 H) 4.54 (br. s., 2 H) 5.15-5.25 (m, 1 H) 7.82 (dd, J=8.66, 2.13 Hz, 1 H) 7.96 (d, J=8.53 Hz, 1 H) 8.16 (d, J=2.01 Hz, 1 H) 8.48 (s, 1 H).

Example 221 methanesulfonic acid 4-tert-butyl-cyclohexyl ester

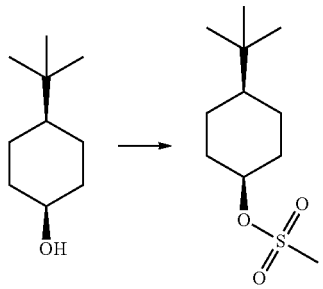

Methanesulfonyl chloride (2.840 mL, 36.70 mmol) was added dropwise to a solution of (1s,4s)-4-(tert-butyl)cyclohexanol (5.120 g, 32.76 mmol) and triethylamine (5.115 mL, 36.70 mmol) in methylene chloride (42.00 mL, 655.3 mmol) at 0° C. The formation of a white precipitate was noted. The solution was stirred overnight, allowing to reach room temperature. The resulting slurry was washed successively with citric acid (5% in water), sodium bicarbonate aqueous solution and then water. The organic layer was dried over MgSO$_4$, filtered and concentrated under reduced pressure to give the desired compound as a white solid.

Example 222

6-Bromo-2-(4-tert-butyl-cyclohexyloxy)-quinazoline

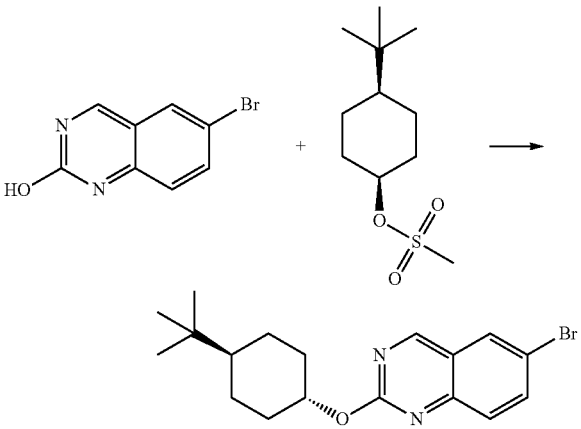

Cesium carbonate (3.1308 g, 9.6089 mmol) was added to a mixture of 6-bromoquinazolin-2-ol (1.0812 g, 4.8044 mmol) in tert-butyl alcohol (15 mL, 160 mmol), toluene (25 mL, 230 mmol) and 2-butanone (10 mL, 100 mmol). The mixture was heated at 110° C. for 1 hour in a sealed tube then cooled to room temperature and methanesulfonic acid 4-tert-butyl-cyclohexyl ester (2.2519 g, 9.6089 mmol) was added. The reaction was then heated at 110° C. overnight. The reaction mixture was cooled to room temperature then filtered through a pad of celite. The filtrate was concentrated under reduced pressure, adsorbed onto silica gel and purified by flash chromatography (80 g SiO$_2$ column; 0-40% EtOAc in heptane eluent) to give the title compound in 20% yield. ESI-MS (M+H$^+$): 365.1

Example 223

1-[2-(4-tert-Butyl-cyclohexyloxy)-quinazolin-6-ylmethyl]-piperidine-4-carboxylic acid ethyl ester

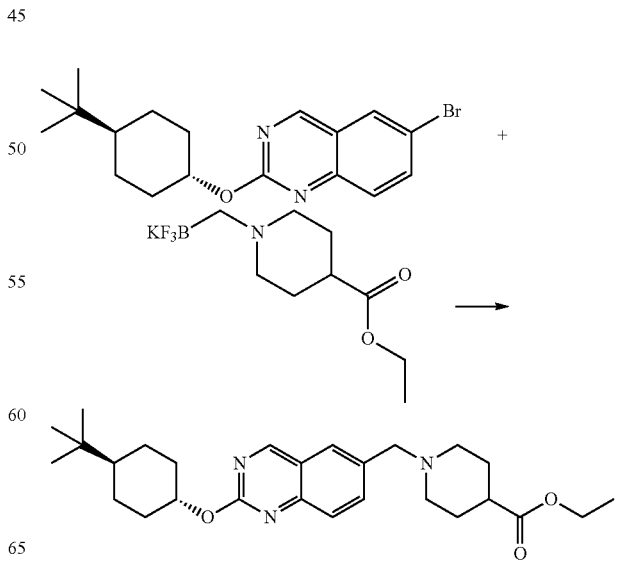

1-[2-(4-tert-Butyl-cyclohexyloxy)-quinazolin-6-ylmethyl]-piperidine-4-carboxylic acid ethyl ester was synthesized similar to 1-[2-(4-tert-Butyl-cyclohexyloxy)-quinoxalin-6-ylmethyl]-piperidine-4-carboxylic acid ethyl ester. ESI-MS (M+H⁺): 454.1

Example 224

1-[2-(4-tert-Butyl-cyclohexyloxy)-quinazolin-6-ylmethyl]-piperidine-4-carboxylic acid

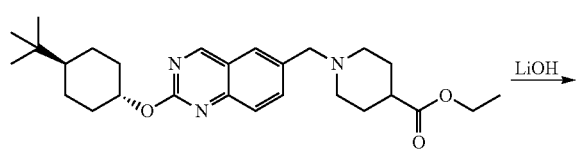

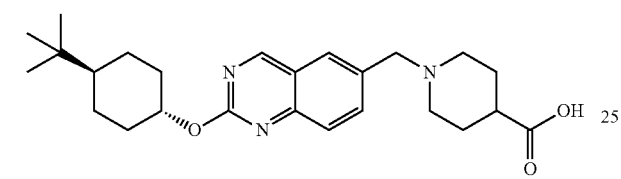

1-[2-(4-tert-Butyl-cyclohexyloxy)-quinazolin-6-ylmethyl]-piperidine-4-carboxylic acid was synthesized similar to 1-[2-(4-tert-Butyl-cyclohexyloxy)-quinoxalin-6-ylmethyl]-piperidine-4-carboxylic acid. ESI-MS (M+H⁺): 426.3. ¹H NMR (400 MHz, METHANOL-d4) δ ppm 0.92 (s, 9 H) 1.06-1.20 (m, 1 H) 1.20-1.34 (m, 2 H) 1.45-1.59 (m, 2 H) 1.76-1.98 (m, 3 H) 2.19-2.36 (m, 4 H) 3.04-3.18 (m, 1 H) 3.55-3.66 (m, 1 H) 4.50 (s, 2 H) 5.08-5.18 (m, 1 H) 7.89 (s, 1 H) 7.94-7.99 (m, 1 H) 8.15 (d, J=1.51 Hz, 1 H) 9.37 (s, 1 H)

Example 225

6-Bromo-2-(4-tert-butyl-cyclohexyloxy)-1,8-naphthyridine

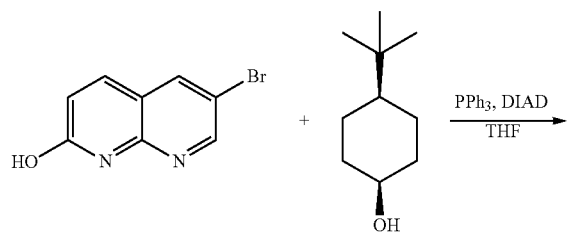

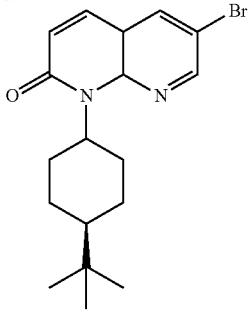

6-Bromo-2-(4-tert-butyl-cyclohexyloxy)-1,8-naphthyridine was synthesized similar to 6-bromo 2-(4-tert butyl-cyclohexyloxy)-quinoxaline. Note that the desired compound was isolated by flash chromatography. ESI-MS (M+H⁺): 365.5

Example 226

1-[7-(4-tert-Butyl-cyclohexyloxy)-[1,8]naphthyridin-3-ylmethyl]-piperidine-4-carboxylic acid ethyl ester

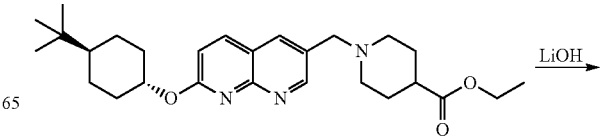

1-[7-(4-tert-Butyl-cyclohexyloxy)-[1,8]naphthyridin-3-ylmethyl]-piperidine-4-carboxylic acid ethyl ester was synthesized similar to 1-[2-(4-tert-Butyl-cyclohexyloxy)-quinoxalin-6-ylmethyl]-piperidine-4-carboxylic acid ethyl ester. ESI-MS (M+H⁺): 454.1

Example 227

1-[7-(4-tert-Butyl-cyclohexyloxy)-[1,8]naphthyridin-3-ylmethyl]-piperidine-4-carboxylic acid

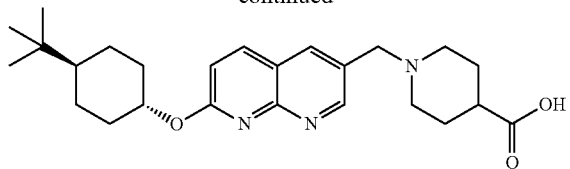

1-[7-(4-tert-Butyl-cyclohexyloxy)-[1,8]naphthyridin-3-ylmethyl]-piperidine-4-carboxylic acid was synthesized similar to 1-[2-(4-tert-Butyl-cyclohexyloxy)-quinoxalin-6-ylmethyl]-piperidine-4-carboxylic acid. ESI-MS (M+H$^+$): 426.2. $^1$H NMR (400 MHz, METHANOL-d4) δ ppm 0.94 (s, 9 H) 1.11-1.22 (m, 1 H) 1.24-1.38 (m, 2 H) 1.45-1.58 (m, 2 H) 1.90-2.00 (m, 2 H) 2.19-2.38 (m, 3 H) 3.09-3.25 (m, 1 H) 3.57-3.72 (m, 1 H) 4.57 (s, 2 H) 5.27-5.37 (m, 1 H) 7.14 (d, J=9.04 Hz, 1 H) 8.30 (d, J=8.78 Hz, 1 H) 8.54 (d, J=2.51 Hz, 1 H) 8.97 (d, J=2.51 Hz, 1 H)

Example 228

(4-Methoxyphenyl)trimethylsilane

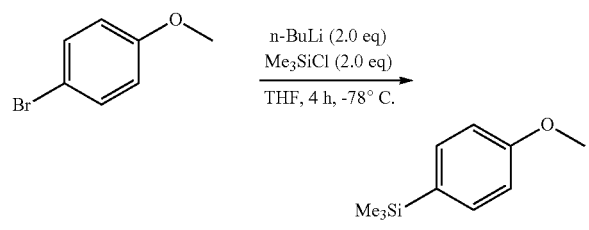

4-Bromoanisole (9.35 g, 50.0 mmol, 1.0 eq) was dissolved in anhydrous THF (200 mL). Me$_3$SiCl (12.7 mL, 100.0 mmol, 2.0 eq) was added at 0° C. followed by n-BuLi (2.5 M in hexanes, 40 mL, 100.0 mmol, 2.0 eq). The reaction mixture was stirred at room temperature for 1 h. Water (150 mL) was then added, the organic layer was separated and the aqueous layer was extracted with Et$_2$O (150 mL×2). The combined organic extracts were dried over anhydrous Na$_2$SO$_4$, filtered and concentrated in vacuo to give (4-methoxyphenyl)trimethylsilane as a light yellow oil (8.1 g, 90% yield). $^1$H NMR (300 MHz, CDCl$_3$) δ: 7.48 (d, J=11.2 Hz, 2H), 6.95 (d, J=11.2 Hz, 2H), 3.84 (s, 3H), 0.27 (s, 9H).

Example 229

4-(Trimethylsilyl)cyclohexanone

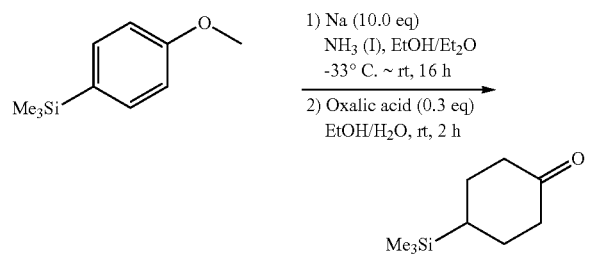

Ammonia (100 mL) was condensed at −78° C. (4-methoxyphenyl)trimethylsilane (18.0 g, 0.1 mol, 1.0 eq) in anhydrous Et$_2$O (110 mL) was added followed by EtOH (80 mL) and sodium (23.0 g, 1.0 mol, 10.0 eq) portionwise at −33° C. Additional EtOH (50 mL) was added and ammonia was allowed to evaporated over 16 h. Then water (250 mL) was added to the residue and the mixture was extracted with Et$_2$O (250 mL×3). The combined organic extracts were dried over anhydrous Na$_2$SO$_4$, filtered and concentrated in vacuo. The crude product was dissolved in EtOH (20 mL) and H$_2$O (20 mL) and oxalic acid (2.71 g, 0.03 mol, 0.3 eq) was then added. The resulting colorless solution was stirred at room temperature for 2 h. Water (100 mL) was then added and the mixture was extracted with Et$_2$O (100 mL×3). The combined organic extracts were washed with brine, dried over anhydrous Na$_2$SO$_4$, filtered and concentrated in vacuo. The residue was purified by column chromatography on silica gel (petroleum ether/EtOAc=10:1) to furnish 4-(trimethylsilyl)cyclohexanone as a light yellow oil (14.0 g, 72% yield). $^1$H NMR (300 MHz, CDCl$_3$) δ: 2.44-2.39 (m, 2H), 2.33-2.22 (m, 2H), 2.11-2.05 (m, 2H), 1.53-1.47 (m, 2H), 0.96-0.87 (m, 1H), 0.00 (s, 9H).

Example 230

Cis-4-(trimethylsilyl)cyclohexanol

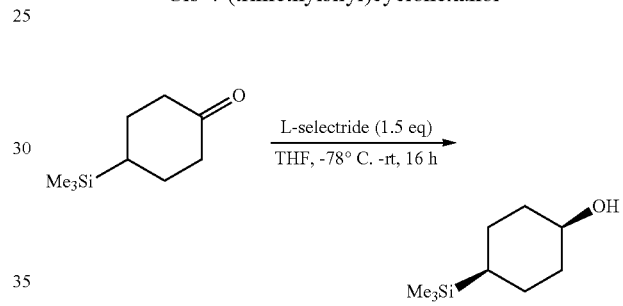

To a solution of L-selectride (165 mL, 0.165 mol, 1.5 eq) in anhydrous THF (200 mL) at −78° C. was added dropwise a solution of 4-(trimethylsilyl)cyclohexanone (20 g, 0.11 mol, 1.0 eq) in anhydrous THF (100 mL). The temperature was maintained for 3 h, and then the reaction mixture was stirred at room temperature for 16 h. Then the mixture was cooled to 0° C. before being quenched with water. The resulting mixture was warmed up to room temperature, and then sodium hydroxide aqueous solution (80 mL, 3 M) was added, followed by hydrogen peroxide (80 mL, 30%). After being stirred for 3 h, the mixture was extracted with EtOAc (300 mL x3), and the combined organic layers were washed with H$_2$O and brine, dried over Na$_2$SO$_4$, concentrated to give a residue which was purified by column chromatography on silica gel (petroleum ether/EtOAc=10:1) to obtain the product cis-4-(trimethylsilyl)cyclohexanol as a white solid (10.0 g, 51% yield). $^1$H NMR (300 MHz, CDCl$_3$) δ: 4.05 (s, 1H), 1.75 (bs, 2H), 1.58-1.43 (m, 7H), 0.55 (bs, 1H), 0.00 (s, 9H).

Example 231

Ethyl 1-((6-((trans-4-(trimethylsityl)cyclohexyl)oxy)naphthalen-2-yl)methyl)piperidine-4-carboxylate

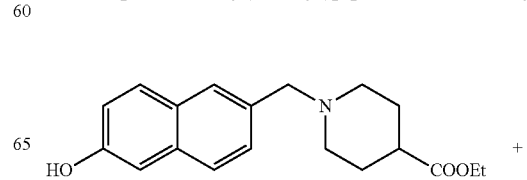

-continued

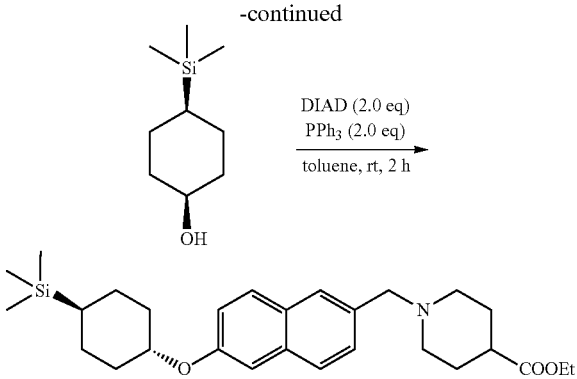

The preparation of ethyl 1-((6-(((trans-4-(trimethylsilyl)cyclohexyl)oxy)naphthalen-2-yl)methyl)piperidine-4-carboxylate was the same as that of ethyl 1-((6-(4-isopropylcyclohexyloxy)naphthalen-2-yl)methyl)piperidine-4-carboxylate. Yellow oil (130 mg, 40% yield). LCMS m/z 468.3 [M+H]$^+$.

Example 232

1-((6-(((trans-4-(trimethylsityl)cyclohexyl)oxy)naphthalen-2-yl)methyl)piperidine-4-carboxylic acid

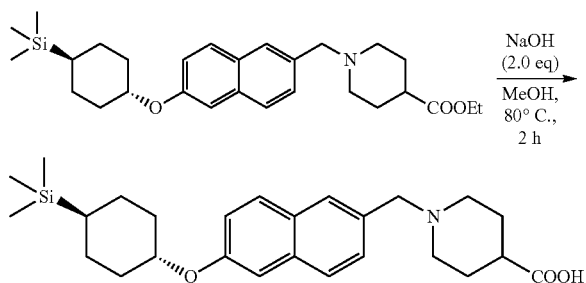

The preparation of 1-((6-(((trans-4-(trimethylsilyl)cyclohexyl)oxy)naphthalen-2-yl)methyl)piperidine-4-carboxylic acid was the same as that of 1-((6-(4-isopropylcyclohexyloxy)naphthalen-2-yl)methyl)piperidine-4-carboxylic acid. The crude product compound was purified with reverse phase prep-HPLC (acetonitrile and H$_2$O with 0.05% TFA as mobile phase) to give the title compound as a yellow oil (40 mg, 35% yield). LCMS m/z 440.3 [M+H]$^+$; $^1$H NMR (400 MHz, CD$_3$OD) δ: 7.91 (s, 1H), 7.85 (d, J=8.4 Hz, 1H), 7.80 (d, J=8.4 Hz, 1H), 7.48 (dd, J=1.6, 8.0 Hz, 1H), 7.30 (s, 1H), 7.18 (dd, J=2.4, 8.8 Hz, 1H), 4.42 (s, 2H), 4.40-4.35 (m, 1H), 3.65-3.40 (m, 2H), 3.26-3.07 (m, 2H), 2.85-2.62 (m, 1H), 2.29-2.21 (m, 4H), 2.02-1.83 (m, 4H), 1.41-1.29 (m, 4H), 0.60-0.55 (m, 1H), 0.00 (s, 9H).

Example 233

Activity Measurements

S1P Receptor Activity Assays

Agonist percentage activation determinations were obtained by assaying sample compounds and referencing the E$_{max}$ control for each receptor profiled. Antagonist percentage inhibition determinations were obtained by assaying sample compounds and referencing the control EC$_{80}$ wells for each receptor profiled. The samples were run using a "Single Addition" assay protocol for the agonist and antagonist assay run. The protocol design was as follows:

Compound Preparation

Master stock solution: Unless specified otherwise, all sample compounds were diluted in 100% anhydrous DMSO including all serial dilutions. All control wells contained identical solvent final concentrations as did the sample compound wells.

Compound plate for assay: The sample compounds were transferred from a master stock solution into a daughter plate that was used in the assay. Each sample compound was diluted into assay buffer (1× HBSS with 20 mM HEPES and 2.5 mM Probenecid) at an appropriate concentration to obtain final concentrations.

Calcium Flux Assay: Agonist Assay Format

Sample compounds were plated in an eight-point, four-fold dilution series in duplicate with a top concentration of 10 μM. The concentrations described here reflect the final concentration of the compounds during the antagonist assay. During the agonist assay the compound concentrations were 1.25 fold higher to allow for the final desired concentration to be achieved with further dilution by EC$_{80}$ of reference agonists during the antagonist assay.

Reference agonists were handled as mentioned above serving as assay control. The reference agonists were handled as described above for E$_{max}$.

Assay was read for 180 seconds using the FLIPR$^{TETRA}$ (This assay run added sample compounds and reference agonist to respective wells). At the completion of the first "Single Addition" assay run, assay plate was removed from the FLIPR$^{TETRA}$ and placed at 25° C. for seven (7) minutes.

Calcium Flux Assay: Antagonist Assay Format

Using the EC$_{80}$ values determined during the agonist assay, stimulated all pre-incubated sample compound and reference antagonist (if applicable) wells with EC$_{80}$ of reference agonist. Read for 180 seconds using the FLIPR$^{TETRA}$ (This assay added reference agonist to respective wells—then fluorescence measurements were collected to calculate percentage inhibition values).

Data Processing

All plates were subjected to appropriate baseline corrections. Once baseline corrections were processed, maximum fluorescence values were exported and data manipulated to calculate percentage activation, percentage inhibition and Z'.

With regard to S1P1 agonist activity, the compounds of examples 32, 34, 42, 56, 58, 60, 61, 75, 77, 100, 106, 131, 139, 145, 153, 171, 177, 179, 183, 187, 204, and 232, had EC$_{50}$ values in the range of 50 nM to 10 μM. With regard to S1P4 antagonist activity, the compounds of examples 15, 26, 28, 30, 32, 34, 36, 38, 42, 56, 57, 58 , 60, 61, 75, 77, 100, 104, 106, 131, 133, 137, 139, 141, 143, 145, 147, 149, 153, 155, 163, 171, 177, 179, 183, 187, 191, 192, 195, 197, 199, 204, 210, 212, 214, and 232, had IC$_{50}$ values in the range of 10 nM to 10 μM. With regard to S1P5 antagonist activity, the compounds of examples 28, 32, 34, 38, 42, 104, 106, 131, 137, 139, 141, 143, 145, 149, 155, 161, 171, 177, 179, 183, 191, 192, 195, 197, 199, and 204 had IC$_{50}$ values in the range of 100 nM to 5 μM.

OPC Differentiation Assay

Enriched populations of oligodendrocytes were grown from post-natal day 2 (P2) female Sprague Dawley rats. The forebrain was dissected out and placed in Hank's buffered saline solution (HBSS; Invitrogen, Grand Island, N.Y.). The tissue was cut into 1 mm fragments and incubated at 37° C. for 15 minutes in 0.01% trypsin and 10 μg/mL DNase. Dissociated cells were plated on poly-L-lysine-coated T75 tissue culture flasks and grown at 37° C. for 10 days in Dulbecco's modified Eagle's medium (DMEM) with 20% fetal calf serum (Invitrogen). A2B5⁺ OPCs were collected by shaking the flask overnight at 200 rpm and 37° C., resulting in a 95% pure population.

For the differentiation assay, 2 μM and 20 μM antagonist or the same concentrations of vehicle (DMSO) were applied to OPCs cultured in CNTF/T3 containing media. After a 3-day incubation, after a 3-day incubation, cell were lysed and then subjected to MSD (Meso Scale Discovery-R) analysis. EC50 was calculated by Prism using a nonlinear sigmoidal dose-response curvecells. Alternatively, cells were lysed in 80 μL lysis buffer (50 mM HEPES [4-(2-hydroxyethyl)-1-piperazineethanesulfonic acid], pH 7.5, 150 mM NaCl, 1.5 mM MgCl2, 1 mM ethylene glycol tetraacetic acid [EGTA], 1% Triton X-100 and 10% glycerol) for 30 minutes at 4° C. After centrifugation at 14,000 g for 15 minutes, the supernatants were boiled in Laemmli sample buffer, subjected to 4-20% SDS-PAGE, and analyzed by Western blotting with anti-MBP, anti-myelin-associated glycoprotein (MAG), or anti-beta actin antibodies. The secondary antibodies used were anti-mouse IgG-HRP (horseradish peroxidase) and anti-rabbit IgG-HRP respectively.

The compounds of examples 22, 26, 30, 32, 34, 36, 38, 42, 48, 52, 57, 58, 61, 62, 75, 77, 81, 83, 85, and 87 showed activity in the range of + to ++++ at 20 micromolar in the OPC assay. The compounds of examples 15, 22, 30, 32, 36, 42, 48, 55, 56, 57, 58, 59, 60, 61, 62, 75, 77, 83, 85, 88 showed activity in the range of + to ++++ at 2 micromolar in the OPC assay. The compounds of examples 22, 24, 26, 30, 32, 42, 58, 60, 61, and 77 had an EC50 value of<10 μM.

OPC Oligodendrocyte Myelination Assay

Embryonic neocortical neurons are dissected from embryonic day 18 (E18) Sprague Dawley rats, and then plated on poly-D-lysine (100 μg/mL)-coated cover slips and grown in neurobasal medium supplemented with B27 (Invitrogen) for one week. A2B5⁺ OPCs are prepared as described above and then added into the cultured neocortical neurons. One day later, different concentrations of an S1P4 receptor antagonist and control reagents are applied into the co-cultures. Fresh media containing the different concentrations of an S1P4 receptor antagonist or control compounds are supplied every three days. After ten days, co-cultures are subjected to sodium dodecyl sulfate polyacrylamide gel electrophoresis (SDS-PAGE)/Western blot analyses to quantify MAG, MBP, and MOG.

Remyelination Assay in Brain Slice Culture

Approximately three to four consecutive 300 μm slices are taken from the junction of the corpus callosum to the hippocampus in post-natal, day 17 Sprague Dawley rats (Charles River, Willmington, Mass.). Slices are cultured in basal DMEM supplemented with 25% horse serum for three days, before being treated with 6 mg/mL LPC (Sigma L-4129) for a further three days. The medium is then changed, and slices incubated with medium containing an S1P4 receptor antagonist or vehicle control for a final period of three days, after which myelination is visualized by black gold staining (Millipore, Bedford, Mass.) following the manufacture's protocol. Images are acquired using a Leica M420 microscope (Bannockburn, Ill.) and the staining intensity of corpus callosum is analyzed using Metamorph software (Molecular Devices, Downingtown, Pa.). Three or four brain slices are used for each treatment group.

Lysolecithin Demyelination Model

Adult Sprague Dawley rats (220-260 g) are anesthetized by intraperitoneal injection of a cocktail, consisting of Ketamine (35 mg/kg), Xylazine (6 mg/kg) and Acepromazine (1 mg/kg). The back of the animal is shaved from the lower thoracic to the lumbar region, subsequently sanitized with 70% isopropanol, Betadine Scrub solution, and 70% isopropanol again. The animal is then placed onto stereotaxic frame.

After ensuring an adequate anesthetic level, the skin is incised along the midline over the thoracic region. The dorsal fascia is incised and the paraspinal muscles separated from the spinous processes of the thoracic vertebrae T-9 through T-11. The T-10 vertebra is demolished, and the lamina removed with micro-rongeurs. Once the dorsal spinal cord region is exposed, a microcapillary glass needle is inserted into the dorsal column to a depth of 0.6 mm. The demyelinating reagent, 1.5 μL of 1% Lysolecithin (LPC, Sigma# L1381) in saline is injected with the infusion rate of 2 nL/sec controlled by a micro-pump (World Precision Instrument #micro4). Once the injection is completed, the needle is placed for additional 1 min before removal. The paraspinal muscles and the lumbar fascia are closed with suture (#5, silk). The skin incision is closed with wound clips. Animals are allowed to recover from the anesthesia and are observed in the humidified incubator.

Buprenorphine (0.05 mg/kg) is administrated subcutaneously (s.c.) twice a day for additional two days following operation.

Three days following the primary surgery, treatments with an S1P4 receptor antagonist (30 pmol), LPA (30 pmol) or control (0.1% DMSO in saline) are injected at the primary injection region in a volume of 1.5 μL with the same infusion speed as indicated above. Nine days following the primary surgery, the animals are anesthetized and perfused transcardially with heparin (10 iu/mL) in saline followed by 4% PFA in PBS. The spinal cords are removed and post fixed in PFA overnight. Then the cords are cut into 100 μM thickness longitudinally and then 1% loxuol fast blue is stained and histological evaluation for remyelination and repair is assessed under microscope.

For systemic treatment, the animals are administered once daily intraperitoneally with either an S1P4 receptor antagonist (10 mg/kg) or control (15% HPCD (hydroxypropyl-β-cyclodextrin)) 2 days following the primary surgery. Nine days after the primary surgery, animals are sacrificed and the spinal cords were processed as indicated above.

Calcium Mobilization

Compounds that are not specific for a particular S1P receptor can cause undesirable side effects. Accordingly, compounds are tested to identify those that are specific. Accordingly, the test compounds are tested in a calcium mobilization assay. The procedure is essentially as described in Davis et al. (2005) *Journal of Biological Chemistry*, vol. 280, pp. 9833-9841, which is incorporated by reference in its entirety with the following modifications. Calcium mobilization assays are performed in recombinant CHEM cells expressing human $S1P_1$, $S1P_2$, $S1P_3$, $S1P_4$, or $S1P_5$ purchased from Millipore (Billerica, Mass.). To detect free intracellular calcium, $S1P_1$, $S1P_2$, $S1P_3$, $S1P_4$, or $SI P_5$ cells are loaded with FLIPR Calcium 4 dye from Molecular Devices (Sunnyvale, Calif.). Cells are imaged for calcium mobilization using a FLIPR$^{TETRA}$ equipped with a 96-well dispense head.

In vivo Screening Assays

Measurement of circulating lymphocytes: Compounds are dissolved in 30% HPCD. Mice (C57bl/6 male, 6-10 week-old) are administered 0.5 and 5 mg/kg of a compound via oral gavage 30% HPCD is included as a negative control.

Blood is collected from the retro-orbital sinus 5 and 24 hours after drug administration under short isoflurane anesthesia. Whole blood samples are subjected to hematology analysis. Peripheral lymphocyte counts are determined using an automated analyzer (HEMAVET™ 3700). Subpopulations of peripheral blood lymphocytes are stained by fluorochrome-conjugated specific antibodies and analyzed using a fluorescent activating cell sorter (FACSCALIBUR™). Three mice are used to assess the lymphocyte depletion activity of each compound screened.

Compounds of formula (I) can induce full lymphopenia at times as short as 4 hours or less to as long as 48 hours or more; for example, 4 to 36 hours, or 5 to 24 hours. In some cases, a compound of formula can induce full lymphopenia at 5 hours and partial lymphopenia at 24 hours. The dosage required to induce lymphopenia can be in the range of, e.g., 0.001 mg/kg to 100 mg/kg; or 0.01 mg/kg to 10 mg/kg. The dosage can be 10 mg/kg or less, such as 5 mg/kg or less, 1 mg/kg or less, or 0.1 mg/kg or less.

Other embodiments are within the scope of the following claims.

What is claimed is:

1. A method for treating stroke in a mammal, comprising administering to said mammal an effective amount of a compound selected from the group consisting of:
    1-((6-(trans-4-tert-butylcyclohexyloxy)quinazolin-2-yl)methyl)piperidine-4-carboxylic acid;
    1-(1-(6-(trans-4-tert-butylcyclohexyloxy)naphthalen-2-yl)-2,2,2-trifluoroethyl)piperidine-4-carboxylic acid;
    1-((6-(4-isopropylcyclohexyloxy)naphthalen-2-yl)methyl)piperidine-4-carboxylic acid;
    1-((6-(cis-4-tert-butylcyclohexyloxy)naphthalen-2-yl)methyl)piperidine-4-carboxylic acid;
    1-((6-(4-(trifluoromethyl)cyclohexyloxy)naphthalen-2-yl)methyl)piperidine-4-carboxylic acid;
    1-((6-(4-ethylcyclohexyloxy)naphthalen-2-yl)methyl)piperidine-4-carboxylic acid;
    1-((6-(4-butylcyclohexyloxy)naphthalen-2-yl)methyl)piperidine-4-carboxylic acid;
    1-((6-(spiro[4.5]decan-8-yloxy)naphthalen-2-yl)methyl)piperidine-4-carboxylic acid;
    1-((6-(cis-4-ethylcyclohexyloxy)naphthalen-2-yl)methyl)piperidine-4-carboxylic acid;
    1-((6-(trans-4-ethylcyclohexyloxy)naphthalen-2-yl)methyl)piperidine-4-carboxylic acid;
    1-((6-(trans-4-tert-butylcyclohexyloxy)quinolin-2-yl)methyl)piperidine-4-carboxylic acid;
    1-(6-(trans-4-tert-butylcyclohexyloxy)-2-naphthoyl)piperidine-4-carboxylic acid;
    1-((6-((4-tert-butylcyclohexylidene)methyl)naphthalen-2-yl)methyl)piperidine-4-carboxylic acid;
    1-((2-(trans-4-tert-butylcyclohexyloxy)quinolin-6-yl)methyl)piperidine-4-carboxylic acid;
    1-[6-(4-tert-butyl-cyclohexyloxy)-naphthalen-2-ylmethyl]-4-ethyl-piperidine-4-carboxylic acid;
    1-[6-(4-tert-butyl-cyclohexyloxy)-naphthalen-2-ylmethyl]-4-propyl-piperidine- 4-carboxylic acid;
    1-[6-(4-tert-butyl-cyclohexyloxy)-naphthalen-2-ylmethyl]-3-methyl-piperidine-4-carboxylic acid;
    1-[6-(4-tert-butyl-cyclohexyloxy)-naphthalen-2-ylmethyl]-4-phenyl-piperidine-4-carboxylic acid;
    1-[6-(4-tert-butyl-cyclohexyloxy)-naphthalen-2-ylmethyl]-perhydro-azepine-4-carboxylic acid;
    1-[6-(4-tert-butyl-cyclohexyloxy)-naphthalen-2-ylmethyl]-4-hydroxy-piperidine-4-carboxylic acid;
    {1-[6-(4-tert-butyl-cyclohexyloxy)-naphthalen-2-ylmethyl]-piperidin-4-yl}-acetic acid;
    1-[7-(trans-4-tert-butyl-cyclohexyloxy)-isoquinolin-3-yl-methyl]-piperidine-4-carboxylic acid;
    1-((6-(trans-4-tert-butylcyclohexyloxy)naphthalen-2-yl)methyl)-4-methylpiperidine-4-carboxylic acid;
    1-((6-(cyclopentyloxy)naphthalen-2-yl)methyl)piperidine-4-carboxylic acid;
    1-((6-(cycloheptyloxy)naphthalen-2-yl)methyl)piperidine-4-carboxylic acid;
    1-((6-(tetrahydro-2H-pyran-4-yloxy)naphthalen-2-yl)methyl)piperidine-4-carboxylic acid;
    1-((6-(spiro[5.5]undecan-3-yloxy)naphthalen-2-yl)methyl)piperidine-4-carboxylic acid;
    1-((6-(spiro[3.5]nonan-7-yloxy)naphthalen-2-yl)methyl)piperidine-4-carboxylic acid; and
    1-[6-(4-tert-butyl-cyclohexyloxy)-naphthalen-2-ylmethyl]-piperidine-2-carboxylic acid;
    or a pharmaceutically acceptable salt thereof.

2. The method of claim 1, wherein the compound is 1-((6-(trans-4-tert-butylcyclohexyloxy)quinazolin-2-yl)methyl)piperidine-4-carboxylic acid, or a pharmaceutically acceptable salt thereof.

3. The method of claim 1, wherein the compound is 1-(1-(6-(trans-4-tert-butylcyclohexyloxy)naphthalen-2-yl)-2,2,2-trifluoroethyl)piperidine-4-carboxylic acid, or a pharmaceutically acceptable salt thereof.

4. The method of claim 1, wherein the compound is 1-((6-(spiro[4.5]decan-8-yloxy)naphthalen-2-yl)methyl)piperidine-4-carboxylic acid, or a pharmaceutically acceptable salt thereof.

5. The method of claim 1, wherein the compound is 1-((6-(cis-4-ethylcyclohexyloxy)naphthalen-2-yl)methyl)piperidine-4-carboxylic acid, or a pharmaceutically acceptable salt thereof.

6. The method of claim 1, wherein the compound is 1-((6-(trans-4-tert-butylcyclohexyloxy)quinolin-2-yl)methyl)piperidine-4-carboxylic acid, or a pharmaceutically acceptable salt thereof.

7. The method of claim 1, wherein the compound is 1-(6-(trans-4-tert-butylcyclohexyloxy)-2-naphthoyl)piperidine-4-carboxylic acid, or a pharmaceutically acceptable salt thereof.

8. The method of claim 1, wherein the compound is 1-((6-((4-tert-butylcyclohexylidene)methyl)naphthalen-2-yl)methyl)piperidine-4-carboxylic acid, or a pharmaceutically acceptable salt thereof.

9. The method of claim 1, wherein the compound is 1-((2-(trans-4-tert-butylcyclohexyloxy)quinolin-6-yl)methyl)piperidine-4-carboxylic acid, or a pharmaceutically acceptable salt thereof.

10. The method of claim 1, wherein the compound is 1-[6-(4-tert-butyl-cyclohexyloxy)-naphthalen-2-ylmethyl]-3-methyl-piperidine-4-carboxylic acid, or a pharmaceutically acceptable salt thereof.

11. The method of claim 1, wherein the compound is 1-[6-(4-tert-butyl-cyclohexyloxy)-naphthalen-2-ylmethyl]-4-phenyl-piperidine-4-carboxylic acid, or a pharmaceutically acceptable salt thereof.

12. The method of claim 1, wherein the compound is 1-[6-(4-tert-butyl-cyclohexyloxy)-naphthalen-2-ylmethyl]-perhydro-azepine-4-carboxylic acid, or a pharmaceutically acceptable salt thereof.

13. The method of claim 1, wherein the compound is {1-[6-(4-tert-butyl-cyclohexyloxy)-naphthalen-2-ylmethyl]-piperidin-4-yl}-acetic acid, or a pharmaceutically acceptable salt thereof.

14. The method of claim 1, wherein the compound is 1-[7-(trans-4-tert-butyl-cyclohexyloxy)-isoquinolin-3-ylmethyl]-piperidine-4-carboxylic acid, or a pharmaceutically acceptable salt thereof.

15. The method of claim 1, wherein the compound is 1-((6-(cyclopentyloxy)naphthalen-2-yl)methyl)piperidine-4-carboxylic acid, or a pharmaceutically acceptable salt thereof.

16. The method of claim 1, wherein the compound is 1-((6-(tetrahydro-2H-pyran-4-yloxy)naphthalen-2-yl)methyl)piperidine-4-carboxylic acid, or a pharmaceutically acceptable salt thereof.

17. The method of claim 1, wherein the compound is 1-[6-(4-tert-butyl-cyclohexyloxy)-naphthalen-2-ylmethyl]-piperidine-2-carboxylic acid, or a pharmaceutically acceptable salt thereof.

18. The method of claim 1, wherein the mammal is a human patient.

* * * * *